US011680246B2

(12) United States Patent
Zhang

(10) Patent No.: US 11,680,246 B2
(45) Date of Patent: Jun. 20, 2023

(54) EX VIVO PROLIFERATION OF EPITHELIAL CELLS

(71) Applicant: PROPAGENIX INC., Gaithersburg, MD (US)

(72) Inventor: Chengkang Zhang, Germantown, MD (US)

(73) Assignee: PROPAGENIX INC., Gaithersburg, MD (US)

( * ) Notice: Subject to any disclaimer, the term of this patent is extended or adjusted under 35 U.S.C. 154(b) by 536 days.

(21) Appl. No.: 16/899,989

(22) Filed: Jun. 12, 2020

(65) Prior Publication Data

US 2021/0032602 A1    Feb. 4, 2021

Related U.S. Application Data

(63) Continuation of application No. 15/921,536, filed on Mar. 14, 2018, now Pat. No. 10,711,250, and a continuation of application No. 15/921,546, filed on Mar. 14, 2018, now Pat. No. 10,711,251, said application No. 15/921,536 is a continuation of application No. 15/685,853, filed on Aug. 24, 2017, now Pat. No. 9,963,680, said application No. 15/921,546 is a continuation of application No. 15/685,853, filed on Aug. 24, 2017, now Pat. No. 9,963,680, which is a continuation of application No. 15/296,831, filed on Oct. 18, 2016, now Pat. No. 9,790,471, which is a continuation of application No. PCT/US2016/025396, filed on Mar. 31, 2016, and a continuation of application No. PCT/US2016/025396, filed on Mar. 31, 2016.

(60) Provisional application No. 62/294,896, filed on Feb. 12, 2016, provisional application No. 62/217,406, filed on Sep. 11, 2015, provisional application No. 62/142,851, filed on Apr. 3, 2015.

(51) Int. Cl.
*C12N 5/071* (2010.01)

(52) U.S. Cl.
CPC ......... *C12N 5/0688* (2013.01); *C12N 5/0629* (2013.01); *C12N 5/0683* (2013.01); *C12N 2500/90* (2013.01); *C12N 2500/99* (2013.01); *C12N 2501/11* (2013.01); *C12N 2501/113* (2013.01); *C12N 2501/117* (2013.01); *C12N 2501/15* (2013.01); *C12N 2501/727* (2013.01); *C12N 2501/999* (2013.01); *C12N 2533/54* (2013.01)

(58) Field of Classification Search
None
See application file for complete search history.

(56) References Cited

U.S. PATENT DOCUMENTS

| | | | |
|---|---|---|---|
| 5,792,752 A | 8/1998 | Cho-Chung et al. | |
| 6,692,961 B1 | 2/2004 | Battista et al. | |
| 7,199,147 B2 | 4/2007 | Imazaki et al. | |
| 7,217,722 B2 | 5/2007 | Takami et al. | |
| 7,846,904 B2 | 12/2010 | Harley et al. | |
| 8,137,662 B2 | 3/2012 | Freeman et al. | |
| 8,148,149 B2 | 4/2012 | Nigam et al. | |
| 8,252,591 B2 | 8/2012 | Ince et al. | |
| 8,476,081 B2 | 7/2013 | Kranz et al. | |
| 8,642,339 B2 | 2/2014 | Sato et al. | |
| 8,822,663 B2 | 9/2014 | Schrum et al. | |
| 8,859,286 B2 | 10/2014 | Agulnick | |
| 8,906,631 B2 | 12/2014 | Clevers et al. | |
| 9,279,106 B2 | 3/2016 | Schlegel et al. | |
| 9,533,013 B2 | 1/2017 | Reid et al. | |
| 9,790,471 B2 | 10/2017 | Zhang | |
| 9,963,680 B2 | 5/2018 | Zhang | |
| 10,066,201 B2 | 9/2018 | Zhang | |
| 10,100,285 B2 | 10/2018 | Zhang et al. | |
| 10,119,121 B2 | 11/2018 | Zhang | |
| 10,514,163 B2 | 12/2019 | Zhang | |
| 10,711,250 B2 | 7/2020 | Zhang | |
| 10,711,251 B2 | 7/2020 | Zhang | |
| 11,060,715 B2 | 7/2021 | Zhang | |
| 2003/0220357 A1 | 11/2003 | Bankston et al. | |
| 2004/0058392 A1 | 3/2004 | Clevers et al. | |
| 2005/0182040 A1 | 8/2005 | Imazaki et al. | |
| 2005/0197328 A1 | 9/2005 | Bailey et al. | |
| 2006/0241127 A1 | 10/2006 | Feurer et al. | |
| 2007/0010008 A1 | 1/2007 | Tseng et al. | |
| 2008/0166327 A1 | 7/2008 | Asahara et al. | |
| 2008/0242594 A1 | 10/2008 | McKay et al. | |
| 2010/0275280 A1 | 10/2010 | Clevers et al. | |
| 2012/0028355 A1 | 2/2012 | Sato et al. | |
| 2012/0196312 A1 | 8/2012 | Sato et al. | |
| 2013/0189327 A1 | 7/2013 | Ortega et al. | |
| 2013/0196369 A1 | 8/2013 | Hikita et al. | |
| 2013/0224857 A1 | 8/2013 | Blak et al. | |
| 2013/0309681 A1 | 11/2013 | Schlegel et al. | |

(Continued)

FOREIGN PATENT DOCUMENTS

| | | |
|---|---|---|
| EP | 0 291 696 A2 | 11/1988 |
| JP | 63-304978 A | 12/1988 |

(Continued)

OTHER PUBLICATIONS

Gibco by Life Technologies, Keratinocyte-SFM (1X), Product Manual, catalog No. 17005-042, publication No. MAN0006271, Rev. 3.00, 2014, www.lifetechnologies.com.

(Continued)

*Primary Examiner* — Robert M Kelly
(74) *Attorney, Agent, or Firm* — Loza & Loza, LLP

(57) ABSTRACT

The technology relates in part to methods and compositions for ex vivo proliferation and expansion of epithelial cells.

20 Claims, 44 Drawing Sheets

Specification includes a Sequence Listing.

(56) References Cited

U.S. PATENT DOCUMENTS

| | | | |
|---|---|---|---|
| 2014/0134733 | A1 | 5/2014 | Wu et al. |
| 2014/0243227 | A1 | 8/2014 | Clevers et al. |
| 2014/0256037 | A1 | 9/2014 | Sato et al. |
| 2014/0328808 | A1 | 11/2014 | Watanabe et al. |
| 2014/0329318 | A1 | 11/2014 | Rajagopal et al. |
| 2014/0335616 | A1 | 11/2014 | Judd et al. |
| 2015/0175964 | A1 | 6/2015 | Clegg et al. |
| 2015/0231201 | A1 | 8/2015 | Clevers et al. |
| 2016/0060594 | A1 | 3/2016 | Xian |
| 2017/0029779 | A1 | 2/2017 | Zhang |
| 2017/0029780 | A1 | 2/2017 | Zhang |
| 2017/0073635 | A1 | 3/2017 | Zhang |
| 2018/0002669 | A1 | 1/2018 | Zhang |
| 2018/0051258 | A1 | 2/2018 | Zhang et al. |
| 2018/0208899 | A1 | 7/2018 | Zhang |
| 2018/0208900 | A1 | 7/2018 | Zhang |
| 2019/0041052 | A1 | 2/2019 | Zhang |
| 2020/0011523 | A1 | 1/2020 | Zhang |

FOREIGN PATENT DOCUMENTS

| | | |
|---|---|---|
| JP | 2008-538180 A | 10/2008 |
| JP | 2014-502151 A | 1/2014 |
| JP | 2016-513469 A | 5/2016 |
| WO | WO 03/059913 A1 | 7/2003 |
| WO | WO 03/062225 A1 | 7/2003 |
| WO | WO 03/062227 A1 | 7/2003 |
| WO | WO 03/064397 A1 | 8/2003 |
| WO | WO 2004/112719 A2 | 12/2004 |
| WO | WO 2005/003101 A2 | 1/2005 |
| WO | 2006/105152 A2 | 10/2006 |
| WO | WO 2007/002900 A1 | 1/2007 |
| WO | WO 2007/127454 A2 | 11/2007 |
| WO | WO 2008/009641 A1 | 1/2008 |
| WO | WO 2009/022907 A2 | 2/2009 |
| WO | WO 2010/090513 A2 | 8/2010 |
| WO | WO 2012/065067 A2 | 5/2012 |
| WO | 2012/168930 A2 | 12/2012 |
| WO | 2012/173207 A1 | 12/2012 |
| WO | 2013/061608 A1 | 5/2013 |
| WO | WO 2014/152321 A1 | 9/2014 |
| WO | 2014/162040 A1 | 10/2014 |
| WO | 2014/165663 A1 | 10/2014 |
| WO | WO 2016/161192 A1 | 10/2016 |
| WO | WO 2017/044454 A1 | 3/2017 |

OTHER PUBLICATIONS

International Preliminary Report on Patentability dated Mar. 22, 2018 in International Patent Application No. PCT/US2016/050496, filed on Sep. 7, 2016, 11 pages.
International Preliminary Report on Patentability dated Oct. 12, 2017 in International Patent Application No. PCT/US2016/025396, filed on Mar. 31, 2016, 9 pages.
International Search Report and Written Opinion dated Jun. 10, 2016 in International Patent Application No. PCT/US2016/025396, filed on Mar. 31, 2016, 14 pages.
International Search Report and Written Opinion dated Nov. 14, 2016 in International Patent Application No. PCT/US2016/050496, filed on Sep. 7, 2016, 15 pages.
Office Action dated Apr. 18, 2018 in U.S. Appl. No. 15/722,327, filed Oct. 2, 2017 and published as US 2018-0051258 on Feb. 22, 2018, 9 pages.
Office Action dated Apr. 25, 2018 in U.S. Appl. No. 15/258,751, filed Sep. 7, 2016 and published as US 2017-0073635 on Mar. 16, 2017, 5 pages.
Office Action dated Aug. 27, 2018 in U.S. Appl. No. 15/296,920, filed Oct. 18, 2016 and published as US 2017-0029780 on Feb. 2, 2017, 7 pages.
Office Action dated Dec. 1, 2017 in U.S. Appl. No. 15/258,751, filed Sep. 7, 2016 and published as US 2017-0073635 on Mar. 16, 2017, 12 pages.
Office Action dated Dec. 15, 2017 in U.S. Appl. No. 15/722,327, filed Oct. 2, 2017 and published as US 2018-0051258 on Feb. 22, 2018, 7 pages.
Office Action dated Dec. 18, 2017 in U.S. Appl. No. 15/685,853, filed Aug. 24, 2017 and published as US 2018-0002669 on Jan. 4, 2018, 17 pages.
Office Action dated Feb. 22, 2018 in U.S. Appl. No. 15/685,853, filed Aug. 24, 2017 and published as US 2018-0002669 on Jan. 4, 2018, 8 pages.
Office Action dated Feb. 25, 2019 in U.S. Appl. No. 16/041,646, filed Jul. 20, 2018 and published as US 2019-0041052 on Feb. 7, 2019, 7 pages.
Office Action dated Feb. 28, 2017 in U.S. Appl. No. 15/296,831, filed Oct. 18, 2016 and published as US 2017-0029779 on Feb. 2, 2017, 8 pages.
Office Action dated Jan. 19, 2018 in U.S. Appl. No. 15/722,327, filed Oct. 2, 2017 and published as US 2018-0051258 on Feb. 22, 2018, 10 pages.
Office Action dated Jul. 14, 2017 in U.S. Apl. No. 15/258,751, filed Sep. 7, 2016 and published as US 2017-0073635 on Mar. 16, 2017, 12 pages.
Office Action dated Jun. 11, 2018 in U.S. Appl. No. 15/722,327, filed Oct. 2, 2017 and published as US 2018-0051258 on Feb. 22, 2018, 5 pages.
Office Action dated Jun. 26, 2017 in U.S. Appl. No. 15/296,831, filed Oct. 18, 2016 and published as US 2017-0029779 on Feb. 2, 2017, 8 pages.
Office Action dated Mar. 2, 2018 in U.S. Appl. No. 15/685,853, filed Aug. 24, 2017 and published as US 2018-0002669 on Jan. 4, 2018, 8 pages.
Office Action dated Mar. 4, 2020 in U.S. Appl. No. 15/921,536, filed Mar. 14, 2018 and published as US 2018-0208899 on Jul. 26, 2018, 5 pages.
Office Action dated Mar. 4, 2020 in U.S. Appl. No. 15/921,546, filed Mar. 14, 2018 and published as US 2018-0208900 on Jul. 26, 2018, 7 pages.
Office Action dated Mar. 5, 2018 in U.S. Appl. No. 15/258,751, filed Sep. 7, 2016 and published as US 2017-0073635 on Mar. 16, 2017, 9 pages.
Office Action dated May 13, 2019 in U.S. Appl. No. 16/041,646, filed Jul. 20, 2018 and published as US 2019-0041052 on Feb. 7, 2019, 8 pages.
Office Action dated May 29, 2018 in U.S. Appl. No. 15/296,920, filed Oct. 18, 2016 and published as US 2017-0029780 on Feb. 2, 2017, 11 pages.
Office Action dated Oct. 18, 2019 in U.S. Appl. No. 15/921,536, filed Mar. 14, 2018 and published as US 2018-0208899 on Jul. 26, 2018, 12 pages.
Office Action dated Oct. 18, 2019 in U.S. Appl. No. 15/921,546, filed Mar. 14, 2018 and published as US 2018-0208900 on Jul. 26, 2018, 12 pages.
Office Action dated Sep. 20, 2018 in U.S. Appl. No. 15/296,920, filed Oct. 18, 2016 and published as US 2017-0029780 on Feb. 2, 2017, 4 pages.
Product Information "Product Name: A 83-01", Tocris—A Biotechne Brand, Nov. 23, 2017, 1 page.
Product Information "Product Name: GW/88388", Tocris—A Biotechne Brand, Jan. 14, 2016, 1 page.
Product Information "Product Name: RepSox", Tocris—A Biotechne Brand, Feb. 14, 2019, 1 page.
Product Information "Product Name: SB 431542", Tocris—A Biotechne Brand, Jun. 6, 2019, 1 page.
UniProt Accession No. B9EGV5, created Dec. 1, 2000.
UniProt Accession No. NM004850, created Jul. 2, 2016.
UniProt Accession No. NM005406, created Aug. 26, 2016.
UniProt Accession No. O14944, created Jan. 1, 1998.
UniProt Accession No. O75116 replacement for P05777, created Nov. 1, 1988.
UniProt Accession No. P04141, created Nov. 1, 1986.
UniProt Accession No. P09919, created: Jul. 1, 1989.
UniProt Accession No. P14210, created Jan. 1, 1990.
UniProt Accession No. P20809, created Feb. 1991.
UniProt Accession No. Q0P6N6, created Sep. 19, 2006.

(56) References Cited

OTHER PUBLICATIONS

UniProt Accession No. Q13464, created May 24, 2004.
UniProt Accession No. Q14487, created Nov. 1, 1996.
UniProt Accession No. Q3MI86, created Oct. 25, 2005.
UniProt Accession No. Q61CV5, created Nov. 23, 2004.
UniProt Accession No. Q86UF5, created Jun. 1, 2003.
Agarwal et al., "Making Every Cell Like HeLa a Giant Step for Cell Culture", The American Journal of Pathology, 2011, 180(2):443-445.
Barrandon et al., "Three Clonal Types of Keratinocyte with Different Capacities for Multiplication", PNAS, 1987, 84:2302-2306.
Bhowmick et al., "TGF-β-Induced RhoA and p160ROCK Activation is Involved in the Inhibition of Cdc25A with Resultant Cell-Cycle Arrest", PNAS, Dec. 23, 2003, 100(26):15548-15553.
Boehm et al., "An Ecosystem of Cancer Cell Line Factories to Support A Cancer Dependency Map", Nature Review Genetics, PMID: 26077369, 2015, 16(7):373-374.
Bokoch Gary M, "Biology of the p21-activated Kinases", Annual Review of Biochemistry, 2003, 72:743-781.
Bove et al., "Breaking The In Vitro Alveolar Type II Cell Proliferation Barrier While Retaining Ion Transport Properties", American Journal of Respiratory Cell and Molecular Biology, Apr. 2014, 50(4):767-776.
Boyce et al., "Calcium-Regulated Differentiation of Normal Human Epidermal Keratinocytes in Chemically Defined Clonal Culture and Serum-Free Serial Culture", Journal of Investigative Dermatology, Aug. 1983, 81(1 Suppl):33s-40s.
Butler, "Rapid Expansion of Human Epithelial Stem Cells Suitable for Airway Tissue Engineering", American Journal of Respiratory and Critical Care Medicine, Feb. 2016, 194(2):156-168.
Castro-Munozledo et al., "Cultivation, Serial Transfer, and Differentiation of Epidermal Keratinocytes in Serum-Free Medium", Biochemical and Biophysical Research Communications, XP002289456, ISSN: 0006-291X, DOI: 10.1006/BBRC.1997.6924 abstract, Jan. 1, 1997, 236(1):167-172.
Chapman et al., "Human Keratinocytes Are Efficiently Immortalized by a Rho Kinase Inhibitor", Journal of Clinical Investigation, Jul. 2010, 120(7):2619-2626.
Chapman et al., "The Effect of Rho Kinase Inhibition on Long-Term Keratinocyte Proliferation Is Rapid and Conditional", Stem Cell Research & Therapy, 2014, 5(2):60.
Chu et al., "CRISPR-Cas9-Mediated Gene Knockout in Primary Human Airway Epithelial Cells Reveals a Proinflammatory Role for MUC18", Gene Therapy, Jul. 2, 2015, 22(10):822-829.
Clevers Hans, "What is an Adult Stem Cell?", Science, Dec. 2015, 350(6266):1319-1320.
Crystal et al., "Patient-Derived Models of Acquired Resistance Can Identify Effective Drug Combinations for Cancer", Science, Dec. 19, 2014, 346(6216):1480-1486.
Dakic et al., "Y-27632 Inhibits Myc-lnduced Apoptosis and Cooperates with Mycto Immortalize Human Keratinocytes", Cancer Research, Abstract, 2015, 75(15):5145.
Denicourt et al., "Another Twist in the Transforming Growth Factor β-Induced Cell-Cycle Arrest Chronicle", PNAS, Dec. 23, 2003, 100(26):15290-15291.
Francis, "Albumin and Mammalian Cell Culture: Implications for Biotechnology Applications", Cytotechnology, Jan. 2010, 62(1):1-16.
Hegab et al., "Mimicking the Niche of Lung Epithelial Stem Cells and Characterization of Several Effectors of Their In Vitro Behavior", Stem Cell Research, Jul. 2015, 15(1):109-121.
Hofner et al., "Defined Conditions for the Isolation and Expansion of Basal Prostate Progenitor Cells of Mouse and Human Origin", Stem Cell Reports, XP055277403, United States ISSN: 2213-6711, DOI: 10.1016/j.stemcr.2015.01.015 abstract, Mar. 1, 2015, 4(3):503-518.
Hu et al., "Rho Kinase as Potential Therapeutic Target for Cardiovascular Diseases: Opportunities and Challenges", Expert Opinion on Therapeutic Targets, 2005, 9(4):715-736.
Huch et al., "In Vitro Expansion of Single Lgr5+ Liver Stem Cells Induced by Wnt-Driven Regeneration", Nature, Feb. 14, 2013, 494(7436):247-250.
Kang et al., "SMAD4 Regulates Cell Motility Through Transcription of N-Cadherin in Human Pancreatic Ductal Epithelium", PLoS One, Sep. 29, 2014, 9(9):11 pages.
Kirshner et al., "Inhibition of Transforming Growth Factor-β1 Signaling Attenuates Ataxia Telangiectasia Mutated Activity in Response to Genotoxic Stress", Cancer Research, Nov. 15, 2006, 66(22):10861-10869.
Kobayashi et al., "New Technique for Culturing Corneal Epithelial Cells of Normal Mice", Molecular Vision, 2009, 15:1589-1593.
Lamb et al., "Keratinocytes Propagated in Serum-Free, Feeder-Free Culture Conditions Fail to Form Stratified Epidermis in a Reconstituted Skin Mode", PLoS One, XP055315202, DOI: 10.1371/journal.pone.0052494 abstract, Jan. 2013, 8(1):8 pages.
Lansdorp Peter M., "Telomere Length and Proliferation Potential of Hematopoietic Stem Cells", Journal of Cell Science, 1995, 108:1-6.
Lebrun, "The Dual Role of TGFβ in Human Cancer: From Tumor Suppression to Cancer Metastasis", ISRN Molecular Biology—Article 381428, 2012, 28 pages.
Ligaba et al., "Multifactorial Analysis of Conditional Reprogramming of Human Keratinocytes", PLoS One, 2015, 10(2):1-11.
Lin et al., "Attenuation of TGF-β Signaling Suppresses Premature Senescence in a p21-Dependent Manner and Promotes Oncogenic Ras-Mediated Metastatic Transformation in Human Mammary Epithelial Cells", Molecular Biology of the Cell, Apr. 15, 2012, 23:1569-1581.
Liu et al., "ROCK Inhibitor and Feeder Cells Induce the Conditional Reprogramming of Epithelial Cells", The American Journal of Pathology, Feb. 2012, 180(2):599-607.
Loirand et al., "Rho Kinases in Cardiovascular Physiology and Pathophysiology", Circulation Research, Feb. 17, 2006, 98(3):322-334.
LU et al., "Isolation of Circulating Epithelial and Tumor Progenitor Cells with an Invasive Phenotype from Breast Cancer Patients", International Journal of Cancer, Feb. 1, 2010, 126(3):669-683.
Mou et al., "Dual SMAD Signaling Inhibition Enables Long-Term Expansion of Diverse Epithelial Basal Cells", Cell Stem Cell, 2016, 19:217-231.
Nagy et al., "Induced Pluripotent Stem Cell Lines Derived from Equine Fibroblasts", Stem Cell Reviews, 2011, 7(3):693-702.
Natarajan et al., "A Keratinocyte Hypermotility/Growth-Arrest Response Involving Laminin 5 and p16INK4A Activated in Wound Healing and Senescence", American Journal of Pathology, Jul. 2006, 168(6):1821-1837.
Ouderkirk et al., "Non-Muscle Myosins in Tumor Progression, Cancer Cell Invasion and Metastasis", Cytoskeleton (Hoboken), 2014, 71(8):447-463.
Ouellette et al., "Telomerase Activity Does Not Always Imply Telomere Maintenance", Biochemical and Biophysical Research Communications, Jan. 27, 1999, 254(3):795-803.
Palechor-Ceron et al., "Radiation Induces Diffusible Feeder Cell Factor(s) That Cooperate with ROCK Inhibitor to Conditionally Reprogram and Immortalize Epithelial Cells", The American Journal of Pathology, Dec. 2013, 183(6):1862-1870.
Park et al., "An Novel Inhibitor of TGF-β Type I Receptor, IN-1130, Blocks Breast Cancer Lung Metastasis Through Inhibition of Epithelial-Mesenchymal Transition", Cancer Letters, May 2014, 351(1):72-80.
Prater, "Mammary Stem Cells Have Myoepithelial Cell Properties", Nature Cell Biology, Aug. 31, 2014, 16(10):942-950.
Reynolds et al., "Airway Progenitor Clone Formation Is Enhanced by Y-27632-Dependent Changes in the Transcriptome", American Journal of Respiratory Cell and Molecular Biology, Sep. 2016, 55(3):323-336.
Riento, "Rocks: Multifunctional Kinases in Cell Behavior", Nature Reviews Molecular Cell Biology, 2003, 4:446-456.
Rollins et al., "Environment-dependent Growth Inhibition of Human Epidermal Keratinocytes by Recombinant Human Transforming Growth Factor-Beta", Journal of Cellular Physiology, Jun. 1989, 139(3):455-462.

(56) References Cited

OTHER PUBLICATIONS

Saenz et al., "Conditionally Reprogrammed Normal and Transformed Mouse Mammary Epithelial Cells Display A Progenitor-Cell-Like Phenotype", PLoS One, 2014, 9(5):10 pages.
Sato et al., "Long-term Expansion of Epithelial Organoids from Human Colon, Adenoma, Adenocarcinoma, and Barrett's Epithelium", Gastroenterology, Sep. 2011, 141(5):1762-1772.
Schukur et al., "Implantable Synthetic Cytokine Converter Cells with And-Gate Logic Treat Experimental Psoriasis", Science Translational Medicine, Dec. 16, 2015, 7(318):12 pages.
Siegel et al., "Cytostatic and Apoptotic Actions of TGF-β in Homeostasis and Cancer", Nature Reviews Cancer, Dec. 2003, 3(11):807-820.
Stasi et al., "Nanotechnology and Regenerative Medicine—Optimal Isolation and Xeno-Free Culture Conditions for Limbal Stem Cell Function", Investigative Ophthalmology & Visual Science, Sep. 2013, 55(1):375-386.
Strudwick et al., "Combination of Low Calcium with Y-27632 Rock Inhibitor Increases the Proliferative Capacity, Expansion Potential and Lifespan of Primary Human Keratinocytes while Retaining Their Capacity to Differentiate into Stratified Epidermis in a 3D Skin Model", PLoS ONE, p. e0123651, XP055315198, DOI: 10.1371/journal.pone.0123651 abstract, Apr. 13, 2015, 10(4): e0123651.
Su et al., "Cell Confluence-induced Activation of Signal Transducer and Activator of Transcription-3 (Stat3) Triggers Epithelial Dome Formation via Augmentation of Sodium Hydrogen Exchanger-3 (NHE3) Expression", The Journal of Biological Chemistry, Mar. 30, 2007, 282(7):9883-9894.
Suprynowicz et al., "Conditionally Reprogrammed Cells Represent a Stem-like State of Adult Epithelial Cells", PNAS, Dec. 4, 2012, 109(49): 20035-20040.
Tojo et al., "The ALK-5 Inhibitor A-83-01 Inhibits Smad Signaling and Epithelial-to-Mesenchymal Transition by Transforming Growth Factor-β", Cancer Science, 2005, 96(11):791-800.
Walters et al., "Pseudo-immortalization of postnatal cochlear progenitor cells yields a scalable cell line capable of transcriptionally regulating mature hair cell genes", Nature Scientific Reports, Dec. 2015, 5:17792-17804.
Wang et al., "Characterization of Ex Vivo Expanded Oral Mucosal Epithelium Cells on Acellular Porcine Corneal Stroma for Ocular Surface Reconstruction", Journal of Ophthalmology, Article ID 6761714, Jan. 1, 2017, 2017:8 pages.
Wang et al., "Cloning and Variation of Ground State Intestinal Stem Cells", Nature, Jun. 11, 2015, 522(7555):173-178.
Watanabe et al., "A ROCK Inhibitor Permits Survival of Dissociated Human Embryonic Stem Cells", Nature Biotechnology, Jun. 2007, 25(6):681-686.
Wei et al., "Modulation of TGF-β-lnducible Hypermotility by EGF and Other Factors in Human Prostate Epithelial Cells and Keratinocytes", In Vitro Cellular & Developmental Biology, Animal, Nov. 2010, 46(10):841-855.
Wong et al., "The Role of Epidermal Growth Factor and Its Receptors in Mammalian CNS", Cytokine & Growth Factor Reviews, Apr.-Jun. 2004, 15(2-3):147-156.
Yu et al., "Circulating Tumor Cells: Approaches to Isolation and Characterization", Journal of Cell Biology, Feb. 7, 2011, 192(3):373-382.
Yuan et al., "Use of Reprogrammed Cells to Identify Therapy for Respiratory Papillomatosis", The New England Journal of Medicine, Sep. 27, 2012, 367(13):1220-1227.
Zamudio et al., "Inhibition of TGFβ Cell Signaling for Limbal Explant Culture in Serumless, Defined Xeno-Free Conditions", Experimental Eye Research, XP029518168, ISSN: 0014-4835, Doi: 10.1016/J.EXER.2015.10.021 abstract, Jul. 11, 2015, 145(7):48-57.
Zhang et al., "TGF-β Inhibition Rescues Hematopoietic Stem Cell Defects and Bone Marrow Failure in Fanconi Anemia", Cell Stem Cell, May 5, 2016, 18(5): 668-681.
Tsuchida et al., "Signal Transduction Pathway Through Activin Receptors as a Therapeutic Target of Musculoskeletal Diseases and Cancer", Endocrine Journal, 2008, 55(1):11-21.
Shahjalal et al., "Generation of Insulin-Producing β-like Cells from Human iPS Cells in a Defined and Completely Xeno-Free Culture System", Journal of Molecular Cell Biology, 2014, 6(5):394-408.
Funakoshi Co., Ltd., "Frontiers in Life Science", Funakoshi Co., Ltd., dobutsuyuraiseibunfrinokumikaetaihitokesseiarubumin (recombinant human serum albumin free of animal-derived component), <URL: https://www.funakoshi.co.jp/contents/4964>, 2011, 6 pages. (A Japanese-language product catalogue for human serum albumin which is expressed and purified from rice (ecoHSA), in which such HSA is suitable for cell culture (e.g., culture of CHO cell line)).
Office Action dated Jan. 4, 2021 in U.S. Appl. No. 16/525,999, filed Jul. 30, 2019 and published as US-2020-0011523-A1 on Jan. 9, 2020, 10 pages.

Prostate epithelial cells in KSFM at PD 18

Bronchial epithelial cells in KSFM at PD 11

PrEC in KSFM+A, passage 6, day 1 day 2 day 3 day 8

HBEC in KSFM+A, passage 7, day 1 day 2 day3 day 7

HBEC in KSFM+Y+A, passage 7, day 1 day 2 day 4 day 7

PrEC in KSFM+Y, passage 7, day 1

HBEC in KSFM+Y, passage 6, day 1

PrEC in KSFM+Y, passage 7, day 9

HBEC in KSFM+Y, passage 6, day 8

| Karotypes of HFK, HBEC and PrEC cells | | | |
|---|---|---|---|
| Cell Line | Donor Age | Early Passage in KSFM+A+Y | Late Passage in KSFM+A+Y |
| HFK | 0 year | 46,XY, P3 (13.5 PD) | 46,XY, P19 (62.0 PD) |
| HBEC | 49 years | 46,XX, P4 (11.1 PD) | 46,XX, P16 (45.1 PD) |
| PrEC | 26 years | 46,XY, P3 (13.5 PD) | 46,XY, P13 (41.1 PD) |

Fig. 21A

| Gene Name | KSFM p2 | KSFM p6 | KSFM+A+Y, p2 | KSFM+A+Y, p13 | KSFM+A+Y, p23 |
|---|---|---|---|---|---|
| *Genes that are involved in stress response and senescence* | | | | | |
| AKT1 | 1 | 26.0 | -2.6 | -3.1 | -3.2 |
| ATM | 1 | 6.1 | -3.2 | -1.6 | -3.2 |
| CDKN2A | 1 | 16.3 | -2.5 | 2.5 | 1.8 |
| GADD45A | 1 | 5.0 | -6.2 | 2.2 | -1.8 |
| GLB1 | 1 | 4.8 | -7.8 | -1.1 | 1.1 |
| PLAU | 1 | 3.8 | -19.4 | -7.1 | -28.8 |
| SERPINE1 | 1 | 3.3 | -16.1 | -2.3 | -13.7 |
| SOD2 | 1 | 5.8 | -1.0 | 1.2 | -1.2 |
| | | | | | |
| *Adhesion molecules and intermediate filament protein* | | | | | |
| FN1 | 1 | 4.7 | -3821.7 | -2149.8 | -982.3 |
| THBS1 | 1 | 2.8 | -99.0 | -3.3 | -16.3 |
| VIM | 1 | 4.1 | -153.3 | -310.8 | -8192.0 |
| | | | | | |
| *Genes that are upregulated in KSFM+A+Y* | | | | | |
| CDKN2B | 1 | -226.0 | 1.2 | 1.9 | 4.5 |
| CITED2 | 1 | 3.2 | -1.4 | 8.5 | 8.5 |
| CREG1 | 1 | 1.0 | 1.5 | 1.9 | 3.1 |
| ID1 | 1 | -1.0 | 4.4 | 3.3 | 11.2 |
| MAP2K6 | 1 | -2.3 | -1.6 | 33.4 | 22.6 |
| IGFBP3 | 1 | 12.7 | 9.3 | 455.1 | 2019.8 |
| IGFBP5 | 1 | 2.0 | 1.8 | 57.3 | 2.6 |

Fig. 27

ZO-1 immunostaining

Day 1

Day 6

Day 10

SEQUENCE LISTING

```
<160> NUMBER OF SEQ ID NOS: 3

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
tgacacctca cctcacccac                                                    20

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 2
cactgtcttc cgcaagttca c                                         21

<210> SEQ ID NO 3
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 3
accctggtcc gaggtgtccc tgag                                      24
```

EX VIVO PROLIFERATION OF EPITHELIAL CELLS

RELATED PATENT APPLICATIONS

This patent application is a continuation of U.S. application Ser. No. 15/921,536 filed on Mar. 14, 2018, now U.S. Pat. No. 10,711,250, entitled EX VIVO PROLIFERATION OF EPITHELIAL CELLS, naming Chengkang Zhang as inventor, which is a continuation application of U.S. patent application Ser. No. 15/685,853 filed on Aug. 24, 2017, now U.S. Pat. No. 9,963,680, entitled EX VIVO PROLIFERATION OF EPITHELIAL CELLS, naming Chengkang Zhang as inventor, which is a continuation of U.S. patent application Ser. No. 15/296,831 filed on Oct. 18, 2016, now U.S. Pat. No. 9,790,471, entitled EX VIVO PROLIFERATION OF EPITHELIAL CELLS, naming Chengkang Zhang as inventor, which is a continuation of international patent application no. PCT/US2016/025396 filed on Mar. 31, 2016, entitled EX VIVO PROLIFERATION OF EPITHELIAL CELLS, naming Chengkang Zhang as inventor. International patent application no. PCT/US2016/025396 claims the benefit of U.S. provisional patent application No. 62/142,851 filed on Apr. 3, 2015, entitled EX VIVO PROLIFERATION OF EPITHELIAL CELLS, naming Chengkang Zhang as inventor. International patent application no. PCT/US2016/025396 also claims the benefit of U.S. provisional patent application No. 62/217,406 filed on Sep. 11, 2015, entitled EX VIVO PROLIFERATION OF EPITHELIAL CELLS, naming Chengkang Zhang as inventor. International patent application no. PCT/US2016/025396 also claims the benefit of U.S. provisional patent application No. 62/294,896 filed on Feb. 12, 2016, entitled EX VIVO PROLIFERATION OF EPITHELIAL CELLS, naming Chengkang Zhang as inventor. The entire content of the foregoing applications is incorporated herein by reference, including all text, tables and drawings, for all purposes.

This patent application is also a continuation of U.S. application Ser. No. 15/921,546 filed on Mar. 14, 2018, now U.S. Pat. No. 10,711,251, entitled EX VIVO PROLIFERATION OF EPITHELIAL CELLS, naming Chengkang Zhang as inventor, which is a continuation application of U.S. patent application Ser. No. 15/685,853 filed on Aug. 24, 2017, now U.S. Pat. No. 9,963,680, entitled EX VIVO PROLIFERATION OF EPITHELIAL CELLS, naming Chengkang Zhang as inventor, which is a continuation of U.S. patent application Ser. No. 15/296,831 filed on Oct. 18, 2016, now U.S. Pat. No. 9,790,471, entitled EX VIVO PROLIFERATION OF EPITHELIAL CELLS, naming Chengkang Zhang as inventor, which is a continuation of international patent application no. PCT/US2016/025396 filed on Mar. 31, 2016, entitled EX VIVO PROLIFERATION OF EPITHELIAL CELLS, naming Chengkang Zhang as inventor. International patent application no. PCT/US2016/025396 claims the benefit of U.S. provisional patent application No. 62/142,851 filed on Apr. 3, 2015, entitled EX VIVO PROLIFERATION OF EPITHELIAL CELLS, naming Chengkang Zhang as inventor. International patent application no. PCT/US2016/025396 also claims the benefit of U.S. provisional patent application No. 62/217,406 filed on Sep. 11, 2015, entitled EX VIVO PROLIFERATION OF EPITHELIAL CELLS, naming Chengkang Zhang as inventor. International patent application no. PCT/US2016/025396 also claims the benefit of U.S. provisional patent application No. 62/294,896 filed on Feb. 12, 2016, entitled EX VIVO PROLIFERATION OF EPITHELIAL CELLS, naming Chengkang Zhang as inventor. The entire content of the foregoing applications is incorporated herein by reference, including all text, tables and drawings, for all purposes.

SEQUENCE LISTING

The instant application contains a Sequence Listing which has been submitted electronically in ASCII format and is hereby incorporated by reference in its entirety. Said ASCII copy, created on Oct. 17, 2016, is named PPG-2001-CTt_SL.txt and is 1,043 bytes in size.

FIELD

The technology relates in part to methods and compositions for ex vivo proliferation and expansion of epithelial cells.

BACKGROUND

Organs such as lung, kidney, liver, pancreas and skin can be characterized by, among other things, the presence of organ-specific epithelial cells. Epithelial cells may be defined by one or more specific functions of each such organ. Specific functions may include, for example, gas exchange in the lung, filtration in the kidney, detoxification and conjugation in the liver, insulin production in the pancreatic islet cells or protection against hazardous conditions in the environment by the skin. Disease or degeneration of such an organ is often debilitating or life threatening because degenerated or lost organ structure is not easily replaced, and because the specialized cells of one organ generally cannot take over the function of another organ.

Certain types of epithelial cells can be difficult to recover and/or regenerate in vivo, and can be challenging to maintain once taken out of their context in the body. Certain types of epithelial cells (e.g., organ-specific epithelial cells harvested from subjects, lineage-committed epithelial cells derived from pluripotent stem cells and/or differentiated epithelial cells) can be challenging to proliferate and expand in vitro and typically have a very limited lifespan in culture. To study epithelial cells in vitro or ex vivo, a form of genetic manipulation such as inserting viral or cellular oncogenes, often is required to allow the cells to survive more than a few passages. These genetic manipulations, however, change the genetic background and physiology of the cells such that these cells may not resemble or function like normal epithelial cells. Moreover, these genetically modified cells would not be candidates for implantation into an animal.

Methods of culturing and expanding epithelial cells (e.g., cells harvested from subjects, cells derived from stem cells) for extended periods of time, without genetically altering the cells, would be useful for a variety of purposes including research applications, personalized medicine applications, and transplantation.

SUMMARY

Provided herein in certain aspects are methods for proliferating differentiated epithelial cells ex vivo, which method comprises a) culturing differentiated epithelial cells under serum-free and feeder-cell free conditions; and b) inhibiting TGF-beta signaling in the differentiated epithelial cells during the culturing in (a).

Also provided herein in certain aspects are methods for proliferating formerly quiescent epithelial cells ex vivo, which method comprises a) culturing formerly quiescent epithelial cells under serum-free and feeder-cell free conditions; and b) inhibiting TGF-beta signaling in the formerly quiescent epithelial cells during the culturing in (a).

Also provided herein in certain aspects are methods for proliferating lineage-committed epithelial cells ex vivo, which method comprises a) culturing lineage-committed epithelial cells under serum-free and feeder-cell free conditions; and b) inhibiting TGF-beta signaling in the lineage-committed epithelial cells during the culturing in (a).

Also provided herein in certain aspects are methods for proliferating epithelial cells ex vivo, which method comprises a) culturing epithelial cells under feeder-cell free conditions; b) inhibiting TGF-beta signaling in the epithelial cells during the culturing in (a); and c) inhibiting the activity of p21-activated kinase (PAK) in the epithelial cells during the culturing in (a). In some embodiments, the epithelial cells are differentiated epithelial cells, formerly quiescent epithelial cells and/or lineage-committed epithelial cells.

Also provided herein in certain aspects are methods for proliferating epithelial cells ex vivo, which method comprises a) culturing epithelial cells under serum-free and feeder-cell free conditions; b) inhibiting TGF-beta signaling in the epithelial cells during the culturing in (a); and c) inhibiting the activity of myosin II in the epithelial cells during the culturing in (a). In some embodiments, the epithelial cells are differentiated epithelial cells, formerly quiescent epithelial cells and/or lineage-committed epithelial cells.

Also provided herein in certain aspects are methods for proliferating differentiated epithelial cells ex vivo, which method comprises a) culturing differentiated epithelial cells under feeder-cell free conditions; b) activating telomerase reverse transcriptase in the differentiated epithelial cells; and c) modulating cytoskeletal structure in the differentiated epithelial cells.

Also provided herein in certain aspects are methods for proliferating formerly quiescent epithelial cells ex vivo, which method comprises a) culturing formerly quiescent epithelial cells under feeder-cell free conditions; b) activating telomerase reverse transcriptase in the formerly quiescent epithelial cells; and c) modulating cytoskeletal structure in the formerly quiescent epithelial cells.

Also provided herein in certain aspects are methods for proliferating lineage-committed epithelial cells ex vivo, which method comprises a) culturing lineage-committed epithelial cells under feeder-cell free conditions; b) activating telomerase reverse transcriptase in the lineage-committed epithelial cells; and c) modulating cytoskeletal structure in the lineage-committed epithelial cells.

Provided herein in certain aspects is a serum-free cell culture medium for proliferating differentiated epithelial cells ex vivo under feeder-cell free conditions, which serum-free medium comprises one or more TGF-beta inhibitors (e.g., one or more TGF-beta signaling inhibitors). Also provided herein in certain aspects is a serum-free cell culture medium for proliferating differentiated epithelial cells ex vivo under feeder-cell free conditions, which serum-free medium comprises a small molecule inhibitor consisting of a TGF-beta inhibitor (e.g., a TGF-beta signaling inhibitor).

Provided herein in certain aspects is a serum-free cell culture medium for proliferating formerly quiescent epithelial cells ex vivo under feeder-cell free conditions, which serum-free medium comprises one or more TGF-beta inhibitors (e.g., one or more TGF-beta signaling inhibitors). Also provided herein in certain aspects is a serum-free cell culture medium for proliferating formerly quiescent epithelial cells ex vivo under feeder-cell free conditions, which serum-free medium comprises a small molecule inhibitor consisting of a TGF-beta inhibitor (e.g., a TGF-beta signaling inhibitor).

Provided herein in certain aspects is a serum-free cell culture medium for proliferating lineage-committed epithelial cells ex vivo under feeder-cell free conditions, which serum-free medium comprises one or more TGF-beta inhibitors (e.g., one or more TGF-beta signaling inhibitors). Also provided herein in certain aspects is a serum-free cell culture medium for proliferating lineage-committed epithelial cells ex vivo under feeder-cell free conditions, which serum-free medium comprises a small molecule inhibitor consisting of a TGF-beta inhibitor (e.g., a TGF-beta signaling inhibitor).

Provided herein in certain aspects is a serum-free cell culture medium for proliferating differentiated epithelial cells ex vivo under feeder-cell free conditions, which serum-free medium comprises one or more telomerase reverse transcriptase activators and one or more cytoskeletal structure modulators. Also provided herein in certain aspects is a serum-free cell culture medium for proliferating differentiated epithelial cells ex vivo under feeder-cell free conditions, which serum-free medium comprises small molecules consisting of a telomerase reverse transcriptase activator and a cytoskeletal structure modulator.

Provided herein in certain aspects is a serum-free cell culture medium for proliferating formerly quiescent epithelial cells ex vivo under feeder-cell free conditions, which serum-free medium comprises one or more telomerase reverse transcriptase activators and one or more cytoskeletal structure modulators. Also provided herein in certain aspects is a serum-free cell culture medium for proliferating formerly quiescent epithelial cells ex vivo under feeder-cell free conditions, which serum-free medium comprises small molecules consisting of a telomerase reverse transcriptase activator and a cytoskeletal structure modulator.

Provided herein in certain aspects is a serum-free cell culture medium for proliferating lineage-committed epithelial cells ex vivo under feeder-cell free conditions, which serum-free medium comprises one or more telomerase reverse transcriptase activators and one or more cytoskeletal structure modulators. Also provided herein in certain aspects is a serum-free cell culture medium for proliferating lineage-committed epithelial cells ex vivo under feeder-cell free conditions, which serum-free medium comprises small molecules consisting of a telomerase reverse transcriptase activator and a cytoskeletal structure modulator.

Also provided herein in certain aspects is a cell culture medium for proliferating epithelial cells ex vivo under feeder-cell free conditions, which medium comprises one or more TGF-beta inhibitors (e.g., one or more TGF-beta signaling inhibitors) and one or more PAK inhibitors. Also provided herein in certain aspects is a cell culture medium for proliferating epithelial cells ex vivo under feeder-cell free conditions, which medium comprises small molecules (e.g., small molecule inhibitors) consisting of a TGF-beta inhibitor (e.g., a TGF-beta signaling inhibitor) and a PAK1 inhibitor. In some embodiments, the epithelial cells are differentiated epithelial cells, formerly quiescent epithelial cells and/or lineage-committed epithelial cells.

Also provided herein in certain aspects is a cell culture medium for proliferating epithelial cells ex vivo under feeder-cell free conditions, which medium comprises one or more TGF-beta inhibitors (e.g., one or more TGF-beta signaling inhibitors) and one or more myosin II inhibitors. Also provided herein in certain aspects is a cell culture medium for proliferating epithelial cells ex vivo under feeder-cell free conditions, which medium comprises small molecules (e.g., small molecule inhibitors) consisting of a TGF-beta inhibitor (e.g., a TGF-beta signaling inhibitor) and a myosin II inhibitor. In some embodiments, the epithelial cells are differentiated epithelial cells, formerly quiescent epithelial cells and/or lineage-committed epithelial cells.

Provided herein in certain aspects is a population of ex vivo proliferated (e.g., expanded) epithelial cells produced by a method comprising a) culturing and proliferating differentiated epithelial cells under serum-free and feeder-cell free conditions; and b) inhibiting TGF-beta signaling in the differentiated epithelial cells during the culturing and proliferating in (a).

Provided herein in certain aspects is a population of ex vivo proliferated (e.g., expanded) epithelial cells produced by a method comprising a) culturing and proliferating formerly quiescent epithelial cells under serum-free and feeder-cell free conditions; and b) inhibiting TGF-beta signaling in the formerly quiescent epithelial cells during the culturing and proliferating in (a).

Provided herein in certain aspects is a population of ex vivo proliferated (e.g., expanded) epithelial cells produced by a method comprising a) culturing and proliferating lineage-committed epithelial cells under serum-free and feeder-cell free conditions; and b) inhibiting TGF-beta signaling in the lineage-committed epithelial cells during the culturing and proliferating in (a).

Also provided herein in certain aspects is a population of ex vivo proliferated (e.g., expanded) epithelial cells produced by a method comprising a) culturing and proliferating epithelial cells under feeder-cell free conditions; b) inhibiting TGF-beta signaling in the epithelial cells during the culturing and proliferating in (a); and c) inhibiting the activity of p21-activated kinase (PAK) in the epithelial cells during the culturing and proliferating in (a). In some embodiments, the epithelial cells are differentiated epithelial cells, formerly quiescent epithelial cells and/or lineage-committed epithelial cells.

Also provided herein in certain aspects is a population of ex vivo proliferated (e.g., expanded) epithelial cells produced by a method comprising a) culturing and proliferating epithelial cells under serum-free and feeder-cell free conditions; b) inhibiting TGF-beta signaling in the epithelial cells during the culturing and proliferating in (a); and c) inhibiting the activity of myosin II in the epithelial cells during the culturing and proliferating in (a). In some embodiments, the epithelial cells are differentiated epithelial cells, formerly quiescent epithelial cells and/or lineage-committed epithelial cells.

Provided herein in certain aspects is a population of ex vivo proliferated (e.g., expanded) epithelial cells produced by a method comprising a) culturing and proliferating differentiated epithelial cells under serum-free and feeder-cell free conditions; b) activating telomerase reverse transcriptase in the differentiated epithelial cells during the culturing and proliferating in (a); and c) modulating cytoskeletal structure in the differentiated epithelial cells during the culturing and proliferating in (a).

Provided herein in certain aspects is a population of ex vivo proliferated (e.g., expanded) epithelial cells produced by a method comprising a) culturing and proliferating formerly quiescent epithelial cells under serum-free and feeder-cell free conditions; b) activating telomerase reverse transcriptase in the formerly quiescent epithelial cells during the culturing and proliferating in (a); and c) modulating cytoskeletal structure in the formerly quiescent epithelial cells during the culturing and proliferating in (a).

Provided herein in certain aspects is a population of ex vivo proliferated (e.g., expanded) epithelial cells produced by a method comprising a) culturing and proliferating lineage-committed epithelial cells under serum-free and feeder-cell free conditions; b) activating telomerase reverse transcriptase in the lineage-committed epithelial cells during the culturing and proliferating in (a); and c) modulating cytoskeletal structure in the lineage-committed epithelial cells during the culturing and proliferating in (a).

Also provided herein in certain aspects are cell culture compositions comprising a defined serum-free cell culture medium, a lipids mix, EGF, FGF, albumin, a TGF-beta inhibitor (e.g., a TGF-beta signaling inhibitor), and a Rho kinase inhibitor (e.g., a Rho-associated protein kinase inhibitor).

Also provided herein in certain aspects are cell culture compositions consisting of a defined serum-free cell culture medium, a lipids mix, EGF, FGF, albumin, a TGF-beta inhibitor (e.g., a TGF-beta signaling inhibitor), and a Rho kinase inhibitor (e.g., a Rho-associated protein kinase inhibitor).

Also provided herein in certain aspects are cell culture compositions comprising a defined serum-free cell culture medium, a lipids mix, EGF, FGF, albumin, a TGF-beta inhibitor (e.g., a TGF-beta signaling inhibitor), a Rho kinase inhibitor (e.g., a Rho-associated protein kinase inhibitor), and a beta-adrenergic agonist (e.g., a beta-adrenergic receptor agonist).

Also provided herein in certain aspects are cell culture compositions consisting of a defined serum-free cell culture medium, a lipids mix, EGF, FGF, albumin, a TGF-beta inhibitor (e.g., a TGF-beta signaling inhibitor), a Rho kinase inhibitor (e.g., a Rho-associated protein kinase inhibitor), and a beta-adrenergic agonist (e.g., a beta-adrenergic receptor agonist).

Also provided herein in certain aspects are methods for proliferating epithelial cells ex vivo, comprising expanding the number of cells in an originating epithelial cell population derived from differentiated tissue under feeder-cell free expansion culture conditions, thereby generating an expanded epithelial cell population, where the expansion culture conditions comprise an agent that activates telomerase reverse transcriptase in the population and/or inhibits transforming growth factor beta (TGF-beta) signaling in the population; the originating epithelial cell population is capable of 25 population doublings or more when cultured under the expansion culture conditions; and the originating epithelial cell population is capable of no more than 20 population doublings when cultured under control culture conditions that do not include the agent.

Also provided herein in certain aspects are methods for proliferating epithelial cells ex vivo, comprising expanding the number of cells in an originating epithelial cell population derived from differentiated tissue under serum-free and feeder-cell free conditions, thereby generating an expanded epithelial cell population, where the expansion culture conditions comprise an agent that activates telomerase reverse transcriptase in the population and/or inhibits transforming growth factor beta (TGF-beta) signaling in the population; and the originating epithelial cell population comprises quiescent and/or formerly quiescent epithelial cells. In certain embodiments, the expansion culture conditions comprise a second agent that modulates cytoskeletal structure in the population and the control culture conditions do not include the second agent.

Also provided herein in certain aspects are methods for proliferating epithelial cells ex vivo, comprising expanding the number of cells in an originating epithelial cell population derived from differentiated tissue, embryonic stem (ES)

cells, or induced pluripotent stem cells (iPSCs) under feeder-cell free expansion culture conditions, thereby generating an expanded epithelial cell population, where the expansion culture conditions comprise an agent that activates telomerase reverse transcriptase in the population and/or inhibits transforming growth factor beta (TGF-beta) signaling in the population; the originating epithelial cell population is capable of 25 population doublings or more when cultured under the expansion culture conditions; and the originating epithelial cell population is capable of no more than 20 population doublings when cultured under control culture conditions that do not include the agent.

Also provided herein in certain aspects are methods for proliferating epithelial cells ex vivo, comprising expanding the number of cells in an originating epithelial cell population under serum-free and feeder-cell free conditions, thereby generating an expanded epithelial cell population, where the expansion culture conditions comprise an agent that activates telomerase reverse transcriptase in the population and/or inhibits transforming growth factor beta (TGF-beta) signaling in the population; and the originating epithelial cell population comprises differentiated epithelial cells.

Also provided herein in certain aspects are methods for proliferating epithelial cells ex vivo, comprising expanding the number of cells in an originating epithelial cell population under serum-free and feeder-cell free conditions, thereby generating an expanded epithelial cell population, where the expansion culture conditions comprise an agent that activates telomerase reverse transcriptase in the population and/or inhibits transforming growth factor beta (TGF-beta) signaling in the population; and the originating epithelial cell population comprises quiescent and/or formerly quiescent epithelial cells epithelial cells.

Also provided herein in certain aspects are methods for proliferating epithelial cells ex vivo, comprising expanding the number of cells in an originating epithelial cell population serum-free and feeder-cell free conditions, thereby generating an expanded epithelial cell population, where the expansion culture conditions comprise an agent that activates telomerase reverse transcriptase in the population and/or inhibits transforming growth factor beta (TGF-beta) signaling in the population; and the originating epithelial cell population comprises lineage-committed epithelial cells.

Certain embodiments are described further in the following description, examples, claims and drawings.

BRIEF DESCRIPTION OF THE DRAWINGS

The drawings illustrate certain embodiments of the technology and are not limiting. For clarity and ease of illustration, the drawings are not made to scale and, in some instances, various aspects may be shown exaggerated or enlarged to facilitate an understanding of particular embodiments.

FIGS. 21A-21C show karyotyping results at early and late passages of various epithelial cells cultured in KSFM plus A83-01 and Y-27632. FIG. 21B shows representative metaphase chromosome spreads of HFK cells at early passage (p3). FIG. 21C shows representative metaphase chromosome spreads of HFK cells at late passage (p19). HFK, human foreskin keratinocytes. HBEC, human bronchial epithelial cells. PrEC, prostate epithelial cells.

FIG. 27 shows a list of representative genes whose expression levels are down-regulated or up-regulated in epithelial cells grown in KSFM plus A83-01 and Y-27632 at different passages, compared to epithelial cells grown in KSFM at different passages. Gene expression levels in KSFM at p2 is set at 1. Positive numbers indicate the folds of up-regulation, negative numbers indicate the folds of down-regulation. A, ALK5 inhibitor A83-01. Y, Rho kinase inhibitor (i.e., Rho-associated protein kinase inhibitor) Y-27632. KSFM, Keratinocyte-SFM (Gibco/Thermo Fisher). p2, passage 2. p6, passage 6. p13, passage 13. p23, passage 23.

FIG. 32A and FIG. 32C are macroscopic images of whole wells. FIG. 32B and FIG. 32D are microscopic images showing 3D-like structures of miniature domes.

DETAILED DESCRIPTION

Figure 1:
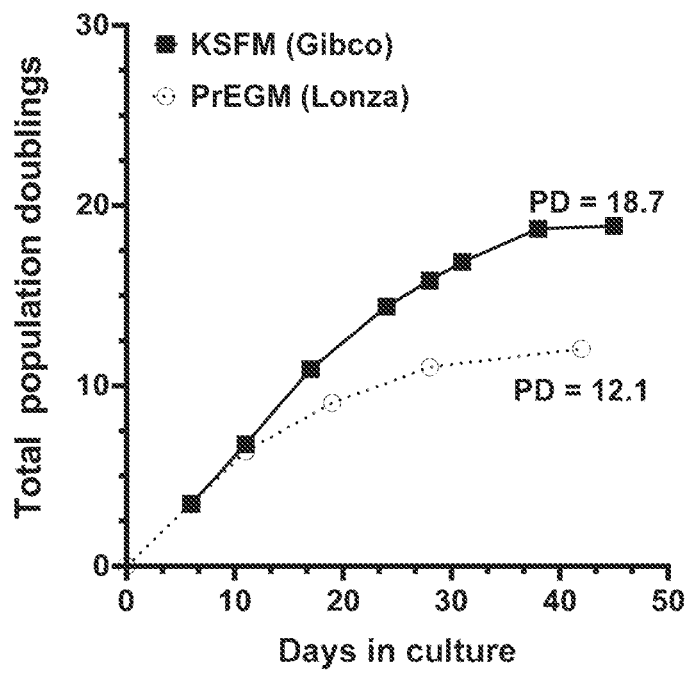
FIG. 1 shows growth of prostate epithelial cells in regular culture medium (i.e., control culture conditions). KSFM, Keratinocyte-SFM (Gibco/Thermo Fisher). PrEGM, Prostate Epithelial Cell Growth Medium (Lonza). PD, population doublings.
Figure 1:
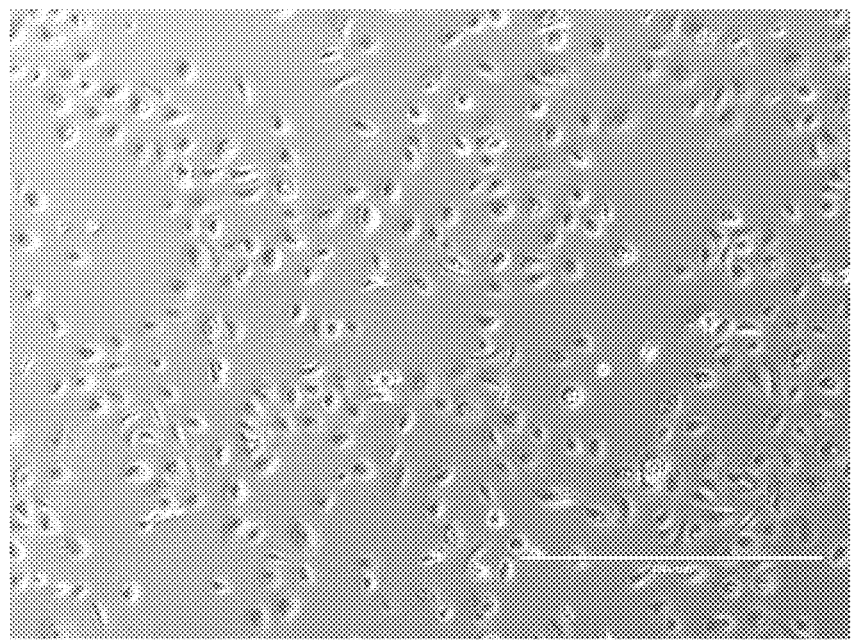

Provided herein are methods and media compositions for proliferating epithelial cells ex vivo. Epithelial cells (e.g., epithelial cells proliferated ex vivo) often are co-cultured with a population of feeder cells and/or cultured in a conditioned media derived from feeder cells. Reliance on feeder cells, however, can limit where and how epithelial cells are cultured, and can significantly increase the cost of culturing epithelial cells. Use of feeder cells also can be problematic due to cell culture variability caused by undefined biological factors derived from the feeder cells. Variability can lead to inconsistent results, which makes data interpretation challenging due to lack of reproducibility. Feeder cells also have the potential to introduce unwanted agents (e.g., retroviruses, other pathogens, and immunogenic nonhuman sialic acid such as Neu5Gc) into the cultured epithelial cells. Such culture conditions may not be desirable for certain applications such as, for example, transplantation.

Epithelial cells are typically cultured in medium supplemented with serum (e.g., fetal bovine serum (FBS)). However, in certain instances, serum can be a source of undefined mitogens, and lot-to-lot variation often is observed. Moreover, serum may be contaminated with infectious agents such as mycoplasma and viruses. Thus, serum can be an undefined and variable component of culture medium, and the use of serum can prevent elucidation of defined nutritional and hormonal requirements for certain cultured cells.

Epithelial cells can be cultured under feeder-cell free conditions with serum-free media that are often supplemented with one or more growth factors and one or more undefined animal organ extracts. However, epithelial cells cultured under these conditions typically stop proliferating after a few passages, have very limited lifespans, and generally cannot be massively expanded ex vivo.

Provided herein are methods and media compositions for proliferating and expanding epithelial cells ex vivo without the use of feeder cells or feeder-cell derived conditioned media, and in certain embodiments, without the use of serum. Also provided herein, in certain embodiments, are methods and media compositions for proliferating and expanding epithelial cells ex vivo under defined cell culture conditions. Also provided herein, in certain embodiments, are populations of epithelial cells proliferated and expanded using the methods and compositions provided herein.

Epithelial Cells

Provided herein are methods and compositions for proliferating and expanding epithelial cells ex vivo. An epithelial cell, or epithelium, typically refers to a cell or cells that line hollow organs, as well as those that make up glands and the outer surface of the body. Epithelial cells can comprise squamous epithelial cells, columnar epithelial cells, adenomatous epithelial cells or transitional epithelial cells. Epithelial cells can be arranged in single layers or can be arranged in multiple layers, depending on the organ and location.

Epithelial cells described herein can comprise keratinocyte (KE) epithelial cells or non-keratinocyte (NKE) epithelial cells. Keratinocytes form the squamous epithelium that is found at anatomic sites such as the skin, ocular surface, oral mucosa, esophagus and cervix. Keratinocytes terminally differentiate into flat, highly keratinized, non-viable cells that help protect against the environment and infection by forming a protective barrier. Examples of keratinocyte epithelial cells include, but are not limited to, dermal keratinocyte, ocular epithelial cells, corneal epithelial cells, oral mucosal epithelial cells, esophagus epithelial cells, and cervix epithelial cells.

NKE cells form the epithelium of the body such as found in the breast, prostate, liver, respiratory tract, retina and gastrointestinal tract. NKE cells typically differentiate into functional, viable cells which function, for example, in absorption and/or secretion. These cells typically do not form highly keratinized structures characteristic of squamous epithelial cells.

NKE cells for use in the methods described herein can be of any type or tissue of origin. Examples of NKE cells include, but are not limited to, prostate cells, mammary cells, hepatocytes, liver epithelial cells, biliary epithelial cells, gall bladder cells, pancreatic islet cells, pancreatic beta cells, pancreatic ductal epithelial cells, pulmonary epithelial cells, airway epithelial cells, nasal epithelial cells, kidney cells, bladder cells, urethral epithelial cells, stomach epithelial cells, large intestinal epithelial cells, small intestinal epithelial cells, testicular epithelial cells, ovarian epithelial cells, fallopian tube epithelial cells, thyroid cells, parathyroid cells, adrenal cells, thymus cells, pituitary cells, glandular cells, amniotic epithelial cells, retinal pigmented epithelial cells, sweat gland epithelial cells, sebaceous epithelial cells and hair follicle cells. In some embodiments, NKE cells do not comprise intestinal epithelial cells.

In some embodiments, epithelial cells comprise basal epithelial cells. Basal epithelial cells generally are cells in the deepest layer of stratified epithelium and multilayered epithelium. Basal epithelial cells may be cells whose nuclei locate close to the basal lamina in a pseudostratified epithelium. In some instances, basal epithelial cells may divide (e.g., by asymmetric cell division or symmetric cell division), giving rise to other basal cells and/or other epithelial cell types (e.g., other cell types in a stratified epithelium, multilayered epithelium or pseudostratified epithelium). A proportion of basal epithelial cells in some epithelia may have lifelong self-renew capability and can give rise to other epithelial cell types and basal cells, and sometimes are considered as epithelial stem cells. The proportion of basal epithelial cells that have lifelong self-renew capability and are considered as epithelial stem cells varies among different tissues.

Epithelial cells may be obtained from a subject and/or a cellular source. Cells obtained from a subject and/or a cellular source may be referred as an originating epithelial cell population. An originating epithelial cell population is the input population of epithelial cells for expansion by culture conditions described herein (e.g., expansion culture conditions, feeder-cell free expansion conditions). A cellular source may include a population of embryonic stem (ES) cells, induced pluripotent stem cells (iPSCs), and the like. In some embodiments, an originating epithelial cell population is isolated from an embryo or a stem cell culture derived from an embryo. In some embodiments, an originating epithelial cell population is isolated from an induced pluripotent stem cell (iPSC) culture. An originating epithelial cell population can be obtained from a subject in a variety of manners (e.g., harvested from living tissue, such as a biopsy, plucked hair follicles, body fluids like urine or body-cavity fluids, or isolated from circulation). A subject may include any animal, including but not limited to any mammal, such as mouse, rat, canine, feline, bovine, equine, porcine, non-human primate and human. In certain embodiments, a subject is a human. In some embodiments, a subject is an animal or human that has gestated longer than an embryo in a uterine environment and often is a post-natal human or a post-natal animal (e.g., neonatal human, neonatal animal, adult human or adult animal). Typically, a subject is not an embryo. A subject sometimes is a juvenile animal, juvenile human, adult animal or adult human.

In some embodiments, an originating epithelial cell population is isolated from a sample from a subject. A sample can include any specimen that is isolated or obtained from a subject or part thereof. Non-limiting examples of specimens include fluid or tissue from a subject, including, without limitation, blood or a blood product (e.g., serum, plasma, or the like), umbilical cord blood, bone marrow, chorionic villi, amniotic fluid, cerebrospinal fluid, spinal fluid, lavage fluid (e.g., bronchoalveolar, gastric, peritoneal, ductal, ear, arthroscopic), biopsy sample or tissue biopsy, buccal swab, celocentesis sample, washings of female reproductive tract, urine, feces, sputum, saliva, nasal mucous, prostate fluid, lavage, semen, lymphatic fluid, bile, tears, sweat, breast milk, breast fluid, hard tissues (e.g., liver, spleen, kidney, lung, or ovary), the like or combinations thereof. The term blood encompasses whole blood, blood product or any fraction of blood, such as serum, plasma, buffy coat, or the like as conventionally defined. Blood plasma refers to the fraction of whole blood resulting from centrifugation of blood treated with anticoagulants. Blood serum refers to the watery portion of fluid remaining after a blood sample has coagulated. In some embodiments, fetal cells are isolated from a maternal sample (e.g., maternal blood, amniotic fluid).

In some embodiments, epithelial cells may comprise normal, healthy cells (e.g., cells that are not diseased). In some embodiments, epithelial cells may comprise cells that are not genetically altered. In some embodiments, epithelial cells may comprise diseased and/or genetically altered. Diseased epithelial cells may include cells from a subject carrying disease-causing mutation(s) (e.g., epithelial cells with genetic mutation(s) in the CFTR gene). Diseased epithelial cells may include cells from abnormal tissue, such as from a neoplasia, a hyperplasia, a malignant tumor or a benign tumor. In certain embodiments, diseased epithelial cells may include cells that are not tumor cells. In certain embodiments, diseased epithelial cells may include cells isolated from circulation (e.g., circulating tumor cells (CTCs)) of a subject. In certain embodiments, diseased epithelial cells may include cells isolated from bodily samples such as, for example, urine, semen, stool (feces), and the like.

In some embodiments, epithelial cells comprise primary cells. In some embodiments, an originating epithelial cell population comprises primary cells. Primary epithelial cells are taken directly from living tissue, such as a biopsy, plucked hair follicles, bodily samples such as a stool sample, body fluids like urine, semen or body-cavity fluids, or isolated from circulation. In certain instances, primary cells have not been passaged. In certain instances, primary cells have been passaged one time. Primary cells may be isolated from differentiated tissue (e.g., isolated from epithelium of various organs). Typically, primary cells have been freshly isolated, for example, through tissue digestion and plated. Primary cells may or may not be frozen and then thawed at a later time. In addition, the tissue from which the primary cells are isolated may or may not have been frozen of preserved in some other manner immediately prior to processing. Typically, cells are no longer primary cells after the cells have been passaged more than once. Cells passaged once or more and immediately frozen after passaging are also not considered as primary cells when thawed. In certain embodiments, epithelial cells are initially primary cells and, through use of the methods described herein, become non-primary cells after passaging. In some embodiments, cells of an originating epithelial cell population are maintained or proliferated in cell culture after the cells are isolated from differentiated tissue and prior to contacting the originating epithelial cell population with culture condition described herein (e.g., an expansion culture condition described herein).

In some embodiments, epithelial cells comprise non-primary cells, such as cells from an established cell line, transformed cells, thawed cells from a previously frozen collection and the like. In certain embodiments, epithelial cells comprise secondary cells. In some embodiments, epithelial cells comprise no cells from an established cell line.

In some embodiments, a culture composition comprises a heterogeneous population of epithelial cells (e.g., comprises a mixture of cell types and/or differentiation states such as epithelial stem cells, epithelial progenitors, epithelial precursor cells, lineage-committed epithelial cells, transit-amplifying epithelial cells, differentiating epithelial cells, differentiated epithelial cells, and terminally differentiated epithelial cells) derived from the same tissue or same tissue compartment. In some embodiments, a culture composition comprises a homogenous population of epithelial cells (e.g., does not include a mixture of cell types and/or differentiation states) derived from the same tissue or same tissue compartment. In some embodiments, a homogeneous population of epithelial cells comprises at least about 90% epithelial cells that are of the same cell type and/or are present at the same differentiation state. For example, a homogeneous population of epithelial cells may comprise at least about 90%, 91%, 92%, 93%, 94%, 95%, 96%, 97%, 98%, 99% or 100% epithelial cells that are of the same cell type and/or are present at the same differentiation state. In some embodiments, a homogeneous population of epithelial cells comprises about 100% epithelial cells that are of the same cell type and/or are present at the same differentiation state. In some embodiments, epithelial cells are a homogenous population of basal epithelial cells. In some embodiments, an originating epithelial cell population may be heterogeneous or may be homogeneous. In some embodiments, an expanded epithelial cell population may be heterogeneous or may be homogeneous.

In some embodiments, epithelial cells are characterized by the cell types and/or differentiation states that are included in, or absent from, a population of epithelial cells. In some embodiments, such cell characterization may be applicable to an originating epithelial cell population. In some embodiments, such cell characterization may be applicable to an expanded epithelial cell population. In some embodiments, such cell characterization may be applicable to an originating epithelial cell population and an expanded epithelial cell population. In some embodiments, epithelial cells that include a particular cell type and/or differentiation state comprise at least about 50% epithelial cells that are of the particular cell type and/or differentiation state. In some embodiments, epithelial cells that include a particular cell type and/or differentiation state comprise at least about 90% epithelial cells that are of the particular cell type and/or differentiation state. For example, epithelial cells that include a particular cell type and/or differentiation state may comprise at least about 90%, 91%, 92%, 93%, 94%, 95%, 96%, 97%, 98%, 99% or 100% epithelial cells that are of the particular type and/or differentiation state. Generally, epithelial cells that do not include a particular cell type and/or differentiation state comprise less than about 10% cells that are of the particular cell type and/or differentiation state. For example, epithelial cells that do not include a particular cell type and/or differentiation state may comprise less than about 10%, 9%, 8%, 7%, 6%, 5%, 4%, 3%, 2%, or 1% cells that are of the particular cell type and/or differentiation state.

In certain embodiments, a culture composition or population consists essentially of a particular type of epithelial cells, referred to hereafter as "the majority cells." Such culture compositions can include a minor amount of one or more other types of epithelial cells, referred to hereafter as "the minority cells." The minority cells typically are from, or are derived from, the same tissue as the majority cells, and often are from, or are derived from, the same tissue compartment, as the majority cells. The majority cells can be greater than 50%, greater than 60%, greater than 70%, or greater than 80% of the total cells in the composition and often are about 90% or more of the total cells in the composition, and sometimes are about 91%, 92%, 93%, 94%, 95%, 96%, 97%, 98% or 99% or more of the total cells in the composition or population.

In some embodiments, a culture composition comprises a heterogeneous population of epithelial cells at different cell cycle phases, such as the M phase, the G1 phase, the S phase, the G2 phase, and the G0 phase which includes senescence and quiescence. In some embodiments, an originating epithelial cell population comprises a heterogeneous population of epithelial cells at different cell cycle phases, such as the M phase, the G1 phase, the S phase, the G2 phase, and the G0 phase which includes senescence and quiescence. In some embodiments, an expanded epithelial cell population comprises a heterogeneous population of epithelial cells at different cell cycle phases, such as the M phase, the G1 phase, the S phase, the G2 phase, and the G0 phase which includes senescence and quiescence. Epithelial cells at a particular cell cycle phase can make up 1% to 100% of the population.

In some embodiments, epithelial cells comprise cells at one or more stages of differentiation. In some embodiments, such stages of differentiation may be described for an originating epithelial cell population. In some embodiments, such stages of differentiation may be described for an expanded epithelial cell population. In some embodiments, such stages of differentiation may be described for an originating epithelial cell population and an expanded epithelial cell population. For example, epithelial cells (or a population of epithelial cells) may comprise epithelial stem cells, epithelial progenitor cells, lineage-restricted epithelial progenitor cells, epithelial precursor cells, lineage-committed epithelial cells, transit-amplifying epithelial cells, proliferating epithelial cells, differentiating epithelial cells, differentiated epithelial cells, quiescent epithelial cells, formerly quiescent epithelial cells, non-proliferating epithelial cells, and terminally differentiated epithelial cells (e.g., cells that are found in tissues and organs). Epithelial cells also may comprise lineage-committed epithelial cells differentiated and/or derived from pluripotent stem cells (embryonic stem (ES) cells or induced pluripotent stem cells (iPSCs)).

In some embodiments, epithelial cells comprise differentiated epithelial cells. Differentiated epithelial cells may divide, but typically do not have the capacity for indefinite self-renewal. In some embodiments, differentiated epithelial cells do not acquire the ability to differentiate into multiple tissue types. Differentiated epithelial cells cultured in conditions described herein generally are more differentiated than undifferentiated cells (e.g., stem cells (embryonic or adult), progenitor cells, precursor cells) and are less differentiated than terminally differentiated cells. Differentiated epithelial cells generally do not include stem cells (embryonic or adult), progenitor cells or precursor cells. In certain instances, differentiated epithelial cells may be referred to as "tissue-specific" and/or "lineage-committed" epithelial cells. In certain instances, differentiated epithelial cells may comprise tissue-specific and/or lineage-committed epithelial cells. In some embodiments, differentiated epithelial cells comprise quiescent epithelial cells. In some embodiments, differentiated epithelial cells comprise basal epithelial cells.

In some embodiments, epithelial cells comprise quiescent or formerly quiescent cells. Quiescent cells generally are non-proliferating cells (i.e., non-cycling cells, cells that have withdrawn from the cell cycle, resting cells), and may be characterized as reversibly growth arrested. Under certain conditions, quiescent cells can be induced to proliferate. Quiescent cells may be characterized as existing in the G0 phase of the cell cycle. Quiescent cells that have been induced to proliferate may be referred to as formerly quiescent cells.

In some embodiments, epithelial cells comprise organ-specific epithelial cells. Organ-specific epithelial cells sometimes are referred to as tissue-specific epithelial cells. In some embodiments, organ-specific epithelial cells may differentiate into more specific cell types within a given organ, but generally do not possess or acquire the ability to differentiate into cells of other types of organs. Organ-specific epithelial cells generally are more differentiated than undifferentiated cells (e.g., stem cells (embryonic or adult)) and are less differentiated than terminally differentiated cells. Organ-specific epithelial cells generally do not include embryonic stem cells. Organ-specific epithelial cells may or may not include adult stem cells (e.g., adult stem cells), and organ-specific epithelial cells may or may not include progenitor cells or precursor cells.

In some embodiments, epithelial cells comprise lineage-committed epithelial cells. In some embodiments, epithelial cells can comprise lineage-committed epithelial cells differentiated from pluripotent stem cells such as embryonic stem (ES) cells and induced pluripotent stem cells (iPSCs). Lineage-committed epithelial cells may divide, but typically do not have the capacity for indefinite self-renewal. In some embodiments, lineage-committed epithelial cells may differentiate into various cell types within a given cell lineage (e.g., respiratory, digestive or integumentary lineages), but generally do not possess or acquire the ability to differentiate into cells of different cell lineages (e.g., integumentary lineage-committed epithelial cells generally do not differentiate into blood cells). Lineage-committed epithelial cells generally are more differentiated than undifferentiated pluripotent stem cells and are less differentiated than terminally differentiated cells. Lineage-committed epithelial cells generally do not include pluripotent stem cells (embryonic or induced pluripotent). In some embodiments, lineage-committed epithelial cells include progenitor cells or precursor cells. In some embodiments, lineage-committed epithelial cells comprise basal epithelial cells.

In some embodiments, epithelial cells do not include terminally differentiated epithelial cells. Terminally differentiated epithelial cells generally do not divide and are committed to a particular function. Terminally differentiated epithelial cells generally are characterized by definitive withdrawal from the cell cycle and typically cannot be induced to proliferate. In some embodiments, epithelial cells do not include terminally differentiated gastric epithelial cells, intestinal epithelial cells, and/or pancreatic epithelial cells. In some embodiments, epithelial cells do not include post-mitotic cells. Post-mitotic cells generally are incapable of or no longer capable of cell division. In some embodiments, epithelial cells do not include senescent cells.

In some embodiments, epithelial cells do not include embryonic stem cells. In some embodiments, epithelial cells are differentiated and/or derived from embryonic stem cells. In some embodiments, epithelial cells are not derived from embryonic stem cells. Generally, embryonic stem cells are undifferentiated cells that have the capacity to regenerate or self-renew indefinitely. Embryonic stem cells sometimes are considered pluripotent (i.e., can differentiate into many or all cell types of an adult organism) and sometimes are considered totipotent (i.e., can differentiate into all cell types, including the placental tissue). In some embodiments, epithelial cells do not include induced pluripotent stem cells (iPSCs). In some embodiments, epithelial cells are differentiated and/or derived from induced pluripotent stem cells (iPSCs). In some embodiments, epithelial cells are not derived from induced pluripotent stem cells (iPSCs). Generally, induced pluripotent stem cells (iPSCs) are a type of pluripotent stem cell that can be generated directly from adult cells. In some embodiments, epithelial cells do not include pluripotent cells. In some embodiments, epithelial cells do not include totipotent cells.

In some embodiments, epithelial cells include adult stem cells. Adult stem cells typically are less differentiated than differentiated cells, organ-specific cells or lineage-committed cells and are more differentiated than embryonic stem cells. Adult stem cells may be referred to as stem cells, undifferentiated stem cells, precursor cells and/or progenitor cells, and are not considered embryonic stem cells as adult stem cells are not isolated from an embryo. Adult epithelial stem cells may be referred to as epithelial stem cells, undifferentiated epithelial stem cells, epithelial precursor cells and/or epithelial progenitor cells.

In some embodiments, epithelial cells do not include adult stem cells or cells derived from adult stem cells. In some embodiments, epithelial cells do not include epithelial stem cells or cells derived from epithelial stem cells. In some embodiments, epithelial cells do not include pluripotent epithelial stem cells or cells derived from pluripotent epithelial stem cells. In some embodiments, epithelial cells do not include progenitor cells or cells derived from progenitor cells. In some embodiments, epithelial cells do not include precursor cells or cells derived from precursor cells. In some embodiments, epithelial cells do not include continuously proliferating (e.g., continuously proliferating in vivo) epithelial stem cells (e.g., intestinal crypt cells; Lgr5+ cells) or cells derived from continuously proliferating epithelial stem cells. In some embodiments, originating cells, or tissue from which originating cells are harvested, do not include continuously proliferating epithelial stem cells (e.g., intestinal crypt cells; Lgr5+ cells) and methods herein may not include selecting for such cell types. For example, in some embodiments, a method does not include selecting for continuously proliferating epithelial stem cells and/or selecting for an in vivo population of continuously proliferating epithelial stem cells (i.e., a population of epithelial stem cells that are continuously proliferating in a subject prior to harvest). In some embodiments, epithelial cells do not acquire the ability to form organoids. In some embodiments, epithelial cells are not completely undifferentiated cells upon initial isolation and plating.

In some embodiments, epithelial cells may be characterized by whether the cells possess one or more markers (e.g., cell surface markers, mRNAs, proteins, epigenetic signatures) and/or do not possess measurable levels of, or possess low levels of, certain markers. In some embodiments, such marker characterization may be applicable to an originating epithelial cell population. In some embodiments, such marker characterization may be applicable to an expanded epithelial cell population. In some embodiments, such marker characterization may be applicable to an originating epithelial cell population and an expanded epithelial cell population.

In certain instances, level of expression (e.g., mRNA expression) is determined for a marker. Levels of mRNA expression may be determined using any suitable method for detecting and measuring mRNA expression. For example, expression level may be determined by quantitative reverse transcription PCR according to a $Ct_{gene}$ value, where $Ct_{gene}$ is the number of cycles required for a fluorescent signal of a quantitative PCR reaction to cross a defined (e.g., detectable) threshold. Generally, expression of a marker is considered absent if the $Ct_{gene}$ is higher than 35. The expression level of a marker is considered low if the $Ct_{gene}$ is less than 35 and greater than or equal to 30. The expression level of a marker is considered medium or moderate if the $Ct_{gene}$ is less than 29 and greater than or equal to 22. The expression level of a marker is considered high if the $Ct_{gene}$ is less than 22.

In some embodiments, epithelial cells possess markers (e.g., cell surface markers, mRNAs, proteins, epigenetic signatures) typically associated with a particular cell type and/or differentiation state. In some embodiments, epithelial cells do not possess markers (e.g., cell surface markers, mRNAs, proteins, epigenetic signatures) typically associated with a particular cell type and/or differentiation state. In some embodiments, epithelial cells possess markers (e.g., cell surface markers, mRNAs, proteins, epigenetic signatures) not typically associated with a particular cell type and/or differentiation state. In some embodiments, epithelial cells possess markers (e.g., cell surface markers, mRNAs, proteins, epigenetic signatures) not typically associated with undifferentiated stem cells. In some embodiments, epithelial cells possess one or more markers (e.g., cell surface markers, mRNAs, proteins, epigenetic signatures) that typically are associated with basal epithelial cells. In some embodiments, epithelial cells possess one or more markers (e.g., cell surface markers, mRNAs, proteins, epigenetic signatures) that typically are associated with differentiated epithelial cells. In some embodiments, epithelial cells possess one or more markers (e.g., cell surface markers, mRNAs, proteins, epigenetic signatures) that typically are associated with airway epithelial cells and/or keratinocyte cells. Moderate levels to high levels of markers may be present in some instances. In some embodiments, epithelial cells do not possess measurable levels of, or possess low levels of, one or more markers (e.g., cell surface markers, mRNAs, proteins, epigenetic signatures) typically associated with certain cell types such as, for example, pluripotent stem cells, terminally differentiated epithelial cells, senescent cells, gastric epithelial cells, intestinal epithelial cells, pancreatic epithelial cells, fibroblast cells, and/or intestinal goblet cells. In some embodiments, epithelial cells do not possess measurable levels of, or possess low levels of, one or more markers (e.g., cell surface markers, mRNAs, proteins, epigenetic signatures) typically associated cell adhesion and/or stress response.

In some embodiments, organ-specific epithelial cells do not possess measurable levels of, or possess low levels of, one or more markers (e.g., cell surface markers, mRNAs, proteins, epigenetic signatures) typically associated with cell types from other organs. For example, airway epithelial cells may not possess measurable levels of, or possess low levels of, one or more markers (e.g., cell surface markers, mRNAs, proteins, epigenetic signatures) typically associated with gastric epithelial cells, intestinal epithelial cells, pancreatic epithelial cells, fibroblast cells, and/or intestinal goblet cells.

In some embodiments, epithelial cells possess one or more markers (e.g., cell surface markers, mRNAs, proteins, epigenetic signatures) that typically are associated with basal epithelial cells such as, for example, ITGA6, ITGB4, KRT14, KRT15, KRT5 and TP63. In some embodiments, epithelial cells possess one or more markers (e.g., cell surface markers, mRNAs, proteins, epigenetic signatures) that typically are associated with differentiated epithelial cells such as, for example, KRT4, KRT6 and KRT8. In some embodiments, epithelial cells possess one or more markers (e.g., cell surface markers, mRNAs, proteins, epigenetic signatures) that typically are associated with airway epithelial cells such as, for example, HEY2, NGFR and BMP7. In some embodiments, epithelial cells possess one or more markers (e.g., cell surface markers, mRNAs, proteins, epigenetic signatures) that typically are associated with keratinocyte cells such as, for example, ZFP42. In some embodiments, epithelial cells possess one or more markers (e.g., cell surface markers, mRNAs, proteins, epigenetic signatures) such as, for example CDKN2B, CITED2, CREG1, ID1, MAP2K6, IGFBP3 and IGFBP5. Moderate levels to high levels of such markers may be present in some instances.

In some embodiments, epithelial cells do not possess a measurable level of, or possess low levels of, one or more markers (e.g., cell surface markers, mRNAs, proteins, epigenetic signatures) typically associated with epithelial stem cells such as, for example, LGR5. In some embodiments, epithelial cells do not possess a measurable level of, or possess low levels of, one or more markers (e.g., cell surface markers, mRNAs, proteins, epigenetic signatures) typically associated with pluripotent stem cells such as, for example, LIN28A, NANOG, POU5F1/OCT4 and SOX2. In some embodiments, epithelial cells do not possess a measurable level of, or possess low levels of, one or more markers (e.g., cell surface markers, mRNAs, proteins, epigenetic signatures) typically associated with terminally differentiated epithelial cells such as, for example, CFTR, FOXJ1, IVL, KRT1, KRT10, KRT20, LOR, MUC1, MUC5AC, SCGB1A1, SFTPB and SFTPD. In some embodiments, epithelial cells do not possess a measurable level of, or possess low levels of, one or more markers (e.g., cell surface markers, mRNAs, proteins, epigenetic signatures) typically associated with cell senescence such as, for example, AKT1, ATM, CDKN2A, GADD45A, GLB1, PLAU, SERPINE1 and SOD2. In some embodiments, epithelial cells do not possess a measurable level of, or possess low levels of, one or more markers (e.g., cell surface markers, mRNAs, proteins, epigenetic signatures) typically associated with cell adhesion such as, for example, adhesion molecules FN1 and THBS1. In some embodiments, epithelial cells do not possess a measurable level of, or possess low levels of, one or more markers (e.g., cell surface markers, mRNAs, proteins, epigenetic signatures) typically associated with cell filaments such as, for example, intermediate filament protein vimentin (VIM). In some embodiments, epithelial cells do not possess a measurable level of, or possess low levels of, one or more markers (e.g., cell surface markers, mRNAs, proteins, epigenetic signatures) typically associated with gastric epithelial cells, intestinal epithelial cells, or pancreatic epithelial cells such as, for example, CD34, HNF1A, HNF4A, IHH, KIT, LGR5, PDX1, and PROM1/CD133. In some embodiments, epithelial cells do not possess a measurable level of, or possess low levels of, one or more markers (e.g., cell surface markers, mRNAs, proteins, epigenetic signatures) typically associated with fibroblast cells such as, for example, ZEB1 and ZEB2. In some embodiments, epithelial cells do not possess a measurable level of, or possess low levels of, one or more markers (e.g., cell surface markers, mRNAs, proteins, epigenetic signatures) typically associated with intestinal goblet cells such as, for example, KRT20.

Cell Culture

Provided herein are methods and compositions for cell culture. In particular, provided herein are expansion culture conditions. Cell culture, or culture, typically refers to the maintenance of cells in an artificial, in vitro environment, or the maintenance of cells in an external, ex vivo environment (i.e., outside of an organism), and can include the cultivation of individual cells and tissues. Certain cell culture systems described herein may be an ex vivo environment and/or an in vitro environment. In some embodiments, primary cells are isolated. In some embodiments, primary cells may be isolated using a single needle biopsy. In some embodiments, primary cells may be isolated using a tissue biopsy. In some embodiments, primary cells may be isolated from a plucked hair. In some embodiments, primary cells may be isolated from body fluids like urine or body-cavity fluids. In some embodiments, primary cells may be isolated from the circulation of a subject.

After isolation, cellular material may be washed (e.g., with saline and/or a PBS solution). Cellular material may be treated with an enzymatic solution such as, for example, collagenase, dispase and/or trypsin, to promote dissociation of cells from the tissue matrix. Dispase, for example, may be used to dissociate epithelium from underlying tissue. An intact epithelium may then be treated with trypsin or collagenase, for example. Such digestion steps often result in a slurry containing dissociated cells and tissue matrix. The slurry can then be centrifuged with sufficient force to separate the cells from the remainder of the slurry. A cell pellet may then be removed and washed with buffer and/or saline and/or cell culture medium. The centrifuging and washing can be repeated any number of times. After a final washing, cells can then be washed with any suitable cell culture medium. In certain instances, digestion and washing steps may not be performed if the cells are sufficiently separated from the underlying tissue upon isolation (e.g., for cells isolated from circulation or using needle biopsy). In some embodiments, cells such as tumor cells may be isolated from the circulation of a subject. In certain embodiments, tumor cells may be isolated according to cell markers specifically expressed on certain types of tumor cells (see e.g., Lu. J., et al., Int'l. J. Cancer, 126(3):669-683 (2010) and Yu, M., et al., J. Cell Biol., 192(3): 373-382 (2011), which are incorporated by reference). Cells may or may not be counted using an electronic cell counter, such as a Coulter Counter, or they can be counted manually using a hemocytometer.

Cell seeding densities may be adjusted according to certain desired culture conditions. For example, an initial seeding density of from about $1 \times 10^3$ to about $1\text{-}10 \times 10^5$ cells per $cm^2$ may be used. In some embodiments, an initial seeding density of from about 1-10 to about $1\text{-}10 \times 10^5$ cells per $cm^2$ may be used. In certain instances, $1 \times 10^6$ cells may be cultured in a 75 $cm^2$ culture flask. Cell density may be altered as needed at any passage.

Cells may be cultivated in a cell incubator at about 37° C. at normal atmospheric pressure. The incubator atmosphere may be humidified and may contain from about 3-10% carbon dioxide in the air. In some instances, the incubator atmosphere may contain from about 0.1-30% oxygen. Temperature, pressure and carbon dioxide and oxygen concentration may be altered as needed. Culture medium pH may be in the range of about 7.1 to about 7.6, or from about 7.1 to about 7.4, or from about 7.1 to about 7.3.

Cell culture medium may be replaced every 1-2 days or more or less frequently as needed. As the cells approach confluence in the culture vessel, they may be passaged. A cell passage is a splitting or dividing of the cells, and a transferring a portion of the cells into a new culture vessel or culture environment. Cells which are adherent to the cell culture surface may require detachment. Methods of detaching adherent cells from the surface of culture vessels are well known and can include the use of enzymes such as trypsin.

A single passage refers to a splitting or manual division of the cells one time, and a transfer of a smaller number of cells into a new container or environment. When passaging, the cells can be split into any ratio that allows the cells to attach and grow. For example, at a single passage the cells can be split in a 1:2 ratio, a 1:3 ratio, a 1:4 ratio, a 1:5 ratio, and so on. In some embodiments, cells are passaged at least about 1 time to at least about 300 times. For example, cells may be passaged at least about 2 times, 5 times, 10 times, 20 times, 30 times, 40 times, 50 times, 60 times, 70 times, 80 times, 90 times, 100 times, 200 times or 300 times. In some embodiments, cells are passaged at least about 15 times. In some embodiments, cells are passaged at least about 25 times.

Cell growth generally refers to cell division, such that one mother cell divides into two daughter cells. Cell growth may be referred to as cell expansion. Cell growth herein generally does not refer to an increase in the actual size (e.g., diameter, volume) of the cells. Stimulation of cell growth can be assessed by plotting cell populations (e.g., cell population doublings) over time. A cell population with a steeper growth curve generally is considered as growing faster than a cell population with a less steep curve. Growth curves can be compared for various treatments between the same cell types, or growth curves can be compared for different cell types with the same conditions, for example.

Expanding a population of cells may be expressed as population doubling. A cell population doubling occurs when the cells in culture divide so that the number of cells is doubled. In some instances, cells are counted to determine if a population of cells has doubled, tripled or multiplied by some other factor. The number of population doublings may not be equivalent to the number of times a cell culture is passaged. For example, passaging the cells and splitting them in a 1:3 ratio for further culturing may not be equivalent to a tripled cell population. A formula that may be used for the calculation of population doublings (PD) is presented in Equation A:

$$n = 3.32 * (\log Y - \log I) + X \qquad \text{Equation A}$$

where n=the final PD number of the cell culture when it is harvested or passaged, Y=the cell yield at the time of harvesting or passaging, I=the cell number used as inoculum to begin that cell culture, and X=the PD number of the originating cell culture that is used to initiate the subculture.

A population of cells may double a certain number of times over a certain period of time. In some embodiments, a population of cells is capable of doubling, or doubles, at least about 1 time to at least about 500 times over a certain period of time. For example, a population of cells may be capable of doubling, or double, at least about 2 times, 5 times, 10 times, 20 times, 30 times, 40 times, 50 times, 60 times, 70 times, 80 times, 90 times, 100 times, 110 times, 120 times, 130 times, 140 times, 150 times, 160 times, 170 times, 180 times, 190 times, 200 times, 250 times, 300 times, 350 times, 400 times, 450 times or 500 times. In some embodiments, the cell population is capable of doubling, or doubles, at least 20 times. In some embodiments, the cell population is capable of doubling, or doubles, at least 50 times. In some embodiments, the cell population is capable of doubling, or doubles, at least 60 times. In some embodiments, the cell population is capable of doubling, or doubles, at least 70 times. In some embodiments, the cell population is capable of doubling, or doubles, at least 80 times. In some embodiments, the cell population is capable of doubling, or doubles, at least 90 times. In some embodiments, the cell population is capable of doubling, or doubles, at least 100 times. In some embodiments, the cell population is capable of doubling, or doubles, at least 120 times. In some embodiments, the cell population is capable of doubling, or doubles, at least 150 times. In some embodiments, the cell population is capable of doubling, or doubles, at least 200 times. In some embodiments, a population of cells doubles, or is capable of doubling, a certain number of times over a period of about 1 day to about 500 days. For example, a population of cells may double, or is capable of doubling, a certain number of times over a period of about 2 days, 5 days, 10 days, 20 days, 30 days, 40 days, 50 days, 60 days, 70 days, 80 days, 90 days, 100 days, 110 days, 120 days, 130 days, 140 days, 150 days, 160 days, 170 days, 180 days, 190 days, 200 days, 250 days, 300 days, 350 days, 400 days, 450 days or 500 days. In some embodiments, a population of cells doubles, or is capable of doubling, a certain number of times over a period of about 50 days. In some embodiments, a population of cells doubles, or is capable of doubling, a certain number of times over a period of about 100 days. In some embodiments, a population of cells doubles, or is capable of doubling, a certain number of times over a period of about 150 days. In some embodiments, a population of cells doubles, or is capable of doubling, a certain number of times over a period of about 200 days.

In some embodiments, a method herein comprises expanding a population of cells. Expanding a population of cells may be referred to as proliferating a population of cells. Expanding a population of cells may be expressed as fold increase in cell numbers. A formula that may be used for the calculation of fold increase as a function of population doublings is presented in Equation B:

$$F=2^n \qquad \text{Equation B}$$

where F=the fold increase in cell numbers after n population doublings. For example, after one (1) population doubling, the number of cells increases by 2 fold, and after two (2) population doublings, the number of cells increases by 4 ($2^2$=4) fold, and after three (3) population doublings, the number of cells increases by 8 ($2^3$=8) fold, and so on. Hence, after twenty (20) population doublings, the number of cells increases by more than one million fold ($2^{20}$=1,048,576), and after thirty (30) population doublings, the number of cells increases by more than one billion fold ($2^{30}$=1,073,741,824), and after forty (40) population doublings, the number of cells increases by more than one trillion fold ($2^{40}$=1,099,511,627,776), and so on. In some embodiments, a population of cells is expanded, or is capable of being expanded, at least about 2-fold to at least about a trillion-fold. For example, a population of cells may be expanded at least about 5-fold, 10-fold, 15-fold, 20-fold, 30-fold, 40-fold, 50-fold, 100-fold, 1,000-fold, 10,000-fold, 100,000-fold, 1 million-fold, 1 billion-fold, or 1 trillion-fold. A particular fold expansion may occur over a certain period of time in culture such as, for example, 2 days, 3 days, 4 days, 5 days, 10 days, 20 days, 30 days, 40 days, 50 days, 100 days or more.

Cells may be continuously proliferated or continuously cultured. Continuous proliferation or continuous culture refers to a continuous dividing of cells, reaching or approaching confluence in the cell culture container such that the cells require passaging and addition of fresh medium to maintain their health. Continuously proliferated cells or continuously cultured cells may possess features that are similar to, or the same as, immortalized cells. In some embodiments, cells continue to grow and divide for at least about 5 passages to at least about 300 passages. For example, cells may continue to grow and divide for at least about 10 passages, 20 passages, 30 passages, 40 passages, 50 passages, 60 passages, 70 passages, 80 passages, 90 passages, 100 passages, 200 passages or 300 passages.

In some embodiments, epithelial cells are a heterogeneous population of epithelial cells upon initial collection and plating and become a homogenous population of epithelial cells after one or more passages. For example, a heterogeneous population of epithelial cells may become a homogeneous population of epithelial cells after 2 passages, after 3 passages, after 4 passages, after 5 passages, after 10 passages, after 20 passages, after 30 passages, after 40 passages, after 50 passages, or after 100 or more passages.

In some embodiments, epithelial cells are characterized by the cell types and/or differentiation states that are included in, or absent from, a population of epithelial cells at initial collection and plating. In some embodiments, epithelial cells are characterized by the cell types and/or differentiation states that are included in, or absent from, a population of epithelial cells after one or more passages. For example, epithelial cells may be characterized by the cell types and/or differentiation states that are included in, or absent from, a population of epithelial cells after 2 passages, after 3 passages, after 4 passages, after 5 passages, after 10 passages, after 20 passages, after 30 passages, after 40 passages, after 50 passages, or after 100 or more passages. In some embodiments, epithelial cells are characterized by the cell types and/or differentiation states that are included in an originating epithelial cell population. In some embodiments, epithelial cells are characterized by the cell types and/or differentiation states that are included in an expanded epithelial cell population.

In some embodiments, cells do not undergo differentiation during expansion, continuous proliferation or continuous culture. For example, cells may not differentiate into terminally differentiated cells or other cell types during expansion, continuous proliferation or continuous culture. In some embodiments, cells of a particular organ or lineage do not differentiate into cells of a different organ or lineage. For example, airway epithelial cells may not differentiate into fibroblast cells, intestinal epithelial cells, intestinal goblet cells, gastric epithelial cells, or pancreatic epithelial cells during expansion, continuous proliferation or continuous culture. In some embodiments, cells undergo some degree of differentiation during expansion, continuous proliferation or continuous culture. For example, lineage-committed epithelial cells may differentiate into cell types within a given lineage and/or organ-specific epithelial cells may differentiate into other cell types within a given organ during expansion, continuous proliferation or continuous culture.

In some embodiments, a certain proportion of the epithelial cells may be at G0 resting phase where the cells have exited cell cycle and have stopped dividing, which includes both quiescence and senescence states. A certain proportion of the epithelial cells may be at G1 phase, in which the cells increase in size and get ready for DNA synthesis. A certain proportion of the epithelial cells may be at S phase, in which DNA replication occurs. A certain proportion of the epithelial cells may be at G2 phase, in which the cells continue to grow and get ready to enter the M (mitosis) phase and divide. A certain proportion of the epithelial cells may be at M (mitosis) phase and complete cell division.

In some embodiments, cells are characterized by telomere length. In some embodiments, cells in an originating epithelial cell population are characterized by telomere length. In some embodiments, cells in an expanded epithelial cell population are characterized by telomere length. Typically, telomere length shortens as cells divide. A cell may normally stop dividing when the average length of telomeres is reduced to a certain length, for example, 4 kb. In some embodiments, average telomere length of cells cultured in media and/or culture conditions described herein may be reduced to a length of less than about 10 kb, and the cells can continue to divide. For example, average telomere length of cells cultured in media and/or culture conditions described herein may be reduced to a length of less than about 9 kb, 8 kb, 7 kb, 6 kb, 5 kb, 4 kb, 3 kb, 2 kb, or 1 kb, and the cells can continue to divide. Average telomere length sometimes is expressed as a mean telomere length or median telomere length. Average telomere length may be determined using any suitable method for determining telomere length, and may vary according to cell type. In some embodiments, average telomere length is determined as relative abundance of telomeric repeats to that of a single copy gene.

In some embodiments, cells are expanded, continuously proliferated or continuously cultured for a certain number of passages without altering cellular karyotype. For example, an alteration in cellular karyotype may include duplication or deletion of chromosomes or portions thereof and/or translocation of a portion of one chromosome to another. Karyotype may be assayed for a population of cells after a certain number of passages which may be compared to a population of cells of the same origin prior to passaging. In some embodiments, cells have an unaltered karyotype after at least about 5 passages to at least about 300 passages. For example, cells may have an unaltered karyotype after at least about 10 passages, 20 passages, 30 passages, 40 passages, 50 passages, 60 passages, 70 passages, 80 passages, 90 passages, 100 passages, 200 passages or 300 passages. In certain instances, cells that have an unaltered karyotype after a certain number of passages may be referred to as conditionally immortalized cells.

In some embodiments, methods herein comprise use of an extracellular matrix (ECM). In some embodiments, methods herein do not comprise use of an extracellular matrix. ECM may contain certain polysaccharides, water, elastin, and certain glycoproteins such as, for example, collagen, entactin (nidogen), fibronectin, and laminin. ECM may be generated by culturing ECM-producing cells, and optionally removing these cells, prior to the plating of epithelial cells. Examples of ECM-producing cells include chondrocytes, which produce collagen and proteoglycans; fibroblast cells, which produce type IV collagen, laminin, interstitial procollagens and fibronectin; and colonic myofibroblasts, which produce collagens (type I, III, and V), chondroitin sulfate proteoglycan, hyaluronic acid, fibronectin, and tenascin-C. ECM also may be commercially provided. Examples of commercially available extracellular matrices include extracellular matrix proteins (Invitrogen), basement membrane preparations from Engelbreth-Holm-Swarm (EHS) mouse sarcoma cells (e.g., Matrigel™ (BD Biosciences)), and synthetic extracellular matrix materials, such as ProNectin (Sigma Z378666). Mixtures of extracellular matrix materials may be used in certain instances. Extracellular matrices may be homogeneous (comprise essentially a single component) or heterogeneous (comprise a plurality of components). Heterogeneous extracellular matrices generally comprise a mixture of ECM components including, for example, a plurality of glycoproteins and growth factors. Example heterogeneous extracellular matrices include basement membrane preparations from Engelbreth-Holm-Swarm (EHS) mouse sarcoma cells (e.g., Matrigel™). In some embodiments, methods herein do not comprise use of a heterogeneous extracellular matrix. Extracellular matrices may be defined (all or substantially all components and amounts thereof are known) or undefined (all or substantially all components and amounts thereof are not known). Example undefined extracellular matrices include basement membrane preparations from Engelbreth-Holm-Swarm (EHS) mouse sarcoma cells (e.g., Matrigel™). In some embodiments, methods herein do not comprise use of an undefined extracellular matrix.

In some embodiments, cells are cultured in a container comprising a coating. For example, cells may be plated onto the surface of culture vessels containing one or more attachment factors. In some embodiments, cells are plated onto the surface of culture vessels without attachment factors. In embodiments where attachment factors are used, a culture container can be precoated with a natural, recombinant or synthetic attachment factor or factors or peptide fragments thereof, such as but not limited to collagen, fibronectin and natural or synthetic fragments thereof. In some embodiments, a culture vessel is precoated with collagen. In some embodiments, a culture vessel is precoated with a basement membrane matrix. In some embodiments, a culture vessel is precoated with a homogeneous and/or defined extracellular matrix.

The cells may maintain one or more functional characteristics throughout the culturing process. In some embodiments, a functional characteristic may be a native functional characteristic. Native functional characteristics generally include traits possessed by a given cell type while in its natural environment (e.g., a cell within the body of a subject before being extracted for cell culture). Examples of native functional characteristics include gas exchange capabilities in airway epithelial cells, detoxification capabilities in liver epithelial cells, filtration capabilities in kidney epithelial cells, and insulin production and/or glucose responsiveness in pancreatic islet cells. In some embodiments, cells do not maintain one or more functional characteristics throughout the culturing process.

A characteristic of cells in culture sometimes is determined for an entire population of cells in culture. For example, a characteristic such as average telomere length, doubling time, growth rate, division rate, gene level or marker level, for example, is determined for the population of cells in culture. A characteristic often is representative of cells in the population, and the characteristic may vary for particular cells in the culture. For example, where a population of cells in a culture exhibits an average telomere length of 4 kb, a portion of cells in the population can have a telomere length of 4 kb, a portion of cells can have a telomere length greater than 4 kb and a portion of cells can have a telomere length less than 4 kb. In another example, where a population of cells is characterized as expressing a high level of a particular gene or marker, all cells in the population express the particular gene or marker at a high level in some embodiments, and in certain embodiments, a portion of cells in the population (e.g., at least 75% of cells) express the particular gene or marker at a high level and a smaller portion of the cells express the particular gene at a moderate level, low level or undetectable level. In another example, where a population of cells is characterized as not expressing, or expressing a low level of a particular gene or marker, no cells in the population express the particular gene or marker at a detectable level in some embodiments, and in certain embodiments, a portion of cells in the population (e.g., less than 10% of cells) express the particular gene or marker at a detectable level.

A characteristic of cells in culture (e.g., population doublings, marker expression) sometimes is compared to the same characteristic observed for cells cultured in control culture conditions. Often, when comparing a characteristic observed for cells cultured in control culture conditions, an equal or substantially equal amount of cells from the same source is added to certain culture conditions and to control culture conditions. Control culture conditions may include the same base medium (e.g., a serum-free base medium) and additional components minus one or more agents (e.g., one or more of a TGF-beta inhibitor (e.g., one or more TGF-beta signaling inhibitors), a ROCK inhibitor, a myosin II inhibitor, a PAK inhibitor). In some embodiments, cell culture conditions consist essentially of certain components necessary to achieve one or more characteristics of cells in culture (e.g., population doublings, marker expression) compared to the same characteristic(s) observed for cells cultured in control culture conditions. When a cell culture condition consists essentially of certain components, additional components or features may be included that do not have a significant effect on the one or more characteristics of cells in culture (e.g., population doublings, marker expression) when compared to control culture conditions. Such additional components or features may be referred to as non-essential components and may include typical cell culture components such as salts, vitamins, amino acids, certain growth factors, fatty acids, and the like.

Feeder Cells

Cells may be cultured with or without feeder cells. Generally, feeder cells are cells co-cultured with other cell types for certain cell culture systems. Feeder cells typically are nonproliferating cells and sometimes are treated to inhibit proliferation, and often are maintained in a live, metabolically active state. For example, feeder cells can be irradiated with gamma irradiation and/or treated with mitomycin C, which can arrest cell division while maintaining the feeder cells in a metabolically active state.

Feeder cells can be from any mammal and the animal source of the feeder cells need not be the same animal source as the cells being cultured. For example feeder cells may be, but are not limited to mouse, rat, canine, feline, bovine, equine, porcine, non-human primate and human feeder cells. Types of feeder cells may include spleenocytes, macrophages, thymocytes and/or fibroblasts. Types of feeder cells may be the same cell type which they support. Types of feeder cells may not be the same cell type which they support. J2 cells are used as feeder cells for certain cell culture systems, and are a subclone of mouse fibroblasts derived from the established Swiss 3T3 cell line.

In some embodiments, cells are cultured in the absence of feeder cells. In some embodiments, cells are not cultured in media conditioned by feeder cells (i.e., not cultured in a conditioned medium). In some embodiments, cells are not cultured in the presence of fractionated feeder cells, or particulate and/or soluble fractions of feeder cells. Any one or all of the above culture conditions (i.e., cultured in the absence of feeder cells; not cultured in a conditioned medium; not cultured in the presence of fractionated feeder cells, or particulate and/or soluble fractions of feeder cells) may be referred to as feeder-cell free conditions or feeder-free conditions. Expansion culture conditions provided herein typically are feeder-cell free culture conditions.

Media and Cell Culture Compositions

Cells typically are cultured in the presence of a cell culture medium. Expansion culture conditions provided herein typically comprise a cell culture medium. A cell culture medium may include any type of medium such as, for example, a serum-free medium; a serum-containing medium; a reduced-serum medium; a protein-free medium; a chemically defined medium; a protein-free, chemically defined medium; a peptide-free, protein-free, chemically defined medium; an animal protein-free medium; a xeno-free medium. A cell culture medium typically is an aqueous-based medium and can include any of the commercially available and/or classical media such as, for example, Dulbecco's Modified Essential Medium (DMEM), Knockout-DMEM (KODMEM), Ham's F12 medium, DMEM/Ham's F12, Advanced DMEM/Ham's F12, Ham's F-10 medium, RPMI 1640, Eagle's Basal Medium (EBM), Eagle's Minimum Essential Medium (MEM), Glasgow Minimal Essential Medium (G-MEM), Medium 199, Keratinocyte-SFM (KSFM; Gibco/Thermo-Fisher), prostate epithelial growth medium (PrEGM; Lonza), CHO cell culture media, PER.C6 media, 293 media, hybridoma media, and the like and combinations thereof.

In some embodiments, a cell culture medium is a serum-containing medium. Serum may include, for example, fetal bovine serum (FBS), fetal calf serum, goat serum or human serum. Generally, serum is present at between about 1% to about 30% by volume of the medium. In some instances, serum is present at between about 0.1% to about 30% by volume of the medium. In some embodiments, a medium contains a serum replacement.

In some embodiments, a cell culture medium is a serum-free medium. A serum-free medium generally does not contain any animal serum (e.g. fetal bovine serum (FBS), fetal calf serum, goat serum or human serum), but may contain certain animal-derived products such as serum albumin (e.g., purified from blood), growth factors, hormones, carrier proteins, hydrolysates, and/or attachment factors. In some embodiments, a serum-free cell culture medium comprises Keratinocyte-SFM (KSFM; Gibco/Thermo-Fisher). KSFM may include insulin, transferrin, hydrocortisone, Triiodothyronine (T3). A representative formulation of KSFM basal medium is described, for example, in U.S. Pat. No. 6,692,961.

In some embodiments, a cell culture medium is a defined serum-free medium. Defined serum-free media, sometimes referred to as chemically-defined serum-free media, generally include identified components present in known concentrations, and generally do not include undefined components such as animal organ extracts (e.g., pituitary extract) or other undefined animal-derived products (e.g., unquantified amount of serum albumin (e.g., purified from blood), growth factors, hormones, carrier proteins, hydrolysates, and/or attachment factors). Defined media may include a basal media such as, for example, DMEM, F12, or RPMI 1640, containing one or more of amino acids, vitamins, inorganic acids, inorganic salts, alkali silicates, purines, pyrimidines, polyamines, alpha-keto acids, organosulphur compounds, buffers (e.g., HEPES), antioxidants and energy sources (e.g., glucose); and may be supplemented with one or more of recombinant albumin, recombinant growth factors, chemically defined lipids, recombinant insulin and/or zinc, recombinant transferrin or iron, selenium and an antioxidant thiol (e.g., 2-mercaptoethanol or 1-thioglycerol). Recombinant albumin and/or growth factors may be derived, for example, from non-animal sources such as rice or *E. coli*, and in certain instances synthetic chemicals are added to defined media such as a polymer polyvinyl alcohol which can reproduce some of the functions of bovine serum albumin (BSA)/human serum albumin (HSA). In some embodiments, a defined serum-free media may be selected from MCDB 153 medium (Sigma-Aldrich M7403), Modified MCDB 153 medium (Biological Industries, Cat. No. 01-059-1), MCDB 105 medium (Sigma-Aldrich M6395), MCDB 110 medium (Sigma-Aldrich M6520), MCDB 131 medium (Sigma-Aldrich M8537), MCDB 201 medium (Sigma-Aldrich M6670), and modified versions thereof. In some embodiments, a defined serum-free media is MCDB 153 medium (Sigma-Aldrich M7403). In some embodiments, a defined serum-free media is Modified MCDB 153 medium (Biological Industries, Cat. No. 01-059-1).

In some embodiments, a cell culture medium is a xeno-free serum-free medium. Xeno-free generally means having no components originating from animals other than the animal from which cells being cultured originate. For example, a xeno-free culture has no components of non-human animal origin when human cells are cultured. In some embodiments, a cell culture medium is a defined xeno-free serum-free medium. Defined xeno-free serum-free media, sometimes referred to as chemically-defined xeno-free serum-free media, generally include identified components present in known concentrations, and generally do not include undefined components such as animal organ extracts (e.g., pituitary extract) or other undefined animal-derived products (e.g., serum albumin (e.g., purified from blood), growth factors, hormones, carrier proteins, hydrolysates, and/or attachment factors). Defined xeno-free serum-free media may or may not include lipids and/or recombinant proteins from animal sources (e.g., non-human sources) such as, for example, recombinant albumin, recombinant growth factors, recombinant insulin and/or recombinant transferrin. Recombinant proteins may be derived, for example, from non-animal sources such as a plant (e.g., rice) or bacterium (e.g., *E. coli*), and in certain instances synthetic chemicals are added to defined media (e.g., a polymer (e.g., polyvinyl alcohol)), which can reproduce some of the functions of bovine serum albumin (BSA)/human serum albumin (HSA). In some embodiments, a defined serum-free medium may comprise a commercially available xeno-free serum substitute, such as, for example, XF-KOSR™ (Invitrogen). In some embodiments, a defined serum-free medium may comprise a commercially available xeno-free base medium such as, for example, mTeSR2™ (Stem Cell Technologies), NutriStem™ (StemGent), X-Vivo 10™ or X-Vivo 15™ (Lonza Biosciences), or HEScGRO™ (Millipore).

Additional ingredients may be added to a cell culture medium herein. For example, such additional ingredients may include amino acids, vitamins, inorganic salts, inorganic acids, adenine, ethanolamine, D-glucose, heparin, N-[2-hydroxyethyl]piperazine-N'-[2-ethanesulfonic acid] (HEPES), hydrocortisone, insulin, lipoic acid, phenol red, phosphoethanolamine, putrescine, sodium pyruvate, pyruvic acid, ammonium metavanadate, molybdic acid, silicates, alkali silicates (e.g., sodium metasilicate), purines, pyrimidines, polyamines, alpha-keto acids, organosulphur compounds, buffers (e.g., HEPES), antioxidants, thioctic acid, triiodothyronine (T3), thymidine and transferrin. In certain instances, insulin and/or transferrin may be replaced by ferric citrate or ferrous sulfate chelates. Amino acid may include, for example, L-alanine, L-arginine, L-asparagine, L-aspartic acid, L-cysteine, L-glutamic acid, L-glutamine, glycine, L-histidine, L-isoleucine, L-leucine, L-lysine, L-methionine, L-phenylalanine, L-proline, L-serine, L-threonine, L-tryptophan, L-tyrosine and L-valine. Vitamins may include, for example, biotin, D-biotin, choline chloride, D-$Ca^{+2}$-pantothenate, D-pantothenic acid, folic acid, i-inositol, myo-inositol, niacinamide, pyridoxine, riboflavin, thiamine and vitamin B12. Inorganic salts may include, for example, calcium salt (e.g., $CaCl_2$), $CuSO_4$, $FeSO_4$, KCl, a magnesium salt (e.g., $MgCl_2$, $MgSO_4$), a manganese salt (e.g., $MnCl_2$), sodium acetate, NaCl, $NaHCO_3$, $Na_2HPO_4$, $Na_2SO_4$, and ions of certain trace elements including selenium, silicon, molybdenum, vanadium, nickel, tin and zinc. These trace elements may be provided in a variety of forms, including the form of salts such as $Na_2SeO_3$, $Na_2SiO_3$, $(NH_4)_6MoO_{24}$, $NH_4VO_3$, $NiSO_4$, SnCl and ZnSO. Additional ingredients may include, for example, heparin, epidermal growth factor (EGF), at least one agent increasing intracellular cyclic adenosine monophosphate (cAMP) levels, at least one fibroblast growth factor (FGF), acidic FGF, granulocyte macrophage colony-stimulating factor (GM-CSF) (uniprot accession number P04141), granulocyte colony stimulating factor (G-CSF) (uniprot accession number P09919), hepatocyte growth factor (HGF) (uniprot accession number P14210), neuregulin 1 (NRG1) (uniprot accession number Q61CV5), neuregulin 2 (NRG2) (uniprot accession number Q3M186), neuregulin 3 (NRG3) (uniprot accession number B9EGV5), neuregulin 4 (NRG4) (uniprot accession number QOP6N6), epiregulin (ERG) (uniprot accession number O14944), beta-cellulin (BC) (uniprot accession number Q86UF5), Interleukin-11 (IL11) (uniprot accession number P20809), a collagen and heparin-binding EGF-like growth factor (HB-EGF) (uniprot accession number Q14487).

In some embodiments, a cell culture medium comprises calcium. In some embodiments, calcium is present at a concentration of about 2 mM. In some embodiments, calcium is present at a concentration below 2 mM. In some embodiments, calcium is present at a concentration of about 1 mM. In some embodiments, calcium is present at a concentration below 1 mM. For example, calcium may be present a concentration below 2 mM, below 1 mM, below 900 µM, below 800 µM, below 700 µM, below 600 µM, below 500 µM, below 400 µM, below 300 µM, below 200 µM, below 100 µM, below 90 µM, below 80 µM, below 70 µM, below 60 µM, below 50 µM, below 40 µM, below 30 µM, below 20 µM, or below 10 µM. In some embodiments, calcium is present at a concentration below 500 µM. In some embodiments, calcium is present at a concentration below 300 µM. In some embodiments, calcium is present at a concentration below 100 µM. In some embodiments, calcium is present at a concentration below 20 µM. In some embodiments, calcium is present at a concentration of about 90 µM.

In some embodiments, a cell culture medium comprises albumin (e.g., serum albumin). Albumin is a protein generally abundant in vertebrate blood. In some embodiments, a cell culture medium comprises bovine serum albumin (BSA). In some embodiments, a cell culture medium comprises human serum albumin (HSA). Albumin may be purified (e.g., from human or bovine serum) or may be recombinantly produced, such as for example, in plants (e.g., rice), bacteria (e.g., *E. coli*), or yeast (e.g., *Pichia pastoris, Saccharomyces cerevisiae*). In some embodiments, a cell culture medium comprises recombinant human serum albumin (rHSA). In some embodiments, a cell culture medium comprises recombinant human serum albumin (rHSA) produced in rice.

In some embodiments, a cell culture medium comprises one or more lipids. Lipids generally refer to oils, fats, waxes, sterols, fat-soluble vitamins (e.g., vitamins A, D, E, and K), fatty acids, monoglycerides, diglycerides, triglycerides, phospholipids, glycerolipids, glycerophospholipids, sphingolipids, saccharolipids, polyketides, prenol lipids and the like, and may include mixtures of lipids (e.g., chemically defined lipids mixtures). In some embodiments, lipids may be selected from arachidonic acid, cholesterol, DL-alpha-tocopherol acetate, linoleic acid, linolenic acid, myristic acid, oleic acid, palmitic acid, palmitoleic acid, pluronic F-68, stearic acid, polysorbate 80 (TWEEN 80), TWEEN 20, cod liver oil fatty acids (methyl esters), polyoxyethylenesorbitan monooleate, D-α-tocopherol acetate. In some embodiments, lipids may include one or more of linoleic acid, linolenic acid, oleic acid, palmitic acid, and stearic acid. In some embodiments, a lipids mix may be a commercially available lipids mix (e.g., Chemically Defined Lipid Concentrate (Gibco, 11905-031); Lipid Mixture (Sigma-Aldrich L5146); Lipid Mixture 1, Chemically Defined (Sigma-Aldrich L0288)). In some embodiments, a lipids mix may include a mixture of lipids supplied with a commercially available albumin (e.g., AlbuMAX® ILipid-Rich BSA (Gibco, 11020-039)).

In some embodiments, a cell culture medium comprises one or more mitogenic growth factors. For example, a mitogenic growth factor may include epidermal growth factor (EGF), transforming growth factor-alpha (TGF-alpha), fibroblast growth factor (FGF), basic fibroblast growth factor (bFGF), acidic fibroblast growth factor (aFGF), brain-derived neurotrophic factor (BDNF), insulin-like growth factor I (IGF-I), insulin-like growth factor II (IGF-II), and/or keratinocyte growth factor (KGF). In some embodiments, a medium does not comprise a mitogenic growth factor.

In some embodiments, a cell culture medium comprises one or more mitogenic supplements. For example, a mitogenic supplement may include bovine pituitary extract (BPE; Gibco/Thermo-Fisher), B27 (Gibco/Thermo-Fisher), N-Acetylcysteine (Sigma), GEM21 NEUROPLEX (Gemini Bio-Products), and N2 NEUROPLEX (Gemini Bio-Products). In some embodiments, a cell culture medium does not comprise a mitogenic supplement.

In some embodiments, a cell culture medium comprises one or more agents that increase intracellular cyclic adenosine monophosphate (cAMP) levels. For example, a cell culture medium may comprise one or more beta-adrenergic agonists (e.g., one or more beta-adrenergic receptor agonists). Beta-adrenergic agonists (e.g., beta-adrenergic receptor agonists) generally are a class of sympathomimetic agents which activate beta adrenoceptors (e.g., beta-1 adrenergic receptor, beta-2 adrenergic receptor, beta-3 adrenergic receptor). The activation of beta adrenoceptors activates adenylate cyclase, which leads to the activation of cyclic adenosine monophosphate (cAMP). Beta-adrenergic agonists (e.g., beta-adrenergic receptor agonists) may include, for example, epinephrine, isoproterenol, dobutamine, xamoterol, salbutamol (ALBUTEROL), levosalbutamol (LEVALBUTEROL), fenoterol, formoterol, metaproterenol, salmeterol, terbutaline, clenbuterol, isoetarine, pirbuterol, procaterol, ritodrine, arbutamine, befunolol, bromoacetylalprenololmenthane, broxaterol, cimaterol, cirazoline, denopamine, dopexamine, etilefrine, hexoprenaline, higenamine, isoxsuprine, mabuterol, methoxyphenamine, nylidrin, oxyfedrine, prenalterol, ractopamine, reproterol, rimiterol, tretoquinol, tulobuterol, zilpaterol, and zinterol. In some embodiments, a cell culture medium comprises isoproterenol. In some embodiments, a cell culture medium comprises isoproterenol at a concentration of between about 0.5 μM to about 20 μM. For example, isoproterenol may be present at a concentration of about 0.5 μM, about 0.6 μM, about 0.7 μM, about 0.8 μM, about 0.9 μM, about 1 μM, about 1.25 μM, about 1.5 μM, about 1.75 μM, about 2 μM, about 2.5 μM, about 3 μM, about 3.5 μM, about 4 μM, about 4.5 μM, about 5 μM, about 5.5 μM, about 6 μM, about 7 μM, about 8 μM, about 9 μM, about 10 μM, about 11 μM, about 12 μM, about 13 μM, about 14 μM, or about 15 μM.

Other agents that increase intracellular cAMP level may include agents which induce a direct increase in intracellular cAMP levels (e.g., dibutyryl cAMP), agents which cause an increase in intracellular cAMP levels by an interaction with a cellular G-protein (e.g., cholera toxin and forskolin), and agents which cause an increase in intracellular cAMP levels by inhibiting the activities of cAMP phosphodiesterases (e.g., isobutylmethylxanthine (IBMX) and theophylline).

In some embodiments, a cell culture medium does not comprise one or more of the following: a Wnt agonist, a beta-catenin agonist, Noggin, DAN, Cerberus, Gremlin, R-spondin, Wnt-3a, EGF, nicotinamide, FGF10, gastrin, a p38 inhibitor, SB202190, DHT, a notch inhibitor, a gamma secretase inhibitor, DBZ, DAPT, Interleukin-6 (IL6), or ephrin A5 (EfnA5).

In some embodiments, a cell culture medium comprises one or more inhibitors. Inhibitors may include, for example, one or more TGF-beta inhibitors (e.g., one or more TGF-beta signaling inhibitors), one or more p21-activated kinase (PAK) inhibitors, one or more myosin II inhibitors (e.g., non-muscle myosin II (NM II) inhibitors), and one or more Rho kinase inhibitors (e.g., one or more Rho-associated protein kinase inhibitors). Such classes of inhibitors are discussed in further detail below. Inhibitors may be in the form of small molecule inhibitors (e.g., small organic molecules), antibodies, RNAi molecules, antisense oligonucleotides, recombinant proteins, natural or modified substrates, enzymes, receptors, peptidomimetics, inorganic molecules, peptides, polypeptides, aptamers, and the like and structural or functional mimetics of these. An inhibitor may act competitively, non-competitively, uncompetitively or by mixed inhibition. For example, in certain embodiments, an inhibitor may be a competitive inhibitor of the ATP binding pocket of a target kinase (e.g., protein kinase). In some embodiments, an inhibitor disrupts the activity of one or more receptors. In some embodiments, an inhibitor disrupts one or more receptor-ligand interactions. In some embodiments, an inhibitor may bind to and reduce the activity of its target. In some embodiments, an inhibitor may bind to and reduce the activity of its target by about 10% or more compared to a control. For example, an inhibitor may bind to and reduce the activity of its target by about 20% or more, 30% or more, 40% or more, 50% or more, 60% or more, 70% or more, 80% or more, 90% or more, 95% or more, or 99% or more compared to a control. Inhibition can be assessed using a cellular assay, for example.

In some embodiments, an inhibitor is a kinase inhibitor (e.g., a protein kinase inhibitor). The effectiveness of a kinase inhibitor inhibiting its target's biological or biochemical function may be expressed as an $IC_{50}$ value. The $IC_{50}$ generally indicates how much of a particular inhibitor is required to inhibit a kinase by 50%. In some embodiments, an inhibitor has an $IC_{50}$ value equal to or less than 1000 nM, equal to or less than 500 nM, equal to or less than 400 nM, equal to or less than 300 nM, equal to or less than 200 nM, equal to or less than 100 nM, equal to or less than 50 nM, equal to or less than 20 nM, or equal to or less than 10 nM.

In some embodiments, an inhibitor may directly or indirectly affect one or more cellular activities, functions or characteristics. For example, an inhibitor may induce telomerase reverse transcriptase expression in cultured cells, for example through the inhibition of the TGF-beta signaling pathway. In certain embodiments, a TGF-beta inhibitor (e.g., a TGF-beta signaling inhibitor) activates telomerase reverse transcriptase expression in cultured cells. In certain embodiments, an ALK5 inhibitor activates telomerase reverse transcriptase expression in cultured cells. In certain embodiments, A83-01 activates telomerase reverse transcriptase expression in cultured cells. In another example, an inhibitor may modulate the cytoskeletal structure within cultured cells, for example through the inhibition of Rho kinase (e.g., Rho-associated protein kinase), p21-activated kinase (PAK), and/or myosin II (e.g., non-muscle myosin II (NM II)). Modulation the cytoskeletal structure may include, for example, a modification of, a disruption to, or a change in any aspect of cytoskeletal structure including actin microfilaments, tubulin microtubules, and intermediate filaments; or interaction with any associated proteins, such as molecular motors, crosslinkers, capping proteins and nucleation promoting factors. In certain embodiments, a ROCK inhibitor modulates the cytoskeletal structure within cultured cells. In certain embodiments, Y-27632 modulates the cytoskeletal structure within cultured cells. In certain embodiments, a PAK1 inhibitor modulates the cytoskeletal structure within cultured cells. In certain embodiments, IPA3 modulates the cytoskeletal structure within cultured cells. In certain embodiments, a myosin II inhibitor (e.g., a non-muscle myosin II (NM II) inhibitor) modulates the cytoskeletal structure within cultured cells. In certain embodiments, blebbistatin modulates the cytoskeletal structure within cultured cells.

TGF-Beta Inhibitors

In some embodiments, a method herein comprises inhibiting transforming growth factor beta (TGF-beta) signaling in cultured epithelial cells. TGF-beta signaling controls proliferation, cellular differentiation, and other functions in a variety of cell types, and can play a role in cell cycle control, regulation of the immune system, and development in certain cell types. Inhibition of TGF-beta signaling may include inhibition of any TGF-beta signaling pathway and/or member of the TGF-beta superfamily including ligands such as TGF-beta1, TGF-beta2, TGF-beta3, inhibins, activin, anti-müllerian hormone, bone morphogenetic protein, decapentaplegic and Vg-1; receptors such as TGF-beta type I receptor, TGF-beta type II receptor, ALK1, ALK2, ALK3, ALK4, ALK5, ALK6, ALK7 and ALK8; and downstream effectors such as R-SMAD and other SMAD proteins (e.g., SMAD1, SMAD2, SMAD3, SMAD4, SMAD5).

In some embodiments, the activity of one or more TGF-beta receptors is inhibited. In some embodiments, one or more TGF-beta receptor-ligand interactions are inhibited. In some embodiments, a TGF-beta type I receptor is inhibited. A TGF-beta type I receptor may include one or more of ALK1, ALK2, ALK3, ALK4, ALK5, ALK6, ALK7 and ALK8. In some embodiments, the TGF-beta receptor is ALK5.

In some embodiments, a cell culture medium comprises one or more TGF-beta inhibitors (e.g., one or more TGF-beta signaling inhibitors). In some embodiments, a TGF-beta inhibitor (e.g., a TGF-beta signaling inhibitor) binds to one or more TGF-beta receptors. In some embodiments, a TGF-beta inhibitor (e.g., a TGF-beta signaling inhibitor) binds to one or more TGF-beta ligands. In some embodiments, a TGF-beta inhibitor (e.g., a TGF-beta signaling inhibitor) binds to one or more SMAD proteins. In some embodiments, a TGF-beta inhibitor (e.g., a TGF-beta signaling inhibitor) binds to one or more TGF-beta receptors and one or more TGF-beta ligands. In some embodiments, a TGF-beta inhibitor (e.g., a TGF-beta signaling inhibitor) binds to one or more TGF-beta receptors and one or more SMAD proteins. In some embodiments, a TGF-beta inhibitor (e.g., a TGF-beta signaling inhibitor) disrupts one or more TGF-beta receptor-ligand interactions. In some embodiments, a TGF-beta inhibitor (e.g., a TGF-beta signaling inhibitor) disrupts one or more TGF-beta receptor-SMAD interactions. In some embodiments, a TGF-beta inhibitor (e.g., a TGF-beta signaling inhibitor) blocks phosphorylation or autophosphorylation of a TGF-beta receptor. In some embodiments, a TGF-beta inhibitor (e.g., a TGF-beta signaling inhibitor) promotes the de-phosphorylation of one or more TGF-beta receptors. In some embodiments, a TGF-beta inhibitor (e.g., a TGF-beta signaling inhibitor) blocks phosphorylation of one or more SMAD proteins. In some embodiments, a TGF-beta inhibitor (e.g., a TGF-beta signaling inhibitor) promotes the de-phosphorylation of one or more SMAD proteins. In some embodiments, a TGF-beta inhibitor (e.g., a TGF-beta signaling inhibitor) promotes the ubiquitin-mediated degradation of one or more TGF-beta receptors. In some embodiments, a TGF-beta inhibitor (e.g., a TGF-beta signaling inhibitor) promotes the ubiquitin-mediated degradation of one or more SMAD proteins. In some embodiments, a TGF-beta inhibitor (e.g., a TGF-beta signaling inhibitor) affects the nuclear translocation of SMADs, nuclear shuffling of SMADs, interactions of SMAD with co-activators, and the like. In certain instances, TGF-beta signaling can be measured by SMAD reporter assays.

A TGF-beta inhibitor (e.g., a TGF-beta signaling inhibitor) may be an ALK5 inhibitor, in some embodiments. An ALK5 inhibitor may bind to ALK5 or one or more ALK5 ligands or both. An ALK5 inhibitor may bind to ALK5 or one or more downstream SMAD proteins or both. An ALK5 inhibitor may disrupt one or more ALK5-ligand interactions or may disrupt one or more ALK5-SMAD interactions. In some embodiments, an ALK5 inhibitor blocks phosphorylation of SMAD2.

ALK5 inhibitors may include one or more small molecule ALK5 inhibitors. In some embodiments, an ALK5 inhibitor is an ATP analog. In some embodiments, an ALK5 inhibitor comprises the structure of Formula A:

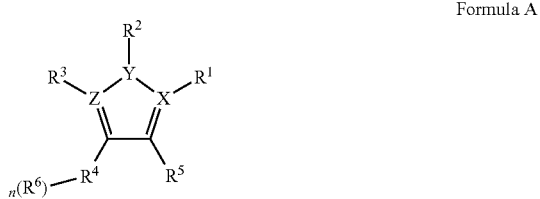

Formula A where:
X, Y and Z independently are chosen from N, C and O;
$R^1$, $R^2$ and $R^3$ independently are chosen from hydrogen, C1-C10 alkyl, substituted C1-C10 alkyl, C3-C9 cycloalkyl, substituted C3-C9 cycloalkyl, C5-C10 aryl, substituted C5-C10 aryl, C5-C10 cycloaryl, substituted C5-C10 cycloaryl, C5-C9 heterocyclic, substituted C5-C9 heterocyclic, C5-C9 hetercycloaryl, substituted C5-C9 heterocycloaryl, -linker-(C3-C9 cycloalkyl), -linker-(substituted C3-C9 cycloalkyl), -linker-(C5-C10 aryl), -linker-(substituted C5-C10 aryl), -linker-(C5-C10 cycloaryl), -linker-(substituted C5-C10 cycloaryl), -linker-(C5-C9 heterocyclic), -linker-(substituted C5-C9 heterocyclic), -linker-(C5-C9 hetercycloaryl), -linker-(substituted C5-C9 heterocycloaryl);
n is 0 or 1;
$R^4$, $R^5$ and $R^6$ independently are chosen from hydrogen, C1-C10 alkyl, substituted C1-C10 alkyl, C1-C10 alkoxy, substituted C1-C10 alkoxy, C1-C6 alkanoyl, C1-C6 alkoxycarbonyl, substituted C1-C6 alkanoyl, substituted C1-C6 alkoxycarbonyl, C3-C9 cycloalkyl, substituted C3-C9 cycloalkyl, C5-C10 aryl, substituted C5-C10 aryl, C5-C10 cycloaryl, substituted C5-C10 cycloaryl, C5-C9 heterocyclic, substituted C5-C9 heterocyclic, C5-C9 hetercycloaryl, substituted C5-C9 heterocycloaryl, -linker-(C3-C9 cycloalkyl), -linker-(substituted C3-C9 cycloalkyl), -linker-(C5-C10 aryl), -linker-(substituted C5-C10 aryl), -linker-(C5-C10 cycloaryl), -linker-(substituted C5-C10 cycloaryl), -linker-(C5-C9 heterocyclic), -linker-(substituted C5-C9 heterocyclic), -linker-(C5-C9 hetercycloaryl), -linker-(substituted C5-C9 heterocycloaryl); and
the substituents on the substituted alkyl, alkoxy, alkanoyl, alkoxycarbonyl cycloalkyl, aryl, cycloaryl, heterocyclic or heterocycloaryl groups are hydroxyl, C1-C10 alkyl, hydroxyl C1-C10 alkylene, C1-C6 alkoxy, C3-C9 cycloalkyl, C5-C9 heterocyclic, C1-6 alkoxy C1-6 alkenyl, amino, cyano, halogen or aryl.

ALK5 inhibitors may include, for example, A83-01 (3-(6-Methyl-2-pyridinyl)-N-phenyl-4-(4-quinolinyl)-1H-pyrazole-1-carbothioamide), GW788388 (4-[4-[3-(2-Pyridinyl)-1H-pyrazol-4-yl]-2-pyridinyl]-N-(tetrahydro-2H-pyran-4-yl)-benzamide), RepSox (2-(3-(6-Methylpyridine-2-yl)-1H-pyrazol-4-yl)-1,5-naphthyridine), and SB 431542 (4-[4-(1,3-benzodioxol-5-yl)-5-(2-pyridinyl)-1H-imidazol-2-yl]benzamide). In some embodiments, the ALK5 inhibitor is A83-01.

p21-Activated Kinase (PAK) Inhibitors

In some embodiments, a method herein comprises inhibiting the activity of p21-activated kinase (PAK) in cultured epithelial cells. PAK proteins, a family of serine/threonine p21-activated kinases, include PAK1, PAK2, PAK3 and PAK4, and generally function to link the Rho family of GTPases to cytoskeleton reorganization and nuclear signaling. These proteins are targets for Cdc42 and Rac and may function in various biological activities. PAK1, for example, can regulate cell motility and morphology. In some embodiments, a method herein comprises inhibiting the activity of PAK in cultured epithelial cells.

In some embodiments, a cell culture medium comprises one or more PAK inhibitors. In some embodiments, a PAK inhibitor binds to a PAK protein. In some embodiments, a PAK inhibitor binds to one or more PAK activators (e.g., Cdc42, Rac). In some embodiments, a PAK inhibitor binds to one or more downstream effectors of PAK1. In some embodiments, a PAK inhibitor binds to a PAK protein and one or more PAK activators (e.g., Cdc42, Rac). In some embodiments, a PAK inhibitor disrupts one or more PAK1-activator interactions. In some embodiments, a PAK1 inhibitor disrupts one or more PAK1-effector interactions. In some embodiments, a PAK1 inhibitor targets an autoregulatory mechanism and promotes the inactive conformation of PAK1.

PAK1 inhibitors may include one or more small molecule PAK1 inhibitors. PAK1 inhibitors may include, for example, IPA3 (1,1'-Dithiodi-2-naphthtol), AG-1478 (N-(3-Chlorophenyl)-6,7-dimethoxy-4-quinazolinanine), FRAX597 (6-[2-chloro-4-(1,3-thiazol-5-yl)phenyl]-8-ethyl-2-[4-(4-methylpiperazin-1-yl)anilino]pyrido[2,3-d]pyrimidin-7-one), FRAX486 (6-(2,4-Dichlorophenyl)-8-ethyl-2-[[3-fluoro-4-(1-piperazinyl)phenyl]amino]pyrido[2,3-d]pyrimidin-7 (8H)-one), and PF-3758309 ((S)—N-(2-(dimethylamino)-1-phenylethyl)-6,6-dimethyl-3-((2-methylthieno[3,2-d]pyrimidin-4-yl)amino)-4,6-dihydropyrrolo[3,4-c]pyrazole-5 (1H)-carboxamide). In some embodiments, the PAK1 inhibitor is IPA3.

Myosin II Inhibitors

In some embodiments, a method herein comprises inhibiting activity of myosin II (e.g., non-muscle myosin II (NM II)) in cultured epithelial cells. Myosin II (e.g., non-muscle myosin II (NM II)) is a member of a family of ATP-dependent motor proteins and plays a role in muscle contraction and other motility processes (e.g., actin-based motility). Non-muscle myosin II (NM II) is an actin-binding protein that has actin cross-linking and contractile properties and is regulated by the phosphorylation of its light and heavy chains. Owing to its position downstream of convergent signaling pathways, non-muscle myosin II (NM II) is involved in the control of cell adhesion, cell migration and tissue architecture. In higher eukaryotes, non-muscle myosin II is activated by phosphorylation of its regulatory light chain (MLC) at Ser19/Thr18. MLC phosphorylation controls both the assembly of the actomyosin contractile apparatus and its contractility. Two groups of enzymes generally control MLC phosphorylation. One group includes kinases that phosphorylate MLC (MLC kinases), promoting activity, and the other is a phosphatase that dephosphorylates MLC, inhibiting activity. Several kinases can phosphorylate MLC at Ser19/Thr18 in vitro and, in some cases, in vivo. These include, for example, MLCK, ROCK, PAK (p21-activated kinase), citron kinase, ILK (integrin-linked kinase), MRCK (myotonic dystrophyprotein kinase-related, cdc42-binding kinase) and DAPKs (death-associated protein kinases including ZIPK). The major myosin phosphatase present in smooth and non-muscle cells includes three subunits: a large subunit of w 130 kDa (referred to as the myosin phosphatase targeting subunit MYPT1 (also called M130/133, M110 or MBS)), a catalytic subunit of 38 kDa (the δ isoform of type 1 protein phosphatase, PP1c) and a small subunit of 20 kDa. Rho-associate protein kinase (ROCK) can activate myosin II by inhibiting MYPT1 and by directly phosphorylating MLC. PAK1 can activate myosin II through the phosphorylation of atypical protein kinase C (aPKCζ).

In some embodiments, a cell culture medium comprises one or more myosin II inhibitors (e.g., non-muscle myosin II (NM II) inhibitors). In some embodiments, a myosin II inhibitor binds to a myosin II protein. In some embodiments, a myosin II inhibitor binds to a myosin head structure. In some embodiments, a myosin II inhibitor binds to the myosin-ADP-$P_i$ complex. In some embodiments, a myosin II inhibitor disrupts myosin II ATPase activity. In some embodiments, a myosin II inhibitor competes with ATP for binding to myosin II. In some embodiments, a myosin II inhibitor competes with nucleotide binding to myosin subfragment-1. In some embodiments, a myosin II inhibitor disrupts myosin II-actin binding. In some embodiments, a myosin II inhibitor disrupts the interaction of the myosin head with actin and/or substrate. In some embodiments, a myosin II inhibitor disrupts ATP-induced actomyosin dissociation. In some embodiments, a myosin II inhibitor interferes with a phosphate release process. In some embodiments, a myosin II inhibitor prevents rigid actomyosin cross-linking.

Myosin II inhibitors (e.g., non-muscle myosin II (NM II) inhibitors) may include one or more small molecule myosin II inhibitors (e.g., small molecule non-muscle myosin II (NM II) inhibitors). Myosin II inhibitors may include, for example, blebbistatin ((±)-1,2,3,3a-Tetrahydro-3a-hydroxy-6-methyl-1-phenyl-4H-pyrrolo[2,3-b]quinolin-4-one) and analogs thereof (e.g., para-nitroblebbistatin, (S)-nitro-Blebbistatin, S-(−)-7-desmethyl-8-nitro blebbistatin, and the like), BTS (N-benzyl-p-toluene sulphonamide), and BDM (2,3-butanedione monoxime). In some embodiments, the myosin II inhibitor is blebbistatin.

ROCK (Rho-Associated Protein Kinase) Inhibitors

In some embodiments, a method herein comprises inhibiting the activity of Rho kinase (e.g., Rho-associated protein kinase) in cultured epithelial cells. In some embodiments, a method herein does not comprise inhibiting the activity of Rho kinase (e.g., Rho-associated protein kinase) in cultured epithelial cells. Rho kinase (e.g., Rho-associated protein kinase) belongs to the Rho GTPase family of proteins, which includes Rho, Rac1 and Cdc42 kinases. An effector molecule of Rho is ROCK, which is a serine/threonine kinase that binds to the GTP-bound form of Rho. The catalytic kinase domain of ROCK, which comprises conserved motifs characteristic of serine/threonine kinases, is found at the N-terminus. ROCK proteins also have a central coiled-coil domain, which includes a Rho-binding domain (RBD). The C-terminus contains a pleckstrin-homology (PH) domain with an internal cysteine-rich domain. The coiled-coil domain is thought to interact with other alpha helical proteins. The RBD, located within the coiled-coil domain, interacts with activated Rho GTPases, including RhoA, RhoB, and RhoC. The PH domain is thought to interact with lipid mediators such as arachidonic acid and sphingosylphosphorylcholine, and may play a role in protein localization. Interaction of the PH domain and RBD with the kinase domain results in an auto-inhibitory loop. In addition, the kinase domain is involved in binding to RhoE, which is a negative regulator of ROCK activity.

The ROCK family includes ROCK1 (also known as ROK-beta or p160ROCK) and ROCK2 (also known as ROK-alpha). ROCK1 is about 1354 amino acids in length and ROCK2 is about 1388 amino acids in length. The amino acid sequences of human ROCK1 and human ROCK2 can be found at UniProt Knowledgebase (UniProtKB) Accession Number Q13464 and O75116, respectively. The nucleotide sequences of human ROCK1 and ROCK2 can be found at GenBank Accession Number NM_005406.2 and NM_004850, respectively. The nucleotide and amino acid sequences of ROCK1 and ROCK2 proteins from a variety of animals can be found in both the UniProt and GenBank databases.

Although both ROCK isoforms are ubiquitously expressed in tissues, they exhibit differing intensities in some tissues. For example, ROCK2 is more prevalent in brain and skeletal muscle, while ROCK1 is more abundant in liver, testes and kidney. Both isoforms are expressed in vascular smooth muscle and heart. In the resting state, both ROCK1 and ROCK2 are primarily cytosolic, but are translocated to the membrane upon Rho activation. Rho-dependent ROCK activation is highly cell-type dependent, and ROCK activity is regulated by several different mechanisms including changes in contractility, cell permeability, migration and proliferation to apoptosis. Several ROCK substrates have been identified (see e.g., Hu and Lee, Expert Opin. Ther. Targets 9:715-736 (2005); Loirand et al, Cir. Res. 98:322-334 (2006); and Riento and Ridley, Nat. Rev. Mol. Cell Biol. 4:446-456 (2003) all of which are incorporated by reference). In some instances, ROCK phosphorylates LIM kinase and myosin light chain (MLC) phosphatase after being activated through binding of GTP-bound Rho.

Inhibiting the activity of Rho kinase (e.g., Rho-associated protein kinase) may include reducing the activity, reducing the function, or reducing the expression of at least one of ROCK1 or ROCK2. The activity, function or expression may be completely suppressed (i.e., no activity, function or expression); or the activity, function or expression may be lower in treated versus untreated cells. In some embodiments, inhibiting the activity of Rho kinase (e.g., Rho-associated protein kinase) involves blocking an upstream effector of a ROCK1 and/or ROCK2 pathway, for example GTP-bound Rho, such that ROCK1 and/or ROCK2 are not activated or its activity is reduced compared to untreated cells. Other upstream effectors include but are not limited to, integrins, growth factor receptors, including but not limited to, TGF-beta and EGFR, cadherins, G protein coupled receptors and the like. In some embodiments, inhibiting the activity of Rho kinase (e.g., Rho-associated protein kinase) involves blocking the activity, function or expression of downstream effector molecules of activated ROCK1 and/or ROCK2 such that ROCK1 and/or ROCK2 cannot propagate any signal or can only propagate a reduced signal compared to untreated cells. Downstream effectors include but are not limited to, vimentin, LIMK, Myosin light chain kinase, NHEI, cofilin and the like.

In some embodiments, inhibiting the activity of Rho kinase (e.g., Rho-associated protein kinase) may comprise the use of one or more Rho kinase inhibitors (e.g., one or more Rho-associated protein kinase inhibitors). Rho kinase inhibitors (e.g., Rho-associated protein kinase inhibitors) may include one or more small molecule Rho kinase inhibitors (e.g., one or more small molecule Rho-associated protein kinase inhibitors). Examples of molecule Rho kinase inhibitors (e.g., Rho-associated protein kinase inhibitors) include, for example, Y-27632 ((R)-(+)-trans-4-(1-Aminoethyl)-N-(4-Pyridyl)cyclohexanecarboxamide dihydrochloride), SR 3677 (N-[2-[2-(Dimethylamino)ethoxy]-4-(1H-pyrazol-4-yl)phenyl-2,3-dihydro-1,4-benzodioxin-2-carboxamide dihydrochloride), thiazovivin (N-Benzyl-[2-(pyrimidin-4-yl)amino]thiazole-4-carboxamide), HA1100 hydrochloride (1-[(1,2-Dihydro-1-oxo-5-isoquinolinyl)sulfonyl]hexahydro-1H-1,4-diazepine hydrochloride), HA1077 (fasudil hydrochloride), and GSK-429286 (4-[4-(Trifluoromethyl)phenyl]-N-(6-Fluoro-1H-indazol-5-yl)-2-methyl-6-oxo-1,4,5,6-tetrahydro-3-pyridinecarboxamide), each of which is commercially available. Additional small molecule Rho kinase inhibitors (e.g., small molecule Rho-associated protein kinase inhibitors) include those described, for example, in International Patent Application Publication Nos. WO 03/059913, WO 03/064397, WO 05/003101, WO 04/112719, WO 03/062225 and WO 03/062227, and described in U.S. Pat. Nos. 7,217,722 and 7,199,147, and U.S. Patent Application Publication Nos. 2003/0220357, 2006/0241127, 2005/0182040 and 2005/0197328, the contents of all of which are incorporated by reference.

Subsequent Environments

In some embodiments, the cells may be removed from the culture conditions described above after a certain amount of time and placed into a subsequent environment. Any of the components described above may be absent in a subsequent environment. In some embodiments, one or more inhibitors described above is absent in a subsequent environment. For example, one or more of a TGF-beta inhibitor (e.g., a TGF-beta signaling inhibitor), ROCK inhibitor, PAK inhibitor and a myosin II inhibitor (e.g., non-muscle myosin II (NM II) inhibitor) may be absent in a subsequent environment.

A subsequent environment may be an environment that promotes differentiation of the cells. A subsequent environment may be an in vivo environment that is similar or identical to the organ or tissue from which the cells were originally derived (e.g., an autologous implant). A subsequent environment may be an in vitro or ex vivo environment that closely resembles certain biochemical or physiological properties of the organ or tissue from which the cells were originally derived. A subsequent environment may be a synthetic environment such that factors known to promote differentiation in vitro or ex vivo are added to the cell culture. For example, calcium or additional calcium may be added to the cell culture to promote differentiation. In some embodiments, calcium may be added such that the calcium concentration in the cell culture medium is at least about 1 mM to promote differentiation. For example, the calcium concentration in the cell culture medium can be at least about 1 mM, 1.1 mM, 1.2 mM, 1.3 mM, 1.4 mM, 1.5 mM, 1.6 mM, 1.7 mM, 1.8 mM, 1.9 mM or 2.0 mM. In some embodiments, calcium is added to a cell culture such that the calcium concentration in the cell culture medium is about 1.5 mM to promote differentiation.

In some embodiments, cells are placed into a subsequent environment that is specific to stimulate differentiation of cells into the cells of the organ or tissue from which the cells were originally derived. In some embodiments, cells can be seeded onto one side of a permeable membrane. In some embodiments, cells cultured on one side of a permeable membrane can be exposed to air while the cells receive nutrients from the other side of the permeable membrane, and such culture may be referred to as an air-liquid-interface. In some instances, cells develop increasing transmembrane electric resistance (TEER) during air-liquid-interface differentiation. In some embodiments, cells can be seeded in a subsequent environment into or onto a natural or synthetic three-dimensional cell culture surface. A non-limiting example of a three-dimensional surface is a Matrigel®-coated culture surface. In some embodiments, the cells can be embedded in Matrigel® or other hydrogels. Other three dimensional culture environments include surfaces comprising collagen gel and/or a synthetic biopolymeric material in any configuration, such as a hydrogel, for example.

In some embodiments, epithelial cells form tight junctions in culture. Tight junctions generally are parts of cell membranes joined together to form an impermeable or substantially impermeable barrier to fluid. Formation of tight junctions may be visualized, for example, by immunofluorescence staining of tight junction proteins (e.g., ZO-1). In some embodiments, epithelial cells can be induced to form tight junctions in culture. For example, epithelial cells can be induced to form tight junctions when exposed to certain concentrations of calcium. In some embodiments, epithelial cells can be induced to form tight junctions when exposed to calcium concentrations that are about 1 mM or higher. For example, epithelial cells can be induced to form tight junctions when exposed to calcium concentrations that are about 1 mM, 1.1 mM, 1.2 mM, 1.3 mM, 1.4 mM, 1.5 mM, 1.6 mM, 1.7 mM, 1.8 mM, 1.9 mM, 2.0 mM, or higher. In some embodiments, epithelial cells can be induced to form tight junctions when exposed to a calcium concentration of about 1.5 mM.

In some embodiments, epithelial cells form domes or dome-like structures in culture. Domes generally are multicellular hemicyst structures unique to polarized epithelia in culture and can be functionally equivalent to differentiated epithelium with trans-epithelial solute transport. Domes can occur sporadically in small areas during cell confluence, and often mark the initial differentiation process of a functional epithelial monolayer. In certain instances, dome formation may include one or more of expression of tight junction proteins, impermeable substratum formation, and diminished cellular adherence to an underlying support (e.g., as a result of liquid accumulation between the cell layer and the underlying support). Dome formation may occur, for example, during development of transepithelial transport systems for morphologically polarized cells (see e.g., Su et al. (2007) J. Biol. Chem. 282(13):9883-9894). In some embodiments, epithelial cells can be induced to form domes or dome-like structures in culture. For example, epithelial cells can be induced to form domes or dome-like structures when exposed to certain concentrations of calcium. In some embodiments, epithelial cells can be induced to form domes or dome-like structures when exposed to calcium concentrations that are about 1 mM or higher. For example, epithelial cells can be induced to form domes or dome-like structures when exposed to calcium concentrations that are about 1 mM, 1.1 mM, 1.2 mM, 1.3 mM, 1.4 mM, 1.5 mM, 1.6 mM, 1.7 mM, 1.8 mM, 1.9 mM, 2.0 mM, or higher. In some embodiments, epithelial cells can be induced to form domes or dome-like structures when exposed to a calcium concentration of about 1.5 mM.

In some embodiments, the cells are placed into a subsequent environment where TGF-beta signaling is not inhibited. In some embodiments, the cells are placed into a subsequent environment where ROCK is not inhibited. In some embodiments, the cells are placed into a subsequent environment where PAK is not inhibited. In some embodiments, the cells are placed into a subsequent environment where myosin II (e.g., non-muscle myosin II (NM II)) is not inhibited. In some embodiments, the cells are placed into a subsequent environment where TGF-beta signaling and ROCK are not inhibited. In some embodiments, the cells are placed into a subsequent environment where TGF-beta signaling and PAK are not inhibited. In some embodiments, the cells are placed into a subsequent environment where TGF-beta signaling and myosin II (e.g., non-muscle myosin II (NM II)) are not inhibited.

In some embodiments, the cells maintain or regain one or more native functional characteristics after placement into the cell culture environment where TGF-beta signaling is not inhibited. In some embodiments, the cells maintain or regain one or more native functional characteristics after placement into the cell culture environment where ROCK is not inhibited. In some embodiments, the cells maintain or regain one or more native functional characteristics after placement into the cell culture environment where PAK is not inhibited. In some embodiments, the cells maintain or regain one or more native functional characteristics after placement into the cell culture environment where myosin II (e.g., non-muscle myosin II (NM II)) is not inhibited. In some embodiments, the cells maintain or regain one or more native functional characteristics after placement into the cell culture environment where TGF-beta signaling and ROCK are not inhibited. In some embodiments, the cells maintain or regain one or more native functional characteristics after placement into the cell culture environment where TGF-beta signaling and PAK are not inhibited. In some embodiments, the cells maintain or regain one or more native functional characteristics after placement into the cell culture environment where TGF-beta signaling and myosin II (e.g., non-muscle myosin II (NM II)) are not inhibited.

Uses of Expanded Cells

In certain embodiments, an expanded epithelial cell population may be used for certain biomedical and laboratory uses such as, for example, biomolecule production (e.g., protein expression), diagnostics (e.g., identifying abnormal epithelial cells) and/or therapeutics (e.g., screening candidate therapeutic agents; cell therapy (e.g., genetically modified cells for cell therapy)). In some instances, an expanded epithelial cell population may be used for autologous applications (e.g., autologous implant), and in certain instances, an expanded epithelial cell population may be used for non-autologous applications (e.g., drug screening). In some instances, an expanded epithelial cell population may be collected and/or isolated and/or stored (e.g., for a cell bank).

In one example, an expanded epithelial cell population may be used for protein expression, virus/vaccine production, and the like. In some instances, an expanded epithelial cell population can be genetically modified to express a protein of interest (e.g., a therapeutic protein). In some instances, an epithelial cell or group of cells can be genetically modified and then expanded using expansion conditions described herein. Such genetic modification of the cells generally would not be a modification intended to increase cell expansion. Rather, such genetic modification of the cells would be designed to, for example, insert a transgene (e.g., a disease-modifying transgene) that codes for a particular protein. A protein expressed by a transgene may act as a functional version of a missing or a defective protein, or may act as a suppressor or inhibitor of genes or other proteins. Cells expressing a particular protein can then be placed in a subsequent environment, for example, such as an autologous implant into a subject, such that the cells will produce the protein in vivo In another example, an expanded epithelial cell population can be useful for identifying candidate treatments for a subject having a condition marked by the presence of abnormal or diseased epithelial cells. Such conditions may include for example neoplasias, hyperplasias, and malignant tumors or benign tumors. In some instances, abnormal epithelial cells obtained from a subject may be expanded according to any of the expansion conditions described herein to produce an in vitro population of abnormal epithelial cells. For example, circulating tumor cells (CTCs) may be isolated from a subject's circulation, and the expansion conditions herein may be utilized to obtain a sufficient number of cells for further analysis, such as, for example, functional, phenotypic and/or genetic characterization of the cells.

In another example, an expanded epithelial cell population may be useful for identifying one or more candidate treatments for a subject. For example, an expanded epithelial cell population may be assayed for generating a response profile. A response profile typically is a collection of one or more data points that can indicate the likelihood that a particular treatment will produce a desired response, for example in normal or abnormal epithelial cells. A response to a therapeutic agent may include, for example, cell death (e.g., by necrosis, toxicity, apoptosis, and the like), and/or a reduction of growth rate for the cells. Methods to assess a response to a therapeutic agent include, for example, determining a dose response curve, a cell survival curve, a therapeutic index and the like. For example, nasal or trachea epithelial cells may be isolated from a subject carrying mutation(s) in the CFTR gene, and the expansion conditions herein may be utilized to obtain a sufficient number of cells for further analysis, such as, for example, assays for generating a response profile to therapeutic agents such as drugs and/or antibodies.

In another example, an expanded epithelial cell population may be useful for identifying one or more abnormal epithelial cells in a subject. For example, at least one candidate abnormal epithelial cell may be expanded according to any of the expansion conditions described herein. Once the cells have been expanded, for example, a tissue origin profile can be determined (e.g., by assaying mRNA and/or protein expression, histological evaluation, immunohistochemical staining) for the cells to determine the likely tissue of origin. At least one feature of the cells can be compared to the same feature of normal epithelial cells from the same tissue of origin. Cell features that may be compared include, for example, cell growth characteristics, colony formation, proteomic profiles, metabolic profiles and genomic profiles. A detected difference in the candidate abnormal epithelial cells and the normal epithelial cells may indicate that the candidate abnormal epithelial cells are abnormal compared to normal epithelial cells.

In another example, an expanded epithelial cell population may be useful for monitoring the progression of a disease or treatment of a disease in a subject. Monitoring the progression of a disease generally means periodically checking an abnormal condition in a subject to determine if an abnormal condition is progressing (worsening), regressing (improving), or remaining static (no detectable change). Expanded epithelial cells from a subject may be assayed for various markers of progression or regression. Monitoring the progression of a disease also may include monitoring the efficacy of one or more treatments.

EXAMPLES

The examples set forth below illustrate certain embodiments and do not limit the technology.

Example 1: Materials and Methods

The materials and methods set forth in this Example were used to perform cell culture and other assays described in Examples 2 to 9, except where otherwise noted.

Cell Culture and Determination of Population Doublings

Epithelial cells (prostate epithelial cells and bronchial epithelial cells) were plated at 3,000-10,000 viable cells/cm$^2$ in tissue culture vessels, using culture medium as indicated in Examples 2 to 5 and FIGS. 1 to 17, and incubated at 37° C. with 5% $CO_2$. The medium was changed every 2 or 3 days. Cells were sub-cultured using standard trypsinization method when they were about 70-90% confluent. Total cell number was determined using the Countess II Automated Cell Counter (Life Technologies, AMQAX1000) following manufacturer's instructions.

Cells and media used for these assays included: PrEC Prostate Epithelial Cells (Lonza CC-2555); Normal human bronchial epithelial cells (Lonza CC-2540); LNCap Clone FGC Cell Line (Sigma-Aldrich, D-073); PrEGM BulletKit containing PrEBM Basal Medium and PrEGM SingleQuot Kit Supplements & Growth Factors (Lonza CC-3166); and Keratinocyte-SFM (Gibco/Thermo-Fisher 17005-042) supplied with prequalified human recombinant Epidermal Growth Factor 1-53 (EGF 1-53, used at 0.2 ng/mL) and Bovine Pituitary Extract (BPE, used at 30 μg/mL). Cell culture materials included Corning® BioCoat™ Cellware, Collagen Type 1, T-25 flask (Corning, 356484).

A formula used for the calculation of population doublings (PD) is presented in Equation A:

$$n = 3.32 * (\log Y - \log I) + X \quad \text{Equation A}$$

where n=the final PD number at end of a given subculture, Y=the cell yield at the time of harvesting, I=the cell number used as inoculum to begin that subculture, and X=the doubling level of the inoculum used to initiate the subculture being quantitated.

Stocks of certain chemicals used in the study were prepared by dissolving in DMSO to 10 mM. The chemical stocks were added to culture media to desired final concentrations, as described in Examples 2 to 5 and shown in FIGS. 1 to 17, from the time when cell culture was initiated. Certain compounds used are listed in Table 1 below.

TABLE 1

Listing of compounds

| Chemical Name | Target | Supplier Cat # | Concentrations used |
|---|---|---|---|
| A 83-01 | TGF-beta RI, ALK4 and ALK7 | Sigma-Aldrich, SML0788; Tocris 2939 | 0.1-10 μM |
| SB 431542 | TGF-beta RI, ALK4 and ALK7 | Tocris 1614 | 0.1-5 μM |
| RepSox | TGF-beta RI, ALK4 and ALK7 | Tocris 3742 | 0.1-5 μM |

TABLE 1-continued

Listing of compounds

| Chemical Name | Target | Supplier Cat # | Concentrations used |
|---|---|---|---|
| GW 788388 | TGF-beta RI, ALK4 and ALK7 | Tocris 3264 | 0.1-5 µM |
| Y-27632 | Rho-kinase (Rho-associated protein kinase, ROCK) | Enzo Life Sciences, ALX-270-333-M025 | 0.1-10 µM |
| SR 3677 dihydrochloride | Rho-kinase (Rho-associated protein kinase, ROCK) | Tocris 3667 | 0.1-5 µM |
| GSK 429286 | Rho-kinase (Rho-associated protein kinase, ROCK) | Tocris 3726 | 0.1-5 µM |
| Thiazovivin | Rho-kinase (Rho-associated protein kinase, ROCK) | Tocris 3845 | 0.1-5 µM |
| IPA-3 | Group I p21-activated kinase (PAK) | Tocris 3622 | 0.1-5 µM |
| Blebbistatin | myosin II ATPase (i.e., non-muscle myosin II (NMII) ATPase) | Tocris 1760 | 0.1-5 µM |
| Isoproterenol | β-adrenoceptor agonist | Sigma-Aldrich 15627 | 0.1-5 µM |

Quantitative RT-PCR

Total RNA was prepared using TRzol® Plus RNA Purification Kit (Life Technologies, 12183-555) and PureLink® RNA Mini Kit (Life Technologies, 12183018A), following the manufacturer's instructions. One hundred nanogram total RNA was used for the determination of human telomerase reverse transcriptase (hTERT) expression using the TaqMan RNA-to-CT™ 1-Step Kit (Life Technologies, 4392938), following the protocol provided by the supplier. hTERT primers and Taqman probe used were as follows: forward primer, 5'-TGACACCTCACCTCACCCAC-3' (SEQ ID NO:1), reverse primer, 5'-CACTGTCTTCCGCAAGTTCAC-3' (SEQ ID NO:2) and Taqman probe, 5'-ACCCTGGTCCGAGGTGTCCCT-GAG-3' (SEQ ID NO:3).

Example 2: Growth of Epithelial Cells in Conventional Cell Culture Medium (i.e., Control Culture Conditions)

In this example, prostate epithelial cells (PrEC) and bronchial epithelial cells (HBEC) were grown in conventional cell culture medium (i.e., control culture conditions) to demonstrate certain properties of epithelial cell growth in vitro and/or ex vivo.

Prostate epithelial cells (PrEC) were cultured in one of two types of regular culture media generally used for culturing prostate epithelial cells: 1) Prostate Epithelial Cell Growth Medium (PrEGM BulletKit containing PrEBM Basal Medium and PrEGM SingleQuot Kit Supplements & Growth Factors (Lonza CC-3166)), or 2) KSFM (Keratinocyte-SFM (Gibco/Thermo-Fisher 17005-042) supplied with prequalified human recombinant Epidermal Growth Factor 1-53 (EGF 1-53, used at 0.2 ng/mL) and Bovine Pituitary Extract (BPE, used at 30 µg/mL)). Population doublings of the cells in each passage were calculated, and total population doublings were plotted against number of days of culture (FIG. 1, top panel). In both media types, prostate epithelial cells showed limited cell replication of only 10 to 20 population doublings before entering senescence. Prostate epithelial cells cultured in KSFM exhibited morphology characteristic of cell senescence at population doubling 18 (PD 18; FIG. 1, bottom panel).

Figure 2:
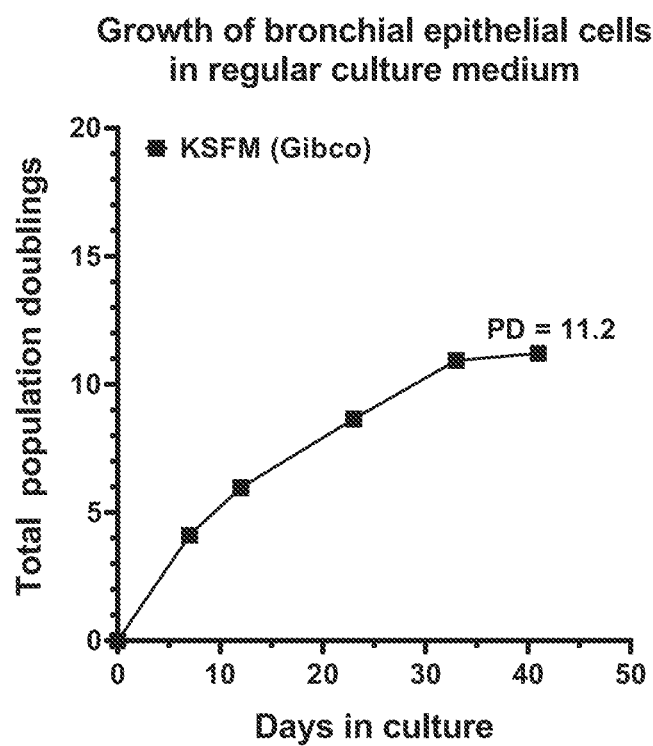
FIG. 2 shows growth of bronchial epithelial cells in regular culture medium (i.e., control culture conditions). KSFM, Keratinocyte-SFM (Gibco/Thermo Fisher). PrEGM, Prostate Epithelial Cell Growth Medium (Lonza). PD, population doublings.
Figure 2:
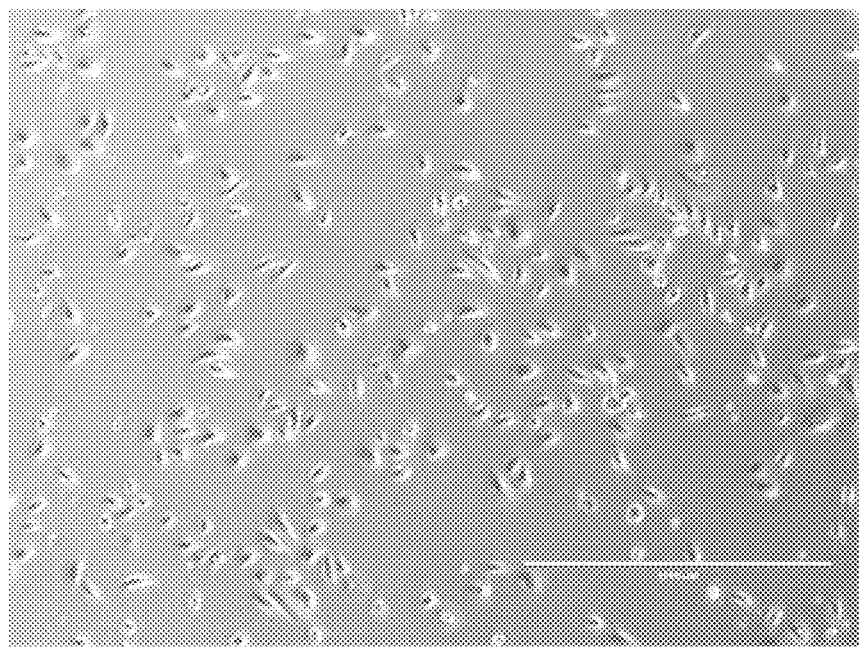

Bronchial epithelial cells (HBEC) were cultured in KSFM. Population doublings of the cells in each passage were calculated, and total population doublings were plotted against number of days of culture (FIG. 2, top panel). The bronchial epithelial cells showed active replication for only 11 population doublings before entering cell senescence. Bronchial epithelial cells cultured in KSFM exhibited characteristic morphology of cell senescence at population doubling 11 (PD 11; FIG. 2, bottom panel).

Figure 3A:
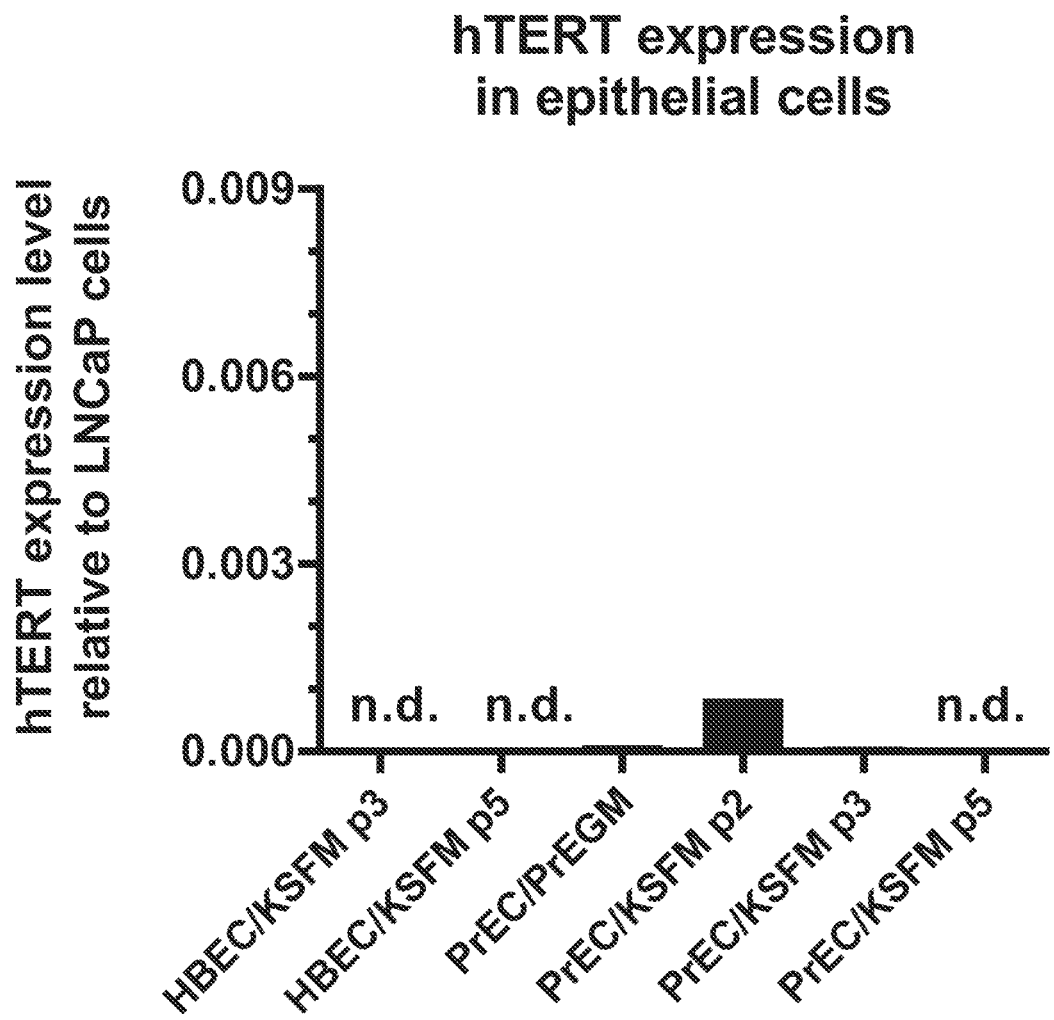
FIG. 3A and FIG. 3B show hTERT expression in epithelial cells. HBEC, human bronchial epithelial cells. hTERT, human telomerase reverse transcriptase gene. KSFM, Keratinocyte-SFM (Gibco/Thermo Fisher). LNCaP, human prostate cancer cell line LNCaP Clone FGC (Sigma-Aldrich). PrEC, prostate epithelial cells. PrEGM, Prostate Epithelial Cell Growth Medium (Lonza). n.d., non-detected. p, passage.
Figure 3B:
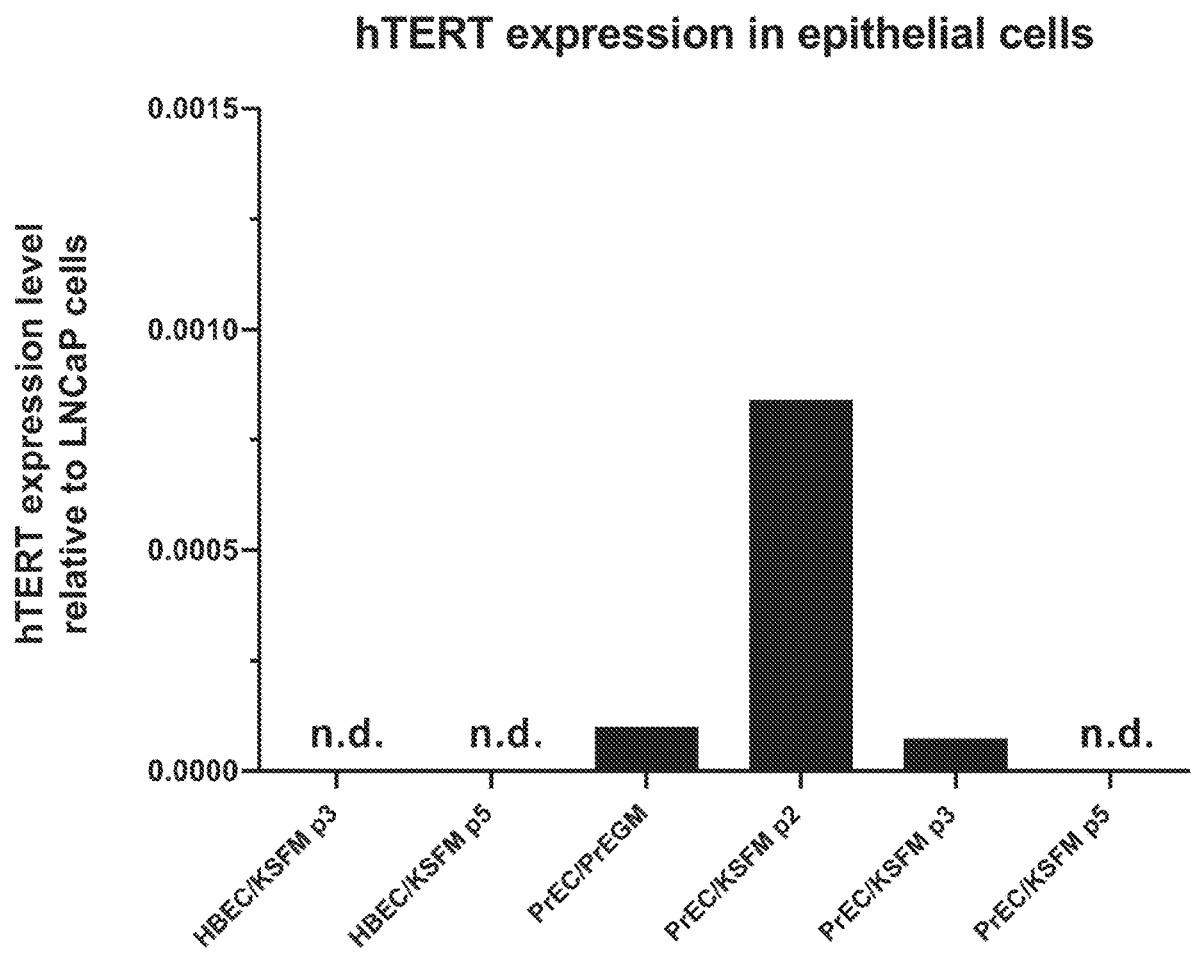

Expression of human telomerase reverse transcriptase (hTERT) gene was examined by quantitative real-time PCR in bronchial epithelial cells and prostate epithelial cells at different passages. The ends of chromosomes are composed of repeated segments of DNA structures called telomeres, which protect chromosomes from abnormally sticking together or breaking down (degrading). In normal epithelial cells, telomeres typically become progressively shorter as the cell divides due to the lack of expression of telomerase reverse transcriptase (TERT). Telomerase is generally active in stem cells and abnormally active in most cancer cells, which grow and divide without limitation. The level of hTERT expression was compared to LNCaP cells, a human prostate cancer cell line (Sigma-Aldrich, D-073), which was used as positive control for hTERT expression. The bronchial epithelial cells did not express hTERT at either early (p3) or late (p5) passages. The prostate epithelial cells at early passage (p2) expressed extremely low level of hTERT, which quickly diminished at passage 3 and become non-detected by passage 5 (FIG. 3A and FIG. 3B). These findings confirmed that both PrEC and HBEC are normal epithelial cells.

Figure 4:
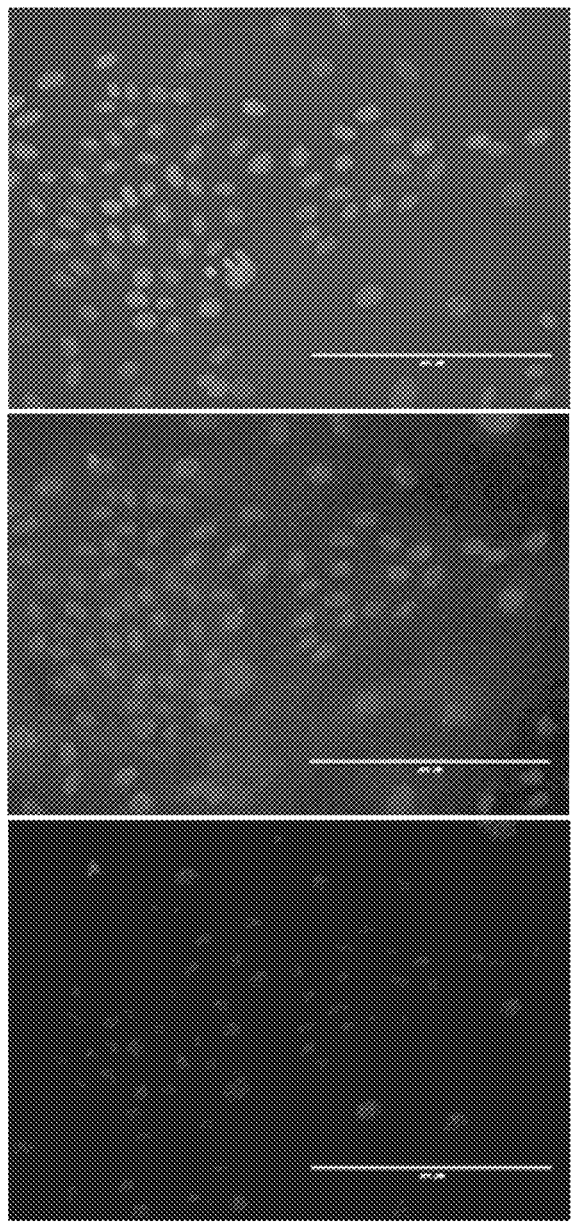
FIG. 4 shows a lack of epithelial stem cell marker LGR5 expression in epithelial cells. Polyclonal Lgr5 antibody (LifeSpan, LS-A1235) was used at 1:50 dilution. Monoclonal TP63 antibody (Santa Cruz, sc-25268) was used at 1:50 dilution. DAPI, DNA fluorescence stain 4',6-diamidino-2-phenylindole.

Expression of certain cell markers was examined in cultured prostate epithelial cells. These cells did not express an epithelial stem cell marker, Lgr5, as examined by immunofluorescence staining (FIG. 4, bottom panel). Instead, all cells stained positive for TP63 expression (FIG. 4, middle panel). The TP63 gene, a transcription factor, is a marker of basal epithelial cells and generally is required for normal function of epithelial tissues. Cell nuclei were visualized using DAPI staining (FIG. 4, top panel). Polyclonal Lgr5 antibody (Anti-GPR49/LGR5 Antibody, LifeSpan Biosciences, LS-A1235) was used at 1:50 dilution. Monoclonal anti-TP63 antibody (Santa Cruz Biotechnology, sc-25268) was used at 1:50 dilution.

The experiments above therefore demonstrated that epithelial cells cultured in conventional cell culture media (i.e., control culture conditions) had limited proliferation capacity in vitro and/or ex vivo, extremely low or undetected expression of the telomerase reverse transcriptase gene, and did not express protein markers typical of epithelial stem cells (i.e., did not express the epithelial stem cell marker LGR5).

Example 3: Human Telomerase Reverse Transcriptase (hTERT) Expression in the Presence of an ALK5 Inhibitor In this example, hTERT expression in epithelial cells was assessed in the presence of an ALK5 inhibitor, a Rho kinase inhibitor (i.e., a Rho-associated protein kinase inhibitor), or both. Expression of hTERT gene was examined by quantitative real-time PCR in bronchial epithelial cells and prostate epithelial cells. The cells were treated with an ALK5 inhibitor, A83-01, or a Rho kinase inhibitor (i.e., a Rho-associated protein kinase inhibitor), Y-27632, or both inhibitors, at different passages in KSFM. A83-01 quickly induced and sustained hTERT expression in epithelial cells as described below.

Figure 5A:
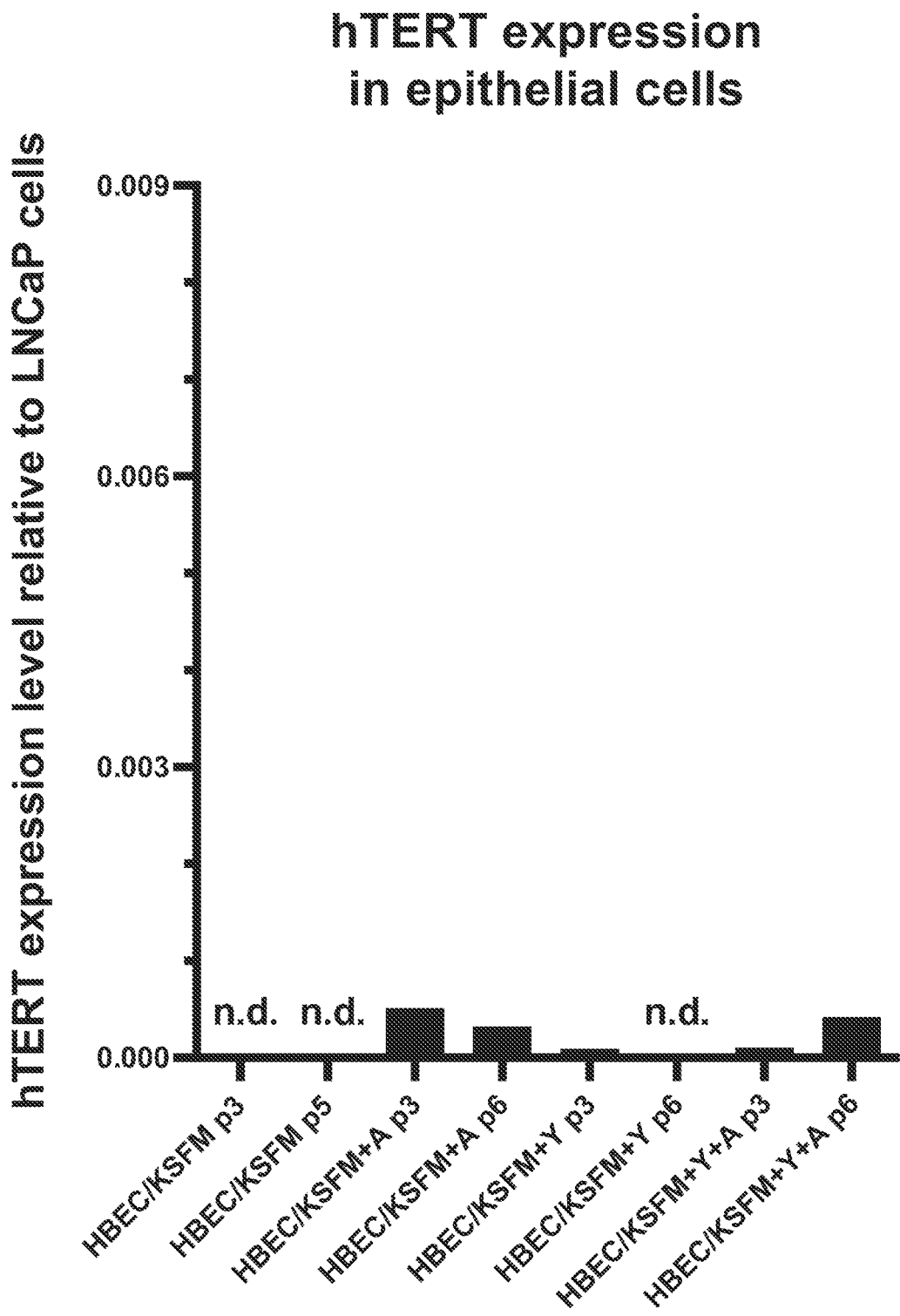
FIG. 5A and FIG. 5B show hTERT expression in bronchial epithelial cells. HBEC, human bronchial epithelial cells. hTERT, human telomerase reverse transcriptase gene. KSFM, Keratinocyte-SFM (Gibco/Thermo Fisher). LNCaP, human prostate cancer cell line LNCaP Clone FGC (Sigma-Aldrich). A, ALK5 inhibitor A83-01. Y, Rho kinase inhibitor (i.e., Rho-associated protein kinase inhibitor) Y-27632. n.d., non-detected. p, passage.
Figure 5B:
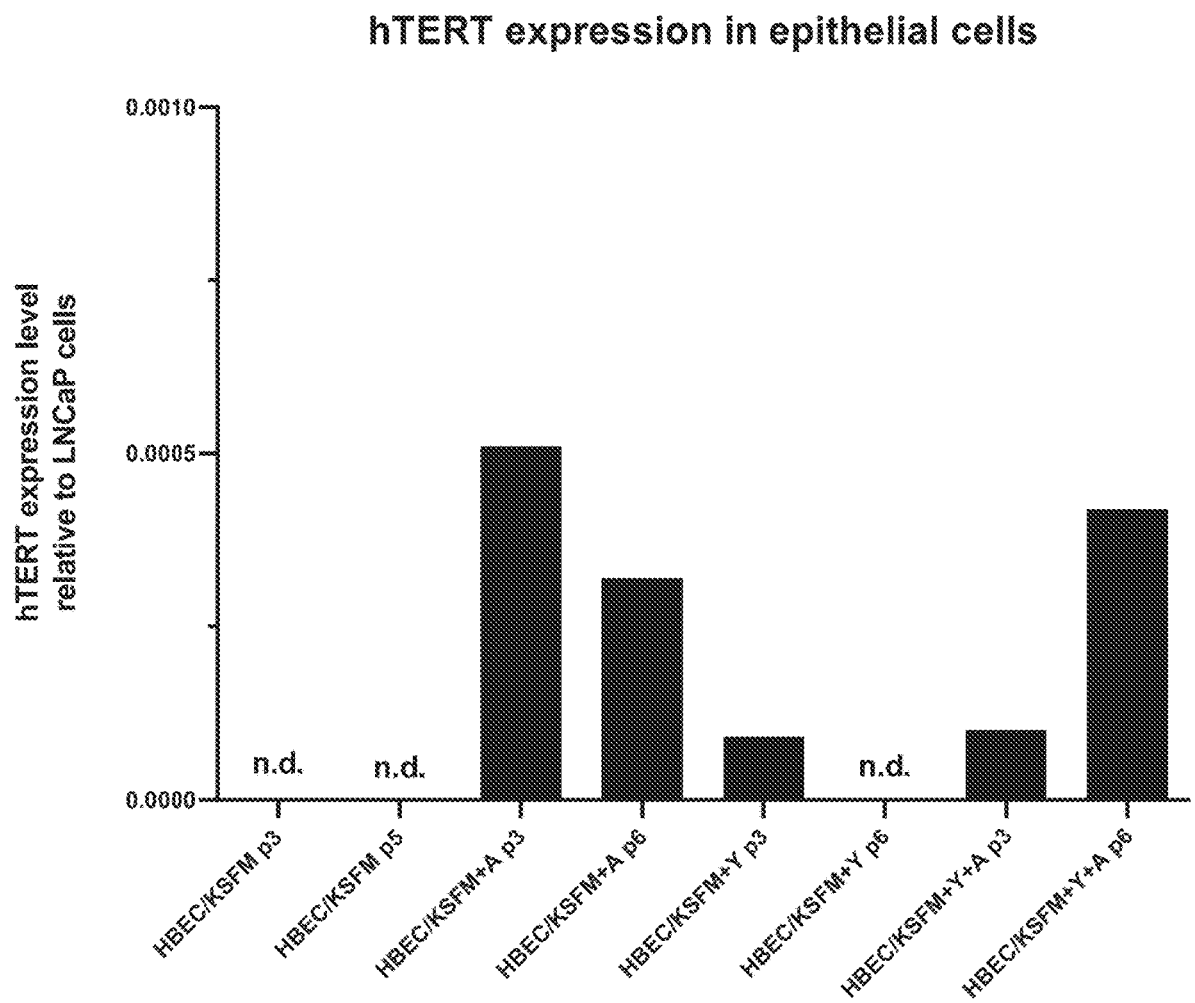

As shown in FIG. 5A and FIG. 5B, bronchial epithelial cells did not express hTERT at both early (p3) and late (p5) passages in KSFM. ALK5 inhibitor A83-01 robustly induced hTERT expression in bronchial epithelial cells at early passage (p3), and sustained measurable hTERT expression at late passage (p6). Rho kinase inhibitor (i.e., Rho-associated protein kinase inhibitor) Y-27632 slightly induced hTERT expression in bronchial epithelial cells at early passage (p3); however, it became non-detectable at late passage (p6). In the presence of both A83-01 and Y-27632, hTERT expression was induced and sustained at late passage (p6) in bronchial epithelial cells.

Figure 6A:
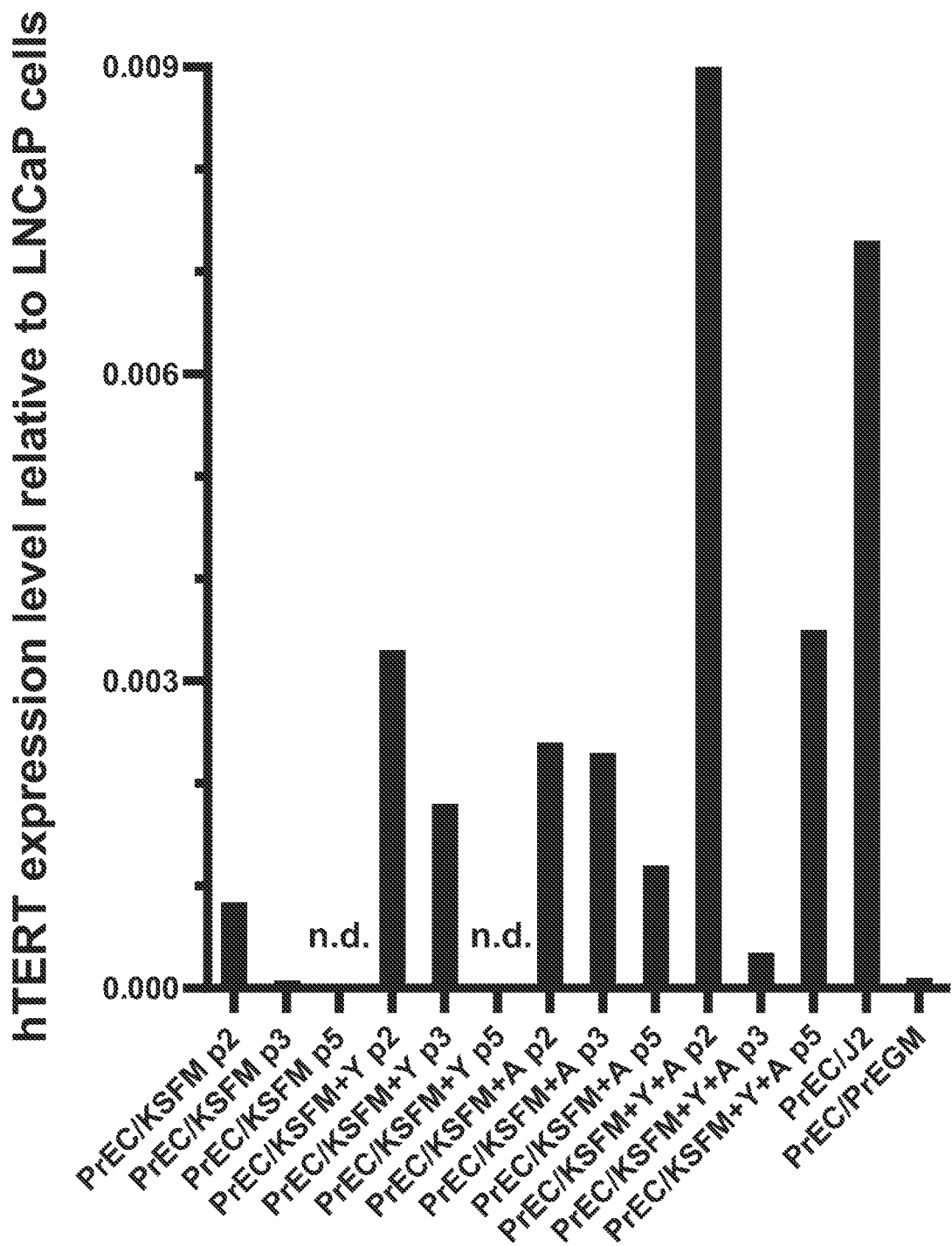
FIG. 6A and FIG. 6B show hTERT expression in prostate epithelial cells. PrEC, prostate epithelial cells. hTERT, human telomerase reverse transcriptase gene. KSFM, Keratinocyte-SFM (Gibco/Thermo Fisher). PrEGM, Prostate Epithelial Cell Growth Medium (Lonza). LNCaP, human prostate cancer cell line LNCaP Clone FGC (Sigma-Aldrich). J2, 3T3-J2 feeder cells. A, ALK5 inhibitor A83-01. Y, Rho kinase inhibitor (i.e., Rho-associated protein kinase inhibitor) Y-27632. n.d., non-detected. p, passage.
Figure 6B:
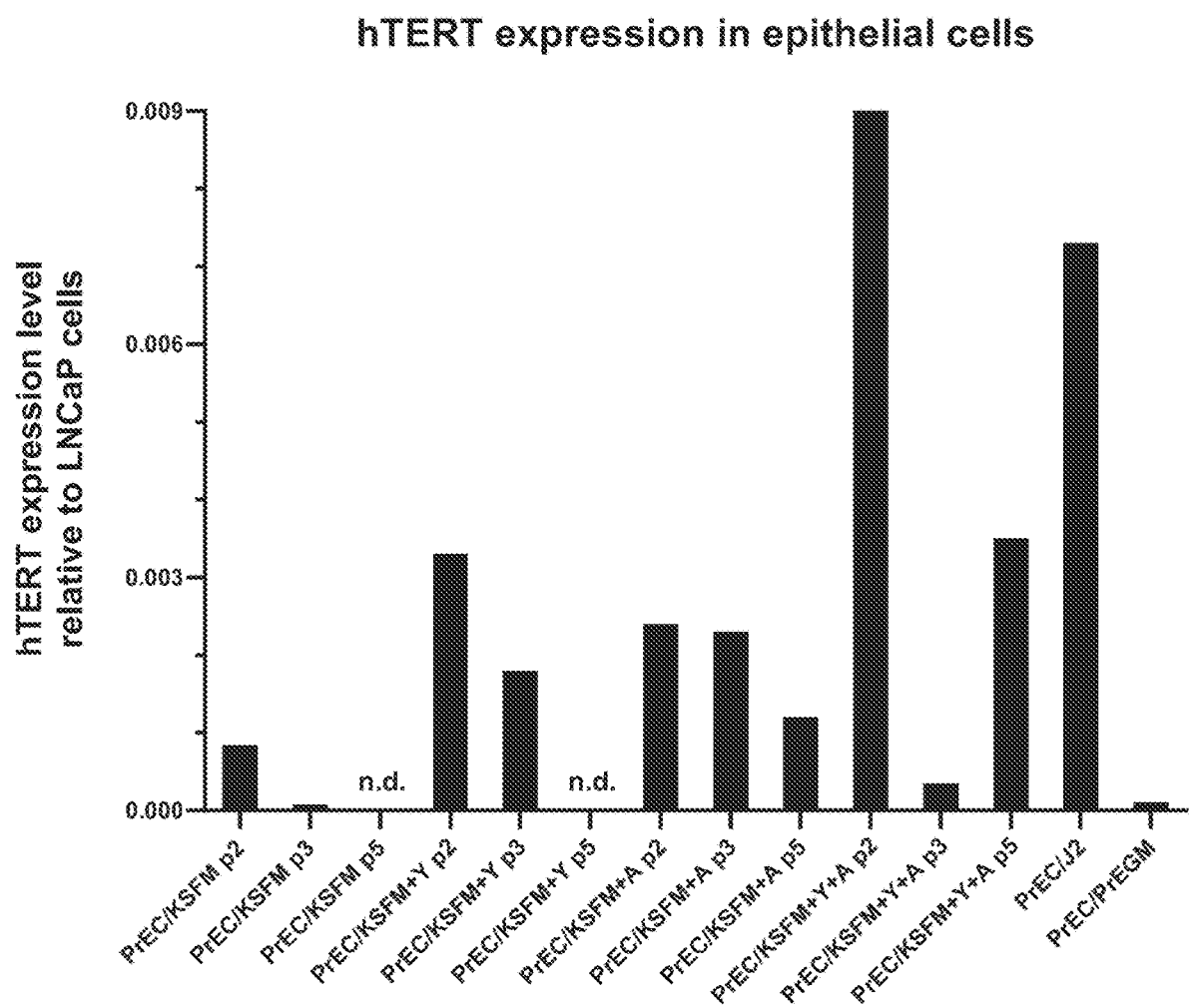

As shown in FIG. 6A and FIG. 6B, prostate epithelial cells at early passage (p2) expressed low level of hTERT, which quickly diminished at passage 3 and became non-detectable by passage 5. ALK5 inhibitor A83-01 quickly induced hTERT expression in prostate epithelial cells at early passage (p2), and sustained measurable hTERT expression at late passage (p5). Rho kinase inhibitor (i.e., Rho-associated protein kinase inhibitor) Y-27632 induced hTERT expression in prostate epithelial cells at early passage (p2); however, it became non-detectable at late passage (p5). In the presence of both A83-10 and Y-27632, hTERT expression was induced significantly in early passage (p2) prostate epithelial cells and sustained at high level even at late passage (p5). This level of hTERT expression was comparable to the level of hTERT expression in prostate epithelial cells co-cultured with 3T3-J2 feeder cells (J2).

Example 4: Epithelial Cell Plating Efficiency

In this example, epithelial cell plating efficiency, i.e., number of cells that efficiently attach to the cell culture surfaces, continue to divide and grow into colonies, was examined under various conditions.

Figure 7:
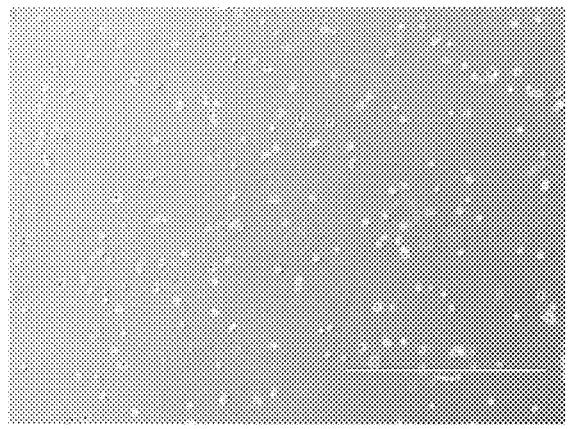
FIG. 7 shows plating efficiency of prostate epithelial cells on regular tissue culture surface in KSFM in the presence of ALK5 inhibitor A83-01. PrEC, prostate epithelial cells. KSFM, Keratinocyte-SFM (Gibco/Thermo Fisher). A, ALK5 inhibitor A83-01.
Figure 7:
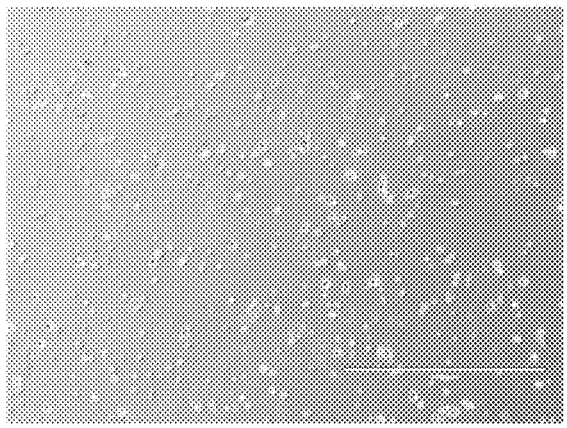
Figure 7:
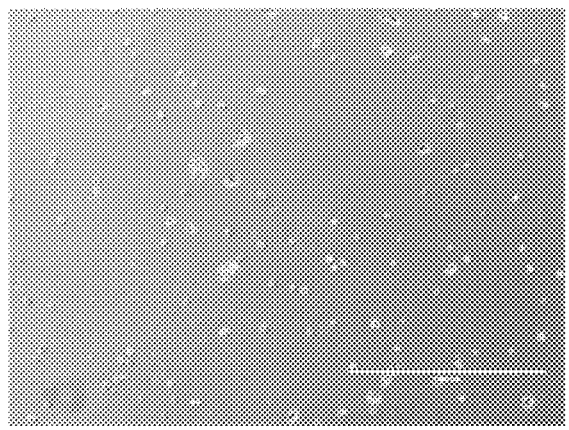
Figure 7:
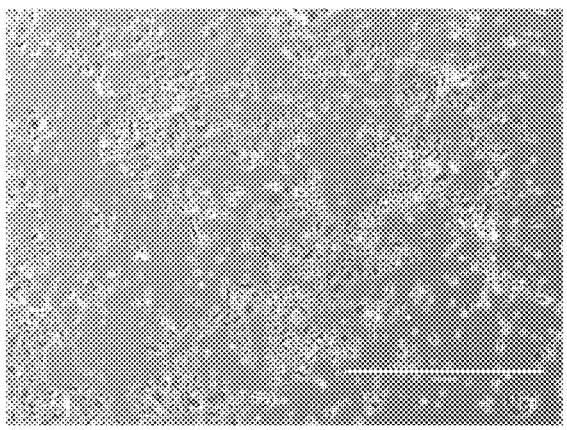

As shown in FIG. 7, ALK5 inhibitor A83-01 interfered with prostate epithelial cell plating efficiency on regular tissue culture surface (i.e., uncoated) in KSFM. In the presence of ALK5 inhibitor A83-01, most prostate epithelial cells failed to attach to the regular tissue culture surface even after 3 days. However, those few cells that did attach continued to proliferate. By day 8, when the cells were passaged, most cells exhibited characteristic morphology of actively dividing cells.

Figure 8:
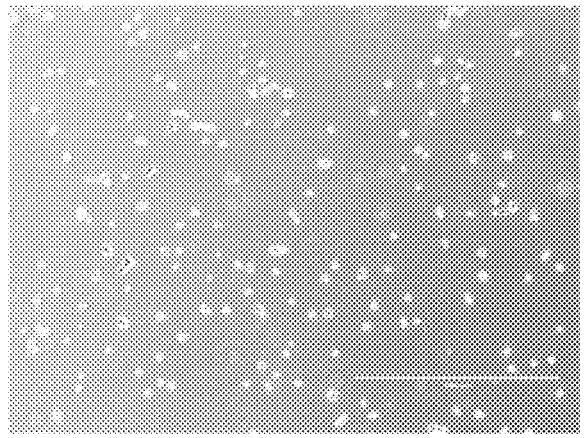
FIG. 8 shows plating efficiency of bronchial epithelial cells on regular tissue culture surface in KSFM in the presence of ALK5 inhibitor A83-01. HBEC, human bronchial epithelial cells. KSFM, Keratinocyte-SFM (Gibco/Thermo Fisher). A, ALK5 inhibitor A83-01.
Figure 8:
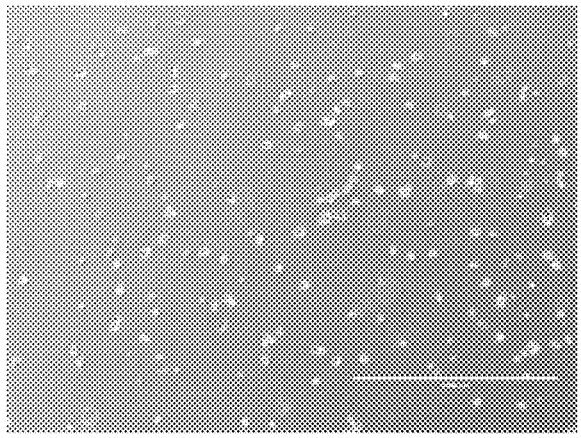
Figure 8:
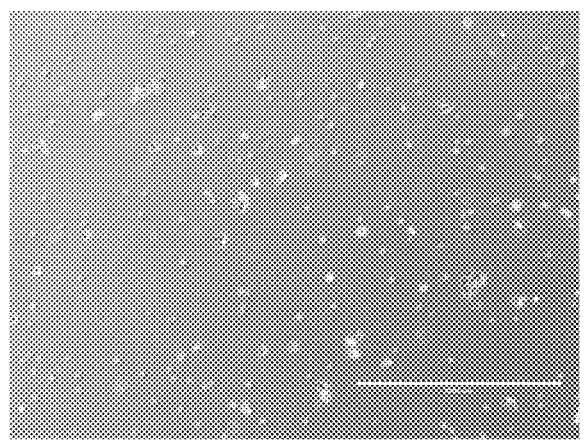
Figure 8:
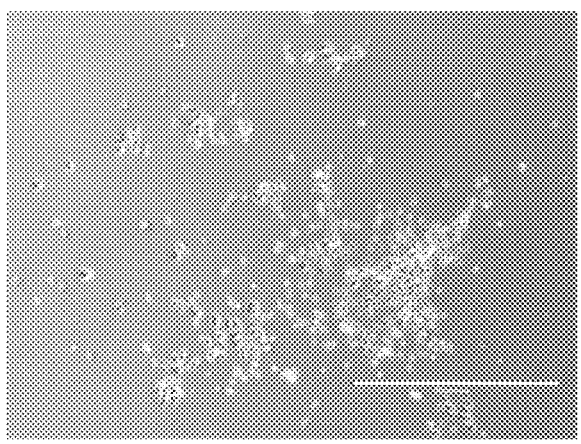

As shown in FIG. 8, ALK5 inhibitor A83-01 interfered with bronchial epithelial cell plating efficiency on regular tissue culture surface (i.e., uncoated) in KSFM. In the presence of ALK5 inhibitor A83-01, most bronchial epithelial cells failed to attach to the regular tissue culture surface even after 3 days. However, those few cells that did attach continued to proliferate. Most cells exhibited characteristic morphology of actively dividing cells at day 7.

Figure 9:
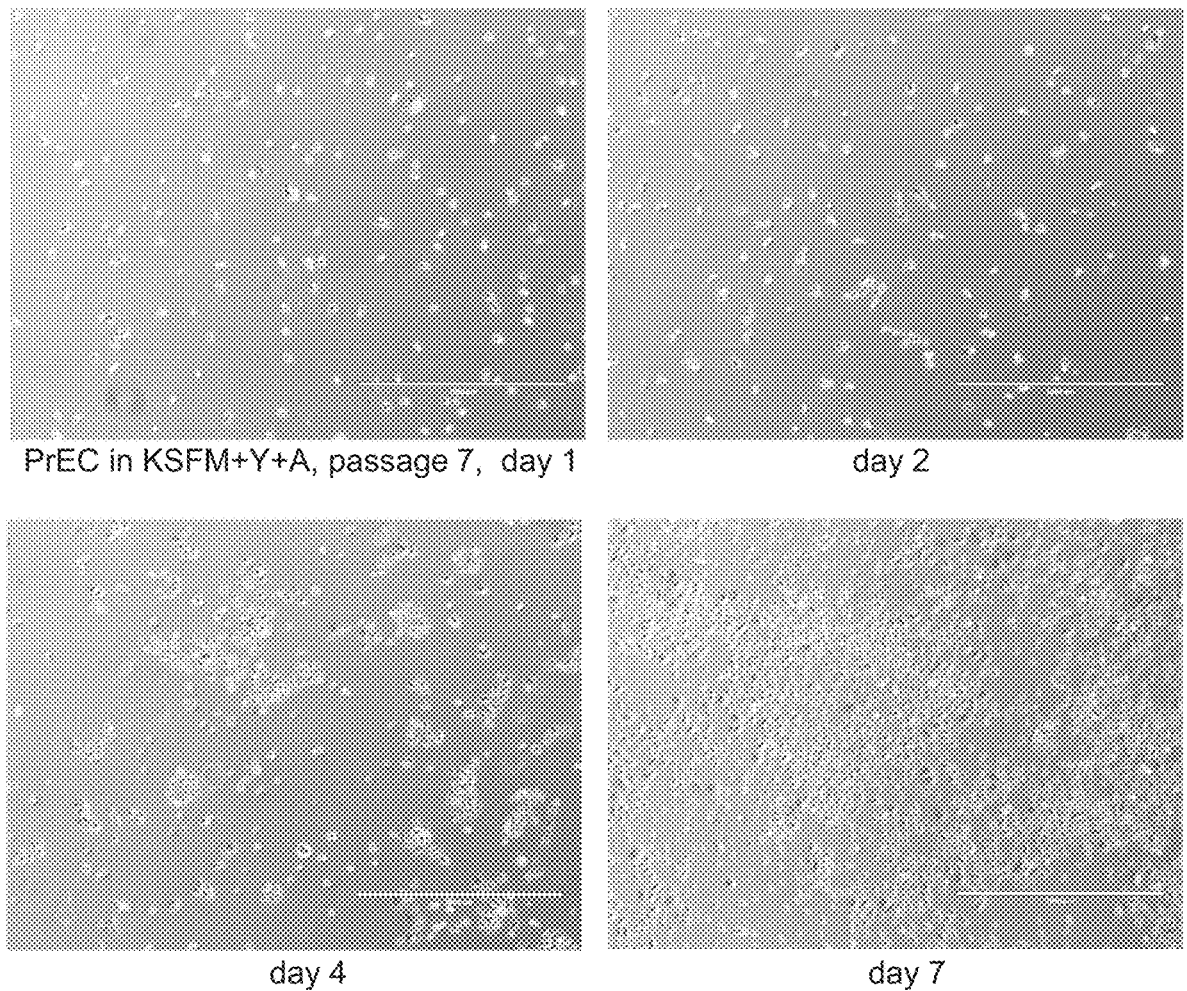
FIG. 9 shows plating efficiency of prostate epithelial cells on regular tissue culture surface in KSFM in the presence of ALK5 inhibitor A83-01 and Rho kinase inhibitor (i.e., Rho-associated protein kinase inhibitor) Y-27632. PrEC, prostate epithelial cells. KSFM, Keratinocyte-SFM (Gibco/Thermo Fisher). A, ALK5 inhibitor A83-01. Y, Rho kinase inhibitor (i.e., Rho-associated protein kinase inhibitor) Y-27632.

As shown in FIG. 9, Rho kinase inhibitor (i.e., Rho-associated protein kinase inhibitor) Y-27632 ameliorated the low plating efficiency of prostate epithelial cells caused by A83-01 in KSFM. Many prostate epithelial cells attached to regular tissue culture surface in the presence of both A83-01 and Y-27632 at day 2 after plating. The cells continued to proliferate and most cells exhibited characteristic morphology of actively dividing cells at day 7.

Figure 10:
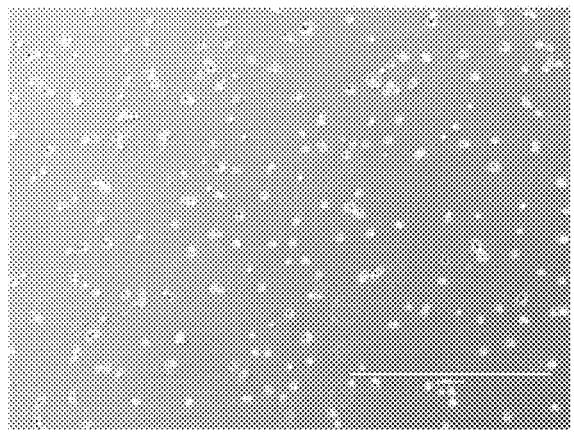
FIG. 10 shows plating efficiency of bronchial epithelial cells on regular tissue culture surface in KSFM in the presence of ALK5 inhibitor A83-01 and Rho kinase inhibitor (i.e., Rho-associated protein kinase inhibitor) Y-27632. HBEC, human bronchial epithelial cells. KSFM, Keratinocyte-SFM (Gibco/Thermo Fisher). A, ALK5 inhibitor A83-01. Y, Rho kinase inhibitor (i.e., Rho-associated protein kinase inhibitor) Y-27632.
Figure 10:
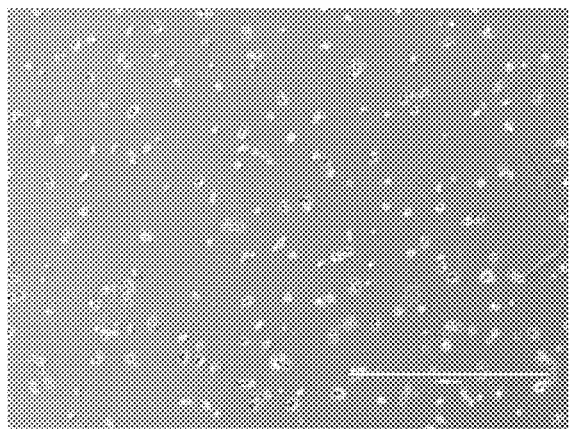
Figure 10:
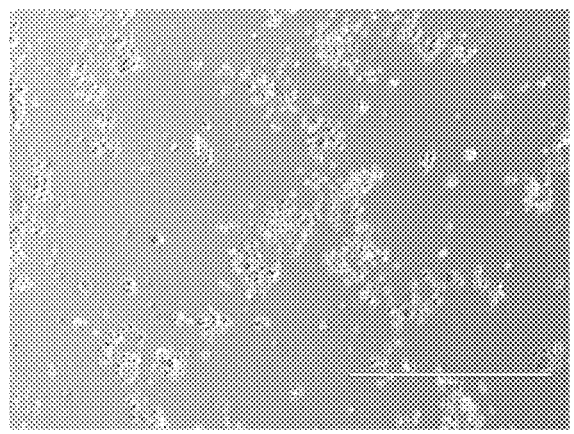
Figure 10:
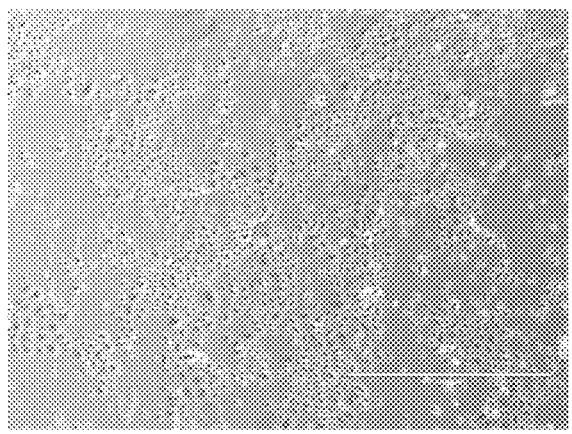

As shown in FIG. 10, Rho kinase inhibitor (i.e., Rho-associated protein kinase inhibitor) Y-27632 ameliorated the low plating efficiency of bronchial epithelial cells caused by A83-01 in KSFM. Many bronchial epithelial cells attached to regular tissue culture surface in the presence of both A83-01 and Y-27632 at day 2 after plating. The cells continued to proliferate and most cells exhibited characteristic morphology of actively dividing cells at day 7.

Figure 11:
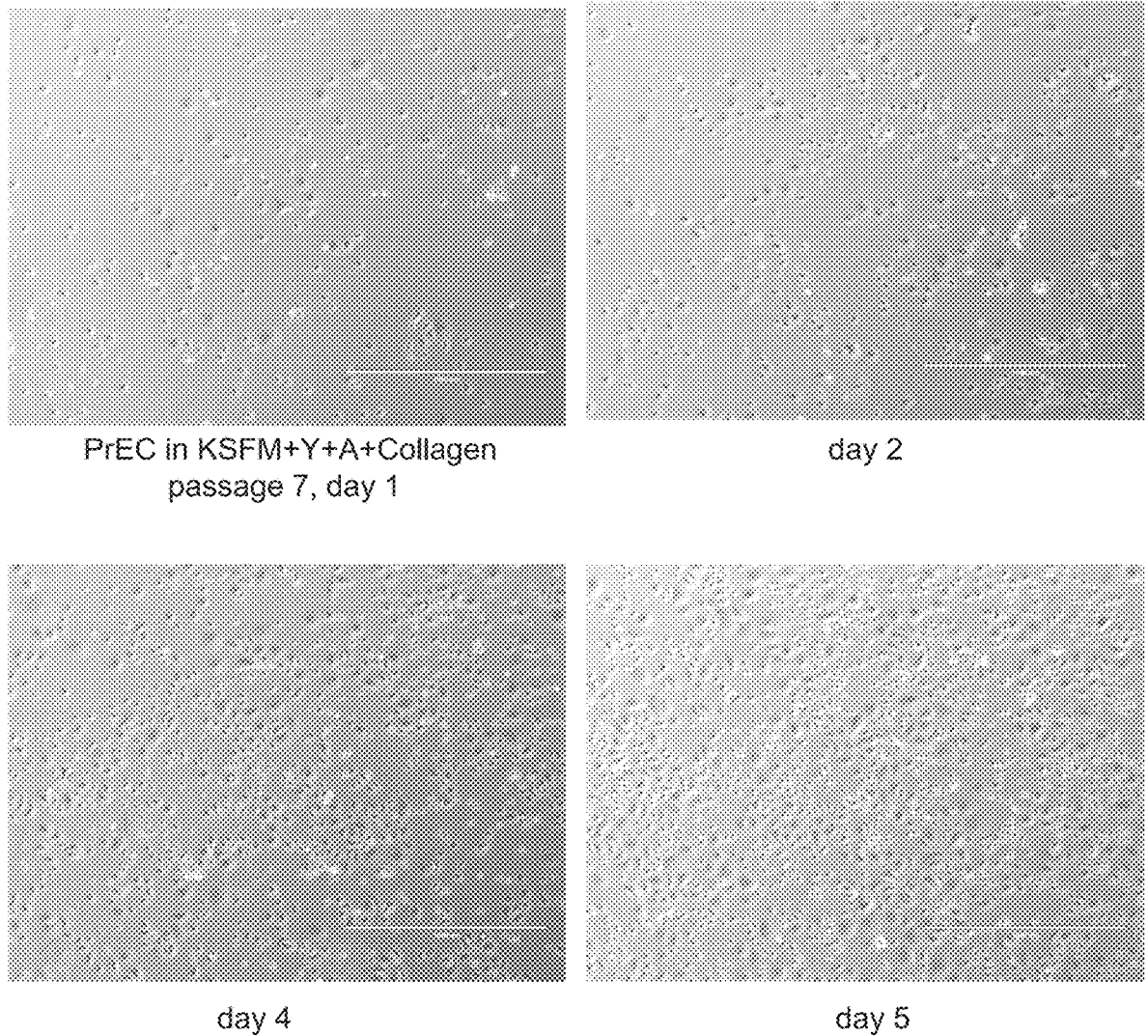
FIG. 11 shows plating efficiency of prostate epithelial cells on collagen I-coated tissue culture surface in KSFM in the presence of ALK5 inhibitor A83-01 and Rho kinase inhibitor (i.e., Rho-associated protein kinase inhibitor) Y-27632. PrEC, prostate epithelial cells. KSFM, Keratinocyte-SFM (Gibco/Thermo Fisher). A, ALK5 inhibitor A83-01. Y, Rho kinase inhibitor (i.e., Rho-associated protein kinase inhibitor) Y-27632.

As shown in FIG. 11, use of collagen I-coated tissue culture surface dramatically increased the plating efficiency of prostate epithelial cells in the presence of A83-01 and Y-27632 in KSFM. Most cells efficiently attached to the surface at day 1 after plating, and proliferated quickly. By day 5, when the cells were passaged, most cells exhibited characteristic morphology of actively dividing cells.

Figure 12:
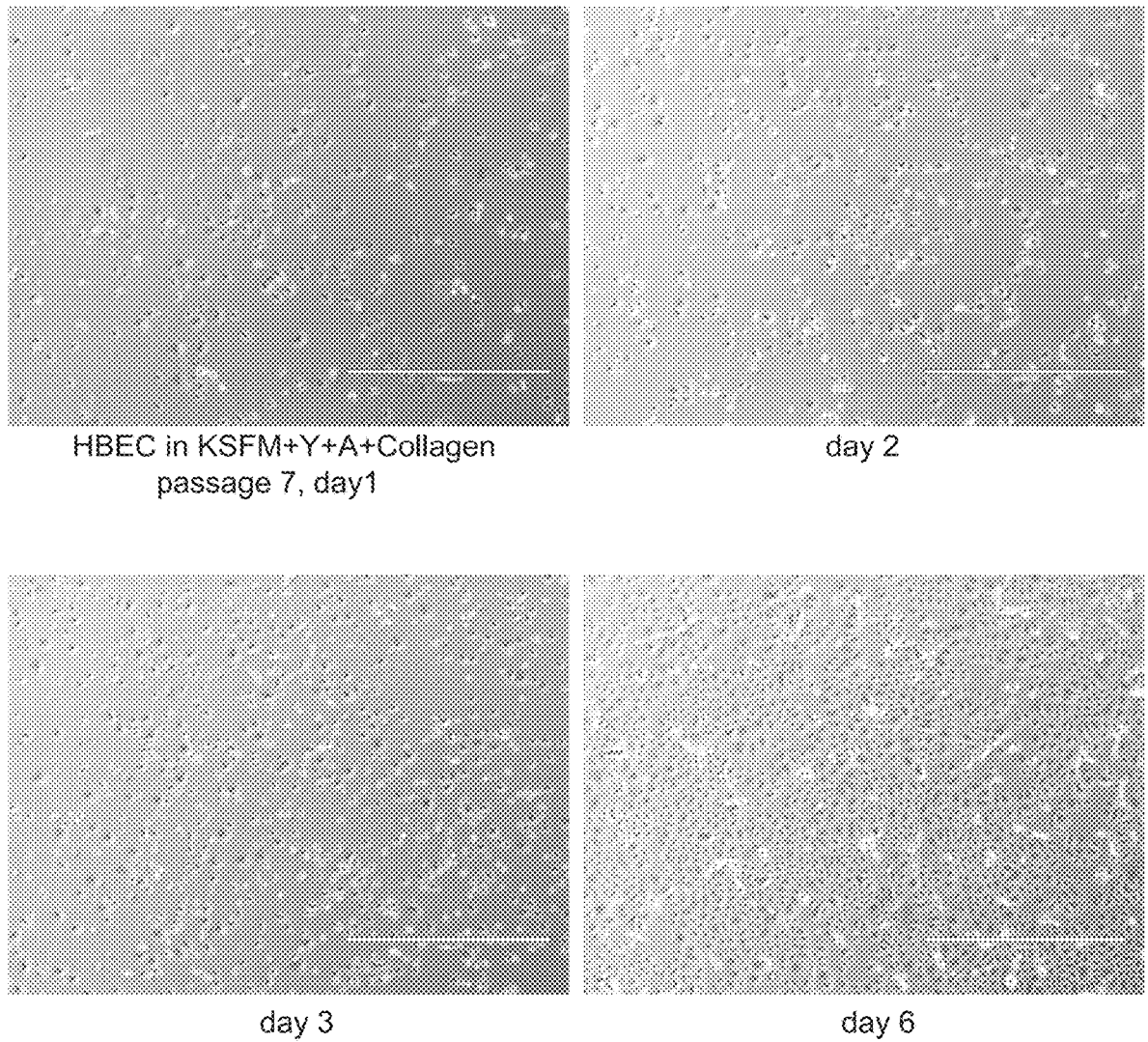
FIG. 12 shows plating efficiency of bronchial epithelial cells on collagen I-coated tissue culture surface in KSFM in the presence of ALK5 inhibitor A83-01 and Rho kinase inhibitor (i.e., Rho-associated protein kinase inhibitor) Y-27632. HBEC, human bronchial epithelial cells. KSFM, Keratinocyte-SFM (Gibco/Thermo Fisher). A, ALK5 inhibitor A83-01. Y, Rho kinase inhibitor (i.e., Rho-associated protein kinase inhibitor) Y-27632.

As shown in FIG. 12, use of collagen I-coated tissue culture surface dramatically increased the plating efficiency of bronchial epithelial cells in the presence of A83-01 and Y-27632 in KSFM. Most cells efficiently attached to the surface at day 1 after plating, and proliferated quickly. By day 6, when the cells were passaged, most cells exhibited characteristic morphology of actively dividing cells.

Example 5: The Effects of Compounds Including ALK5 Inhibitors, Rho Kinase Inhibitors, and Other Compounds on Epithelial Cell Proliferation In this example, proliferation of prostate and bronchial epithelial cells was assessed in the presence of compounds including ALK5 inhibitors, Rho kinase inhibitors (i.e., Rho-associated protein kinase inhibitors), and other compounds.

Figure 13:
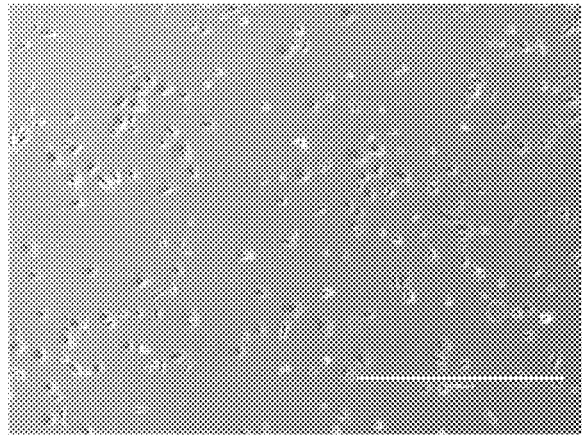
FIG. 13 shows cell senescence of late passage prostate epithelial cells and bronchial epithelial cells in KSFM in the presence of Rho kinase inhibitor (i.e., Rho-associated protein kinase inhibitor) Y-27632. PrEC, prostate epithelial cells. HBEC, human bronchial epithelial cells. KSFM, Keratinocyte-SFM (Gibco/Thermo Fisher). Y, Rho kinase inhibitor (i.e., Rho-associated protein kinase inhibitor) Y-27632.
Figure 13:
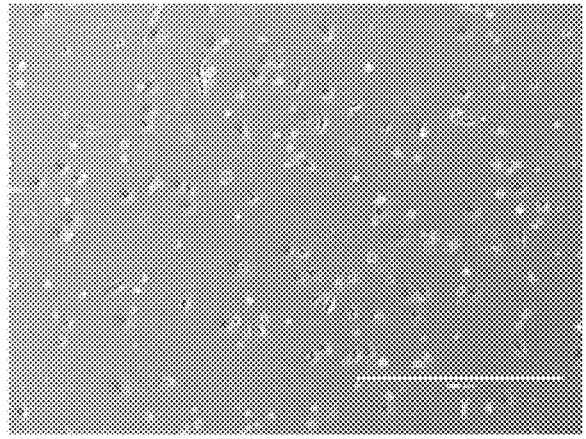
Figure 13:
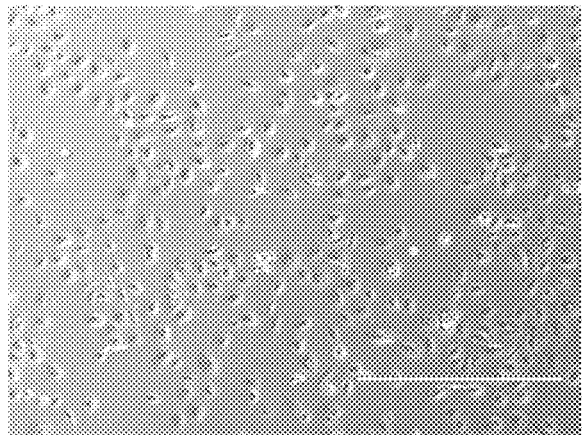
Figure 13:
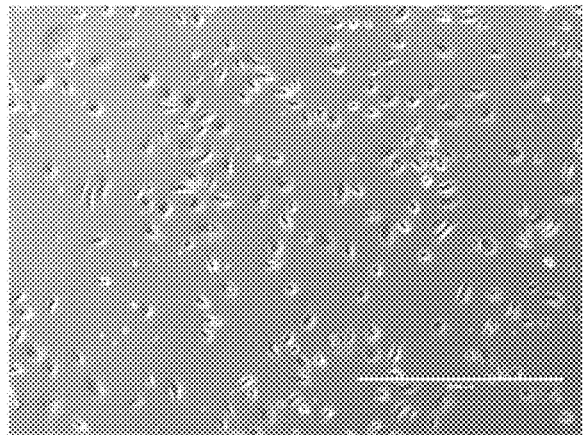

Prostate and bronchial epithelial cells were grown in KSFM in the presence of Rho kinase inhibitor (i.e., Rho-associated protein kinase inhibitor) Y-27632. As shown in FIG. 13, both prostate and bronchial epithelial cells entered senescence at late passage despite the continuous use of Rho kinase inhibitor (i.e., Rho-associated protein kinase inhibitor) Y-27632. By day 8 or day 9, late passages of prostate epithelial cells and bronchial epithelial cells exhibited characteristic morphology of cell senescence such as a flat and enlarged cell shape. Thus, when it was used alone, Y-27632 did not promote the proliferation of prostate epithelial cells or bronchial epithelial cells.

Figure 14:
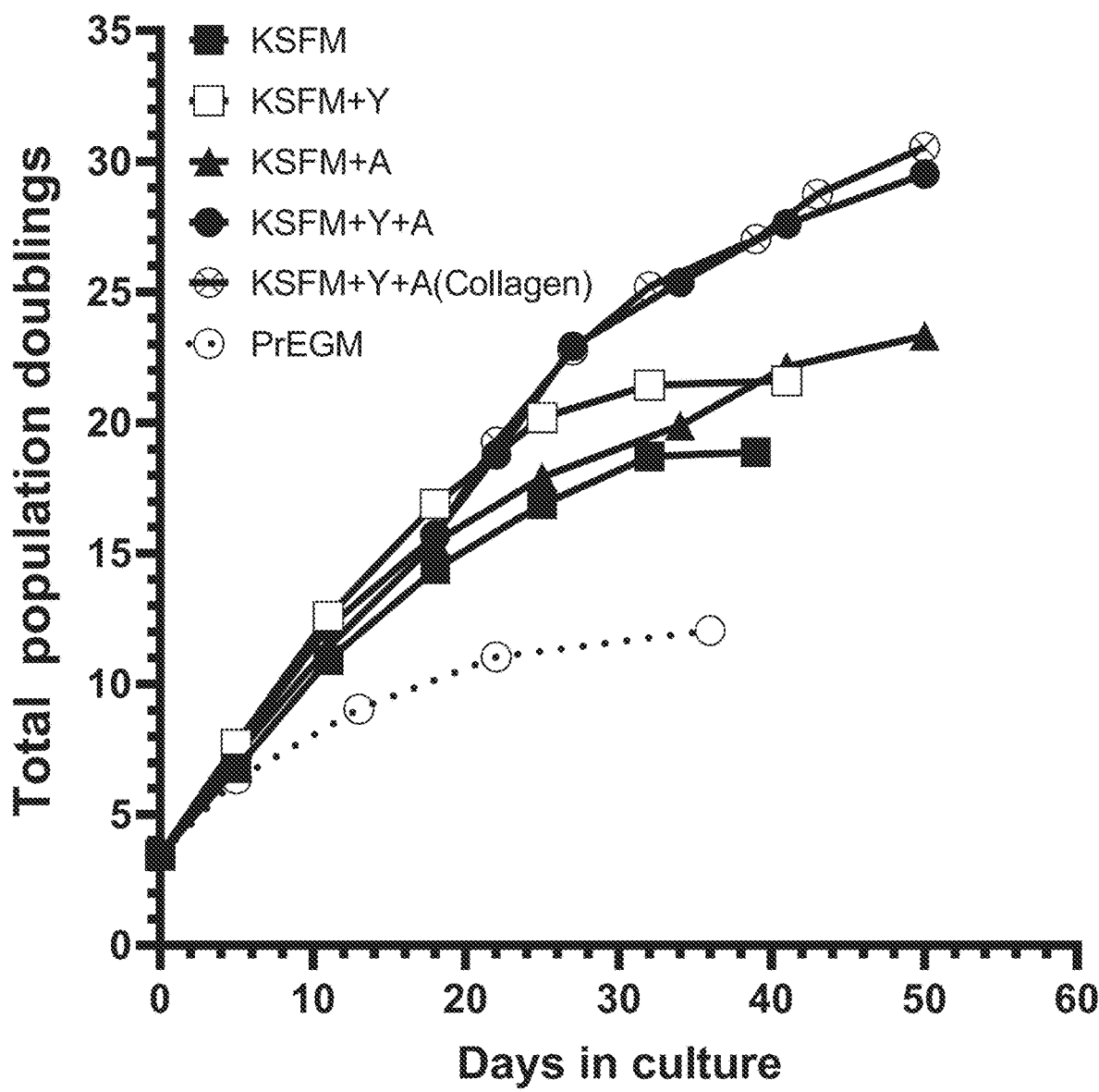
FIG. 14 shows growth of prostate epithelial cells. KSFM, Keratinocyte-SFM (Gibco/Thermo Fisher). PrEGM, Prostate Epithelial Cell Growth Medium (Lonza). A, ALK5 inhibitor A83-01. Y, Rho kinase inhibitor (i.e., Rho-associated protein kinase inhibitor) Y-27632.

To examine the effects of additional in vitro and/or ex vivo growth conditions, prostate epithelial cells were grown in KSFM or PrEGM in the presence of media alone, ALK5 inhibitor A83-01, Rho kinase inhibitor (i.e., Rho-associated protein kinase inhibitor) Y-27632, or both (with or without collagen). As shown in FIG. 14, prostate epithelial cells entered senescence after 10 to 20 population doublings in PrEGM or KSFM. Rho kinase inhibitor (i.e., Rho-associated protein kinase inhibitor) Y-27632 slightly increased the total population doublings of prostate epithelial cells, although the cells still entered senescence shortly after reaching over PD20. A83-01 also increased the total population doublings; however, since A83-01 can interfere with the plating efficiency on regular tissue culture surface (see Example 4), the increase in cell number is slow. Adding both A83-01 and Y-27632 to KSFM significantly increased the total population doublings of prostate epithelial cells at a much faster pace, on both regular tissue culture vessel and collagen-coated tissue culture vessels. Thus, total population doublings of prostate epithelial cells increased significantly when ALK5 inhibitor A83-01 and Rho kinase inhibitor (i.e., Rho-associated protein kinase inhibitor) Y-27632 were used in combination.

Figure 15:
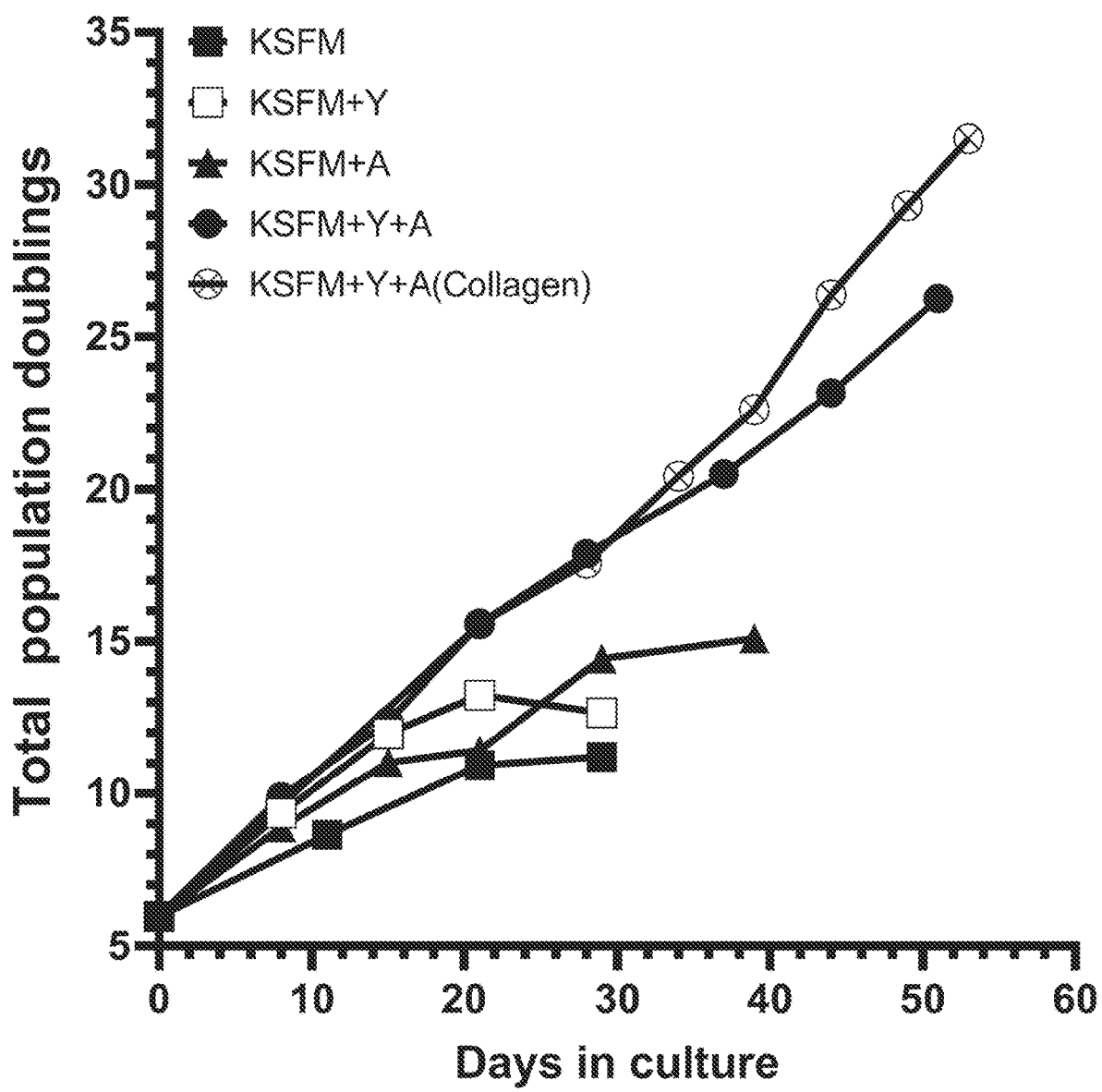
FIG. 15 shows growth of bronchial epithelial cells. KSFM, Keratinocyte-SFM (Gibco/Thermo Fisher). A, ALK5 inhibitor A83-01. Y, Rho kinase inhibitor (i.e., Rho-associated protein kinase inhibitor) Y-27632.

Similar to the experiment above, bronchial epithelial cells were grown in KSFM in the presence of media alone, ALK5 inhibitor A83-01, Rho kinase inhibitor (i.e., Rho-associated protein kinase inhibitor) Y-27632, or both (with or without collagen). As shown in FIG. 15, bronchial epithelial cells entered senescence after 11 population doublings in KSFM. Rho kinase inhibitor (i.e., Rho-associated protein kinase inhibitor) Y-27632 slightly increased the total population doublings of bronchial epithelial cells, although the cells still entered senescence shortly after reaching over PD13. A83-01 also increased the total population doublings; however, since A83-01 can interfere with the plating efficiency on regular tissue culture surface (see Example 4), the increase in cell number is slow. Adding both A83-01 and Y-27632 to KSFM significantly increased the total population doublings of bronchial epithelial cells at a much faster pace, on both regular tissue culture surfaces and collagen-coated tissue culture surfaces, the latter of which showed an even faster pace. Thus, total population doublings of bronchial epithelial cells increased significantly when ALK5 inhibitor A83-01 and Rho kinase inhibitor (i.e., Rho-associated protein kinase inhibitor) Y-27632 were used in combination.

Figure 16:
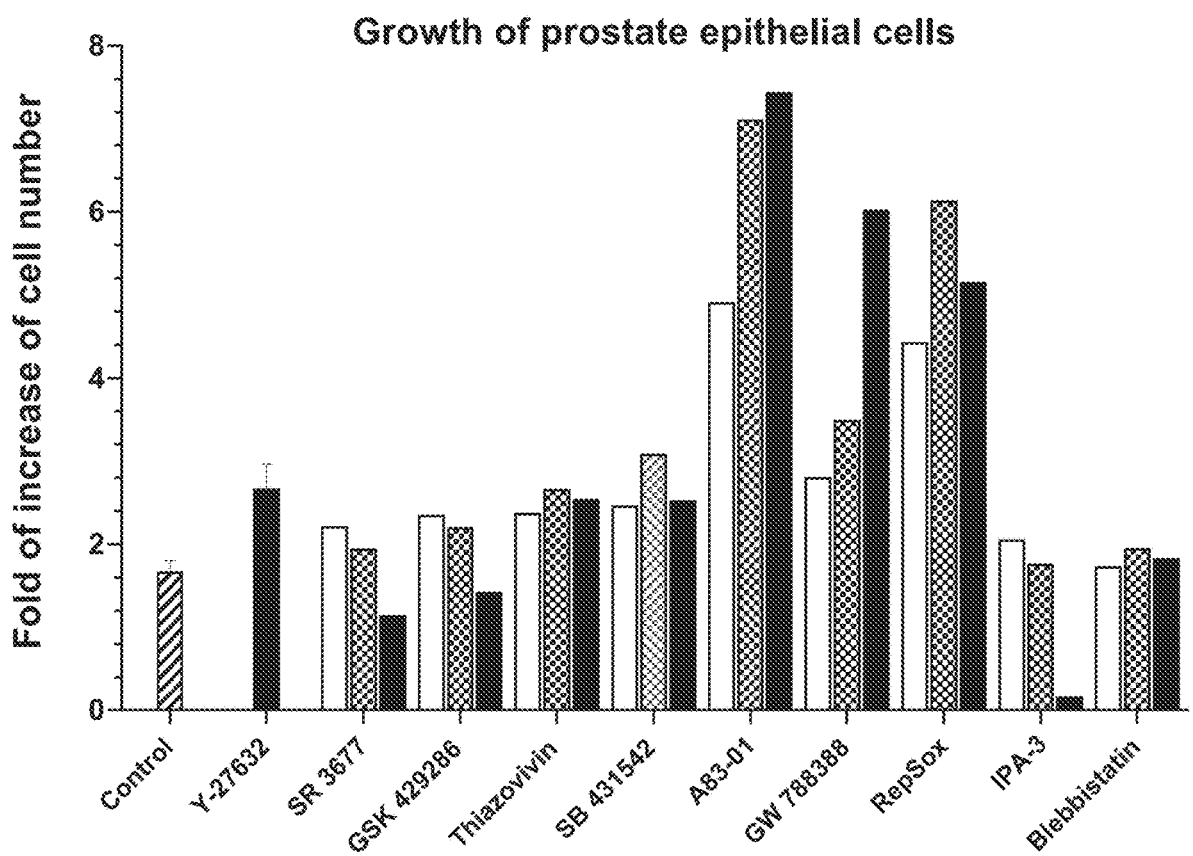
FIG. 16 shows growth of prostate epithelial cells in the presence of various compounds (5 µM, filled bar; 1 µM, checkered bar; and 0.2 µM, open bar). Control is KSFM (Keratinocyte-SFM (Gibco/Thermo Fisher)) with no compound.

In another experiment, late passage prostate epithelial cells were cultured in KSFM plus individual compounds as indicated in FIG. 16, which were tested at various concentrations (i.e., 5 µM, filled bar; 1 µM, checkered bar; and 0.2 µM, open bar). In a control experiment with no added compound, there was minimum increase of cell numbers after 5 days. Rho kinase inhibitors (i.e., Rho-associated protein kinase inhibitors) such as Y-27632, SR 3677, GSK 429286 and Thiazovivin lead to slight increase of total cell numbers. In contrast, ALK5 inhibitors such as A83-01, SB 431542, GW 788388 and RepSox resulted in a pronounced increase of total cell number after 5 days. Neither PAK inhibitor IPA-3 nor myosin II inhibitor (i.e., non-muscle myosin II (NM II) inhibitor) Blebbistatin resulted in any increase of cell proliferation, and IPA-3 caused nearly total cell death at the highest concentration tested (5 µM). Thus, when used alone, ALK5 inhibitors significantly increased the proliferation of late-passage prostate epithelial cells in KSFM; when used alone, Rho kinase inhibitors (i.e., Rho-associated protein kinase inhibitors) slightly increased proliferation; and when used alone, a PAK inhibitor or a myosin II inhibitor (i.e., non-muscle myosin II (NM II) inhibitor) did not increase proliferation.

Figure 17:
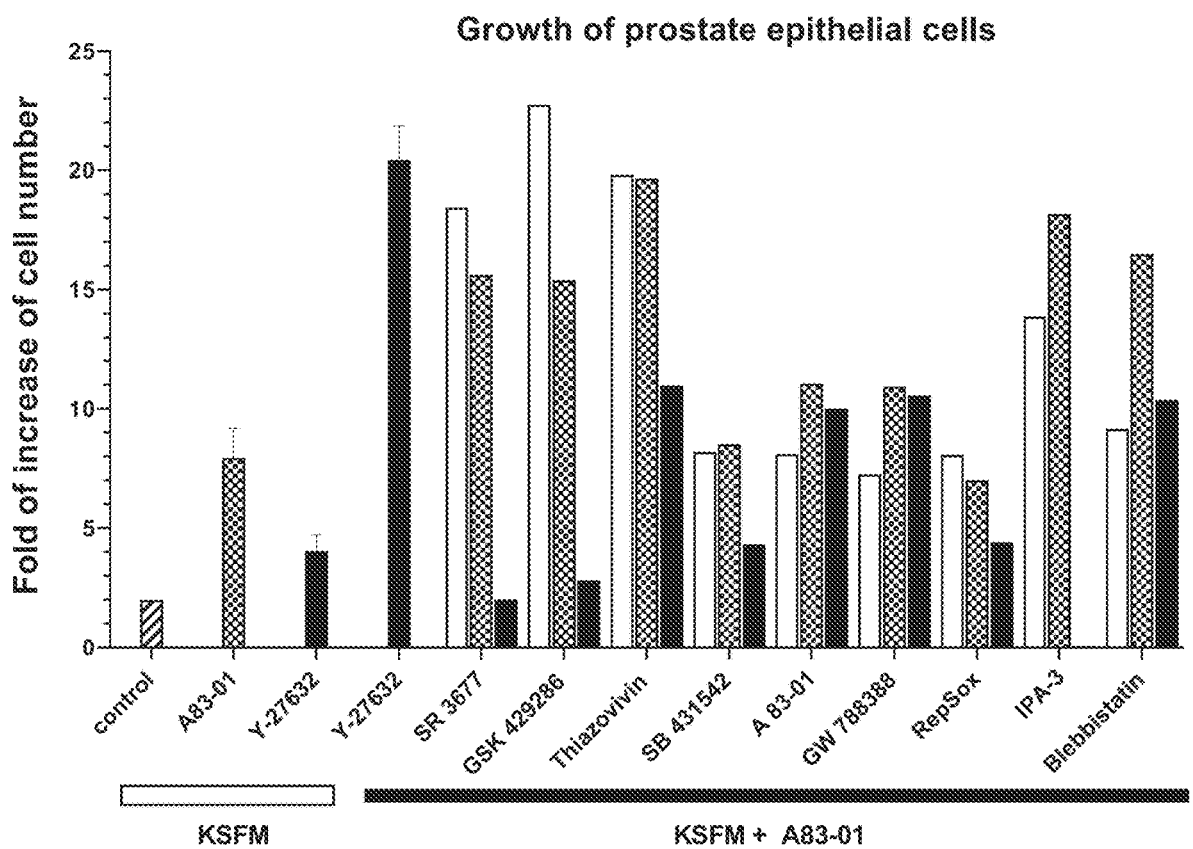
FIG. 17 shows growth of prostate epithelial cells in the presence of various compounds (5 µM, filled bar; 1 µM, checkered bar; and 0.2 µM, open bar). Control is KSFM (Keratinocyte-SFM (Gibco/Thermo Fisher)) with no compound.

In a further experiment, late passage prostate epithelial cells were cultured in KSFM, or KSFM supplemented with A83-01, plus individual compounds as indicated in FIG. 17, which were tested at various concentrations (5 µM, filled bar; 1 µM, checkered bar; and 0.2 µM, open bar). In control experiment with no inhibitor added to KSFM, there was minimum increase of cell numbers after 5 days. A83-01 significantly increased late-passage prostate epithelial cell proliferation, while Rho kinase inhibitor (i.e., Rho-associated protein kinase inhibitor) Y-27632 lead to a slight increase of cell proliferation. When both A83-01 and Y-27632 were used, they synergistically increased the proliferation of prostate epithelial cells. Such synergistic effect also was observed for other Rho kinase inhibitors such as SR 3677, GSK 429286 and Thiazovivin. PAK inhibitor IPA-3 and myosin II inhibitor (i.e., non-muscle myosin II (NM II) inhibitor) Blebbistatin also synergistically increased prostate epithelial cell proliferation when used together with A83-01 in KSFM. In contrast, there was little extra increase of prostate epithelial cell proliferation when other ALK5 inhibitors such as GW 788388, SB 431542 or RepSox were used together with A83-01. Thus, several classes of inhibitors that modulate cytoskeleton integrity synergistically increased late-passage prostate cell proliferation in KSFM, when they were used together with A83-01. As described above, these include Rho kinase inhibitors (i.e., Rho-associated protein kinase inhibitors) such as Y-27632, SR 3677, GSK 429286 and Thiazovivin; PAK inhibitor IPA-3; and myosin II inhibitor (i.e., non-muscle myosin II (NM II) inhibitor) Blebbistatin.

Example 6: Additional Studies on the Effects of Compounds Including ALK5 Inhibitors, Rho Kinase Inhibitors, and Other Compounds on Epithelial Cell Proliferation and Other Properties In this example, proliferation of foreskin keratinocytes, prostate epithelial cells, and bronchial epithelial cells was assessed in the presence of compounds including ALK5 inhibitors, Rho kinase inhibitors (i.e., Rho-associated protein kinase inhibitors), and other compounds.

Figure 18:
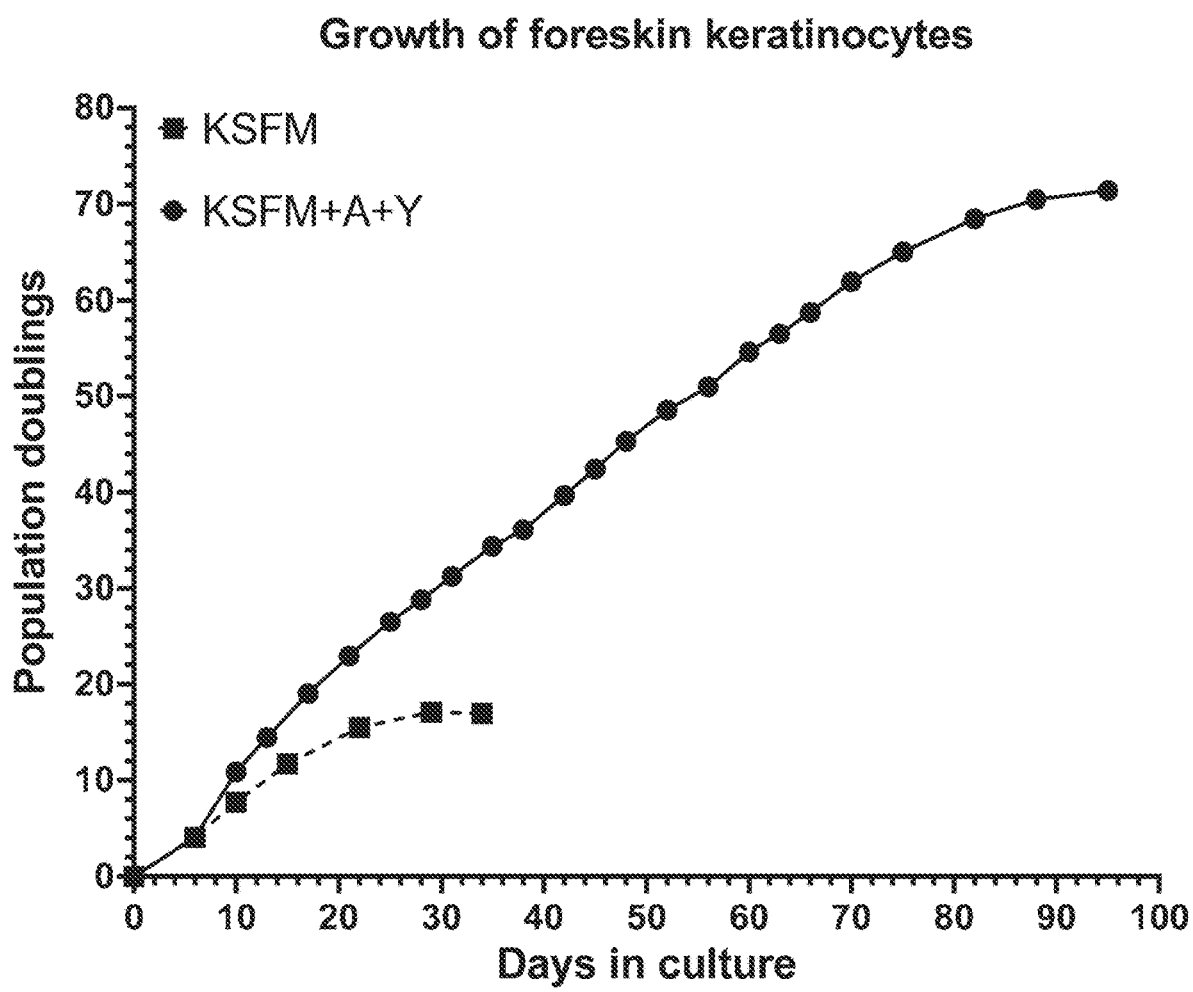
FIG. 18 shows growth of human foreskin keratinocytes in the presence of KSFM and KSFM+A+Y. A, ALK5 inhibitor A83-01. Y, Rho kinase inhibitor (i.e., Rho-associated protein kinase inhibitor) Y-27632. KSFM, Keratinocyte-SFM (Gibco/Thermo Fisher).
Figure 19:
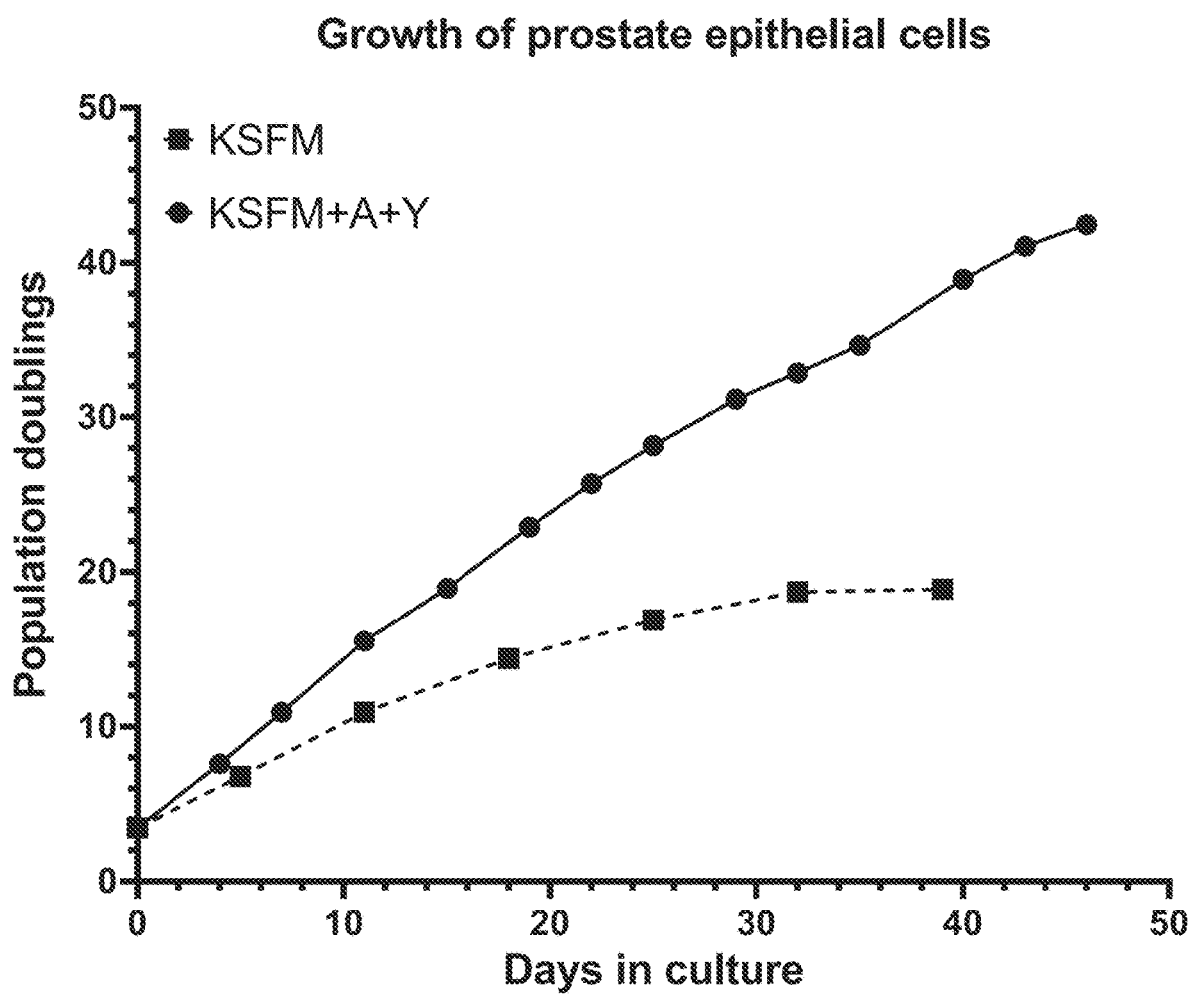
FIG. 19 shows growth of prostate epithelial cells in the presence of KSFM and KSFM+A+Y. A, ALK5 inhibitor A83-01. Y, Rho kinase inhibitor (i.e., Rho-associated protein kinase inhibitor) Y-27632. KSFM, Keratinocyte-SFM (Gibco/Thermo Fisher).
Figure 20:
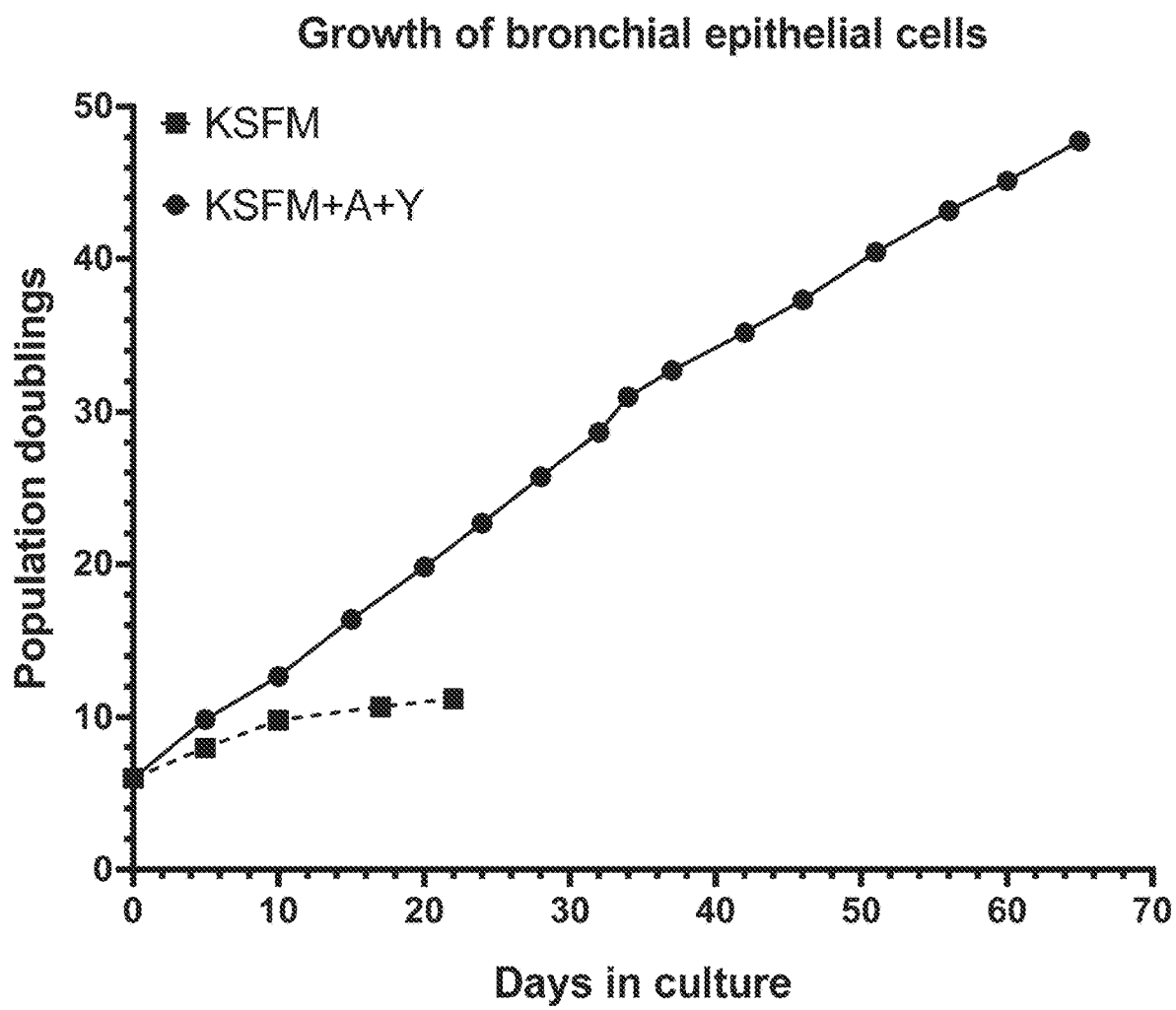
FIG. 20 shows growth of bronchial epithelial cells in the presence of KSFM and KSFM+A+Y. A, ALK5 inhibitor A83-01. Y, Rho kinase inhibitor (i.e., Rho-associated protein kinase inhibitor) Y-27632. KSFM, Keratinocyte-SFM (Gibco/Thermo Fisher).

Foreskin keratinocytes (FIG. 18), prostate epithelial cells (FIG. 19), and bronchial epithelial cells (FIG. 20) were cultured in either KSFM alone, or KSFM supplemented with 1 µM ALK5 inhibitor A83-01 and 5 µM Rho kinase inhibitor (i.e., Rho-associated protein kinase inhibitor) Y-27632 on collagen-coated culture vessels. Population doublings of the cells in each passage were assessed, and total population doublings were plotted against number of days of culture (FIGS. 18, 19 and 20). In KSFM, the epithelial cells showed limited cell replication for only 10 to 20 population doublings before ceasing growth. In KSFM with A83-01 and Y-27632, the epithelial cells continued to proliferate for 40 to 60 additional population doublings. Thus, population doublings of foreskin keratinocytes, prostate epithelial cells and bronchial epithelial cells increased significantly when ALK5 inhibitor A83-01 and Rho kinase inhibitor (i.e., Rho-associated protein kinase inhibitor) Y-27632 were used together, which shows that A83-01 and Y-27632 together significantly extend the lifespan of various epithelial cells in culture.

Figure 30:
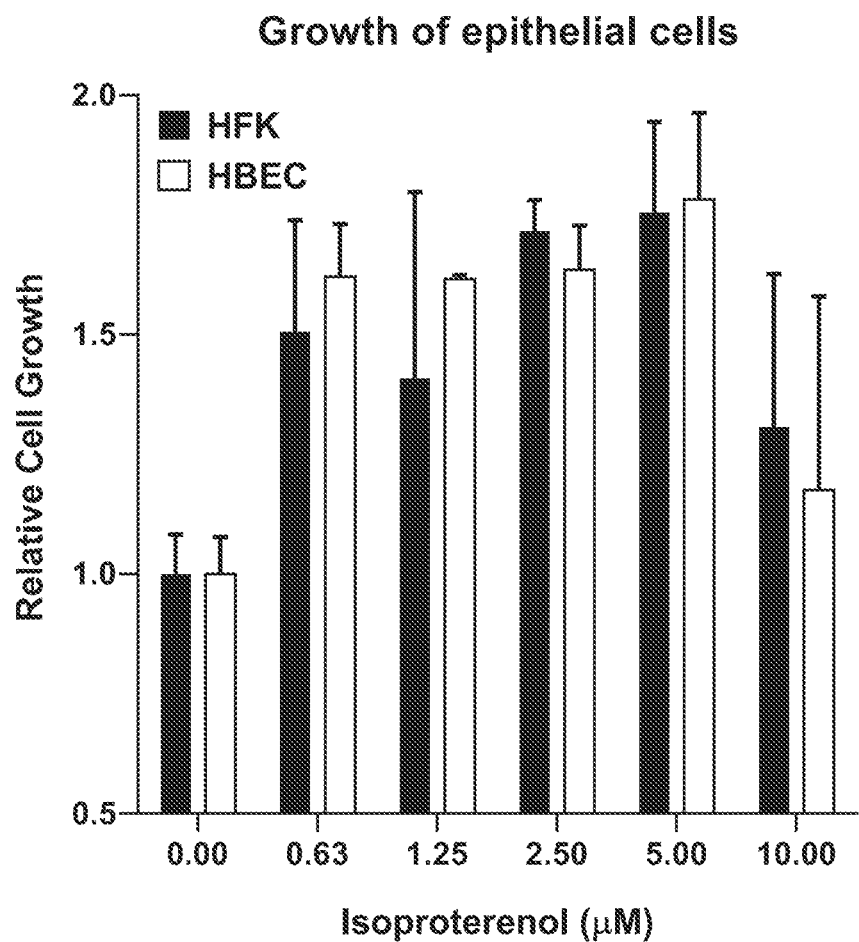
FIG. 30 shows growth of human foreskin keratinocytes (HFK) and human bronchial epithelial cells (HBEC) cultured in KSFM (Keratinocyte-SFM) plus with A83-01 and Y-27632, supplemented with increasing concentrations of isoproterenol.

In a further investigation, epithelial cell growth was assessed in the presence of a beta-adrenergic agonist (i.e., a beta-adrenergic receptor agonist). Human foreskin keratinocytes (HFK) and human bronchial epithelial cells (HBEC) were cultured in KSFM plus 1 µM A83-01 and 5 µM Y-27632, supplemented with increasing concentrations of isoproterenol (a beta-adrenergic receptor agonist that increases cytosolic cAMP levels). Cell numbers were counted after six days to calculate cell growth relative to control. As shown in FIG. 30, isoproterenol further increased epithelial cells growth in KSFM plus A83-01 and Y-27632.

Figure 23:
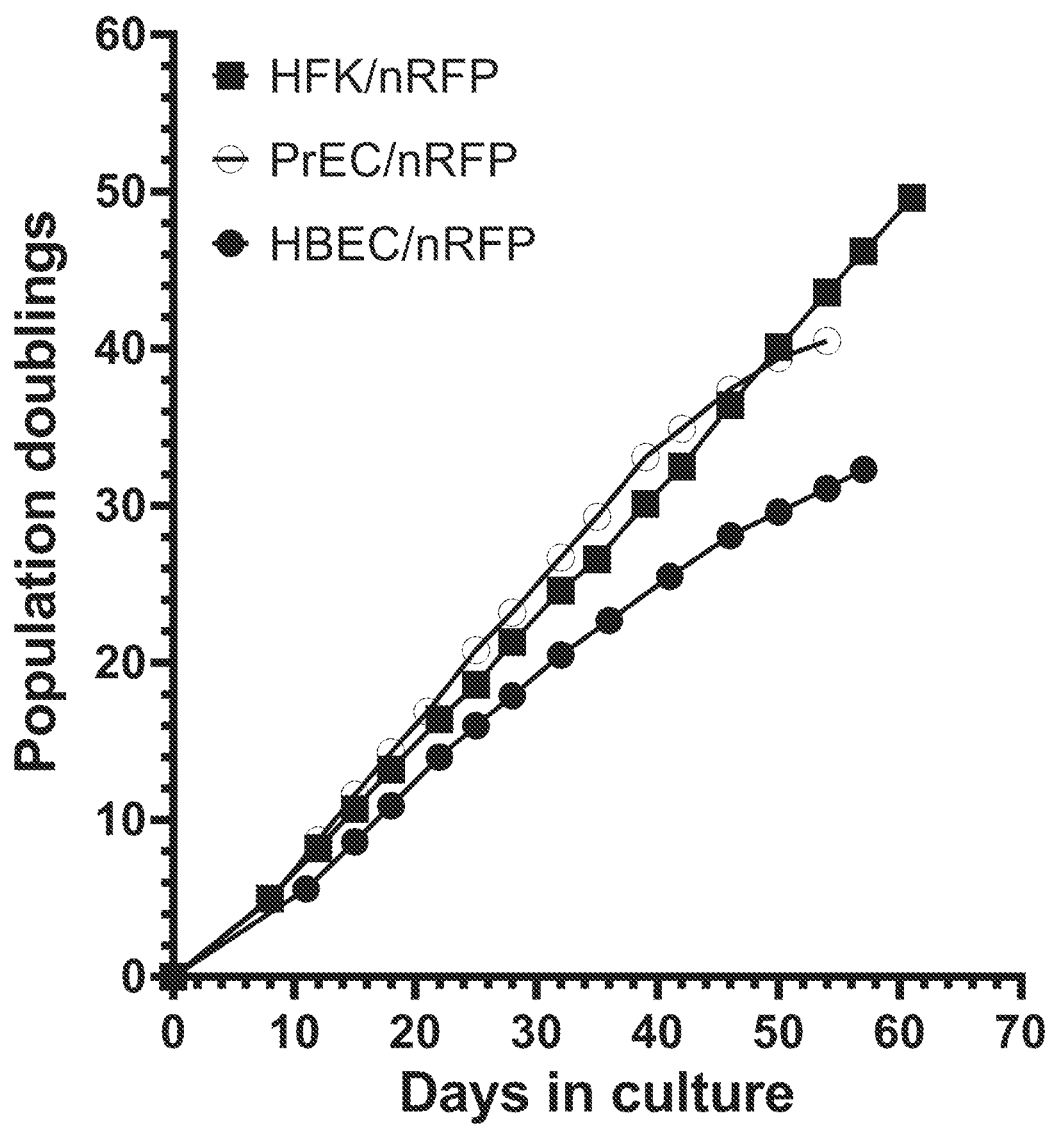
FIG. 23 shows growth of transgenic nuclear-localized Red Fluorescence Protein (nRFP)-expressing epithelial cell lines in KSFM with A83-01 and Y-27632. HFK, human foreskin keratinocytes. HBEC, human bronchial epithelial cells. PrEC, prostate epithelial cells. nRFP, nuclear-localized Red Fluorescence Protein.
Figure 24:
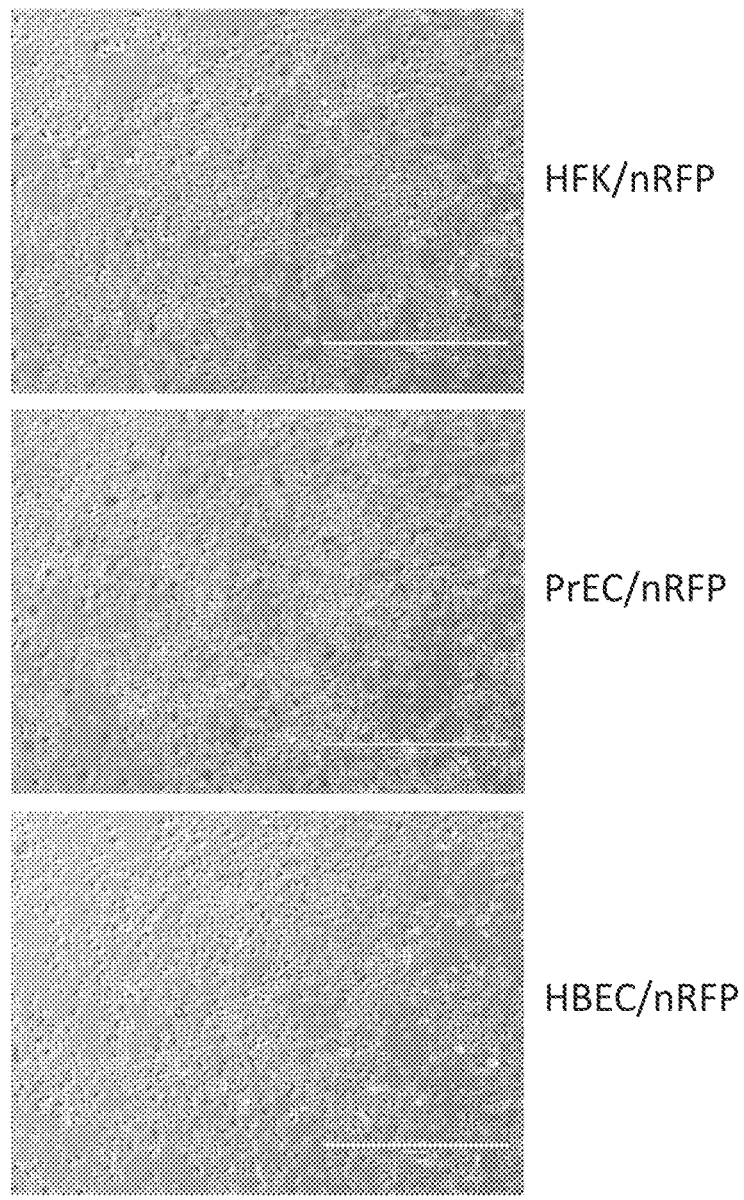
FIG. 24 shows images of transgenic nuclear-localized Red Fluorescence Protein (nRFP)-expressing epithelial cell lines grown in KSFM with A83-01 and Y-27632. HFK, human foreskin keratinocytes. HBEC, human bronchial epithelial cells. PrEC, prostate epithelial cells. nRFP, nuclear-localized Red Fluorescence Protein.

Stable transgenic cell lines were established for various epithelial cells (i.e., human foreskin keratinocytes (HFK), prostate epithelial cells (PrEC), and human bronchial epithelial cells (HBEC)) using a lentivirus vector expressing nucleus-localized Red Fluorescence Protein (nRFP). Such transgenic cell lines (e.g., shown in FIG. 24) ubiquitously express the nRFP reporter gene and are selected through standard antibiotic selection. HFK/nRFP, PrEC/nRFP and HBEC/nRFP cells were cultured for extended periods in KSFM with A83-01 and Y-27632, as shown in FIG. 23.

Figure 21B:
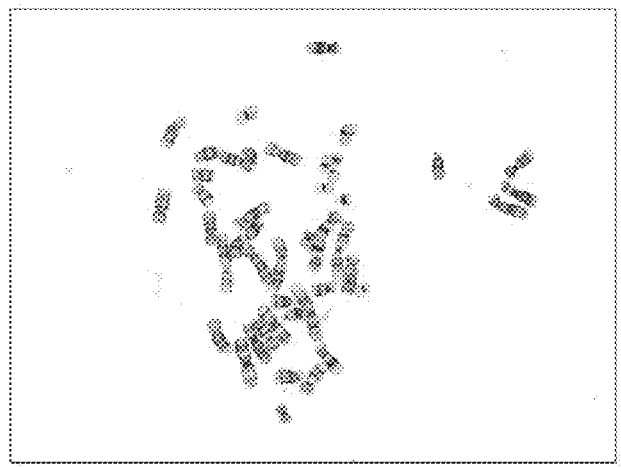
Figure 21B:
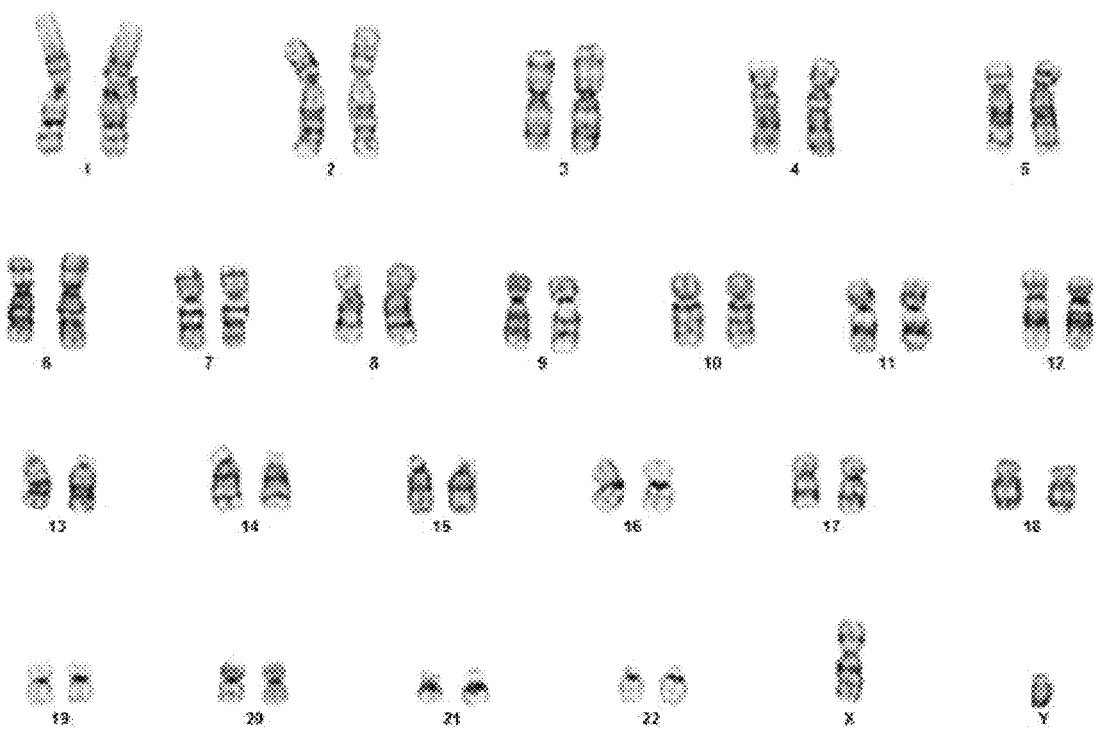
Figure 21C:
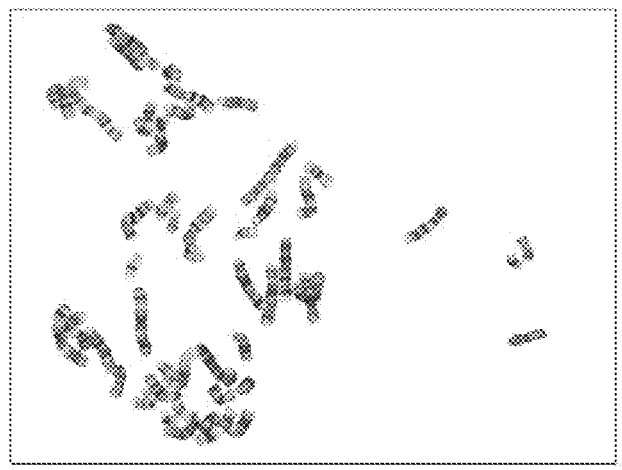
Figure 21C:
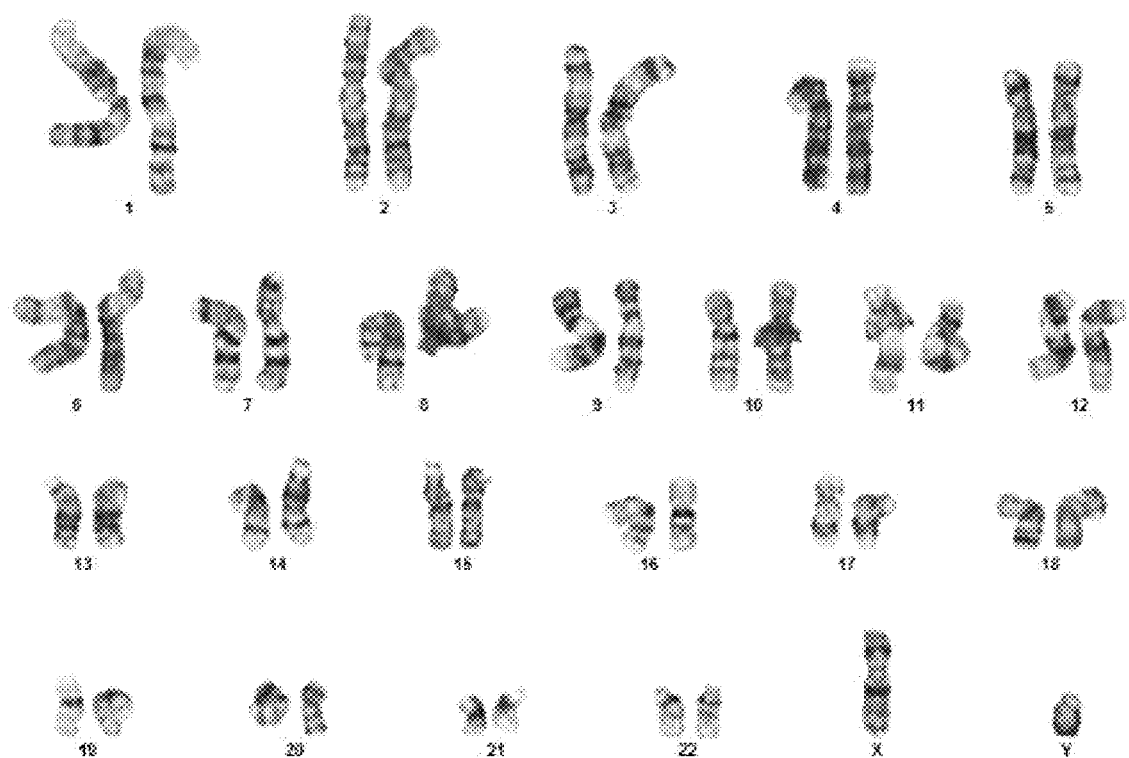

Karyotypes for various epithelial cells cultured in KSFM plus A83-01 and Y-27632 were assessed at early and late passages. Specifically, karyotype analysis was performed on human foreskin keratinocytes (HFK) at passage 3 (13.5 population doublings) and passage 19 (62.0 population doublings); human bronchial epithelial cells (HBEC) at passage 4 (11.1 population doublings) and passage 16 (45.1 population doublings); and prostate epithelial cells (PrEC) at passage 3 (13.5 population doublings) and passage 13 (41.1 population doublings), using metaphase chromosome spreading. The results of the karyotype analysis are presented in FIGS. 21A-21C. The cells showed 46 normal chromosomes with no gross karyotypic abnormality after extended culture in the presence of A83-01 and Y-27632. FIG. 21B shows representative metaphase chromosome spreads of HFK cells at early passage (p3), and FIG. 21C shows representative metaphase chromosome spreads of HFK cells at late passage (p19).

Figure 22:
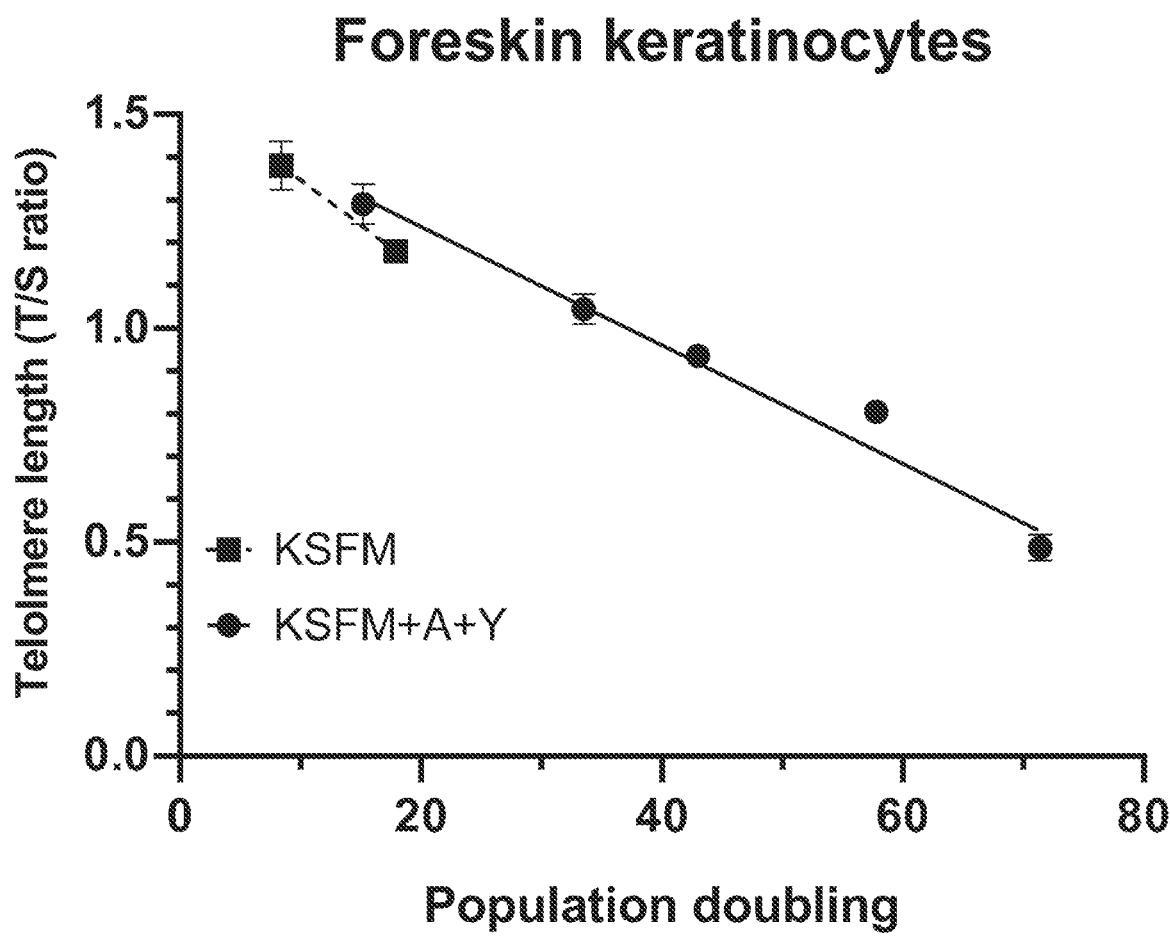
FIG. 22 shows average relative length of telomeres in foreskin keratinocytes cultured in KSFM plus A83-01 and Y-27632 at various population doublings. The relative length of telomeres is represented as ratio (T/S ratio) of telomeric repeats (T) to single copy gene (S) using quantitative PCR. KSFM, Keratinocyte-SFM (Gibco/Thermo Fisher). A, ALK5 inhibitor A83-01. Y, Rho kinase inhibitor (i.e., Rho-associated protein kinase inhibitor) Y-27632.

Average telomere length was assessed for cells cultured in KSFM alone or KSFM plus A83-01 and Y-27632 over several population doublings. Specifically, average telomere length in foreskin keratinocytes cultured in KSFM alone or KSFM plus A83-01 and Y-27632 was determined using a quantitative PCR assay and is represented as a T/S ratio (T, telomere; S, single copy gene) in FIG. 22. The average length of telomeres in foreskin keratinocytes cultured in KSFM plus A83-01 and Y-27632 decreased steadily as the population doublings of the culture increased.

Expression of certain genes was assessed at various passages for epithelial cells cultured in KSFM alone or KSFM plus A83-01 and Y-27632. FIG. 27 provides a list of representative genes whose expression levels are down-regulated or up-regulated in KSFM plus A83-01 and Y-27632. Total RNA was extracted from foreskin keratinocytes cultured in KSFM alone, or KSFM plus A83-01 and Y-27632 at different passages. Gene expression levels were analyzed by quantitative PCR using $RT^2$ Profiler™ PCR Array Human Cellular Senescence assay (Qiagen, PAHS-050Z). Several genes that are involved in stress response and senescence showed increased expression when the cells entered senescence at 6th passage in KSFM (i.e., AKT1, ATM, CDKN2A, GADD45A, GLB1, PLAU, SERPINE1 and SOD2), while the expression of these genes was suppressed in KSFM plus A83-01 and Y-27632. Likewise, adhesion molecule genes (FN1, THBS1) and an intermediate filament protein (VIM) gene showed increased expression when the cells entered senescence at 6th passage in KSFM, while the expression of these genes was suppressed in KSFM plus A83-01 and Y-27632. The expression of certain genes, CDKN2B, CITED2, CREG1, ID1, MAP2K6, IGFBP3 and IGFBP5 was significantly up-regulated in KSFM plus A83-01 and Y-27632, especially at late passages. Thus, a few genes sometimes associated with cellular senescence (such as CDKN2B, CITED2, CREG1, ID1, MAP2K6, IGFBP3 and IGFBP5) showed increased expression in late passage epithelial cell population cultured in KSFM plus A83-01 and Y-27632. Together with the normal karyotype and shorter telomeres observed in late passage normal epithelial cells cultured in KSFM plus A83-01 and Y-27632, this indicates that normal epithelial cells expanded in KSFM plus A83-01 and Y-27632 gained features such that they are different than the originating epithelial cell population, however they are not transformed into abnormal cells.

Figure 28:
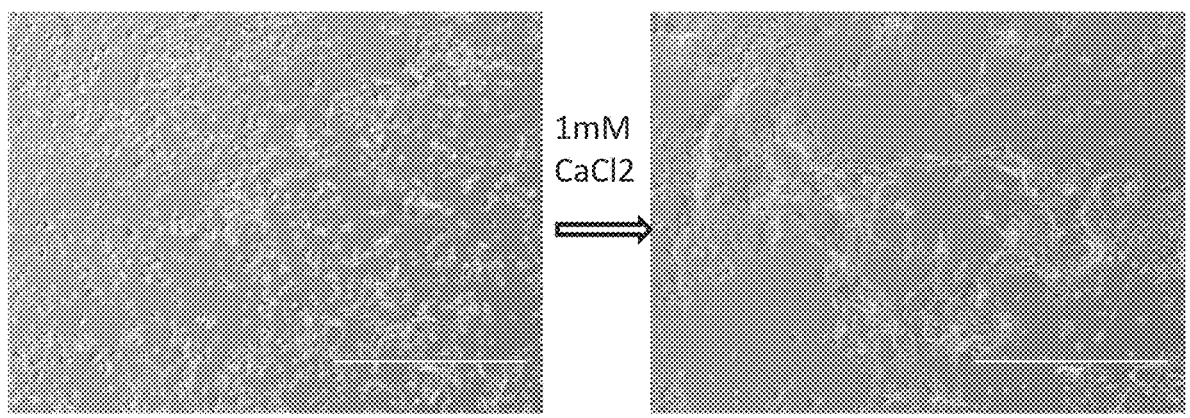
FIG. 28 shows changes in the behavior of epithelial cells cultured in KSFM with A83-01 and Y-27632 (image on the left side) after the addition of 1 mM CaCl2 (image on the right side). A, ALK5 inhibitor A83-01. Y, Rho kinase inhibitor (i.e., Rho-associated protein kinase inhibitor) Y-27632. KSFM, Keratinocyte-SFM (Gibco/Thermo Fisher).

Effects of culture media calcium content on cell behavior were assessed for epithelial cells cultured in KSFM plus A83-01 and Y-27632. Human bronchial epithelial cells were grown KSFM (with 90 µM $CaCl_2$) plus A83-01 and Y-27632. These cells dispersed throughout the culture vessel (FIG. 28, left panel), and few cells formed intercellular connections, even when they were in close proximity to each other. Adding high concentration (1 mM) of $CaCl_2$ into KSFM plus A83-01 and Y-27632 caused the bronchial epithelial cells to aggregate into tight clusters (FIG. 28, right panel). Cells in the center of the patches tended to pile up, and boundaries between individual cells generally were not discernable. In certain instances, abnormal elongations formed between clusters.

Figure 29:
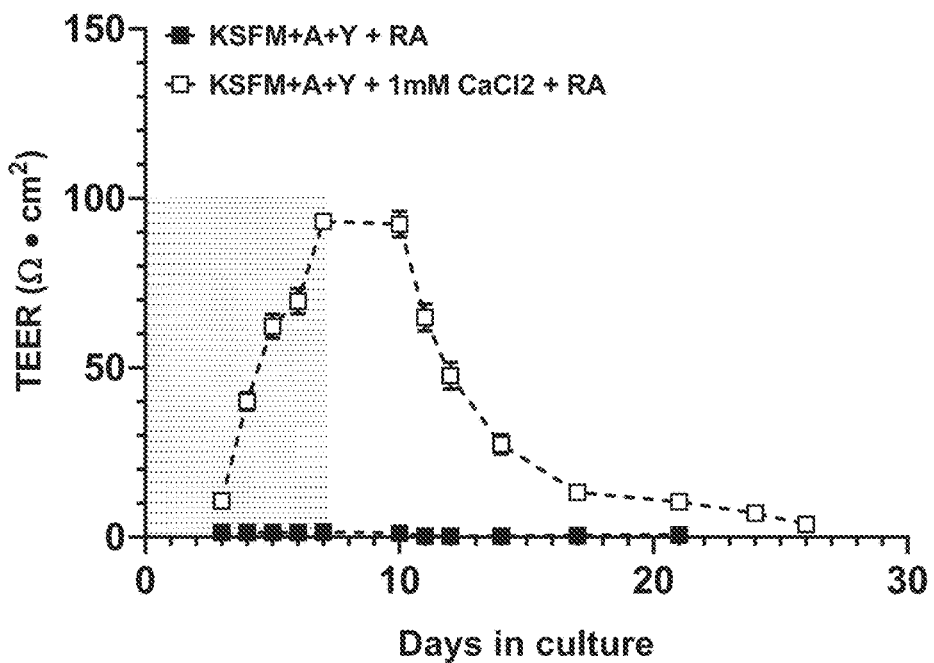
FIG. 29 shows electric resistance across TRANSWELL membrane for bronchial epithelial cells cultured in KSFM with A83-01 and Y-27632 and different calcium concentrations. A, ALK5 inhibitor A83-01. Y, Rho kinase inhibitor (i.e., Rho-associated protein kinase inhibitor) Y-27632. KSFM, Keratinocyte-SFM (Gibco/Thermo Fisher). RA, all-trans-Retinoic acid (Sigma).
Figure 29:
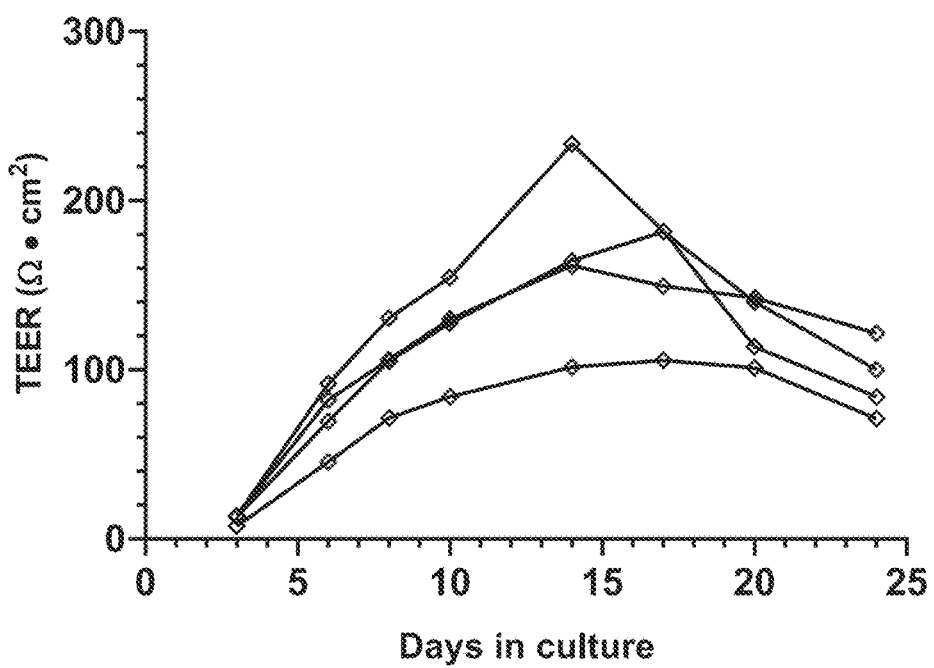

In a further investigation, effects of culture media calcium content on intercellular junctions was assessed for bronchial epithelial cells cultured in KSFM plus A83-01 and Y-27632. Intercellular junctions were assessed according to paracellular flow of ions as measured by trans-epithelium electric resistance (TEER). As shown in FIG. 29 (top panel), bronchial epithelial cells established tight intercellular junctions which minimized the paracellular flow of ions, as shown by an increasing TEER in the presence of high concentration (1 mM) of $CaCl_2$ in KSFM plus A 83-01 and Y-27632. On contrary, bronchial epithelial cells failed to establish tight intercellular junctions under a low concentration (90 µM) of $CaCl_2$ in KSFM plus A 83-01 and Y-27632. Bronchial epithelial cells were plated on porous membrane support (TRANSWELL, Corning, 354474) and maintained for 7 days when the membrane was covered with culture medium (submerged phase, grayed box in FIG. 29, top panel). On day 8, the medium was removed from the apical side of the membrane, and the cells were exposed to air to induce further differentiation. Further, as shown in FIG. 29 (bottom panel), bronchial epithelial cells established increasing transmembrane electric resistance (TEER) over time in the presence of high concentration (1 mM) of CaCl2 in KSFM plus A 83-01 and Y-27632. Bronchial epithelial cells were plated on a porous membrane support (TRANSWELL, Corning, 354474) and maintained for 24 days, with the membrane covered by culture medium for the duration of the culture. Trans-epithelium electric resistance (TEER) remained at a high level throughout the culture period. Each trace in FIG. 29 (bottom panel) shows a measurement of TEER across one porous membrane.

Example 7: Identification of Defined Media Compositions for Epithelial Cell Proliferation Bovine pituitary extract is used as a mitogenic supplement in KSFM and in many serum-free cell culture media. In addition to its mitogenic activity, BPE contains a variety of undefined proteins, lipids and hormones. To identify one or more defined media compositions in which epithelial cells are capable of proliferating, additional culture media compositions were tested. Specifically, epithelial cells were proliferated in a variety of defined media compositions containing ALK5 inhibitors and Rho kinase inhibitors (i.e., Rho-associated protein kinase inhibitors), and the growth of these cell populations was assessed. Defined media compositions included one or more components selected from M* (MCDB-153 (Modified) Medium (Biological Industries, Cat. No. 01-059-1, which formulation can be found at world wide web address bioind.com/page_16682 and in Table 2B below)+epithelial growth factor (EGF)+acidic fibroblast growth factor (aFGF)+A83-01+Y-27632); fatty-acid free bovine serum albumin (BSA; Sigma, A8806); recombinant human serum albumin expressed in Rice (rHA; Sigma, A9731); lipids mix (Chemically Defined Lipid Concentrate; Gibco, 11905-031); and ALBUMAX I Lipid-Rich BSA (Gibco, 11020-039). Certain components in MCDB-153 (Sigma Aldrich, M7403) and Modified MCDB-153 (Biological Industries, Cat. No. 01-059-1) and their concentrations are presented in Tables 2A and 2B below. The lipids mix includes ethyl alcohol and components listed in Table 3 below. ALBUMAX includes BSA and the following fatty acids at between about 0.5 to 2.2 mg each/gSA: Apha-linolenic acid, Linoleic acid, Oleic acid, Stearic acid, and Palmitic acid.

TABLE 2A

MCDB-153 Components

| Component | Concentration (g/L) |
|---|---|
| Ammonium Metavanadate | 0.000000585 |
| Calcium Chloride•Anhydrous | 0.00333 |
| Cupric Sulfate•5H$_2$O | 0.00000275 |
| Ferrous Sulfate•7H$_2$O | 0.00139 |
| Magnesium Chloride | 0.05713 |
| Manganese Sulfate | 0.000000151 |
| Molybdic Acid•4H$_2$O (ammonium) | 0.00000124 |
| Nickel Chloride•6H$_2$O | 0.00000012 |
| Potassium Chloride | 0.11183 |
| Sodium Acetate (anhydrous) | 0.30153 |
| Sodium Chloride | 7.599 |
| Sodium Metasilicate•9H$_2$O | 0.000142 |
| Sodium Phosphate Dibasic (anhydrous) | 0.284088 |
| Sodium Selenite | 0.0000038 |
| Stannous Chloride•2H$_2$O | 0.000000113 |
| Zinc Sulfate•7H$_2$O | 0.000144 |
| L-Alanine | 0.00891 |
| L-Arginine•HCl | 0.2107 |
| L-Asparagine•H$_2$O | 0.015 |
| L-Aspartic Acid | 0.00399 |
| L-Cysteine•HCl•H$_2$O | 0.04204 |
| L-Glutamic Acid | 0.01471 |
| L-Glutamine | 0.8772 |
| Glycine | 0.00751 |
| L-Histidine•HCl•H$_2$O | 0.01677 |
| L-Isoleucine | 0.001968 |
| L-Leucine | 0.0656 |
| L-Lysine•HCl | 0.01827 |
| L-Methionine | 0.00448 |
| L-Phenylalanine | 0.00496 |
| L-Proline | 0.03453 |
| L-Serine | 0.06306 |
| L-Threonine | 0.01191 |
| L-Tryptophan | 0.00306 |
| L-Tyrosine•2Na | 0.00341 |
| L-Valine | 0.03513 |
| D-Biotin | 0.0000146 |
| Choline Chloride | 0.01396 |
| Folic Acid | 0.00079 |
| myo-Inositol | 0.01802 |
| Niacinamide | 0.00003663 |
| D-Pantothenic Acid (hemicalcium) | 0.000238 |
| Pyridoxine•HCl | 0.00006171 |
| Riboflavin | 0.0000376 |
| Thiamine•HCl | 0.000337 |
| Vitamin B-12 | 0.000407 |
| Adenine•HCl | 0.03088 |
| D-Glucose | 1.081 |
| HEPES | 6.6 |
| Phenol Red•Na | 0.001242 |
| Putrescine•2HCl | 0.000161 |
| Pyruvic Acid•Na | 0.055 |
| Thioctic Acid | 0.000206 |
| Thymidine | 0.000727 |

TABLE 2B

Modified MCDB-153 Components

| Component | Concentration (g/L*) |
|---|---|
| Ammonium Metavanadate | 0.000000585 |
| Calcium Chloride•Anhydrous | 0.00333 |
| Cupric Sulfate•5H$_2$O | 0.00000275 |
| Ferrous Sulfate•7H$_2$O | 0.00139 |
| Magnesium Chloride | 0.05713 |
| Molybdic Acid•4H$_2$O (ammonium) | 0.00000124 |
| Nickel Chloride•6H$_2$O | 0.00000012 |
| Potassium Chloride | 0.11183 |
| Sodium Acetate (anhydrous) | 0.30153 |
| Sodium Chloride | 7.599 |
| Sodium Metasilicate•9H$_2$O | 0.000142 |
| Sodium Phosphate Dibasic (anhydrous) | 0.284088 |
| Sodium Selenite | 0.0000038 |
| Stannous Chloride•2H$_2$O | 0.000000113 |
| Zinc Sulfate•7H$_2$O | 0.000144 |
| L-Alanine | 0.0178 |
| L-Arginine•HCl | 0.2107 |
| L-Asparagine•H$_2$O | 0.030 |
| L-Aspartic Acid | 0.01729 |
| L-Cystine•HCl•H$_2$O | 0.04204 |
| L-Glutamic acid | 0.0294 |
| L-Glutamine | 0.8772 |
| Glycine | 0.0150 |
| L-Histidine•HCl•H$_2$O | 0.01677 |
| L-Isoleucine | 0.001968 |
| L-Leucine | 0.0656 |
| L-Lysine•HCl | 0.01827 |
| L-Methionine | 0.00448 |
| L-Phenylalanine | 0.00496 |
| L-Proline | 0.04603 |
| L-Serine | 0.07356 |
| L-Threonine | 0.01191 |
| L-Tryptophan | 0.00306 |
| L-Tyrosine•2Na | 0.00341 |
| L-Valine | 0.03513 |
| D-Biotin | 0.0000146 |
| Choline Chloride | 0.01396 |
| Folic Acid | 0.00079 |
| myo-Inositol | 0.01802 |
| Niacinamide | 0.00003663 |
| D-Pantothenic Acid (hemicalcium) | 0.000238 |
| Pyridoxine•HCl | 0.00006171 |
| Riboflavin | 0.0000376 |
| Thiamine•HCl | 0.000337 |
| Vitamin B-12 | 0.000407 |
| Adenine•HCl | 0.03088 |
| D-Glucose | 1.081 |
| HEPES | 6.6 |
| Phenol Red•Na | 0.001242 |
| Putrescine•2HCl | 0.000161 |
| Pyruvic Acid•Na | 0.055 |
| Thioctic Acid | 0.000206 |
| Thymidine | 0.000727 |
| Hydrocortisone | 200 nM |
| Triiodothyronine | 10 nM |
| Testosteron | 10 nM |
| Insulin | 5.0 mg/L |
| Transferrin (Iron-free) | 5.0 mg/L |
| Sodium selenite | 5.0 µg/L |

*Concentration is in g/L except where noted otherwise.

TABLE 3

Lipids Mix Components

| Component | Concentration (mg/L) |
|---|---|
| Arachidonic Acid | 2.0 |
| Cholesterol | 220.0 |
| DL-alpha-Tocopherol Acetate | 70.0 |
| Linoleic Acid | 10.0 |
| Linolenic Acid | 10.0 |
| Myristic Acid | 10.0 |
| Oleic Acid | 10.0 |
| Palmitic Acid | 10.0 |
| Palmitoleic Acid | 10.0 |
| Pluronic F-68 | 90000.0 |
| Stearic Acid | 10.0 |

TABLE 3-continued

Lipids Mix Components

| Component | Concentration (mg/L) |
|---|---|
| Tween 80 ® (polysorbate 80) | 2200.0 |

Figure 25:
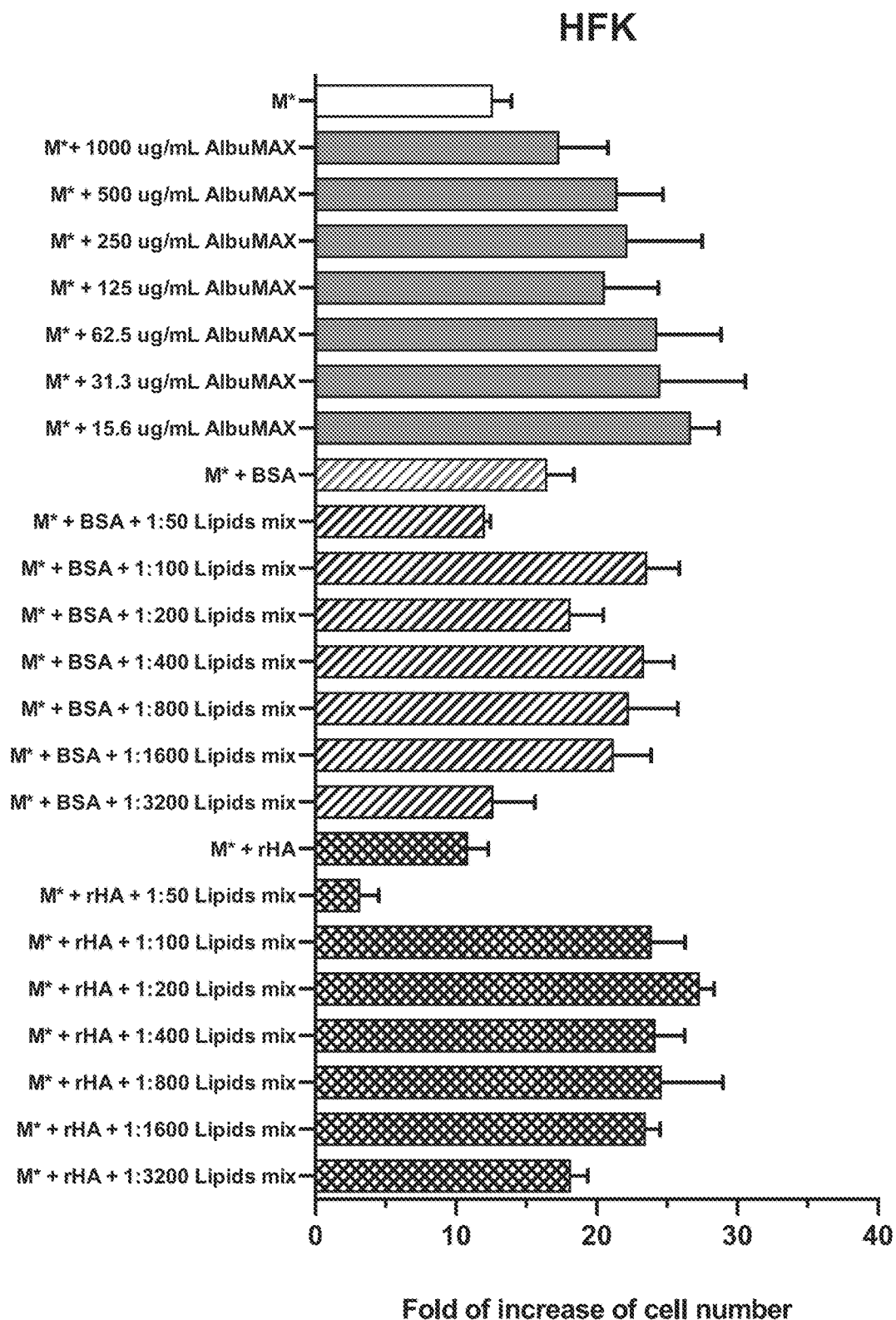
FIG. 25 shows growth of human foreskin keratinocytes in the presence of various compounds and conditions. HFK, human foreskin keratinocytes. M*, Modified MCDB-153 medium (with 90 µM CaCl2) plus EGF, aFGF, A83-01, and Y-27632. EGF, epithelial growth factor. aFGF, acidic fibroblast growth factor. BSA, Fatty-acid free BSA (Sigma, A8806). rHA, recombinant human serum albumin expressed in Rice (Sigma, A9731). Lipids mix, Chemically Defined Lipid Concentrate (Gibco, 11905-031). AlbuMAX, AlbuMAX® ILipid-Rich BSA (Gibco, 11020-039).
Figure 26:
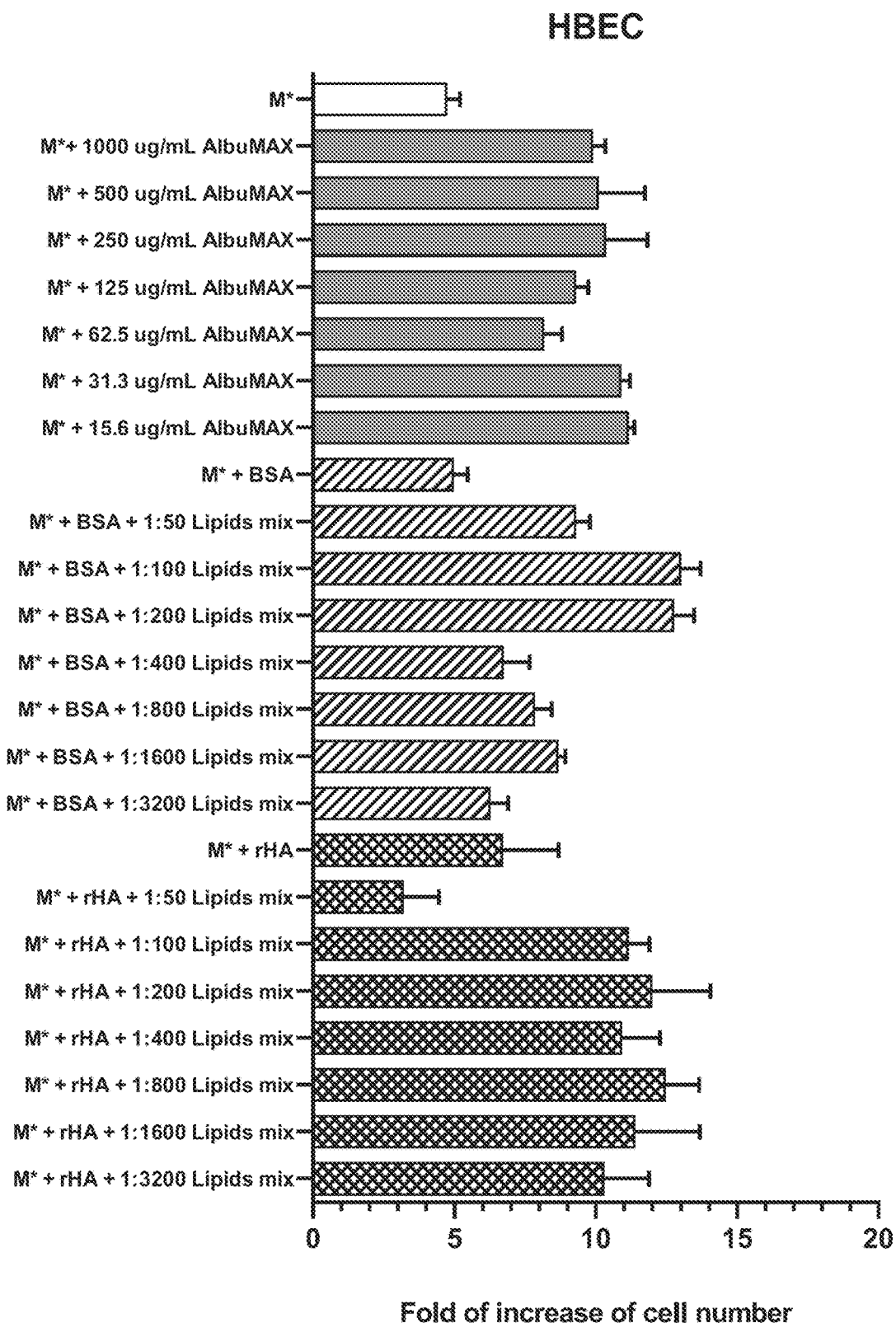
FIG. 26 shows growth of human bronchial epithelial cells in the presence of various compounds and conditions. HBEC, human bronchial epithelial cells. M*, Modified MCDB-153 medium (with 90 µM CaCl2) plus EGF, aFGF, A83-01, and Y-27632. EGF, epithelial growth factor. aFGF, acidic fibroblast growth factor. BSA, Fatty-acid free BSA (Sigma, A8806). rHA, recombinant human serum albumin expressed in Rice (Sigma, A9731). Lipids mix, Chemically Defined Lipid Concentrate (Gibco, 11905-031). AlbuMAX, AlbuMAX® ILipid-Rich BSA (Gibco, 11020-039).

HFK cells and HBEC cells were grown in M*; M*+ALBUMAX (at 1000 µg/mL, 500 µg/mL, 250 µg/mL, 125 µg/mL, 62.5 µg/mL, 31.3 µg/mL and 15.6 µg/mL); M*+BSA+lipids mix (at 1:50 dilution, 1:100 dilution, 1:200 dilution, 1:400 dilution, 1:800 dilution, 1:1600 dilution, and 1:3200 dilution); or M*+rHA+lipids mix (at 1:50 dilution, 1:100 dilution, 1:200 dilution, 1:400 dilution, 1:800 dilution, 1:1600 dilution, and 1:3200 dilution). Growth of the cell populations was assessed and the results are presented as fold increase of cell number in FIG. 25 for HFK cells and FIG. 26 for HBEC cells. The results show that albumin and a lipids mixture can be used to support epithelial cell proliferation without the need for bovine pituitary extract (BPE) supplementation.

Example 8: Epithelial Cell Gene Expression Profiles

In this example, gene expression profiles are described for epithelial cells grown in various serum-free media conditions.

Total RNAs were extracted from human foreskin keratinocytes cultured in KSFM at passages 2 and 6, or KSFM plus A 83-01 (1 µM) and Y-27632 (5 µM) at passages 2, 13 and 23; and airway epithelial cells cultured in KSFM plus A 83-01 (1 µM) and Y-27632 (5 µM) at passages 2 and 8. The cell culture media for the airway epithelial cells also included isoproterenol (3 µM). Gene expression levels were analyzed by quantitative RT-PCR using customized RT$^2$ Profiler™ PCR Array (Qiagen). Total RNAs from human small intestine or lung tissues (Clontech) were included as controls. Gene expression levels relative to that of Actin B were calculated using $2\hat{}(Ct_{actinB}-Ct_{gene})$, where $Ct_{actinB}$ or $Ct_{gene}$ is the number of cycles required for the fluorescent signal of quantitative PCR reaction to cross a defined threshold. $Ct_{actinB}$ was generally around 18. The expression level of a gene was considered non-detectable (ND) if the $Ct_{gene}$ was higher than 35. The expression level of a gene was considered low if the $Ct_{gene}$ was less than 35 and greater than or equal to 30. The expression level of a gene was considered medium or moderate if the $Ct_{gene}$ was less than 29 and greater than or equal to 22. The expression level of a gene was considered high if the $Ct_{gene}$ was less than 22.

As shown in Table 4 below, epithelial cells grown in KSFM plus A 83-01 and Y-27632 expressed high levels of genes that typically are expressed in basal epithelial cells (ITGA6, ITGB4, KRT14, KRT15, KRT5 and TP63). These cells also lacked expression of certain pluripotent stem cell markers such as LIN28A, NANOG, POU5F1/OCT4 and SOX2, and they expressed a moderate level of KLF4. The cells also did not express or expressed very low levels of genes that typically are expressed in terminally differentiated epithelial cells, including CFTR, FOXJ1, IVL, KRT1, KRT10, KRT20, LOR, MUC1, MUC5AC, SCGB1A1, SFTPB and SFTPD. None of the genes highly expressed in gastric, intestinal, or pancreatic epithelial cells were detected in the cells grown in KSFM plus A 83-01 and Y-27632, including CD34, HNF1A, HNF4A, IHH, KIT, LGR5, PDX1, and PROM1/CD133.

TABLE 4

Gene expression profile of epithelial cells grown in KSFM plus A83-01 and Y-27632

| | | | | | | | Foreskin Keratinocyte | | | Airway Epithelial Cells | |
|---|---|---|---|---|---|---|---|---|---|---|---|
| Gene Name | GenBank | Description | Small Intestine | Lung | KSFM (p2) | KSFM (p6) | KSFM + A + Y (p2) | KSFM + A + Y (p13) | KSFM + A + Y (p23) | KSFM + A + Y (p2) | KSFM + A + Y (p8) |
| *Genes that are enriched in basal epithelial cells* | | | | | | | | | | | |
| ITGA6 | NM_000210 | Integrin, Alpha 6 | 0.032 | 0.015 | 0.25 | 0.27 | 0.17 | 0.21 | 0.39 | 0.22 | 0.21 |
| ITGB4 | NM_000213 | Integrin, Beta 4 | 0.0041 | 0.0019 | 0.039 | 0.047 | 0.031 | 0.027 | 0.018 | 0.034 | 0.026 |
| KRT14 | NM_000526 | Keratin 14, Type I | 0.00016 | 0.00021 | 1.45 | 0.85 | 2.53 | 2.19 | 2.63 | 1.19 | 1.21 |
| KRT15 | NM_002275 | Keratin 15, Type I | 0.0002 | 0.0015 | 0.058 | 0.053 | 0.35 | 0.086 | 1.03 | 0.25 | 0.13 |
| KRT5 | NM_000424 | Keratin 5, Type II | 0.00013 | 0.0028 | 0.73 | 0.91 | 1.52 | 1.53 | 1.66 | 1.47 | 1.03 |
| TP63 | NM_003722 | Tumor Protein P63 | ND | 0.00057 | 0.046 | 0.043 | 0.092 | 0.047 | 0.033 | 0.066 | 0.03 |
| *Markers for pluripotent stem cells* | | | | | | | | | | | |
| KLF4 | NM_004235 | Kruppel-Like Factor 4 | 0.022 | 0.038 | 0.014 | 0.011 | 0.044 | 0.028 | 0.036 | 0.024 | 0.012 |
| LIN28A | NM_024674 | Lin-28 Homolog A | 0.00085 | 0.00031 | ND | ND | 0.00012 | ND | 0.00016 | ND | ND |
| NANOG | NM_024865 | Nanog Homeobox | 0.0013 | 0.00057 | ND | 0.00031 | ND | ND | 0.00013 | 0.00044 | ND |
| POU5F1 | NM_002701 | POU Class 5 Homeobox 1 | 0.0011 | 0.00066 | 0.00046 | 0.00091 | 0.00040 | 0.00051 | 0.0015 | 0.00036 | 0.00039 |
| SOX2 | NM_003106 | SRY (Sex Determining Region Y)-Box 2 | 0.00036 | 0.00021 | ND | ND | ND | ND | ND | 0.0026 | 0.00097 |
| *Genes that are enriched in airway epithelial cells* | | | | | | | | | | | |
| BMP7 | NM_001719 | Bone Morphogenetic Protein 7 | 0.00058 | 0.00045 | ND | ND | ND | 0.00023 | 0.00095 | 0.0041 | 0.0041 |
| HEY2 | NM_012259 | Hes-Related Family BHLH Transcription Factor With YRPW Motif 2 | 0.0022 | 0.0022 | 0.00025 | ND | 0.00081 | ND | ND | 0.24 | 0.074 |
| NGFR | NM_002507 | Nerve Growth Factor Receptor | 0.00084 | 0.00011 | 0.00019 | 0.00011 | 0.0018 | 0.00095 | 0.000091 | 0.0046 | 0.0022 |

TABLE 4-continued

Gene expression profile of epithelial cells grown in KSFM plus A83-01 and Y-27632

| | | | | | Foreskin Keratinocyte | | | | | Airway Epithelial Cells | |
|---|---|---|---|---|---|---|---|---|---|---|---|
| Gene Name | GenBank | Description | Small Intestine | Lung | KSFM (p2) | KSFM (p6) | KSFM + A + Y (p2) | KSFM + A + Y (p13) | KSFM + A + Y (p23) | KSFM + A + Y (p2) | KSFM + A + Y (p8) |
| | | Gene that is enriched in keratinocytes | | | | | | | | | |
| ZFP42 | NM_174900 | ZFP42 Zinc Finger Protein | ND | ND | 0.00096 | 0.0012 | 0.00077 | 0.0013 | 0.0022 | ND | ND |
| | | Genes that make up keratin intermediate filaments | | | | | | | | | |
| KRT1 | NM_006121 | Keratin 1, Type II | 0.00029 | 0.00011 | ND | 0.00014 | ND | 0.00058 | 0.0015 | ND | ND |
| KRT10 | NM_000421 | Keratin 10, Type I | ND | ND | ND | ND | 0.00024 | 0.00078 | 0.020 | 0.00051 | ND |
| KRT14 | NM_000526 | Keratin 14, Type I | 0.00015 | 0.00021 | 1.45 | 0.84 | 2.53 | 2.19 | 2.62 | 1.19 | 1.21 |
| KRT15 | NM_002275 | Keratin 15, Type I | 0.0002 | 0.0015 | 0.057 | 0.053 | 0.35 | 0.085 | 1.03 | 0.25 | 0.13 |
| KRT16 | NM_005557 | Keratin 16, Type I | ND | 0.00016 | 0.0045 | 0.032 | 0.088 | 0.038 | 0.050 | 0.024 | 0.015 |
| KRT18 | NM_000224 | Keratin 18, Type I | 0.058 | 0.015 | 0.075 | 0.063 | 0.13 | 0.043 | 0.024 | 0.048 | 0.025 |
| KRT19 | NM_002276 | Keratin 19, Type I | 0.13 | 0.043 | 0.16 | 0.39 | 0.077 | 0.33 | 0.81 | 0.62 | 0.41 |
| KRT20 | NM_019010 | Keratin 20, Type I | 0.078 | ND | ND | ND | ND | ND | ND | ND | ND |
| KRT4 | NM_002272 | Keratin 4, Type II | 0.00029 | 0.00076 | ND | 0.00015 | 0.00013 | 0.0048 | 0.40 | 0.0039 | 0.0098 |
| KRT5 | NM_000424 | Keratin 5, Type II | 0.00012 | 0.0027 | 0.72 | 0.91 | 1.51 | 1.52 | 1.66 | 1.47 | 1.032 |
| KRT6A | NM_005554 | Keratin 6A, Type II | 0.00015 | 0.086 | 0.54 | 1.34 | 0.75 | 0.87 | 2.87 | 0.85 | 0.75 |
| KRT7 | NM_005556 | Keratin 7, Type II | ND | 0.023 | 0.041 | 0.11 | 0.0049 | 0.00014 | 0.0011 | 0.023 | 0.045 |
| KRT8 | NM_002273 | Keratin 8, Type II | 0.0080 | 0.0017 | 0.0011 | 0.0011 | 0.0010 | 0.00097 | 0.00023 | 0.0010 | 0.00023 |
| | | Genes that are expressed in terminally differentiated cells | | | | | | | | | |
| CFTR | NM_000492 | Cystic Fibrosis Transmembrane Conductance Regulator | 0.0013 | 0.00069 | ND | ND | ND | ND | ND | ND | ND |
| FOXJ1 | NM_001454 | Forkhead Box J1 | ND | 0.0043 | ND | ND | ND | ND | ND | ND | ND |
| IVL | NM_005547 | Involucrin | ND | ND | 0.00066 | 0.022 | 0.00085 | 0.0027 | 0.19 | 0.00039 | 0.0023 |
| KRT1 | NM_006121 | Keratin 1, Type II | 0.00029 | 0.00011 | ND | 0.00014 | ND | 0.00058 | 0.0015 | ND | ND |
| KRT10 | NM_000421 | Keratin 10, Type I | ND | ND | ND | ND | 0.00024 | 0.00078 | 0.020 | 0.00051 | 0.000083 |
| KRT20 | NM_019010 | Keratin 20, Type I | 0.078 | ND | ND | ND | ND | ND | ND | ND | ND |
| LOR | NM_000427 | Loricrin | ND | ND | ND | ND | ND | ND | 0.00016 | ND | ND |
| MUC1 | NM_001018016 | Mucin 1, Cell Surface Associated | 0.00066 | 0.018 | ND | 0.00047 | 0.00034 | 0.00022 | 0.0030 | 0.00021 | 0.00023 |
| MUC5AC | XM_003403450 | Mucin 5AC, Oligomeric Mucus/Gel-Forming | ND | ND | ND | ND | ND | ND | ND | ND | ND |
| SCGB1A1 | NM_003357 | Secretoglobin, Family 1A, Member 1 | ND | 0.18 | ND | ND | ND | ND | ND | ND | ND |
| SFTPB | NM_000542 | Surfactant Protein B | ND | 0.082 | ND | ND | ND | ND | ND | ND | ND |
| SFTPD | NM_003019 | Surfactant Protein D | 0.00017 | 0.038 | ND | ND | ND | ND | 0.00027 | ND | ND |
| | | Markers for gastric/intestinal/pancreatic epithelium stem cells | | | | | | | | | |
| AXIN2 | NM_004655 | Axin 2 | 0.0050 | 0.0029 | ND | ND | ND | ND | ND | ND | ND |
| BMP4 | NM_130851 | Bone Morphogenetic Protein 4 | 0.0031 | 0.0017 | 0.00014 | 0.00014 | ND | 0.00022 | 0.00048 | 0.00035 | 0.00032 |
| BMP5 | NM_021073 | Bone Morphogenetic Protein 5 | 0.0043 | 0.017 | ND | ND | ND | ND | ND | ND | ND |
| BMP6 | NM_001718 | Bone Morphogenetic Protein 6 | 0.0019 | 0.0034 | ND | 0.00011 | ND | ND | ND | ND | ND |
| CD34 | NM_001773 | CD34 Molecule | 0.035 | 0.085 | ND | ND | 0.00010 | ND | ND | ND | ND |
| CFTR | NM_000492 | Cystic Fibrosis Transmembrane Conductance Regulator | 0.0013 | 0.00069 | ND | ND | ND | ND | ND | ND | ND |
| DLL4 | NM_019074 | Delta-Like 4 | 0.00039 | 0.0029 | ND | ND | ND | ND | ND | ND | ND |
| HNF1A | NM_000545 | HNF1 Homeobox A | 0.0046 | ND | ND | ND | ND | ND | ND | ND | ND |
| HNF4A | NM_178849 | Hepatocyte Nuclear Factor 4, Alpha | 0.0055 | ND | ND | ND | ND | ND | ND | ND | ND |
| IHH | NM_002181 | Indian Hedgehog | 0.00025 | ND | ND | ND | ND | ND | ND | ND | ND |
| KIT | NM_000222 | V-Kit Hardy-Zuckerman 4 Feline Sarcoma Viral Oncogene Homolog | 0.0021 | 0.0026 | ND | ND | ND | ND | ND | ND | ND |
| KRT20 | NM_019010 | Keratin 20, Type I | 0.078 | ND | ND | ND | ND | ND | ND | ND | ND |
| LGR5 | NM_003667 | Leucine-Rich Repeat Containing G Protein-Coupled Receptor 5 | 0.0017 | 0.00073 | ND | ND | ND | ND | ND | ND | ND |
| PDX1 | NM_000209 | Pancreatic And Duodenal Homeobox 1 | 0.0082 | ND | ND | ND | ND | ND | ND | ND | ND |
| PROM1 | NM_006017 | Prominin 1 | 0.0039 | 0.0017 | ND | ND | ND | ND | ND | ND | ND |

Example 9: Characterization of Epithelial Cells in Culture

In this example, certain characteristics are described for epithelial cells grown in various feeder-free and serum-free media conditions.

Differentiation of Bronchial Epithelial Cells into Bronchospheres

Figure 31:
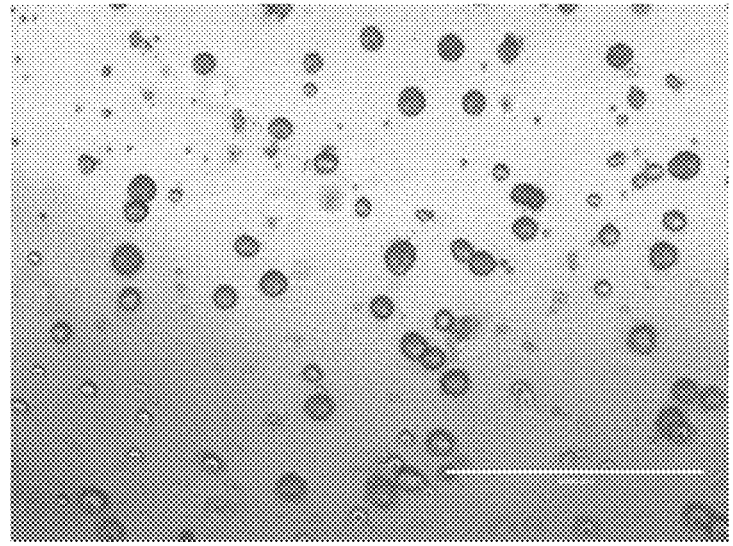
FIG. 31 shows differentiation of human bronchial epithelial cells (HBEC) into bronchospheres. The top panel shows cells viewed at lower (4x) magnification, and the bottom panel shows cells viewed at higher (20x) magnification. Large bronchospheres with visible lumen are shown in the bottom panel.
Figure 31:
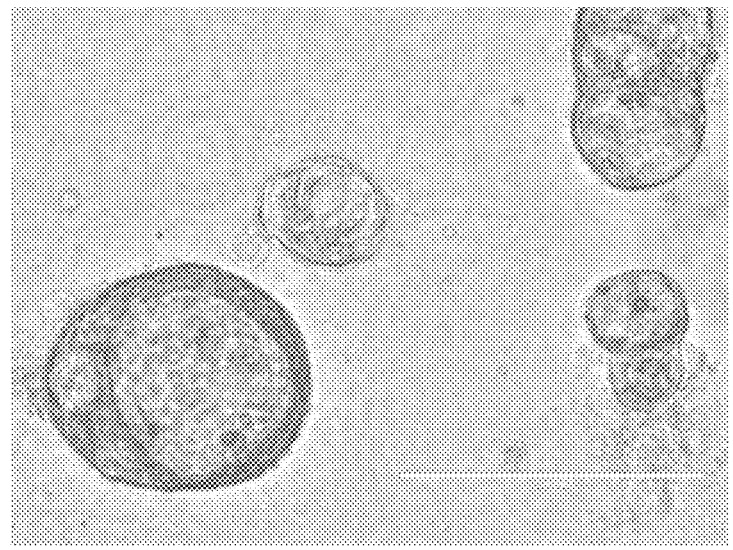
Figure 32A:
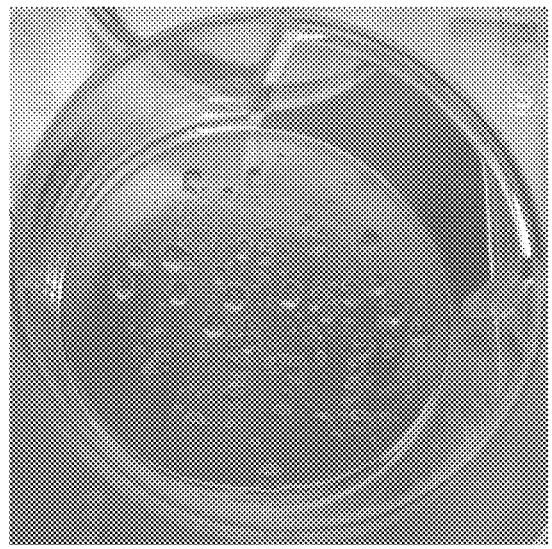
FIG. 32A to FIG. 32D show dome-like structures that form in human bronchial epithelial cell (HBEC) culture (FIG. 32A, FIG. 32B) and human foreskin keratinocyte (HFK) culture (FIG. 32C, FIG. 32D) in the presence of high concentration of $CaCl_2$.
Figure 32B:
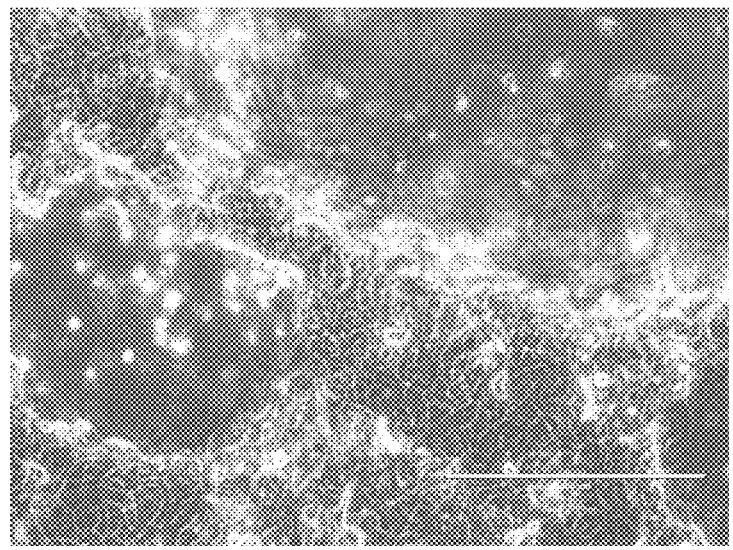
Figure 32C:
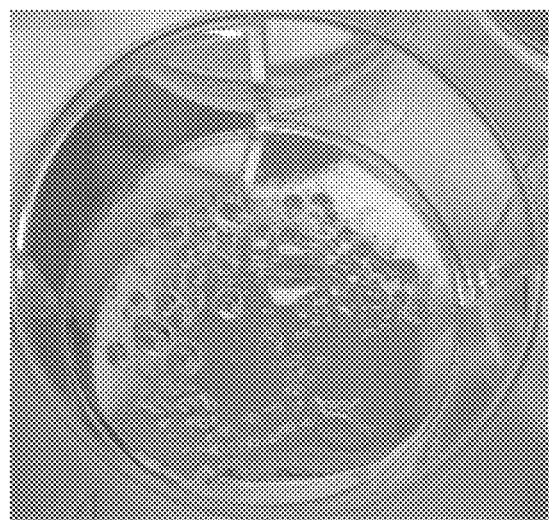
Figure 32D:
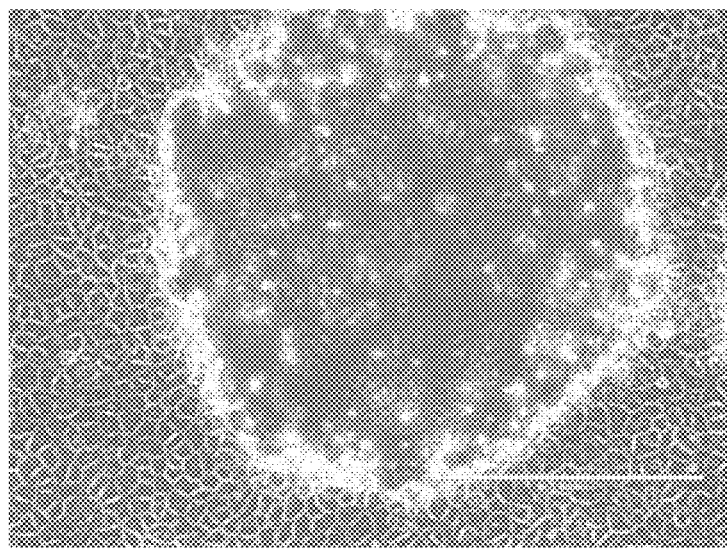

Passage 2 human bronchial epithelial cells cultured in KSFM supplemented with 1 µM A 83-01 and 5 µM Y-27632 (KSFM+A+Y) were removed from KSFM+A+Y conditions and embedded in Matrigel® as single cells, and cultured in Clonetics™ B-ALI™ air-liquid interface medium (high calcium differentiation medium, Lonza) for 14 days. FIG. 31 shows bronchial epithelial cells differentiated into bronchospheres. The top panel of FIG. 31 shows cells viewed at lower (4×) magnification, and the bottom panel of FIG. 31 shows cells viewed at higher (20×) magnification. Large bronchospheres with visible lumen are shown in the bottom panel of FIG. 31.

Characterization of Epithelial Cells after Exposure to High Calcium Concentrations Dome-like structures formed in keratinocyte and bronchial epithelial cell cultures in the presence of high concentration of $CaCl_2$. Specifically, late passage human bronchial epithelial cells (HBEC) and late passage human foreskin keratinocytes (HFK) cultured in KSFM supplemented with 1 µM A 83-01 and 5 µM Y-27632 (KSFM+A+Y) at low $CaCl_2$ (90 µM) were allowed to reach confluence in 6-well plates. The cells remained in the KSFM+A+Y conditions and the $CaCl_2$ concentration was raised to 1.5 mM to induce differentiation of the epithelial cells. Many dome-like structures were formed after 7 to 10 days and are shown in FIG. 32A to FIG. 32D.

Figure 33:
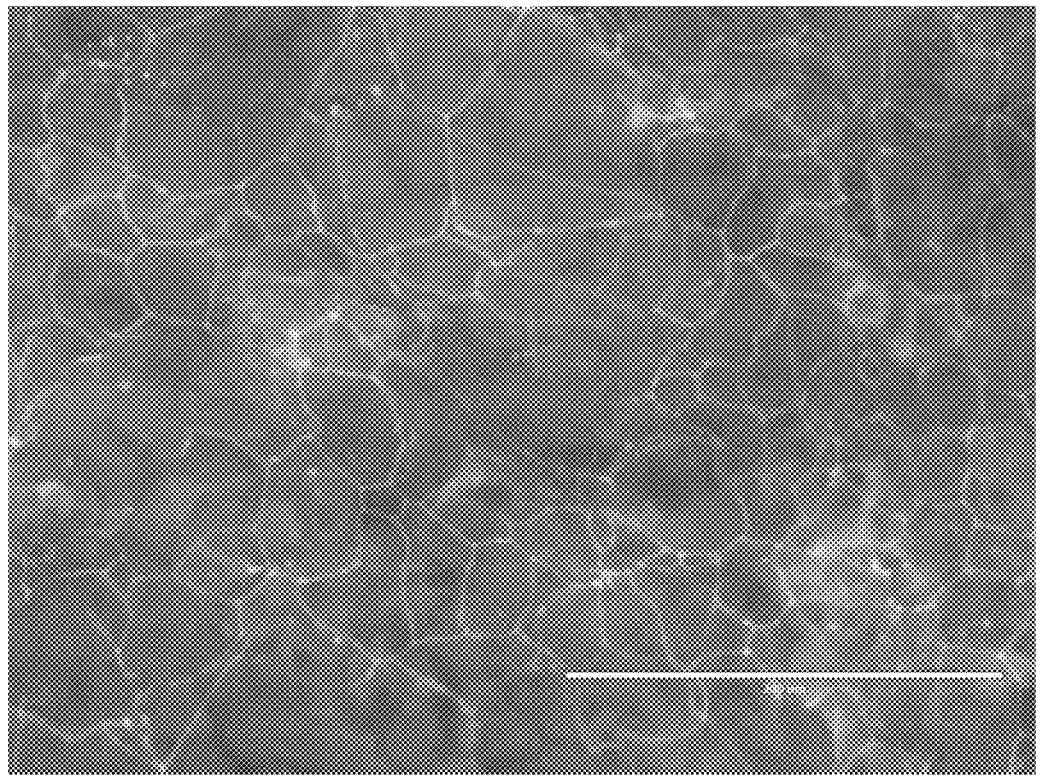
FIG. 33 shows tight junctions that form between human foreskin keratinocytes (HFK) after induced differentiation in the presence of high concentration of $CaCl_2$. The presence of intercellular tight junctions is revealed by immunofluorescence staining of tight junction protein ZO-1 using a monoclonal antibody conjugated to Alexa Fluor@ 488 (ThermoFisher, 339188).

Tight junction formation was observed between keratinocytes after exposure to a high concentration of $CaCl_2$. Specifically, late passage human foreskin keratinocytes (HFK) cultured in KSFM supplemented with 1 µM A83-01 and 5 µM Y-27632 (KSFM+A+Y) at low $CaCl_2$ (90 µM) were allowed to reach confluence. The cells remained in the KSFM+A+Y conditions and the $CaCl_2$ concentration was raised to 1.5 mM to induce differentiation. The presence of intercellular tight junctions was revealed by immunofluorescence staining of tight junction protein ZO-1 using a monoclonal antibody conjugated to Alexa Fluor® 488 (ThermoFisher, 339188), and is shown in FIG. 33.

Figure 34:
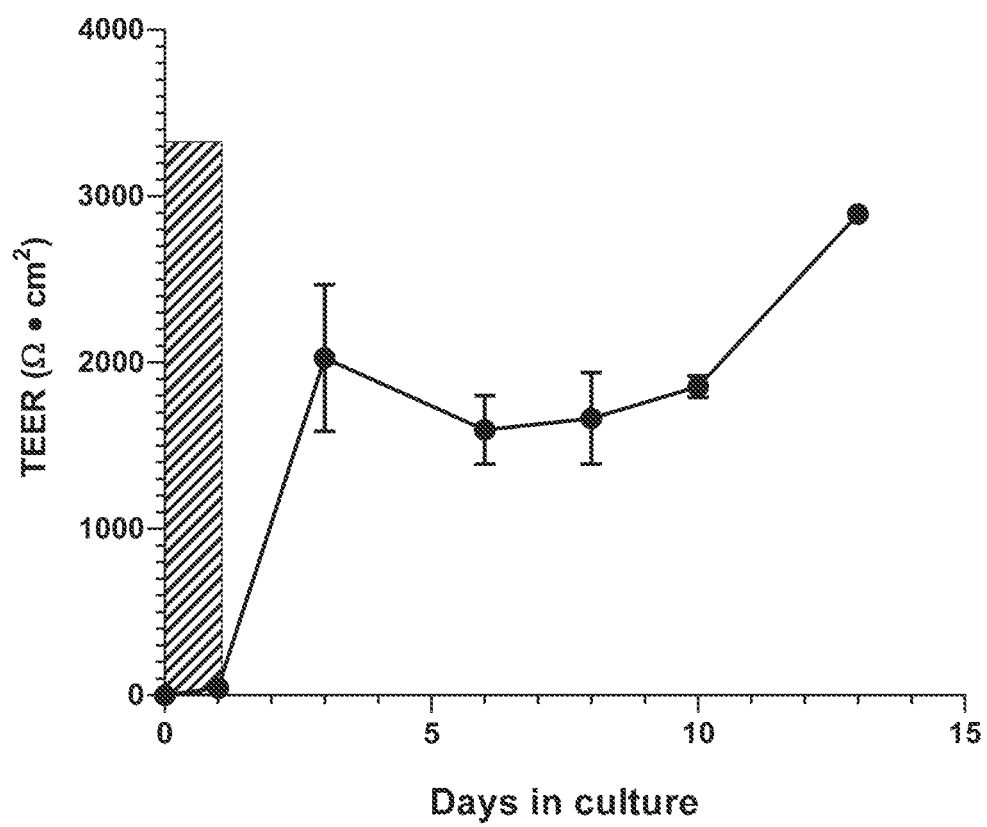
FIG. 34 shows human foreskin keratinocytes (HFK) with increasing transmembrane electric resistance (TEER) over time in air-liquid-interface differentiation, in the presence of high concentration of $CaCl_2$ in KSFM plus A 83-01 and Y-27632. Submerged phase is indicated by the grayed box.

Keratinocytes established increasing transmembrane electric resistance (TEER) over time in air-liquid-interface differentiation, in the presence of high concentration (1.5 mM) of $CaCl_2$ in KSFM plus A 83-01 and Y-27632. Specifically, human foreskin keratinocytes (HFK) previously cultured in KSFM supplemented with 1 µM A83-01 and 5 µM Y-27632 (KSFM+A+Y) at low $CaCl_2$ (90 µM) were plated on a porous membrane support (TRANSWELL, Corning, 354474) and maintained for 14 days. The cells were covered by culture medium (KSFM+A+Y and 1.5 mM of $CaCl_2$) for the first day (submerged phase, grayed box in FIG. 34) and exposed to air for the remaining days. As shown in FIG. 34, trans-epithelium electric resistance (TEER) reached very high levels throughout the culture period.

Figure 35:
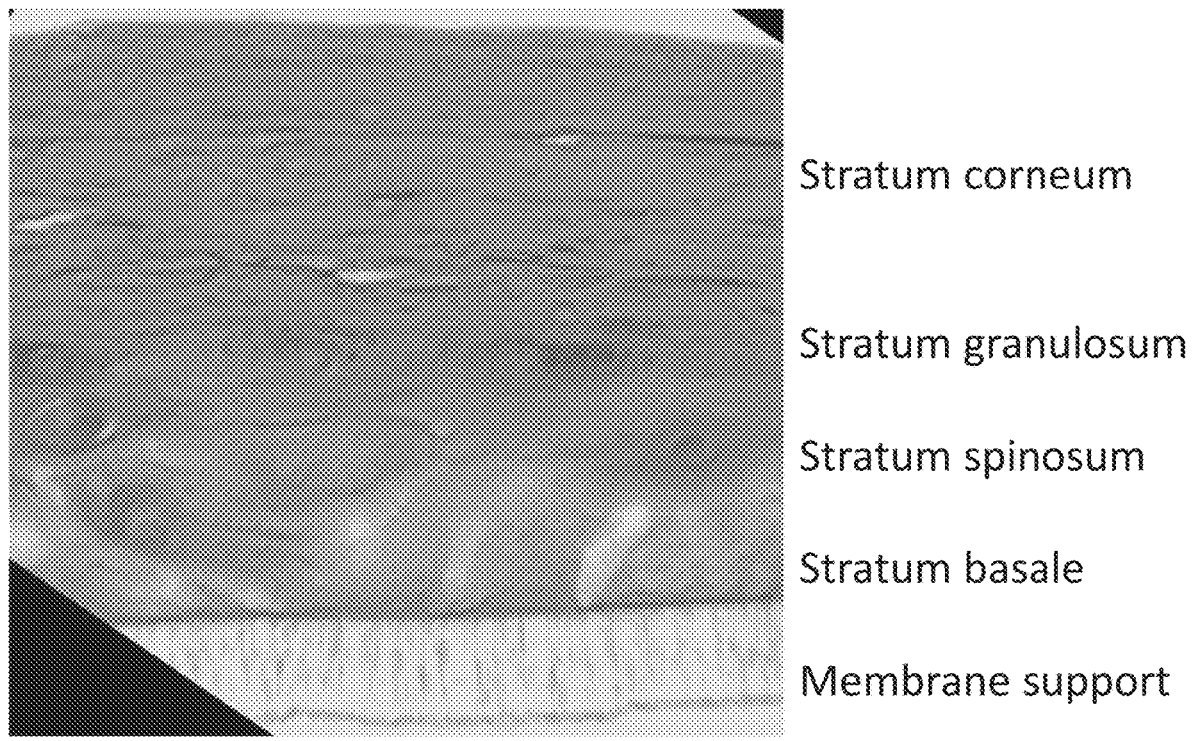
FIG. 35 shows human foreskin keratinocytes (HFK) form an epidermal-like structure over time in air-liquid-interface differentiation, in the presence of high concentration of $CaCl_2$ in KSFM plus A 83-01 and Y-27632. A multi-layer structure is shown, with layers resembling stratum corneum, stratum granulosm, stratum spinosum, and stratum basale.

Keratinocytes formed an epidermal-like structure over time in air-liquid-interface differentiation, in the presence of high concentration (1.5 mM) of $CaCl_2$ in KSFM plus A 83-01 and Y-27632. Specifically, human foreskin keratinocytes (HFK) previously cultured in KSFM supplemented with 1 µM A 83-01 and 5 µM Y-27632 (KSFM+A+Y) at low $CaCl_2$ (90 µM) were plated on a porous membrane support (TRANSWELL, Corning, 354474) and maintained for 14 days. The cells were covered by culture medium (KSFM+A+Y and 1.5 mM of $CaCl_2$) for the first day and exposed to air for the remaining days. At the end of experiment (i.e., on day 14), the culture was fixed in 4% paraformaldehyde, embedded in paraffin and sectioned for haematoxylin and eosin staining (H&E) to reveal its structure. As shown in FIG. 35, the cells had differentiated into multi-layer structures, with layers resembling stratum corneum, stratum granulosm, stratum spinosum, and stratum basale.

Further Characterization of Epithelial Cell Culture

Figure 36:
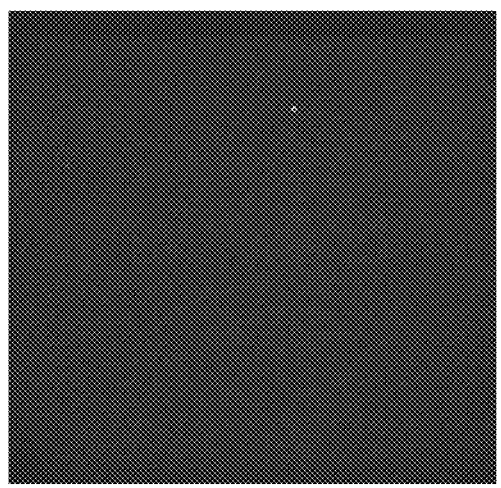
FIG. 36 shows single cell cloning of human foreskin keratinocytes (HFK) in KSFM plus A 83-01, Y-27632 and isoproterenol.
Figure 36:
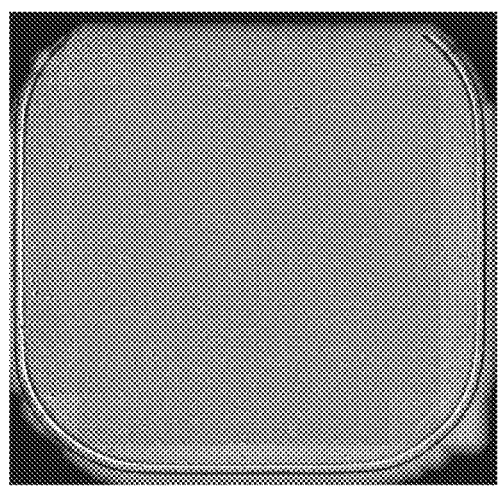
Figure 36:
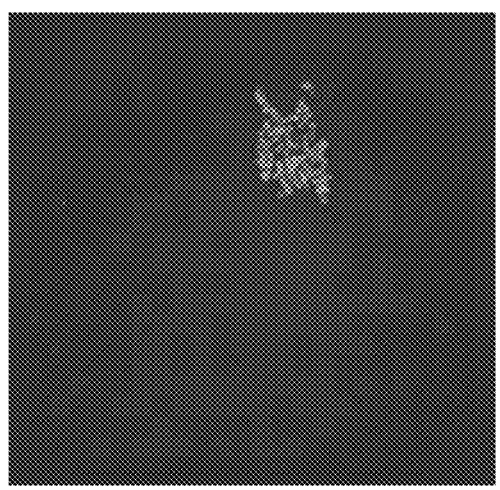
Figure 36:
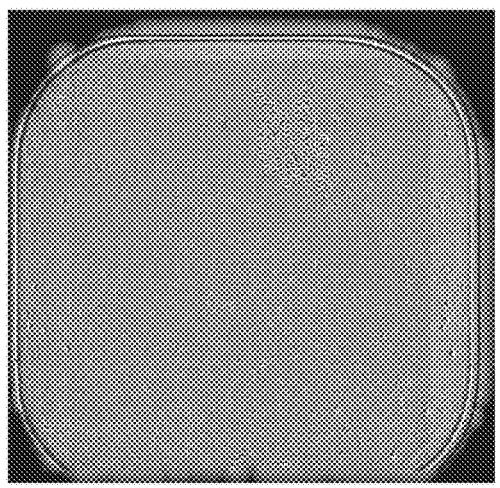
Figure 36:
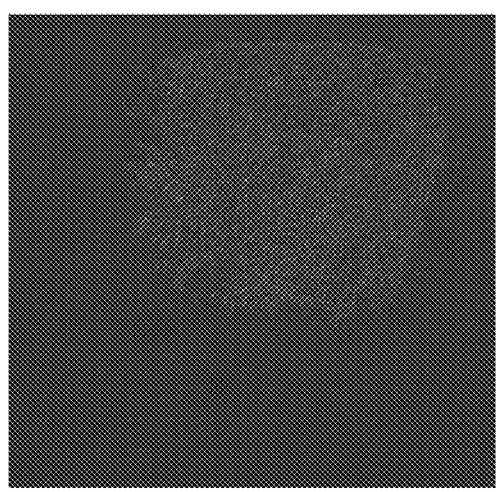
Figure 36:
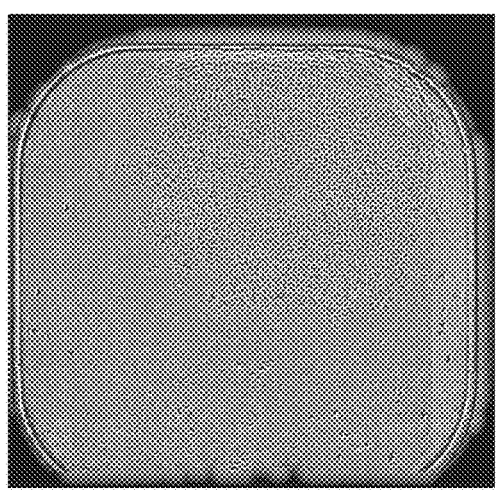

Single cell cloning and expansion of keratinocytes was examined. Specifically, a single human foreskin keratinocyte (HFK) at late passage (previously cultured in KSFM plus 1 µM A 83-01, 5 µM Y-27632 and 3 µM isoproterenol) was plated onto a collagen I coated 384-well plate and cultured in KSFM plus 1 µM A 83-01, 5 µM Y-27632 and 3 µM isoproterenol. Over 10 days, the cell divided into more than 1000 cells and formed a colony, as shown in FIG. 36.

Figure 37:
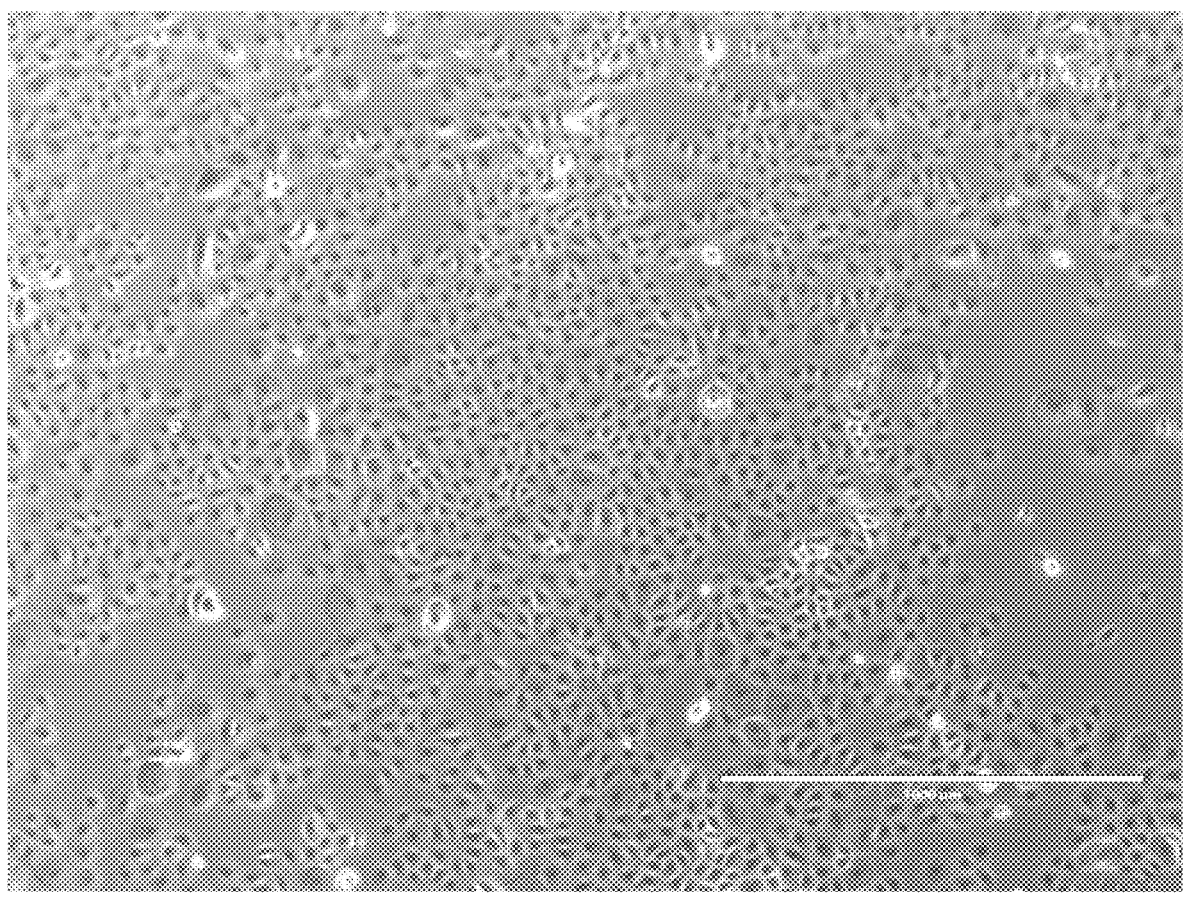
FIG. 37 shows heterogeneity in cellular morphology of human foreskin keratinocyte (HFK) progeny derived from a single cell.

Heterogeneity in cellular morphology was observed for keratinocyte progeny derived from a single cell. Specifically, the single-cell derived colony described above and shown in FIG. 36 was further expanded in a T-25 flask in KSFM plus 1 µM A 83-01, 5 µM Y-27632 and 3 µM isoproterenol. Heterogeneity in cellular morphology (e.g., cell size) was observed and is shown in FIG. 37. Mitotic cells were identified by a characteristic rounded morphology, a phase bright halo, and a central dark band (indicating condensed chromosomes).

Figure 38:
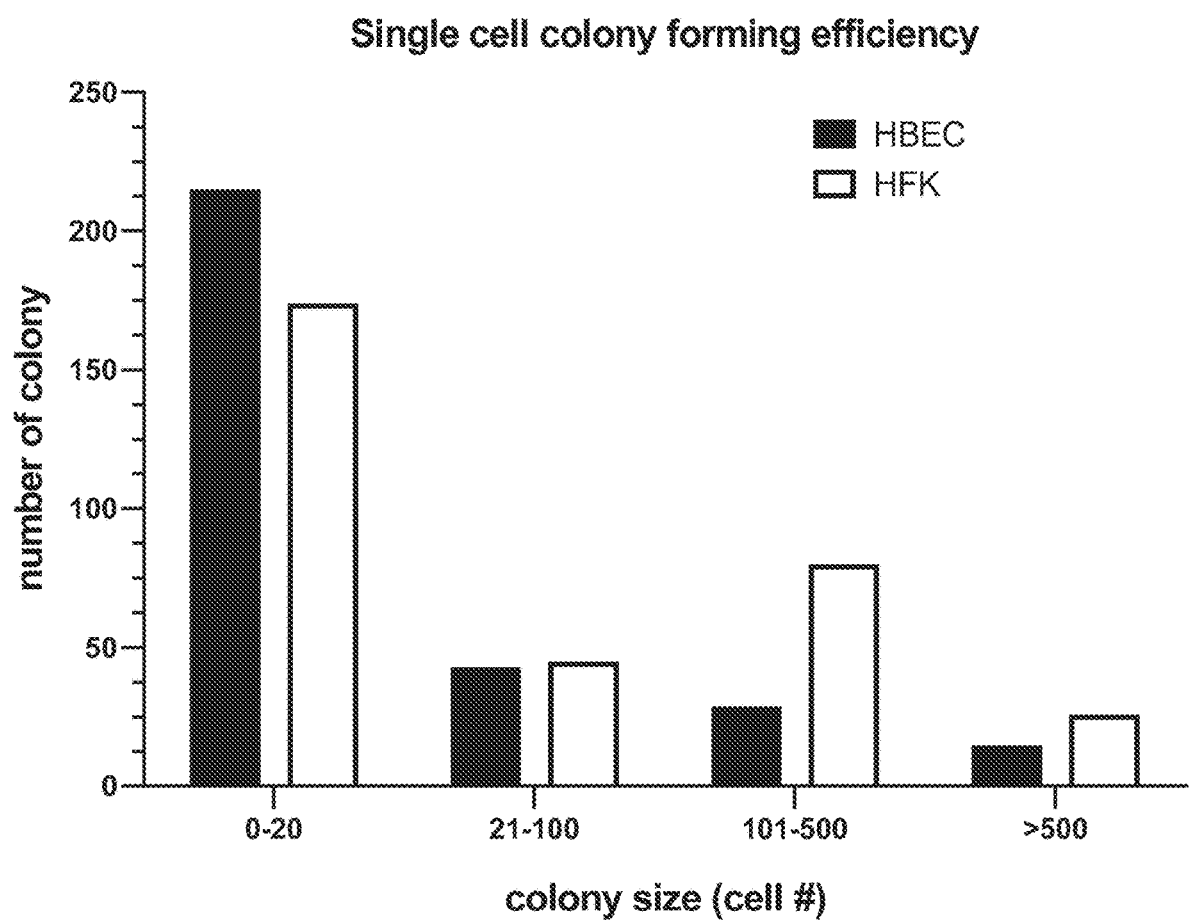
FIG. 38 shows single cell colony forming efficiency for human foreskin keratinocytes (HFK) and human bronchial epithelial cells (HBEC) cultured in KSFM plus A 83-01, Y-27632 and isoproterenol.

Single cell colony forming efficiency was examined for certain epithelial cell types cultured in KSFM plus A 83-01, Y-27632 and isoproterenol. Specifically, late passage human foreskin keratinocytes (HFK) and human bronchial epithelial cells (HBEC) previously cultured in KSFM plus 1 µM A 83-01, 5 µM Y-27632 and 3 µM isoproterenol were seeded onto collagen coated 384-well plates at one cell per well and allowed to grow for 10 days in KSFM plus 1 µM A 83-01, 5 µM Y-27632 and 3 µM isoproterenol. On day 10, the number of cells in each well was determined. The number of wells (i.e., colonies) having less than 20 cells, having 21-100 cells, having 101-500 cells, or having more than 500 cells were tallied and plotted, and the results are presented in FIG. 38.

Expansion of Epithelial Cells Cultured in Different Media Conditions

Epithelial cells from different tissues were cultured to evaluate their potential for expansion in different culture media. The cells were obtained from ThermoFisher/Gibco (HFKn and HEKa) or Lonza (HMEC, PrEC, HBEC, SAEC and DHBE-CF). Fold expansion was calculated using the formula $F=2^n$, where F=the fold of expansion after n population doublings, and the results are presented in Table 5 below.

TABLE 5

Fold expansion of epithelial cells

| Cell Type | Donor Age | Medium | Fold expansion | Population doublings |
|---|---|---|---|---|
| HFKn | neonatal | KSFM | 122,295 | 16.9 |
| HFKn | neonatal | KSFM + A + Y (*) | 3,115,599,965,857,640,000,000 | 71.4 |
| HFKn | neonatal | KSFM + A + IPA | 3,333,095,978,582 | 41.6 |

TABLE 5-continued

Fold expansion of epithelial cells

| Cell Type | Donor Age | Medium | Fold expansion | Population doublings |
|---|---|---|---|---|
| HFKn | neonatal | KSFM + A + B | 1,744,298,739 | 30.7 |
| HFKn | neonatal | KSFM + A + GSK | 315,751,799,532 | 38.2 |
| HEKa | adult | KSFM | 2,896 | 11.5 |
| HEKa | adult | KSFM + A + Y | 67,232,112,528,152,800 | 55.9 |
| HEKa | adult | KSFM + A + B | 416,636,997,323 | 38.6 |
| HEKa | adult | KSFM + A + GSK | 90,675,893,177 | 36.4 |
| HMEC | adult | KSFM | 5 | 2.3 |
| HMEC | adult | KSFM + A + Y | 15,314,887,470,577 | 43.8 |
| PrEC | adult | KSFM | 489,178 | 18.9 |
| PrEC | adult | PrGM | 4,390 | 12.1 |
| PrEC | adult | KSFM + A | 10,327,588 | 23.3 |
| PrEC | adult | KSFM + Y | 3,178,688 | 21.6 |
| PrEC | adult | KSFM + A + Y | 7,657,443,735,288 | 42.8 |
| PrEC | adult | KSFM + A + IPA | 9,206,463,941 | 33.1 |
| HBEC | adult | KSFM | 2,353 | 11.2 |
| HBEC | adult | KSFM + A | 1,123,836 | 20.1 |
| HBEC | adult | KSFM + Y | 561,918 | 19.1 |
| HBEC | adult | KSFM + A + Y | 228,628,724,347,545 | 47.7 |
| HBEC | adult | KSFM + A + IPA | 15,314,887,470,577 | 43.8 |
| SAEC | adult | KSFM | 21 | 4.4 |
| SAEC | adult | KSFM + A + Y (*) | 38,543,921 | 25.2 |
| DHBE-CF | adult (cystic fibrosis) | KSFM + A + Y | 5,173,277,483,525,740 | 52.2 |

HFKn, neonatal human foreskin keratinocyte.
HEKa, adult human epidermal keratinocyte.
HMEC, human mammary epithelial cells (female).
PrEC, human prostate epithelial cells.
HBEC, human bronchial epithelial cells.
SAEC, human small airway epithelial cells.
DHBE-CF, diseased human bronchial epithelial cells from cystic fibrosis patient.
*notes that the cell culture was voluntarily suspended after it achieved much more folds of expansion than in KSFM, the population was still undergoing active divisions when the experiment was suspended.
KSFM, Keratinocyte-SFM (Gibco/Thermo Fisher).
PrGM, Prostate Epithelial Cell Growth Medium (Lonza). A, ALK5 inhibitor A83-01.
Y, Rho kinase inhibitor (i.e., Rho-associated protein kinase inhibitor) Y-27632.
B, myosin II inhibitor blebbistatin.
IPA, Group I p21-activated kinase (PAK1) inhibitor.
GSK, Rho kinase inhibitor (i.e., Rho-associated protein kinase inhibitor) GSK-429286.

Example 10: Examples of Embodiments

The examples set forth below illustrate certain embodiments and do not limit the technology.

A1. A method for proliferating differentiated epithelial cells ex vivo, which method comprises:
 a) culturing differentiated epithelial cells under serum-free and feeder-cell free conditions; and
 b) inhibiting TGF-beta signaling in the differentiated epithelial cells during the culturing in (a).

A1.1 A method for proliferating formerly quiescent epithelial cells ex vivo, which method comprises:
 a) culturing formerly quiescent epithelial cells under serum-free and feeder-cell free conditions; and
 b) inhibiting TGF-beta signaling in the formerly quiescent epithelial cells during the culturing in (a).

A1.2 A method for proliferating lineage-committed epithelial cells ex vivo, which method comprises:
 a) culturing lineage-committed epithelial cells under serum-free and feeder-cell free conditions; and
 b) inhibiting TGF-beta signaling in the lineage-committed epithelial cells during the culturing in (a).

A2. A method for proliferating epithelial cells ex vivo, which method comprises:
 a) culturing epithelial cells under feeder-cell free conditions;
 b) inhibiting TGF-beta signaling in the epithelial cells during the culturing in (a); and
 c) inhibiting the activity of p21-activated kinase (PAK) in the epithelial cells during the culturing in (a).

A2.1 The method of embodiment A2, wherein the epithelial cells comprise differentiated epithelial cells.

A2.2 The method of embodiment A2, wherein the epithelial cells comprise formerly quiescent epithelial cells.

A2.3 The method of embodiment A2, wherein the epithelial cells comprise lineage-committed epithelial cells.

A3. A method for proliferating epithelial cells ex vivo, which method comprises:
 a) culturing epithelial cells under serum-free and feeder-cell free conditions;
 b) inhibiting TGF-beta signaling in the epithelial cells during the culturing in (a); and
 c) inhibiting the activity of myosin II in the epithelial cells during the culturing in (a).

A3.1 The method of embodiment A3, wherein the epithelial cells comprise differentiated epithelial cells.

A3.2 The method of embodiment A3, wherein the epithelial cells comprise formerly quiescent epithelial cells.

A3.3 The method of embodiment A3, wherein the epithelial cells comprise lineage-committed epithelial cells.

A3.4 The method of any one of embodiments A3 to A3.3, wherein the myosin II is a non-muscle myosin II (NM II).

A4. The method of any one of embodiments A2 to A3.4, wherein the culturing in (a) is performed in the presence of a serum containing medium.

A4.1 The method of any one of embodiments A2 to A3.4, wherein the culturing in (a) is performed in the presence of a serum-free medium.

A5. A method for proliferating differentiated epithelial cells ex vivo, which method comprises:
 a) culturing differentiated epithelial cells under feeder-cell free conditions;
 b) activating telomerase reverse transcriptase in the differentiated epithelial cells; and
 c) modulating cytoskeletal structure in the differentiated epithelial cells.

A5.1 A method for proliferating formerly quiescent epithelial cells ex vivo, which method comprises:
 a) culturing formerly quiescent epithelial cells under feeder-cell free conditions;
 b) activating telomerase reverse transcriptase in the formerly quiescent epithelial cells; and
 c) modulating cytoskeletal structure in the formerly quiescent epithelial cells.

A5.2 A method for proliferating lineage-committed epithelial cells ex vivo, which method comprises:
 a) culturing lineage-committed epithelial cells under feeder-cell free conditions;
 b) activating telomerase reverse transcriptase in the lineage-committed epithelial cells; and
 c) modulating cytoskeletal structure in the lineage-committed epithelial cells.

A5.3 The method of embodiment A5, A5.1 or A5.2, wherein TGF-beta signaling is inhibited in (b).

A5.4 The method of any one of embodiments A1 to A5.3, wherein (a) and (b) are performed at the same time; or wherein (a), (b) and (c) are performed at the same time.

A5.5 The method of any one of embodiments A1 to A5.4, wherein the epithelial cells are frozen and thawed prior to (a).

A6. The method of any one of embodiments A1 to A5.5, wherein the activity of one or more TGF-beta receptors is inhibited in (b).

A7. The method of embodiment A6, wherein one or more TGF-beta receptor-ligand interactions are inhibited in (b).

A8. The method of embodiment A6 or A7, wherein the one or more TGF-beta receptors comprise a TGF-beta type I receptor.

A9. The method of embodiment A8, wherein the TGF-beta type I receptor is selected from ALK1, ALK2, ALK3, ALK4, ALK5, ALK6, ALK7 and ALK8.

A10. The method of embodiment A8, wherein the one or more TGF-beta receptors comprise ALK5.

A11. The method of any one of embodiments A1 to A10, wherein inhibiting TGF-beta signaling comprises use of one or more TGF-beta inhibitors and/or one or more TGF-beta signaling inhibitors.

A12. The method of embodiment A11, wherein the one or more TGF-beta inhibitors and/or the one or more TGF-beta signaling inhibitors bind to one or more TGF-beta receptors or one or more TGF-beta ligands or both.

A13. The method embodiment A11 or A12, wherein the one or more TGF-beta inhibitors and/or the one or more TGF-beta signaling inhibitors disrupt one or more TGF-beta receptor-ligand interactions.

A14. The method of embodiment A11, A12 or A13, wherein the one or more TGF-beta inhibitors and/or the one or more TGF-beta signaling inhibitors do not comprise a recombinant protein.

A15. The method of any one of embodiments A11 to A14, wherein the one or more TGF-beta inhibitors and/or the one or more TGF-beta signaling inhibitors do not comprise Noggin, DAN, Cerberus or Gremlin.

A16. The method of any one of embodiments A11 to A15, wherein the one or more TGF-beta inhibitors and/or the one or more TGF-beta signaling inhibitors comprise one or more ALK5 inhibitors.

A17. The method of embodiment A16, wherein the one or more ALK5 inhibitors comprise one or more small molecule ALK5 inhibitors.

A18. The method of embodiment A17, wherein the one or more ALK5 inhibitors comprise one or more ATP analogs.

A19. The method of any one of embodiments A16 to A18, wherein at least one of the one or more ALK5 inhibitors comprises the structure of Formula A:

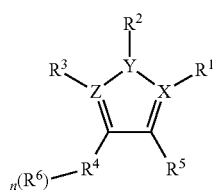

Formula A wherein:
X, Y and Z independently are chosen from N, C and O;
$R^1$, $R^2$ and $R^3$ independently are chosen from hydrogen, C1-C10 alkyl, substituted C1-C10 alkyl, C3-C9 cycloalkyl, substituted C3-C9 cycloalkyl, C5-C10 aryl, substituted C5-C10 aryl, C5-C10 cycloaryl, substituted C5-C10 cycloaryl, C5-C9 heterocyclic, substituted C5-C9 heterocyclic, C5-C9 hetercycloaryl, substituted C5-C9 heterocycloaryl, -linker-(C3-C9 cycloalkyl), -linker-(substituted C3-C9 cycloalkyl), -linker-(C5-C10 aryl), -linker-(substituted C5-C10 aryl), -linker-(C5-C10 cycloaryl), -linker-(substituted C5-C10 cycloaryl), -linker-(C5-C9 heterocyclic), -linker-(substituted C5-C9 heterocyclic), -linker-(C5-C9 hetercycloaryl), -linker-(substituted C5-C9 heterocycloaryl);
n is 0 or 1;
$R^4$, $R^5$ and $R^6$ independently are chosen from hydrogen, C1-C10 alkyl, substituted C1-C10 alkyl, C1-C10 alkoxy, substituted C1-C10 alkoxy, C1-C6 alkanoyl, C1-C6 alkoxycarbonyl, substituted C1-C6 alkanoyl, substituted C1-C6 alkoxycarbonyl, C3-C9 cycloalkyl, substituted C3-C9 cycloalkyl, C5-C10 aryl, substituted C5-C10 aryl, C5-C10 cycloaryl, substituted C5-C10 cycloaryl, C5-C9 heterocyclic, substituted C5-C9 heterocyclic, C5-C9 hetercycloaryl, substituted C5-C9 heterocycloaryl, -linker-(C3-C9 cycloalkyl), -linker-(substituted C3-C9 cycloalkyl), -linker-(C5-C10 aryl), -linker-(substituted C5-C10 aryl), -linker-(C5-C10 cycloaryl), -linker-(substituted C5-C10 cycloaryl), -linker-(C5-C9 heterocyclic), -linker-(substituted C5-C9 heterocyclic), -linker-(C5-C9 hetercycloaryl), -linker-(substituted C5-C9 heterocycloaryl); and
the substituents on the substituted alkyl, alkoxy, alkanoyl, alkoxycarbonyl cycloalkyl, aryl, cycloaryl, heterocyclic or heterocycloaryl groups are hydroxyl, C1-C10 alkyl, hydroxyl C1-C10 alkylene, C1-C6 alkoxy, C3-C9 cycloalkyl, C5-C9 heterocyclic, C1-6 alkoxy C1-6 alkenyl, amino, cyano, halogen or aryl.

A20. The method of anyone of embodiments A16 to A19, wherein the one or more ALK5 inhibitors are selected from A83-01, GW788388, RepSox, and SB 431542.

A21. The method of embodiment A20, wherein the one or more ALK5 inhibitors comprise A83-01.

A22. The method of any one of embodiments A16 to A21, wherein the one or more ALK5 inhibitors binds to ALK5 or one or more ALK5 ligands or both.

A23. The method of any one of embodiments A16 to A22, wherein the one or more ALK5 inhibitors disrupt one or more ALK5-ligand interactions.

A24. The method of any one of embodiments A1 to A23, wherein the method comprises activating telomerase reverse transcriptase the epithelial cells.

A24.1 The method of any one of embodiments A1 to A24, wherein the method comprises modulating cytoskeletal structure in the epithelial cells.

A24.2 The method of any one of embodiments A1 to A24.1, wherein the method comprises:
a) activating telomerase reverse transcriptase the epithelial cells; and
b) modulating cytoskeletal structure in the epithelial cells.

A25. The method of any one of embodiments A1 to A24.2, further comprising inhibiting the activity of Rho kinase and/or Rho-associated protein kinase in the epithelial cells during the culturing in (a).

A26. The method of embodiment A25, wherein Rho kinase and/or Rho-associated protein kinase is selected from Rho kinase 1 (ROCK 1) and Rho kinase 2 (ROCK 2).

A27. The method of embodiment A25 or A26, wherein inhibiting the activity of Rho kinase and/or Rho-associated protein kinase comprises use of one or more Rho kinase inhibitors and/or one or more Rho-associated protein kinase inhibitors.

A28. The method of embodiment A27, wherein the one or more Rho kinase inhibitors and/or the one or more Rho-associated protein kinase inhibitors comprise one or more small molecule Rho kinase inhibitors and/or one or more small molecule Rho-associated protein kinase inhibitors.

A29. The method of embodiment A28, wherein the one or more Rho kinase inhibitors and/or the one or more Rho-associated protein kinase inhibitors is selected from Y-27632, SR 3677, thiazovivin, HA1100 hydrochloride, HA1077 and GSK-429286.

A30. The method of embodiment A29, wherein the one or more Rho kinase inhibitors and/or the one or more Rho-associated protein kinase inhibitors comprise Y-27632.

A30.1 The method of any one of embodiments A1 to A24, which does not comprise inhibiting the activity of Rho kinase and/or Rho-associated protein kinase in the epithelial cells during the culturing in (a).

A31. The method of any one of embodiments A1 to A30.1, further comprising inhibiting the activity of p21-activated kinase (PAK) in the epithelial cells during the culturing in (a).

A32. The method of embodiment A31, wherein the PAK is selected from PAK1, PAK2, PAK3 and PAK4.

A33. The method of embodiment A32, wherein the PAK is PAK1.

A34. The method of embodiment A33, wherein inhibiting the activity of PAK1 comprises use of one or more PAK1 inhibitors.

A35. The method of embodiment A34, wherein the one or more PAK1 inhibitors comprise one or more small molecule PAK1 inhibitors.

A36. The method of embodiment A35, wherein the one or more PAK1 inhibitors comprise IPA3.

A37. The method of any one of embodiments A1 to A36, further comprising inhibiting the activity of myosin II in the epithelial cells during the culturing in (a).

A37.1 The method of embodiment A37, wherein the myosin II is a non-muscle myosin II (NM 1*l*).

A37.2 The method of embodiment A37 or A37.1, wherein inhibiting the activity of myosin comprises use of one or more myosin II inhibitors.

A37.3 The method of embodiment A37.2, wherein the one or more myosin II inhibitors comprise one or more small molecule myosin II inhibitors.

A37.4. The method of embodiment A37.2 or A37.3, wherein the one or more myosin II inhibitors comprise blebbistatin.

A38. The method of any one of embodiments A1 to A37.4, further comprising increasing intracellular cyclic adenosine monophosphate (cAMP) levels in the epithelial cells during the culturing in (a).

A39. The method of embodiment A38, wherein increasing intracellular cyclic adenosine monophosphate (cAMP) levels comprises use of one or more beta-adrenergic agonists and/or one or more beta-adrenergic receptor agonists.

A39.1 The method of embodiment A39, where the one or more beta-adrenergic agonists and/or the one or more beta-adrenergic receptor agonists comprise isoproterenol.

A40. The method of any one of embodiments A1 to A39.1, wherein the epithelial cells are obtained from a subject prior to (a).

A40.1 The method of embodiment A40, wherein the subject is a mammal.

A40.2 The method of embodiment A40, wherein the subject is a human.

A40.3 The method of any one of embodiments A40 to A40.2, wherein the epithelial cells are from tissue from a subject.

A40.4 The method of embodiment A40.3, wherein the epithelial cells are from differentiated tissue from a subject.

A40.5 The method of any one of embodiments A40 to A40.2, wherein the epithelial cells are from circulating cells from a subject.

A41. The method of any one of embodiments A40 to A40.5, wherein the epithelial cells comprise primary cells from a subject.

A42. The method of any one of embodiments A40 to A40.5, wherein the epithelial cells do not comprise primary cells from a subject.

A43. The method of any one of embodiments A40 to A42, wherein the epithelial cells comprise tumor cells from a subject.

A44. The method of any one of embodiments A41 to A43, wherein the epithelial cells from a subject are selected from squamous cells, columnar cells, adenomatous cells and transitional epithelial cells.

A44.1 The method of any one of embodiments A41 to A43, wherein the epithelial cells from a subject comprise one or more of squamous cells, columnar cells, adenomatous cells and transitional epithelial cells.

A45. The method of any one of embodiments A41 to A44.1, wherein the epithelial cells from a subject comprise keratinocyte epithelial cells.

A45.1 The method of embodiment A45, wherein the keratinocyte epithelial cells are selected from dermal keratinocytes, ocular epithelial cells, corneal epithelial cells, oral mucosal epithelial cells, esophagus epithelial cells, and cervix epithelial cells.

A46. The method of any one of embodiments A41 to A44, wherein the epithelial cells from a subject comprise non-keratinocyte epithelial cells.

A47. The method of embodiment A46, wherein the non-keratinocyte epithelial cells comprise glandular epithelial cells.

A48. The method of embodiment A46 or A47, wherein the non-keratinocyte epithelial cells are selected from prostate cells, mammary cells, hepatocytes, liver epithelial cells, biliary epithelial cells, gall bladder cells, pancreatic islet cells, pancreatic beta cells, pancreatic ductal epithelial cells, pulmonary epithelial cells, airway epithelial cells, nasal epithelial cells, kidney cells, bladder cells, urethral epithelial cells, stomach epithelial cells, large intestinal epithelial cells, small intestinal epithelial cells, testicular epithelial cells, ovarian epithelial cells, fallopian tube epithelial cells, thyroid cells, parathyroid cells, adrenal cells, thymus cells, pituitary cells, glandular cells, amniotic epithelial cells, retinal pigmented epithelial cells, sweat gland epithelial cells, sebaceous epithelial cells and hair follicle cells.

A48.1 The method of any one of embodiments A1 to A47, wherein the epithelial cells comprise basal epithelial cells.

A48.2 The method of any one of embodiments A1 to A47, wherein the epithelial cells are not intestinal epithelial cells.

A49. The method of any one of embodiments A1 to A48.2, wherein the culturing in (a) is performed in the presence of a serum-free medium.

A49.1 The method of embodiment A49, wherein the serum-free medium is a defined serum-free medium.

A49.2 The method of embodiment A49, wherein the serum-free medium is a xeno-free serum-free medium.

A49.3 The method of embodiment A49, wherein the serum-free medium is a defined xeno-free serum-free medium.

A50. The method of any one of embodiments A49 to A49.3, wherein the serum-free medium comprises calcium.

A51. The method of embodiment A50, wherein the serum-free medium comprises calcium at a concentration below 1 mM.

A52. The method of embodiment A50, wherein the serum-free medium comprises calcium at a concentration below 500 μM.

A53. The method of embodiment A50, wherein the serum-free medium comprises calcium at a concentration below 100 μM.

A53.1 The method of embodiment A53, wherein the serum-free medium comprises calcium at a concentration of about 90 μM.

A54. The method of embodiment A50, wherein the serum-free medium comprises calcium at a concentration below 20 μM.

A54.1 The method of any one of embodiments A49 to A54, wherein the serum-free medium comprises a buffer and one or more components selected from inorganic acids, salts, alkali silicates, amino acids, vitamins, purines, pyrimidines, polyamines, alpha-keto acids, organosulphur compounds and glucose.

A54.2 The method of embodiment A54.1, wherein the one or more salts are selected from sodium chloride, potassium chloride, sodium acetate, and sodium phosphate.

A54.3 The method of embodiment A54.1 or A54.2, wherein the one or more amino acids are selected from arginine and glutamine.

A54.4 The method of any one of embodiments A54.1 to A54.3, wherein the buffer is HEPES buffer.

A54.5 The method any one of embodiments A49 to A54.4, wherein the serum-free medium comprises albumin.

A54.6 The method of embodiment A54.5, wherein the albumin is selected from bovine serum albumin and recombinant human serum albumin.

A54.7 The method any one of embodiments A49 to A54.6, wherein the serum-free medium comprises one or more lipids.

A54.8 The method of embodiment A54.7, wherein the one or more lipids are selected from arachidonic acid, cholesterol, DL-alpha-tocopherol acetate, linoleic acid, linolenic acid, myristic acid, oleic acid, palmitic acid, palmitoleic acid, pluronic F-68, stearic acid, and polysorbate 80.

A54.9 The method of embodiment A54.8, wherein the one or more lipids are selected from linoleic acid, linolenic acid, oleic acid, palmitic acid, and stearic acid.

A55. The method of any one of embodiments A1 to A54.9, which comprises use of one or more mitogenic growth factors.

A56. The method of embodiment A55, wherein the one or more mitogenic growth factors comprise EGF.

A56.1 The method of embodiment A55, wherein the one or more mitogenic growth factors comprise FGF.

A56.2 The method of embodiment A55, wherein the one or more mitogenic growth factors comprise EGF and FGF.

A56.3 The method of embodiment A56.1 or A56.2, wherein the FGF comprises acidic FGF.

A57. The method of any one of embodiments A1 to A54.9, which does not comprise use of a mitogenic growth factor.

A58. The method of any one of embodiments A1 to A57, which comprises use of one or more mitogenic supplements.

A59. The method of embodiment A58, wherein the one or more mitogenic supplements comprise bovine pituitary extract (BPE).

A59.1 The method of any one of embodiments A1 to A57, which does not comprise use of a mitogenic supplement.

A60. The method of any one of embodiments A1 to A59.1, which does not comprise use of a Wnt agonist or a beta-catenin agonist.

A60.1 The method of any one of embodiments A1 to A60, which does not comprise use of one or more of components selected from: noggin, R-spondin, Wnt-3a, EGF, nicotinamide, FGF10, gastrin, a p38 inhibitor, SB202190, DHT, a notch inhibitor, a gamma secretase inhibitor, DBZ and DAPT.

A61. The method of any one of embodiments A1 to A60.1, which does not comprise use of an extracellular matrix.

A62. The method of any one of embodiments A1 to A60.1, wherein the culturing in (a) is performed in a container comprising a coating.

A63. The method of embodiment A62, wherein the coating comprises collagen.

A64. The method of embodiment A62, wherein the coating comprises a basement membrane matrix.

A65. The method of any one of embodiments A1 to A64, wherein the culturing in (a) comprises expanding the epithelial cells.

A66. The method of embodiment A65, wherein the epithelial cells are expanded at least about 2-fold.

A67. The method of embodiment A65, wherein the epithelial cells are expanded at least about 5-fold.

A68. The method of embodiment A65, wherein the epithelial cells are expanded at least about 10-fold.

A69. The method of embodiment A65, wherein the epithelial cells are expanded at least about 15-fold.

A70. The method of embodiment A65, wherein the epithelial cells are expanded at least about 20-fold.

A70.1 The method of embodiment A65, wherein the epithelial cells are expanded at least about 100-fold.

A70.2 The method of embodiment A65, wherein the epithelial cells are expanded at least about 1,000-fold.

A70.3 The method of embodiment A65, wherein the epithelial cells are expanded at least about 10,000-fold.

A70.4 The method of embodiment A65, wherein the epithelial cells are expanded at least about 100,000-fold.

A70.5 The method of embodiment A65, wherein the epithelial cells are expanded at least about 1 million-fold.

A70.6 The method of embodiment A65, wherein the epithelial cells are expanded at least about 1 billion-fold.

A70.7 The method of embodiment A65, wherein the epithelial cells are expanded at least about 1 trillion-fold.

A71. The method of any one of embodiments A65 to A70.7, wherein the epithelial cells are cultured for about 4 days.

A72. The method of any one of embodiments A65 to A70.7, wherein the epithelial cells are cultured for about 5 days.

A73. The method of any one of embodiments A1 to A72, wherein the epithelial cells are continuously proliferated.

A74. The method of any one of embodiments A1 to A73, comprising passaging the epithelial cells at least 15 times.

A75. The method of any one of embodiments A1 to A73, comprising passaging the epithelial cells at least 25 times.

A76. The method of any one of embodiments A1 to A75, wherein a population of the epithelial cells doubles over a period of time.

A77. The method of embodiment A76, wherein the epithelial cell population doubles at least 20 times.

A78. The method of embodiment A76, wherein the epithelial cell population doubles at least 50 times.

A78.1 The method of embodiment A76, wherein the epithelial cell population doubles at least 80 times.

A79. The method of embodiment A76, wherein the epithelial cell population doubles at least 100 times.
A80. The method of embodiment A76, wherein the epithelial cell population doubles at least 120 times.
A81. The method of embodiment A76, wherein the epithelial cell population doubles at least 150 times.
A82. The method of embodiment A76, wherein the epithelial cell population doubles at least 200 times.
A83. The method of any one of embodiments A76 to A82, wherein the period of time is about 50 days.
A84. The method of any one of embodiments A76 to A82, wherein the period of time is about 100 days.
A85. The method of any one of embodiments A76 to A82, wherein the period of time is about 150 days.
A86. The method of any one of embodiments A76 to A82, wherein the period of time is about 200 days.
A87. The method of any one of embodiments A1 to A86, wherein the epithelial cells maintain one or more native functional characteristics during (b).
A88. The method of any one of embodiments A1 to A86, wherein the epithelial cells do not maintain one or more native functional characteristics during (b).
A89. The method of any one of embodiments A1 to A88, wherein the epithelial cells are placed after (b) into a cell culture environment wherein TGF-beta signaling is not inhibited.
A90. The method of embodiment A89, wherein the epithelial cells maintain or regain one or more native functional characteristics after placement into the cell culture environment wherein TGF-beta signaling is not inhibited.
A91. The method of any one of embodiments A1 to A90, wherein the epithelial cells can be induced to differentiate into multiple tissue types.
A91.1 The method of any one of embodiments A1 to A90, wherein the epithelial cells do not acquire the ability to differentiate into multiple tissue types.
A92. The method of any one of embodiments A1 to A91.1, wherein the epithelial cells do not acquire the ability to form organoids.
A93. The method of any one of embodiments A1 to A92, wherein the epithelial cells are not derived from embryonic stem cells.
A93.1 The method of any one of embodiments A1 to A93, wherein the epithelial cells are not derived from continuously proliferating epithelial stem cells.
A93.2 The method of any one of embodiments A1 to A93.1, wherein the epithelial cells are derived from epithelial tissue comprising quiescent epithelial cells.
A93.3 The method of any one of embodiments A1 to A93.2, which method does not comprise selecting for continuously proliferating epithelial stem cells.
A93.4 The method of any one of embodiments A1 to A93.3, which method does not comprise selecting for intestinal crypt cells.
A93.5 The method of any one of embodiments A1 to A93.4, which method does not comprise selecting for LGR5+ cells.
A94. The method of any one of embodiments A40 to A93.5, wherein the epithelial cells obtained from a subject and/or the epithelial cells in culture do not comprise continuously proliferating epithelial stem cells or cells derived from continuously proliferating epithelial stem cells.
A94.1 The method of any one of embodiments A40 to A94, wherein the epithelial cells obtained from a subject and/or the epithelial cells in culture do not comprise pluripotent stem cells or cells derived from pluripotent stem cells.
A94.2 The method of any one of embodiments A40 to A94.1, wherein the epithelial cells obtained from a subject and/or the epithelial cells in culture do not comprise terminally differentiated epithelial cells.
A94.3 The method of any one of embodiments A40 to A94.2, wherein the epithelial cells obtained from a subject and/or the epithelial cells in culture do not comprise gastric epithelial cells, intestinal epithelial cells, and/or pancreatic epithelial cells.
A94.4 The method of any one of embodiments A40 to A94.3, wherein the epithelial cells obtained from a subject and/or the epithelial cells in culture do not comprise intestinal crypt cells.
A94.5 The method of any one of embodiments A40 to A94.4, wherein the epithelial cells obtained from a subject and/or the epithelial cells in culture do not comprise LGR5+ cells.
A95. The method of any one of embodiments A40 to A94.5, wherein the epithelial cells obtained from a subject and/or the epithelial cells in culture are a homogenous population of epithelial cells.
A95.1 The method of any one of embodiments A40 to A95, wherein the epithelial cells obtained from a subject and/or the epithelial cells in culture are a homogenous population of basal epithelial cells.
A95.2 The method of any one of embodiments A40 to A94.5, wherein the epithelial cells obtained from a subject and/or the epithelial cells in culture are a heterogeneous population of epithelial cells.
A96. The method of any one of embodiments A40 to A95.2, wherein the epithelial cells obtained from a subject and/or the epithelial cells in culture are less differentiated than terminally differentiated cells and are more differentiated than embryonic stem cells or adult stem cells.
A97. The method of any one of embodiments A40 to A96, wherein the epithelial cells obtained from a subject and/or the epithelial cells in culture express one or more basal epithelial cell markers.
A98. The method of any one of embodiments A40 to A97, wherein the epithelial cells obtained from a subject and/or the epithelial cells in culture express one or more of ITGA6, ITGB4, KRT14, KRT15, KRT5 and TP63.
A99. The method of any one of embodiments A40 to A98, wherein the epithelial cells obtained from a subject and/or the epithelial cells in culture do not express one or more epithelial stem cell markers.
A100. The method of any one of embodiments A40 to A99, wherein the epithelial cells obtained from a subject and/or the epithelial cells in culture do not express Lgr5.
A101. The method of any one of embodiments A40 to A100, wherein the epithelial cells obtained from a subject and/or the epithelial cells in culture do not express one or more pluripotent stem cell markers.
A102. The method of any one of embodiments A40 to A101, wherein the epithelial cells obtained from a subject and/or the epithelial cells in culture do not express one or more of LIN28A, NANOG, POU5F1/OCT4 and SOX2.
A103. The method of any one of embodiments A40 to A102, wherein the epithelial cells obtained from a subject and/or the epithelial cells in culture do not express one or more terminally differentiated epithelial cell markers.
A104. The method of any one of embodiments A40 to A103, wherein the epithelial cells obtained from a subject and/or the epithelial cells in culture do not express one or more of CFTR, FOXJ1, IVL, KRT1, KRT10, KRT20, LOR, MUC1, MUC5AC, SCGB1A1, SFTPB and SFTPD.
A105. The method of any one of embodiments A40 to A104, wherein the epithelial cells obtained from a subject and/or the epithelial cells in culture do not express one or more gastric epithelial cell markers, one or more intestinal epithelial cell markers, and/or one or more pancreatic epithelial cell markers.

A106. The method of any one of embodiments A40 to A105, wherein the epithelial cells obtained from a subject and/or the epithelial cells in culture do not express one or more of CD34, HNF1A, HNF4A, IHH, KIT, LGR5, PDX1, and PROM1/CD133.

A107. The method of any one of embodiments A1 to A106, further comprising isolating a population of ex vivo proliferated epithelial cells.

A108. The method of any one of embodiments A1 to A107, further comprising storing a population of ex vivo proliferated epithelial cells in a cell bank.

A109. A population of ex vivo proliferated epithelial cells produced by a method according to any one of embodiments A1 to A108.

A110. Use of the population of ex vivo proliferated epithelial cells of embodiment A109 for production of genetically modified cells.

A111. Use of the population of ex vivo proliferated epithelial cells of embodiment A109 for identifying one or more candidate treatments for a subject.

A112. Use of the population of ex vivo proliferated epithelial cells of embodiment A109 for identifying one or more abnormal epithelial cells in a subject.

A113. Use of the population of ex vivo proliferated epithelial cells of embodiment A109 for monitoring the progression of a disease or treatment of a disease in a subject.

B1. A serum-free cell culture medium for proliferating differentiated epithelial cells ex vivo under feeder-cell free conditions, which serum-free medium comprises one or more TGF-beta inhibitors and/or one or more TGF-beta signaling inhibitors.

B1.1 A serum-free cell culture medium for proliferating formerly quiescent epithelial cells ex vivo under feeder-cell free conditions, which serum-free medium comprises one or more TGF-beta inhibitors and/or one or more TGF-beta signaling inhibitors.

B1.2 A serum-free cell culture medium for proliferating lineage-committed epithelial cells ex vivo under feeder-cell free conditions, which serum-free medium comprises one or more TGF-beta inhibitors and/or one or more TGF-beta signaling inhibitors.

B1.3 A serum-free cell culture medium for proliferating differentiated epithelial cells ex vivo under feeder-cell free conditions, which serum-free medium comprises a small molecule inhibitor consisting of a TGF-beta inhibitor or a TGF-beta signaling inhibitor.

B1.4 A serum-free cell culture medium for proliferating formerly quiescent epithelial cells ex vivo under feeder-cell free conditions, which serum-free medium comprises a small molecule inhibitor consisting of a TGF-beta inhibitor or a TGF-beta signaling inhibitor.

B1.5 A serum-free cell culture medium for proliferating lineage-committed epithelial cells ex vivo under feeder-cell free conditions, which serum-free medium comprises a small molecule inhibitor consisting of a TGF-beta inhibitor or a TGF-beta signaling inhibitor.

B1.6 The serum-free cell culture medium of any one of embodiments 1 to 1.5, which is a defined serum-free cell culture medium.

B1.7 The serum-free cell culture medium of any one of embodiments 1 to 1.5, which is a xeno-free serum-free cell culture medium.

B1.8 The serum-free cell culture medium of any one of embodiments 1 to 1.5, which is a defined xeno-free serum-free cell culture medium.

B2. A cell culture medium for proliferating epithelial cells ex vivo under feeder-cell free conditions, which medium comprises one or more TGF-beta inhibitors and/or one or more TGF-beta signaling inhibitors, and one or more PAK1 inhibitors.

B2.1 A cell culture medium for proliferating epithelial cells ex vivo under feeder-cell free conditions, which medium comprises small molecule inhibitors consisting of a TGF-beta inhibitor or a TGF-beta signaling inhibitor and a PAK1 inhibitor.

B3. A cell culture medium for proliferating epithelial cells ex vivo under feeder-cell free conditions, which medium comprises one or more TGF-beta inhibitors and/or one or more TGF-beta signaling inhibitors, and one or more myosin II inhibitors.

B3.1 The cell culture medium of embodiment B3, wherein the myosin II is a non-muscle myosin II (NM II).

B3.2 A cell culture medium for proliferating epithelial cells ex vivo under feeder-cell free conditions, which medium comprises small molecule inhibitors consisting of a TGF-beta inhibitor or a TGF-beta signaling inhibitor and a myosin II inhibitor.

B3.3 The cell culture medium of embodiment B3.2, wherein the myosin II is a non-muscle myosin II (NM II).

B4. The cell culture medium of any one of embodiments B2 to B3.3, wherein the epithelial cells comprise differentiated epithelial cells.

B4.1 The cell culture medium of any one of embodiments B2 to B3.3, wherein the epithelial cells comprise formerly quiescent epithelial cells.

B4.2 The cell culture medium of any one of embodiments B2 to B3.3, wherein the epithelial cells comprise lineage-committed epithelial cells.

B5. The cell culture medium of any one of embodiments B2 to B4, which is a serum containing medium.

B5.1 The cell culture medium of any one of embodiments B2 to B4, which is a serum-free medium.

B5.2 The cell culture medium of embodiment B5.1, which is a defined serum-free medium.

B5.3 The cell culture medium of embodiment B5.1, which is a xeno-free serum-free medium.

B5.4 The cell culture medium of embodiment B5.1, which is a defined xeno-free serum-free medium.

B6. The cell culture medium of any one of embodiments B1 to B5.3, wherein the one or more TGF-beta inhibitors and/or the one or more TGF-beta signaling inhibitors bind to one or more TGF-beta receptors or one or more TGF-beta ligands or both.

B7. The cell culture medium of any one of embodiments B1 to B6, wherein the one or more TGF-beta inhibitors and/or the one or more TGF-beta signaling inhibitors disrupt one or more TGF-beta receptor-ligand interactions.

B8. The cell culture medium of any one of embodiments B1 to B7, wherein the one or more TGF-beta inhibitors and/or the one or more TGF-beta signaling inhibitors do not comprise a recombinant protein.

B9. The cell culture medium of any one of embodiments B1 to B8, wherein the one or more TGF-beta inhibitors and/or the one or more TGF-beta signaling inhibitors do not comprise Noggin, DAN, Cerberus or Gremlin.

B10. The cell culture medium of any one of embodiments B1 to B9, wherein the one or more TGF-beta inhibitors and/or the one or more TGF-beta signaling inhibitors comprise one or more TGF-beta receptor inhibitors.

B11. The cell culture medium of embodiment B10, wherein the one or more TGF-beta receptor inhibitors comprise one or more TGF-beta type I receptor inhibitors.

B12. The cell culture medium of embodiment 11, wherein the one or more TGF-beta type I receptor inhibitors are selected from an ALK1 inhibitor, an ALK2 inhibitor, an ALK3 inhibitor, an ALK4 inhibitor, an ALK5 inhibitor, an ALK6 inhibitor, an ALK7 inhibitor, and an ALK8 inhibitor.

B13. The cell culture medium of embodiment B12, wherein the one or more TGF-beta type 1 receptor inhibitors comprise one or more ALK5 inhibitors.

B14. The cell culture medium of embodiment B13, wherein the one or more ALK5 inhibitors comprise one or more small molecule ALK5 inhibitors.

B15. The cell culture medium of embodiment B15, wherein the one or more ALK5 inhibitors comprise one or more ATP analogs.

B16. The cell culture medium of embodiment B14 or B15, wherein at least one of the one or more ALK5 inhibitors comprises the structure of Formula A:

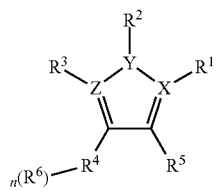

Formula A wherein:
  X, Y and Z independently are chosen from N, C and O;
  $R^1$, $R^2$ and $R^3$ independently are chosen from hydrogen, C1-C10 alkyl, substituted C1-C10 alkyl, C3-C9 cycloalkyl, substituted C3-C9 cycloalkyl, C5-C10 aryl, substituted C5-C10 aryl, C5-C10 cycloaryl, substituted C5-C10 cycloaryl, C5-C9 heterocyclic, substituted C5-C9 heterocyclic, C5-C9 hetercycloaryl, substituted C5-C9 heterocycloaryl, -linker-(C3-C9 cycloalkyl), -linker-(substituted C3-C9 cycloalkyl), -linker-(C5-C10 aryl), -linker-(substituted C5-C10 aryl), -linker-(C5-C10 cycloaryl), -linker-(substituted C5-C10 cycloaryl), -linker-(C5-C9 heterocyclic), -linker-(substituted C5-C9 heterocyclic), -linker-(C5-C9 hetercycloaryl), -linker-(substituted C5-C9 heterocycloaryl);
  n is 0 or 1;
  $R^4$, $R^5$ and $R^6$ independently are chosen from hydrogen, C1-C10 alkyl, substituted C1-C10 alkyl, C1-C10 alkoxy, substituted C1-C10 alkoxy, C1-C6 alkanoyl, C1-C6 alkoxycarbonyl, substituted C1-C6 alkanoyl, substituted C1-C6 alkoxycarbonyl, C3-C9 cycloalkyl, substituted C3-C9 cycloalkyl, C5-C10 aryl, substituted C5-C10 aryl, C5-C10 cycloaryl, substituted C5-C10 cycloaryl, C5-C9 heterocyclic, substituted C5-C9 heterocyclic, C5-C9 hetercycloaryl, substituted C5-C9 heterocycloaryl, -linker-(C3-C9 cycloalkyl), -linker-(substituted C3-C9 cycloalkyl), -linker-(C5-C10 aryl), -linker-(substituted C5-C10 aryl), -linker-(C5-C10 cycloaryl), -linker-(substituted C5-C10 cycloaryl), -linker-(C5-C9 heterocyclic), -linker-(substituted C5-C9 heterocyclic), -linker-(C5-C9 hetercycloaryl), -linker-(substituted C5-C9 heterocycloaryl); and
  the substituents on the substituted alkyl, alkoxy, alkanoyl, alkoxycarbonyl cycloalkyl, aryl, cycloaryl, heterocyclic or heterocycloaryl groups are hydroxyl, C1-C10 alkyl, hydroxyl C1-C10 alkylene, C1-C6 alkoxy, C3-C9 cycloalkyl, C5-C9 heterocyclic, C1-6 alkoxy C1-6 alkenyl, amino, cyano, halogen or aryl.

B17. The cell culture medium of embodiment B14, B15 or B16, wherein the one or more ALK5 inhibitors are selected from A83-01, GW788388, RepSox, and SB 431542.

B18. The cell culture medium of embodiment B17, wherein the one or more ALK5 inhibitors comprise A83-01.

B19. The cell culture medium of any one of embodiments B13 to B18, wherein the one or more ALK5 inhibitors binds to ALK5 or one or more ALK5 ligands or both.

B20. The cell culture medium of any one of embodiments B13 to B19, wherein the one or more ALK5 inhibitors disrupt one or more ALK5-ligand interactions.

B21. The cell culture medium of any one of embodiments B1 to B20, further comprising one or more Rho kinase inhibitors and/or one or more Rho-associated protein kinase inhibitors.

B22. The cell culture medium of embodiment B21, wherein the one or more Rho kinase inhibitors and/or the one or more Rho-associated protein kinase inhibitors are selected from a Rho kinase 1 (ROCK 1) inhibitor and a Rho kinase 2 (ROCK 2) inhibitor.

B23. The cell culture medium of embodiment B21 or B22, wherein the one or more Rho kinase inhibitors and/or the one or more Rho-associated protein kinase inhibitors comprise one or more small molecule Rho kinase inhibitors and/or one or more small molecule Rho-associated protein kinase inhibitors.

B24. The cell culture medium of embodiment B23, wherein the one or more Rho kinase inhibitors and/or the one or more Rho-associated protein kinase inhibitors is selected from Y-27632, SR 3677, thiazovivin, HA1100 hydrochloride, HA1077 and GSK-429286.

B25. The cell culture medium of embodiment B14, wherein the one or more Rho kinase inhibitors and/or the one or more Rho-associated protein kinase inhibitors comprise Y-27632.

B25.1 The cell culture medium of any one of embodiments B1 to B20, which does not comprise a Rho kinase inhibitor and/or a Rho-associated protein kinase inhibitor.

B26. The cell culture medium of any one of embodiments B1 to B25.1, further comprising one or more PAK1 inhibitors.

B27. The cell culture medium of embodiment B26, wherein the one or more PAK inhibitors comprise one or more small molecule PAK inhibitors.

B28. The cell culture medium of embodiment B27, wherein the one or more PAK inhibitors comprise IPA3.

B29. The cell culture medium of any one of embodiments B1 to B28, further comprising one or more myosin II inhibitors.

B29.1 The cell culture medium of embodiment B29, wherein the one or more myosin II inhibitors comprise one or more non-muscle myosin II (NM II) inhibitors.

B30. The cell culture medium of embodiment B29 or B29.1, wherein the one or more myosin II inhibitors comprise one or more small molecule myosin II inhibitors.

B30.1 The cell culture medium of embodiment B30, wherein the one or more myosin II inhibitors comprise blebbistatin.

B31. The cell culture medium of any one of embodiments B1 to B30.1, further comprising one or more beta-adrenergic agonists and/or one or more beta-adrenergic receptor agonists.

B31.1 The cell culture medium of embodiment B31, wherein the one or more beta-adrenergic agonists and/or the one or more beta-adrenergic receptor agonists comprise isoproterenol.
B32. The cell culture medium of any one of embodiments B1 to B31.1, wherein the epithelial cells are from a subject.
B32.1 The cell culture medium of embodiment B32, wherein the epithelial cells are from tissue from a subject.
B32.2 The cell culture medium of embodiment B32.1, wherein the epithelial cells are from differentiated tissue from a subject.
B32.3 The cell culture medium of any one of embodiments B32 to B32.2, wherein the epithelial cells comprise primary cells.
B33. The cell culture medium of any one of embodiments B32 to B32.2, wherein the epithelial cells do not comprise primary cells.
B34. The cell culture medium of any one of embodiments B32 to B33, wherein the epithelial cells comprise tumor cells.
B35. The cell culture medium of any one of embodiments B32 to B34, wherein the epithelial cells from a subject are selected from squamous cells, columnar cells, adenomatous cells and transitional epithelial cells.
B35.1 The cell culture medium of any one of embodiments B32 to B34, wherein the epithelial cells from a subject comprise one or more of squamous cells, columnar cells, adenomatous cells and transitional epithelial cells.
B36. The cell culture medium of any one of embodiments B32 to B35.1, wherein the epithelial cells from a subject comprise keratinocyte epithelial cells.
B36.1 The cell culture medium of embodiment B36, wherein the keratinocyte epithelial cells are selected from dermal keratinocyte, ocular epithelial cells, corneal epithelial cells, oral mucosal epithelial cells, esophagus epithelial cells, and cervix epithelial cells.
B37. The cell culture medium of any one of embodiments B32 to B35, wherein the epithelial cells from a subject comprise non-keratinocyte epithelial cells.
B38. The cell culture medium of embodiment B37, wherein the non-keratinocyte epithelial cells comprise glandular epithelial cells.
B39. The cell culture medium of embodiment B37 or B38, wherein the non-keratinocyte epithelial cells are selected from prostate cells, mammary cells, hepatocytes, liver epithelial cells, biliary epithelial cells, gall bladder cells, pancreatic islet cells, pancreatic beta cells, pancreatic ductal epithelial cells, pulmonary epithelial cells, airway epithelial cells, nasal epithelial cells, kidney cells, bladder cells, urethral epithelial cells, stomach epithelial cells, large intestinal epithelial cells, small intestinal epithelial cells, testicular epithelial cells, ovarian epithelial cells, fallopian tube epithelial cells, thyroid cells, parathyroid cells, adrenal cells, thymus cells, pituitary cells, glandular cells, amniotic epithelial cells, retinal pigmented epithelial cells, sweat gland epithelial cells, sebaceous epithelial cells and hair follicle cells.
B39.1 The cell culture medium of any one of embodiments B1 to B39, wherein the epithelial cells comprise basal epithelial cells.
B39.2 The cell culture medium of any one of embodiments B1 to B39, wherein the epithelial cells are not intestinal epithelial cells.
B40. The cell culture medium of any one of embodiments B1 to B39.2, which comprises calcium.
B41. The cell culture medium of embodiment B40, wherein the calcium is present at a concentration below 1 mM.
B42. The cell culture medium of embodiment B40, wherein the calcium is present at a concentration below 500 μM.
B43. The cell culture medium of embodiment B40, wherein the calcium is present at a concentration below 100 μM.
B43.1 The cell culture medium of embodiment B43, wherein the calcium is present at a concentration of about 90 μM.
B44. The cell culture medium of embodiment B40, wherein the calcium is present at a concentration below 20 μM.
B44.1 The cell culture medium of any one of embodiments B1 to B44, which comprises a buffer and one or more components selected from inorganic acids, salts, alkali silicates, amino acids, vitamins, purines, pyrimidines, polyamines, alpha-keto acids, organosulphur compounds and glucose.
B44.2 The cell culture medium of embodiment B44.1, wherein the one or more salts are selected from sodium chloride, potassium chloride, sodium acetate, and sodium phosphate.
B44.3 The cell culture medium of embodiment B44.1 or B44.2, wherein the one or more amino acids are selected from arginine and glutamine.
B44.4 The cell culture medium of any one of embodiments B44.1 to B44.3, wherein the buffer is HEPES buffer.
B44.5 The cell culture medium any one of embodiments B1 to B44.4, which comprises albumin.
B44.6 The cell culture medium of embodiment B44.5, wherein the albumin is selected from bovine serum albumin and recombinant human serum albumin.
B44.7 The cell culture medium any one of embodiments B1 to B44.6, which comprises one or more lipids.
B44.8 The cell culture medium of embodiment B44.7, wherein the one or more lipids are selected from arachidonic acid, cholesterol, DL-alpha-tocopherol acetate, linoleic acid, linolenic acid, myristic acid, oleic acid, palmitic acid, palmitoleic acid, pluronic F-68, stearic acid, and polysorbate 80.
B44.9 The cell culture medium of embodiment B44.8, wherein the one or more lipids are selected from linoleic acid, linolenic acid, oleic acid, palmitic acid, and stearic acid.
B45. The cell culture medium of any one of embodiments B1 to B44.9, which comprises one or more mitogenic growth factors.
B46. The cell culture medium of embodiment B45, wherein the one or more mitogenic growth factors comprise EGF.
B46.1 The cell culture medium of embodiment B45, wherein the one or more mitogenic growth factors comprise FGF.
B46.2 The cell culture medium of embodiment B45, wherein the one or more mitogenic growth factors comprise EGF and FGF.
B46.3 The cell culture medium of embodiment B46.1 or B46.2, wherein the FGF comprises acidic FGF.
B47. The cell culture medium of any one of embodiments B1 to B44.9, which does not comprise a mitogenic growth factor.
B48. The cell culture medium of any one of embodiments B1 to B47, which comprises one or more mitogenic supplements.
B49. The cell culture medium of embodiment B48, wherein the one or more mitogenic supplements comprise bovine pituitary extract (BPE).
B49.1 The cell culture medium of any one of embodiments B1 to B47, which does not comprise a mitogenic supplement.

B50. The cell culture medium of any one of embodiments B1 to B49.1, which does not comprise a Wnt agonist or a beta-catenin agonist.

B50.1 The cell culture medium of any one of embodiments B1 to B50, which does not comprise one or more of components selected from: noggin, R-spondin, Wnt-3a, EGF, nicotinamide, FGF10, gastrin, a p38 inhibitor, SB202190, DHT, a notch inhibitor, a gamma secretase inhibitor, DBZ and DAPT.

B51. The cell culture medium of any one of embodiments B1 to B50.1, which does not comprise an extracellular matrix.

C1. A population of ex vivo proliferated epithelial cells produced by a method comprising:
   a) culturing differentiated epithelial cells under serum-free and feeder-cell free conditions; and
   b) inhibiting TGF-beta signaling in the differentiated epithelial cells during the culturing in (a).

C1.1 A population of ex vivo proliferated epithelial cells produced by a method comprising:
   a) culturing formerly quiescent epithelial cells under serum-free and feeder-cell free conditions; and
   b) inhibiting TGF-beta signaling in the formerly quiescent epithelial cells during the culturing in (a).

C1.2 A population of ex vivo proliferated epithelial cells produced by a method comprising:
   a) culturing lineage-committed epithelial cells under serum-free and feeder-cell free conditions; and
   b) inhibiting TGF-beta signaling in the lineage-committed epithelial cells during the culturing in (a).

C2. A population of ex vivo proliferated epithelial cells produced by a method comprising:
   a) culturing epithelial cells under feeder-cell free conditions;
   b) inhibiting TGF-beta signaling in the epithelial cells during the culturing in (a); and
   c) inhibiting the activity of p21-activated kinase (PAK) in the epithelial cells during the culturing in (a).

C2.1 The epithelial cells of embodiment C2, which comprise differentiated epithelial cells.

C2.2 The epithelial cells of embodiment C2, which comprise formerly quiescent epithelial cells.

C2.3 The epithelial cells of embodiment C2, which comprise lineage-committed epithelial cells.

C3. A population of ex vivo proliferated epithelial cells produced by a method comprising:
   a) culturing epithelial cells under serum-free and feeder-cell free conditions;
   b) inhibiting TGF-beta signaling in the epithelial cells during the culturing in (a); and
   c) inhibiting the activity of myosin II in the epithelial cells during the culturing in (a).

C3.1 The epithelial cells of embodiment C3, which comprise differentiated epithelial cells.

C3.2 The epithelial cells of embodiment C3, which comprise formerly quiescent epithelial cells.

C3.3 The epithelial cells of embodiment C3, which comprise lineage-committed epithelial cells.

C3.4 The epithelial cells of any one or embodiments C3 to C3.3, wherein the myosin II is a non-muscle myosin II (NM 1$l$).

C4. The epithelial cells of any one of embodiments C2 to C3.4, wherein the culturing in (a) is performed in the presence of a serum containing medium.

C5. The epithelial cells of any one of embodiments C2 to C3.4, wherein the culturing in (a) is performed in the presence of a serum-free medium.

C5.1 The epithelial cells of any one of embodiments C1 to C5, wherein (a) and (b) are performed at the same time; or (a), (b) and (c) are performed at the same time.

C5.2 The epithelial cells of any one of embodiments C1 to C5.1, wherein the epithelial cells are frozen and thawed prior to (a).

C6. The epithelial cells of any one of embodiments C1 to C5.2, wherein the activity of one or more TGF-beta receptors is inhibited in (b).

C7. The epithelial cells of embodiment C6, wherein one or more TGF-beta receptor-ligand interactions are inhibited in (b).

C8. The epithelial cells of embodiment C6 or C7, wherein the one or more TGF-beta receptors comprise a TGF-beta type I receptor.

C9. The epithelial cells of embodiment C8, wherein the TGF-beta type I receptor is selected from ALK1, ALK2, ALK3, ALK4, ALK5, ALK6, ALK7 and ALK8.

C10. The epithelial cells of embodiment C8, wherein the one or more TGF-beta receptors comprise ALK5.

C11. The epithelial cells of any one of embodiments C1 to C10, wherein inhibiting TGF-beta signaling comprises use of one or more TGF-beta inhibitors and/or one or more TGF-beta signaling inhibitors.

C12. The epithelial cells of embodiment C11, wherein the one or more TGF-beta inhibitors and/or the one or more TGF-beta signaling inhibitors bind to one or more TGF-beta receptors or one or more TGF-beta ligands or both.

C13. The epithelial cells embodiment C11 or C12, wherein the one or more TGF-beta inhibitors and/or the one or more TGF-beta signaling inhibitors disrupt one or more TGF-beta receptor-ligand interactions.

C14. The epithelial cells of embodiment C11, C12 or C13, wherein the one or more TGF-beta inhibitors and/or the one or more TGF-beta signaling inhibitors do not comprise a recombinant protein.

C15. The epithelial cells of any one of embodiments C11 to C14, wherein the one or more TGF-beta inhibitors and/or the one or more TGF-beta signaling inhibitors do not comprise Noggin, DAN, Cerberus or Gremlin.

C16. The epithelial cells of any one of embodiments C11 to C15, wherein the one or more TGF-beta inhibitors and/or the one or more TGF-beta signaling inhibitors comprise one or more ALK5 inhibitors.

C17. The epithelial cells of embodiment C16, wherein the one or more ALK5 inhibitors comprise one or more small molecule ALK5 inhibitors.

C18. The epithelial cells of embodiment C17, wherein the one or more ALK5 inhibitors comprise one or more ATP analogs.

C19. The epithelial cells of anyone of embodiments C16 to C18, wherein at least one of the one or more ALK5 inhibitors comprises the structure of Formula A:

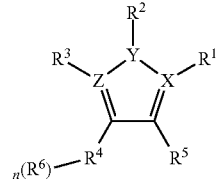

Formula A wherein:
X, Y and Z independently are chosen from N, C and O;
R$^1$, R$^2$ and R$^3$ independently are chosen from hydrogen, C1-C10 alkyl, substituted C1-C10 alkyl, C3-C9 cycloalkyl, substituted C3-C9 cycloalkyl, C5-C10 aryl, substituted C5-C10 aryl, C5-C10 cycloaryl, substituted C5-C10 cycloaryl, C5-C9 heterocyclic, substituted C5-C9 heterocyclic, C5-C9 hetercycloaryl, substituted C5-C9 heterocycloaryl, -linker-(C3-C9 cycloalkyl), -linker-(substituted C3-C9 cycloalkyl), -linker-(C5-C10 aryl), -linker-(substituted C5-C10 aryl), -linker-(C5-C10 cycloaryl), -linker-(substituted C5-C10 cycloaryl), -linker-(C5-C9 heterocyclic), -linker-(substituted C5-C9 heterocyclic), -linker-(C5-C9 hetercycloaryl), -linker-(substituted C5-C9 heterocycloaryl);
n is 0 or 1;
R$^4$, R$^5$ and R$^6$ independently are chosen from hydrogen, C1-C10 alkyl, substituted C1-C10 alkyl, C1-C10 alkoxy, substituted C1-C10 alkoxy, C1-C6 alkanoyl, C1-C6 alkoxycarbonyl, substituted C1-C6 alkanoyl, substituted C1-C6 alkoxycarbonyl, C3-C9 cycloalkyl, substituted C3-C9 cycloalkyl, C5-C10 aryl, substituted C5-C10 aryl, C5-C10 cycloaryl, substituted C5-C10 cycloaryl, C5-C9 heterocyclic, substituted C5-C9 heterocyclic, C5-C9 hetercycloaryl, substituted C5-C9 heterocycloaryl, -linker-(C3-C9 cycloalkyl), -linker-(substituted C3-C9 cycloalkyl), -linker-(C5-C10 aryl), -linker-(substituted C5-C10 aryl), -linker-(C5-C10 cycloaryl), -linker-(substituted C5-C10 cycloaryl), -linker-(C5-C9 heterocyclic), -linker-(substituted C5-C9 heterocyclic), -linker-(C5-C9 hetercycloaryl), -linker-(substituted C5-C9 heterocycloaryl); and
the substituents on the substituted alkyl, alkoxy, alkanoyl, alkoxycarbonyl cycloalkyl, aryl, cycloaryl, heterocyclic or heterocycloaryl groups are hydroxyl, C1-C10 alkyl, hydroxyl C1-C10 alkylene, C1-C6 alkoxy, C3-C9 cycloalkyl, C5-C9 heterocyclic, C1-6 alkoxy C1-6 alkenyl, amino, cyano, halogen or aryl.

C20. The epithelial cells of any one of embodiments C16 to C19, wherein the one or more ALK5 inhibitors are selected from A83-01, GW788388, RepSox, and SB 431542.

C21. The epithelial cells of embodiment C20, wherein the one or more ALK5 inhibitors comprise A83-01.

C22. The epithelial cells of any one of embodiments C16 to C21, wherein the one or more ALK5 inhibitors bind to ALK5 or one or more ALK5 ligands or both.

C23. The epithelial cells of any one of embodiments C16 to C22, wherein the one or more ALK5 inhibitors disrupt one or more ALK5-ligand interactions.

C24. The epithelial cells of any one of embodiments C16 to C23, wherein the method comprises activating telomerase and/or modulating cytoskeletal structure in the epithelial cells.

C25. The epithelial cells of any one of embodiments C1 to C24, wherein the method further comprises inhibiting the activity of Rho kinase and/or Rho-associated protein kinase in the epithelial cells during the culturing in (a).

C26. The epithelial cells of embodiment C25, wherein Rho kinase and/or the Rho-associated protein kinase is selected from Rho kinase 1 (ROCK 1) and Rho kinase 2 (ROCK 2).

C27. The epithelial cells of embodiment C25 or C26, wherein inhibiting the activity of Rho kinase and/or Rho-associated protein kinase comprises use of one or more Rho kinase inhibitors and/or one or more Rho-associated protein kinase inhibitors.

C28. The epithelial cells of embodiment C27, wherein the one or more Rho kinase inhibitors and/or the one or more Rho-associated protein kinase inhibitors comprise one or more small molecule Rho kinase inhibitors.

C29. The epithelial cells of embodiment C28, wherein the one or more Rho kinase inhibitors and/or the one or more Rho-associated protein kinase inhibitors is selected from Y-27632, SR 3677, thiazovivin, HA1100 hydrochloride, HA1077 and GSK-429286.

C30. The epithelial cells of embodiment C29, wherein the one or more Rho kinase inhibitors and/or the one or more Rho-associated protein kinase inhibitors comprise Y-27632.

C30.1 The epithelial cells of any one of embodiments C1 to C24, wherein the method does not comprise inhibiting the activity of Rho kinase and/or Rho-associated protein kinase in the epithelial cells during the culturing in (a).

C31. The epithelial cells of any one of embodiments C1 to C30.1, wherein the method further comprises inhibiting the activity of p21-activated kinase (PAK) in the epithelial cells during the culturing in (a).

C32. The epithelial cells of embodiment C31, wherein the PAK is selected from PAK1, PAK2, PAK3 and PAK4.

C33. The epithelial cells of embodiment C32, wherein the PAK is PAK1.

C34. The epithelial cells of embodiment C33, wherein inhibiting the activity of PAK1 comprises use of one or more PAK1 inhibitors.

C35. The epithelial cells of embodiment C34, wherein the one or more PAK1 inhibitors comprise one or more small molecule PAK1 inhibitors.

C36. The epithelial cells of embodiment C35, wherein the one or more PAK1 inhibitors comprise IPA3.

C37. The epithelial cells of any one of embodiments C1 to C36, wherein the method further comprises inhibiting the activity of myosin II in the epithelial cells during the culturing in (a).

C37.1 The epithelial cells of embodiment C37, wherein the myosin II is a non-muscle myosin II (NM II).

C37.2 The epithelial cells of embodiment C37 or C37.1, wherein inhibiting the activity of myosin II comprises use of one or more myosin II inhibitors.

C37.3 The epithelial cells of embodiment C37.2, wherein the one or more myosin II inhibitors comprise one or more small molecule myosin II inhibitors.

C37.4 The epithelial cells of embodiment C37.2 or C37.3, wherein the one or more myosin II inhibitors comprise blebbistatin.

C38. The epithelial cells of any one of embodiments C1 to C37.4, wherein the method further comprises increasing intracellular cyclic adenosine monophosphate (cAMP) levels in the epithelial cells during the culturing in (a).

C39. The epithelial cells of embodiment C38, wherein increasing intracellular cyclic adenosine monophosphate (cAMP) levels comprises use of one or more beta-adrenergic agonists and/or one or more beta-adrenergic receptor agonists.

C39.1 The epithelial cells of embodiment C39, where the one or more beta-adrenergic agonists and/or the one or more beta-adrenergic receptor agonists comprise isoproterenol.

C40. The epithelial cells of any one of embodiments C1 to C40, wherein the epithelial cells are obtained from a subject prior to (a).

C40.1 The epithelial cells of embodiment C40, wherein the subject is a mammal.

C40.2 The epithelial cells of embodiment C40, wherein the subject is a human.

C40.3 The epithelial cells of any one of embodiments C40 to C40.2, wherein the epithelial cells are from tissue from a subject.

C40.4 The epithelial cells of embodiment C40.3, wherein the epithelial cells are from differentiated tissue from a subject.
C40.5 The epithelial cells of any one of embodiments C40 to C40.2, wherein the epithelial cells are from circulating cells from a subject.
C41. The epithelial cells of any one of embodiments C40 to C40.5, wherein the epithelial cells comprise primary cells from a subject.
C42. The epithelial cells of any one of embodiments C40 to C40.5, wherein the epithelial cells do not comprise primary cells from a subject.
C43. The epithelial cells of any one of embodiments C40 to C42, wherein the epithelial cells comprise tumor cells from a subject.
C44. The epithelial cells of any one of embodiments C41 to C43, wherein the epithelial cells from a subject are selected from squamous cells, columnar cells, adenomatous cells and transitional epithelial cells.
C44.1 The epithelial cells of any one of embodiments C41 to C43, wherein the epithelial cells from a subject comprise one or more of squamous cells, columnar cells, adenomatous cells and transitional epithelial cells.
C45. The epithelial cells of any one of embodiments C41 to C44.1, wherein the epithelial cells from a subject comprise keratinocyte epithelial cells.
C45.1 The epithelial cells of embodiment C45, wherein the keratinocyte epithelial cells are selected from dermal keratinocyte, ocular epithelial cells, corneal epithelial cells, oral mucosal epithelial cells, esophagus epithelial cells, and cervix epithelial cells.
C46. The epithelial cells of any one of embodiments C41 to C44, wherein the epithelial cells from a subject comprise non-keratinocyte epithelial cells.
C47. The epithelial cells of embodiment C46, wherein the non-keratinocyte epithelial cells comprise glandular epithelial cells.
C48. The epithelial cells of embodiment C46 or C47, wherein the non-keratinocyte epithelial cells are selected from prostate cells, mammary cells, hepatocytes, liver epithelial cells, biliary epithelial cells, gall bladder cells, pancreatic islet cells, pancreatic beta cells, pancreatic ductal epithelial cells, pulmonary epithelial cells, airway epithelial cells, nasal epithelial cells, kidney cells, bladder cells, urethral epithelial cells, stomach epithelial cells, large intestinal epithelial cells, small intestinal epithelial cells, testicular epithelial cells, ovarian epithelial cells, fallopian tube epithelial cells, thyroid cells, parathyroid cells, adrenal cells, thymus cells, pituitary cells, glandular cells, amniotic epithelial cells, retinal pigmented epithelial cells, sweat gland epithelial cells, sebaceous epithelial cells and hair follicle cells.
C48.1 The epithelial cells of any one of embodiments C1 to C48, wherein the epithelial cells comprise basal epithelial cells.
C48.2 The epithelial cells of any one of embodiments C1 to C48, wherein the epithelial cells are not intestinal epithelial cells.
C49. The epithelial cells of any one of embodiments C1 to C48.2, wherein the culturing in (a) is performed in the presence of a serum-free medium.
C49.1 The epithelial cells of embodiment C49, wherein the serum-free medium is a defined serum-free medium.
C49.2 The epithelial cells of embodiment C49, wherein the serum-free medium is a xeno-free serum-free medium.
C49.3 The epithelial cells of embodiment C49, wherein the serum-free medium is a defined xeno-free serum-free medium.
C50. The epithelial cells of any one of embodiments C49 to C49.3, wherein the serum-free medium comprises calcium.
C51. The epithelial cells of embodiment C50, wherein the serum-free medium comprises calcium at a concentration below 1 mM.
C52. The epithelial cells of embodiment C50, wherein the serum-free medium comprises calcium at a concentration below 500 µM.
C53. The epithelial cells of embodiment C50, wherein the serum-free medium comprises calcium at a concentration below 100 µM.
C53.1 The epithelial cells of embodiment C53, wherein the serum-free medium comprises calcium at a concentration of about 90 µM.
C54. The epithelial cells of embodiment C50, wherein the serum-free medium comprises calcium at a concentration below 20 µM.
C54.1 The epithelial cells of any one of embodiments C49 to C54, wherein the serum-free medium comprises a buffer and one or more of inorganic acids, salts, alkali silicates, amino acids, vitamins, purines, pyrimidines, polyamines, alpha-keto acids, organosulphur compounds and glucose.
C54.2 The epithelial cells of embodiment C54.1, wherein the one or more salts are selected from sodium chloride, potassium chloride, sodium acetate, and sodium phosphate.
C54.3 The epithelial cells of embodiment C54.1 or C54.2, wherein the one or more amino acids are selected from arginine and glutamine.
C54.4 The epithelial cells of any one of embodiments C54.1 to C54.3, wherein the buffer is HEPES buffer.
C54.5 The epithelial cells any one of embodiments C49 to C54.4, wherein the serum-free medium comprises albumin.
C54.6 The epithelial cells of embodiment C54.5, wherein the albumin is selected from bovine serum albumin and recombinant human serum albumin.
C54.7 The epithelial cells any one of embodiments C49 to C54.6, wherein the serum-free medium comprises one or more lipids.
C54.8 The epithelial cells of embodiment C54.7, wherein the one or more lipids are selected from arachidonic acid, cholesterol, DL-alpha-tocopherol acetate, linoleic acid, linolenic acid, myristic acid, oleic acid, palmitic acid, palmitoleic acid, pluronic F-68, stearic acid, and polysorbate 80.
C54.9 The epithelial cells of embodiment C54.8, wherein the one or more lipids are selected from linoleic acid, linolenic acid, oleic acid, palmitic acid, and stearic acid.
C55. The epithelial cells of any one of embodiments C1 to C54, wherein the method comprises use of one or more mitogenic growth factors.
C56. The epithelial cells of embodiment C55, wherein the one or more mitogenic growth factors comprise EGF.
C56.1 The epithelial cells of embodiment C55, wherein the one or more mitogenic growth factors comprise FGF.
C56.2 The epithelial cells of embodiment C55, wherein the one or more mitogenic growth factors comprise EGF and FGF.
C56.3 The epithelial cells of embodiment C56.1 or C56.2, wherein the FGF comprises acidic FGF.
C57. The epithelial cells of any one of embodiments C1 to C54.9, wherein the method does not comprise use of a mitogenic growth factor.
C58. The epithelial cells of any one of embodiments C1 to C57, wherein the method comprises use of one or more mitogenic supplements.

C59. The epithelial cells of embodiment C58, wherein the one or more mitogenic supplements comprise bovine pituitary extract (BPE).

C59.1 The epithelial cells of any one of embodiments C1 to C57, wherein the method does not comprise use of a mitogenic supplement.

C60. The epithelial cells of any one of embodiments C1 to C59.1, wherein the method does not comprise use of a Wnt agonist or a beta-catenin agonist.

C60.1 The epithelial cells of any one of embodiments C1 to C60, wherein the method does not comprise use of one or more of components selected from: noggin, R-spondin, Wnt-3a, EGF, nicotinamide, FGF10, gastrin, a p38 inhibitor, SB202190, DHT, a notch inhibitor, a gamma secretase inhibitor, DBZ and DAPT.

C61. The epithelial cells of any one of embodiments C1 to C60.1, wherein the method does not comprise use of an extracellular matrix.

C62. The epithelial cells of any one of embodiments C1 to C60.1, wherein the culturing in (a) is performed in a container comprising a coating.

C63. The epithelial cells of embodiment C62, wherein the coating comprises collagen.

C64. The epithelial cells of embodiment C62, wherein the coating comprises a basement membrane matrix.

C65. The epithelial cells of any one of embodiments C1 to C64, wherein the culturing in (a) comprises expanding the epithelial cells.

C66. The epithelial cells of embodiment C65, wherein the epithelial cells are expanded at least about 2-fold.

C67. The epithelial cells of embodiment C65, wherein the epithelial cells are expanded at least about 5-fold.

C68. The epithelial cells of embodiment C65, wherein the epithelial cells are expanded at least about 10-fold.

C69. The epithelial cells of embodiment C65, wherein the epithelial cells are expanded at least about 15-fold.

C70. The epithelial cells of embodiment C65, wherein the epithelial cells are expanded at least about 20-fold.

C70.1 The epithelial cells of embodiment A65, wherein the epithelial cells are expanded at least about 100-fold.

C70.2 The epithelial cells of embodiment A65, wherein the epithelial cells are expanded at least about 1,000-fold.

C70.3 The epithelial cells of embodiment A65, wherein the epithelial cells are expanded at least about 10,000-fold.

C70.4 The epithelial cells of embodiment A65, wherein the epithelial cells are expanded at least about 100,000-fold.

C70.5 The epithelial cells of embodiment A65, wherein the epithelial cells are expanded at least about 1 million-fold.

C70.6 The epithelial cells of embodiment A65, wherein the epithelial cells are expanded at least about 1 billion-fold.

C70.7 The epithelial cells of embodiment A65, wherein the epithelial cells are expanded at least about 1 trillion-fold.

C71. The epithelial cells of any one of embodiments C65 to C70.7, wherein the epithelial cells are cultured for about 4 days.

C72. The epithelial cells of any one of embodiments C65 to C70.7, wherein the epithelial cells are cultured for about 5 days.

C73. The epithelial cells of any one of embodiments C1 to C72, wherein the epithelial cells are continuously proliferated.

C74. The epithelial cells of any one of embodiments C1 to C73, wherein the method comprises passaging the epithelial cells at least 15 times.

C75. The epithelial cells of any one of embodiments C1 to C73, wherein the method comprises passaging the epithelial cells at least 25 times.

C76. The epithelial cells of any one of embodiments C1 to C75, wherein a population of the epithelial cells doubles over a period of time.

C77. The epithelial cells of embodiment C76, wherein the epithelial cell population doubles at least 20 times.

C78. The epithelial cells of embodiment C76, wherein the epithelial cell population doubles at least 50 times.

C78.1 The epithelial cells of embodiment C76, wherein the epithelial cell population doubles at least 80 times.

C79. The epithelial cells of embodiment C76, wherein the epithelial cell population doubles at least 100 times.

C80. The epithelial cells of embodiment C76, wherein the epithelial cell population doubles at least 120 times.

C81. The epithelial cells of embodiment C76, wherein the epithelial cell population doubles at least 150 times.

C82. The epithelial cells of embodiment C76, wherein the epithelial cell population doubles at least 200 times.

C83. The epithelial cells of any one of embodiments C76 to C82, wherein the period of time is about 50 days.

C84. The epithelial cells of any one of embodiments C76 to C82, wherein the period of time is about 100 days.

C85. The epithelial cells of any one of embodiments C76 to C82, wherein the period of time is about 150 days.

C86. The epithelial cells of any one of embodiments C76 to C82, wherein the period of time is about 200 days.

C87. The epithelial cells of any one of embodiments C1 to C86, which cells maintain one or more native functional characteristics during (b).

C88. The epithelial cells of any one of embodiments C1 to C86, which cells do not maintain one or more native functional characteristics during (b).

C89. The epithelial cells of any one of embodiments C1 to C88, which cells are placed after (b) into a cell culture environment wherein TGF-beta signaling is not inhibited.

C90. The epithelial cells of embodiment C89, which cells maintain or regain one or more native functional characteristics after placement into the cell culture environment wherein TGF-beta signaling is not inhibited.

C91. The epithelial cells of any one of embodiments C1 to C90, which cells can be induced to differentiate into multiple tissue types.

C91.1 The epithelial cells of any one of embodiments C1 to C90, which cells do not acquire the ability to differentiate into multiple tissue types.

C92. The epithelial cells of any one of embodiments C1 to C91.1, which cells do not acquire the ability to form organoids.

C93. The epithelial cells of any one of embodiments C1 to C92, which cells are not derived from embryonic stem cells.

C93.1 The epithelial cells of any one of embodiments C1 to C93, which cells are not derived from continuously proliferating epithelial stem cells.

C93.2 The epithelial cells of any one of embodiments C1 to C93.1, which cells are derived from epithelial tissue comprising quiescent epithelial cells.

C93.3 The epithelial cells of any one of embodiments C1 to C93.2, which method does not comprise selecting for continuously proliferating epithelial stem cells.

C93.4 The epithelial cells of any one of embodiments C1 to C93.3, which method does not comprise selecting for intestinal crypt cells.

C93.5 The epithelial cells of any one of embodiments C1 to C93.4, which method does not comprise selecting for LGR5+ cells.

C94. The epithelial cells of any one of embodiments C40 to C93.5, wherein the cells obtained from a subject and/or the population of ex vivo proliferated cells do not comprise continuously proliferating epithelial stem cells or cells derived from continuously proliferating epithelial stem cells.

C94.1 The epithelial cells of any one of embodiments C40 to C94, wherein the cells obtained from a subject and/or the population of ex vivo proliferated cells do not comprise pluripotent stem cells or cells derived from pluripotent stem cells.

C94.2 The epithelial cells of any one of embodiments C40 to C94.1, wherein the cells obtained from a subject and/or the population of ex vivo proliferated cells do not comprise terminally differentiated epithelial cells.

C94.3 The epithelial cells of any one of embodiments C40 to C94.2, wherein the cells obtained from a subject and/or the population of ex vivo proliferated cells do not comprise gastric epithelial cells, intestinal epithelial cells, and/or pancreatic epithelial cells.

C94.4 The epithelial cells of any one of embodiments C40 to C94.3, wherein the cells obtained from a subject and/or the population of ex vivo proliferated cells do not comprise intestinal crypt cells.

C94.5 The epithelial cells of any one of embodiments C40 to C94.4, wherein the cells obtained from a subject and/or the population of ex vivo proliferated cells do not comprise LGR5+ cells.

C95. The epithelial cells of any one of embodiments C40 to C94.5, wherein the cells obtained from a subject and/or the population of ex vivo proliferated cells are a homogenous population of epithelial cells.

C95.1 The epithelial cells of any one of embodiments C40 to C95, wherein the cells obtained from a subject and/or the population of ex vivo proliferated cells are a homogenous population of basal epithelial cells.

C95.2 The epithelial cells of any one of embodiments C40 to C94.5, wherein the cells obtained from a subject and/or the population of ex vivo proliferated cells are a heterogeneous population of epithelial cells.

C96. The epithelial cells of any one of embodiments C40 to C95.2, wherein the cells obtained from a subject and/or the population of ex vivo proliferated cells are less differentiated than terminally differentiated cells and are more differentiated than embryonic stem cells or adult stem cells.

C97. The epithelial cells of any one of embodiments C40 to C96, wherein the cells obtained from a subject and/or the population of ex vivo proliferated cells express one or more basal epithelial cell markers.

C98. The epithelial cells of any one of embodiments C40 to C97, wherein the cells obtained from a subject and/or the population of ex vivo proliferated cells express one or more of ITGA6, ITGB4, KRT14, KRT15, KRT5 and TP63.

C99. The epithelial cells of any one of embodiments C40 to C98, wherein the cells obtained from a subject and/or the population of ex vivo proliferated cells do not express one or more epithelial stem cell markers.

C100. The epithelial cells of any one of embodiments C40 to C99, wherein the cells obtained from a subject and/or the population of ex vivo proliferated cells do not express Lgr5.

C101. The epithelial cells of any one of embodiments C40 to C100, wherein the cells obtained from a subject and/or the population of ex vivo proliferated cells do not express one or more pluripotent stem cell markers.

C102. The epithelial cells of any one of embodiments C40 to C101, wherein the cells obtained from a subject and/or the population of ex vivo proliferated cells do not express one or more of LIN28A, NANOG, POU5F1/OCT4 and SOX2.

C103. The epithelial cells of any one of embodiments C40 to C102, wherein the cells obtained from a subject and/or the population of ex vivo proliferated cells do not express one or more terminally differentiated epithelial cell markers.

C104. The epithelial cells of any one of embodiments C40 to C103, wherein the cells obtained from a subject and/or the population of ex vivo proliferated cells do not express one or more of CFTR, FOXJ1, IVL, KRT1, KRT10, KRT20, LOR, MUC1, MUC5AC, SCGB1A1, SFTPB and SFTPD.

C105. The epithelial cells of any one of embodiments C40 to C104, wherein the cells obtained from a subject and/or the population of ex vivo proliferated cells do not express one or more gastric epithelial cell markers, one or more intestinal epithelial cell markers, and/or one or more pancreatic epithelial cell markers.

C106. The epithelial cells of any one of embodiments C40 to C105, wherein the cells obtained from a subject and/or the population of ex vivo proliferated cells do not express one or more of CD34, HNF1A, HNF4A, IHH, KIT, LGR5, PDX1, and PROM1/CD133.

C107. Use of the epithelial cells of any one of embodiments C1 to C106 for production of genetically modified cells.

C108. Use of the epithelial cells of any one of embodiments C1 to C106 for identifying one or more candidate treatments for a subject.

C109. Use of the epithelial cells of any one of embodiments C1 to C106 for identifying one or more abnormal epithelial cells in a subject.

C110. Use of the epithelial cells of any one of embodiments C1 to C106 for monitoring the progression of a disease or treatment of a disease in a subject.

D1. A cell culture composition comprising a defined serum-free cell culture medium, a lipids mix, EGF, FGF, albumin, a TGF-beta inhibitor or a TGF-beta signaling inhibitor, and a Rho kinase inhibitor or a Rho-associated protein kinase inhibitor.

D2. A cell culture composition consisting of a defined serum-free cell culture medium, a lipids mix, EGF, FGF, albumin, a TGF-beta inhibitor or a TGF-beta signaling inhibitor, and a Rho kinase inhibitor or a Rho-associated protein kinase inhibitor.

D3. A cell culture composition comprising a defined serum-free cell culture medium, a lipids mix, EGF, FGF, albumin, a TGF-beta inhibitor or a TGF-beta signaling inhibitor, a Rho kinase inhibitor or a Rho-associated protein kinase inhibitor, and a beta-adrenergic agonist or a beta-adrenergic receptor agonist.

D4. A cell culture composition consisting of a defined serum-free cell culture medium, a lipids mix, EGF, FGF, albumin, a TGF-beta inhibitor or a TGF-beta signaling inhibitor, a Rho kinase inhibitor or a Rho-associated protein kinase inhibitor, and a beta-adrenergic agonist or a beta-adrenergic receptor agonist.

D5. A cell culture composition comprising a xeno-free serum-free cell culture medium, a lipids mix, EGF, FGF, albumin, a TGF-beta inhibitor or a TGF-beta signaling inhibitor, and a Rho kinase inhibitor or a Rho-associated protein kinase inhibitor.

D6. A cell culture composition consisting of a xeno-free serum-free cell culture medium, a lipids mix, EGF, FGF, albumin, a TGF-beta inhibitor or a TGF-beta signaling inhibitor, and a Rho kinase inhibitor or a Rho-associated protein kinase inhibitor.

D7. A cell culture composition comprising a xeno-free serum-free cell culture medium, a lipids mix, EGF, FGF, albumin, a TGF-beta inhibitor or a TGF-beta signaling inhibitor, a Rho kinase inhibitor or a Rho-associated protein kinase inhibitor, and a beta-adrenergic agonist or a beta-adrenergic receptor agonist.

D8. A cell culture composition consisting of a xeno-free serum-free cell culture medium, a lipids mix, EGF, FGF, albumin, a TGF-beta inhibitor or a TGF-beta signaling inhibitor, a Rho kinase inhibitor or a Rho-associated protein kinase inhibitor, and a beta-adrenergic agonist or a beta-adrenergic receptor agonist.

D9. A cell culture composition comprising a defined xeno-free serum-free cell culture medium, a lipids mix, EGF, FGF, albumin, a TGF-beta inhibitor or a TGF-beta signaling inhibitor, and a Rho kinase inhibitor or a Rho-associated protein kinase inhibitor.

D10. A cell culture composition consisting of a defined xeno-free serum-free cell culture medium, a lipids mix, EGF, FGF, albumin, a TGF-beta inhibitor or a TGF-beta signaling inhibitor, and a Rho kinase inhibitor or a Rho-associated protein kinase inhibitor.

D11. A cell culture composition comprising a defined xeno-free serum-free cell culture medium, a lipids mix, EGF, FGF, albumin, a TGF-beta inhibitor or a TGF-beta signaling inhibitor, a Rho kinase inhibitor or a Rho-associated protein kinase inhibitor, and a beta-adrenergic agonist or a beta-adrenergic receptor agonist.

D12. A cell culture composition consisting of a defined xeno-free serum-free cell culture medium, a lipids mix, EGF, FGF, albumin, a TGF-beta inhibitor or a TGF-beta signaling inhibitor, a Rho kinase inhibitor or a Rho-associated protein kinase inhibitor, and a beta-adrenergic agonist or a beta-adrenergic receptor agonist.

E1. A method for proliferating epithelial cells ex vivo, comprising:
  expanding the number of cells in an originating epithelial cell population derived from differentiated tissue under feeder-cell free expansion culture conditions, thereby generating an expanded epithelial cell population, wherein:
  the expansion culture conditions comprise an agent that activates telomerase reverse transcriptase in the population and/or inhibits transforming growth factor beta (TGF-beta) signaling in the population;
  the originating epithelial cell population is capable of 25 population doublings or more when cultured under the expansion culture conditions; and the originating epithelial cell population is capable of no more than 20 population doublings when cultured under control culture conditions that do not include the agent.

E1.1 A method for proliferating epithelial cells ex vivo, comprising:
  expanding the number of cells in an originating epithelial cell population derived from differentiated tissue under serum-free and feeder-cell free conditions, thereby generating an expanded epithelial cell population, wherein:
  the expansion culture conditions comprise an agent that activates telomerase reverse transcriptase in the population and/or inhibits transforming growth factor beta (TGF-beta) signaling in the population; and
  the originating epithelial cell population comprises quiescent and/or formerly quiescent epithelial cells.

E1.2 The method of embodiment E1, wherein:
  agent that activates telomerase reverse transcriptase in the population and/or inhibits transforming growth factor beta (TGF-beta) signaling in the population is a first agent,
  the expansion culture conditions further comprise a second agent that modulates cytoskeletal structure in the population, and
  the control culture conditions do not include the first agent and the second agent.

E1.3 The method of embodiment E1.1, wherein the expansion culture conditions further comprise an agent that modulates cytoskeletal structure in the population.

E2. The method of any one of embodiments E1 to E1.3, comprising isolating the originating epithelial cell population from the differentiated tissue.

E3. The method of any one of embodiments E1 to E2, comprising maintaining or proliferating cells of the originating epithelial cell population in cell culture after the cells are isolated from the differentiated tissue and prior to contacting the originating epithelial cell population to the feeder-cell free expansion culture conditions.

E4. The method of any one of embodiments E1 to E3, wherein the originating epithelial cell population and the expanded epithelial cell population contain no embryonic stem cells.

E5. The method of any one of embodiments E1 to E4, wherein:
  the originating epithelial cell population, or
  the expanded epithelial cell population, or
  the originating epithelial cell population and the expanded epithelial cell population,
  express one or more basal epithelial cell markers.

E6. The method of any one of embodiments E1 to E5, wherein:
  the originating epithelial cell population, or
  the expanded epithelial cell population, or
  the originating epithelial cell population and the expanded epithelial cell population,
  express one or more of ITGA6, ITGB4, KRT14, KRT15, KRT5 and TP63.

E7. The method of any one of embodiments E1 to E6, wherein:
  the originating epithelial cell population, or
  the expanded epithelial cell population, or
  the originating epithelial cell population and the expanded epithelial cell population,
  do not express one or more epithelial stem cell markers.

E8. The method of any one of embodiments E1 to E7, wherein:
  the originating epithelial cell population, or
  the expanded epithelial cell population, or
  the originating epithelial cell population and the expanded epithelial cell population,
  do not express Lgr5.

E9. The method of any one of embodiments E1 to E8, wherein:
  the originating epithelial cell population, or
  the expanded epithelial cell population, or
  the originating epithelial cell population and the expanded epithelial cell population,
  do not express one or more pluripotent stem cell markers.

E10. The method of any one of embodiments E1 to E9, wherein:
  the originating epithelial cell population, or
  the expanded epithelial cell population, or
  the originating epithelial cell population and the expanded epithelial cell population, do not express one or more of LIN28A, NANOG, POU5F1/OCT4 and SOX2.

E11. The method of any one of embodiments E1 to E10, wherein:
  the originating epithelial cell population, or
  the expanded epithelial cell population, or
  the originating epithelial cell population and the expanded epithelial cell population,
  do not express one or more terminally differentiated epithelial cell markers.

E12. The method of any one of embodiments E1 to E11, wherein:
the originating epithelial cell population, or
the expanded epithelial cell population, or
the originating epithelial cell population and the expanded epithelial cell population,
do not express one or more of CFTR, FOXJ1, IVL, KRT1, KRT10, KRT20, LOR, MUC1, MUC5AC, SCGB1A1, SFTPB and SFTPD.

E13. The method of any one of embodiments E1 to E12, wherein:
the originating epithelial cell population, or
the expanded epithelial cell population, or
the originating epithelial cell population and the expanded epithelial cell population,
do not express one or more gastric epithelial cell markers, one or more intestinal epithelial cell markers, and/or one or more pancreatic epithelial cell markers.

E14. The method of any one of embodiments E1 to E13, wherein:
the originating epithelial cell population, or
the expanded epithelial cell population, or
the originating epithelial cell population and the expanded epithelial cell population,
do not express one or more of CD34, HNF1A, HNF4A, IHH, KIT, LGR5, PDX1, and PROM1/CD133.

E15. The method of any one of embodiments E1 to E14, wherein:
the originating epithelial cell population, or
the expanded epithelial cell population, or
the originating epithelial cell population and the expanded epithelial cell population,
comprise quiescent and/or formerly quiescent epithelial cells.

E16. The method of any one of embodiments E1 to E15, wherein the agent that activates telomerase reverse transcriptase in the population and/or inhibits transforming growth factor beta (TGF-beta) signaling comprises one or more TGF-beta signaling inhibitors.

E17. The method of embodiment E16, wherein the one or more TGF-beta signaling inhibitors comprise one or more ALK5 inhibitors.

E18. The method of embodiment E17, wherein the one or more ALK5 inhibitors comprise one or more small molecule ALK5 inhibitors.

E19. The method of embodiment E17, wherein the one or more ALK5 inhibitors are selected from A83-01, GW788388, RepSox, and SB 431542.

E20. The method of any one of embodiments E1 to E19, wherein the agent that modulates cytoskeletal structure comprises one or more of a Rho-associated protein kinase inhibitor, a p21-activated kinase (PAK) inhibitor, and a myosin II inhibitor.

E21. The method of embodiment E20, wherein the Rho kinase inhibitor is selected from a Rho-associated protein kinase 1 (ROCK 1) inhibitor and a Rho-associated protein kinase 2 (ROCK 2) inhibitor.

E22. The method of embodiment E20 or E21, wherein the Rho-associated protein kinase inhibitor comprises one or more small molecule Rho-associated protein kinase inhibitors.

E23. The method of embodiment E22, wherein the one or more Rho-associated protein kinase inhibitors is selected from Y-27632, SR 3677, thiazovivin, HA1100 hydrochloride, HA1077 and GSK-429286.

E24. The method of any one of embodiments E20 to E23, wherein the p21-activated kinase (PAK) inhibitor is selected from a PAK1 inhibitor, a PAK2 inhibitor, a PAK3 inhibitor and a PAK4 inhibitor.

E25. The method of embodiment E24, wherein the p21-activated kinase (PAK) inhibitor comprises one or more small molecule PAK1 inhibitors.

E26. The method of embodiment E25, wherein the one or more small molecule PAK inhibitors comprise IPA3.

E27. The method of any one of embodiments E20 to E26, wherein the myosin II inhibitor comprises one or more non-muscle myosin II (NM II) inhibitors.

E28. The method of embodiment E27, wherein the one or more non-muscle myosin II (NM II) inhibitors comprise one or more small molecule non-muscle myosin II (NM II) inhibitors.

E29. The method of embodiment E28, wherein the one or more small molecule non-muscle myosin II (NM II) inhibitors comprise blebbistatin.

E30. The method of any one of embodiments E1 to E29, wherein the expansion culture conditions further comprise an agent that increases intracellular cyclic adenosine monophosphate (cAMP) levels in the population.

E31. The method of embodiment E30, wherein the agent that increases intracellular cyclic adenosine monophosphate (cAMP) levels comprises one or more beta-adrenergic receptor agonists.

E32. The method of embodiment E31, wherein the one or more beta-adrenergic receptor agonists comprise isoproterenol.

E33. The method of any one of embodiments E1 to E32, wherein the expansion culture conditions are serum-free culture conditions.

E34. The method of any one of embodiments E1 to E33, wherein the expansion culture conditions are defined serum-free culture conditions.

E35. The method of any one of embodiments E1 to E34, wherein the expansion culture conditions are xeno-free culture conditions.

E36. The method of any one of embodiments E1 to E35, wherein the expansion culture conditions are defined xeno-free culture conditions.

E37. The method of any one of embodiments E1 to E36, wherein the expansion culture conditions comprise calcium at a concentration below 100 µM.

E38. The method of embodiment E37, wherein the calcium is present at a concentration of about 90 µM.

E39. The method of any one of embodiments E1 to E38, wherein the expansion culture conditions comprise one or more mitogenic growth factors.

E40. The method of embodiment E39, wherein one or more mitogenic growth factors comprise EGF, FGF, or EGF and FGF.

E41. The method of any one of embodiments E1 to E40, wherein the expansion culture conditions comprise no extracellular matrix.

E42. The method of any one of embodiments E1 to E41, wherein the originating epithelial cell population is capable of 30 population doublings or more when cultured under the expansion culture conditions.

E43. The method of any one of embodiments E1 to E41, wherein the originating epithelial cell population is capable of 50 population doublings or more when cultured under the expansion culture conditions.

E44. The method of any one of embodiments E1 to E41, wherein the originating epithelial cell population is capable of 80 population doublings or more when cultured under the expansion culture conditions.

E45. The method of any one of embodiments E1 to E41, wherein the originating epithelial cell population is capable of 100 population doublings or more when cultured under the expansion culture conditions.

E46. The method of any one of embodiments E1 to E45, wherein the method does not comprise selecting for continuously proliferating epithelial stem cells in the originating epithelial cell population.

E47. The method of any one of embodiments E1 to E45, wherein the originating epithelial cell population does not comprise continuously proliferating epithelial stem cells.

E48. The method of any one of embodiments E1 to E47, further comprising isolating a population of ex vivo expanded epithelial cells.

E49. The method of any one of embodiments E1 to E48, further comprising storing a population of ex vivo expanded epithelial cells in a cell bank.

E50. A population of ex vivo expanded epithelial cells produced by a method according to any one of embodiments E1 to E49.

E51. Use of the population of ex vivo expanded epithelial cells of embodiment E50 for production of genetically modified cells.

E52. Use of the population of ex vivo expanded epithelial cells of embodiment E50 for identifying one or more candidate treatments for a subject.

E53. Use of the population of ex vivo expanded epithelial cells of embodiment E50 for identifying one or more abnormal epithelial cells in a subject.

E54. Use of the population of ex vivo expanded epithelial cells of embodiment E50 for monitoring the progression of a disease or treatment of a disease in a subject.

The entirety of each patent, patent application, publication and document referenced herein hereby is incorporated by reference. Citation of the above patents, patent applications, publications and documents is not an admission that any of the foregoing is pertinent prior art, nor does it constitute any admission as to the contents or date of these publications or documents. Their citation is not an indication of a search for relevant disclosures. All statements regarding the date(s) or contents of the documents is based on available information and is not an admission as to their accuracy or correctness.

Modifications may be made to the foregoing without departing from the basic aspects of the technology. Although the technology has been described in substantial detail with reference to one or more specific embodiments, those of ordinary skill in the art will recognize that changes may be made to the embodiments specifically disclosed in this application, yet these modifications and improvements are within the scope and spirit of the technology.

The technology illustratively described herein suitably may be practiced in the absence of any element(s) not specifically disclosed herein. Thus, for example, in each instance herein any of the terms "comprising," "consisting essentially of," and "consisting of" may be replaced with either of the other two terms. The terms and expressions which have been employed are used as terms of description and not of limitation, and use of such terms and expressions do not exclude any equivalents of the features shown and described or portions thereof, and various modifications are possible within the scope of the technology claimed. The term "a" or "an" can refer to one of or a plurality of the elements it modifies (e.g., "a reagent" can mean one or more reagents) unless it is contextually clear either one of the elements or more than one of the elements is described. The term "about" as used herein refers to a value within 10% of the underlying parameter (i.e., plus or minus 10%), and use of the term "about" at the beginning of a string of values modifies each of the values (i.e., "about 1, 2 and 3" refers to about 1, about 2 and about 3). For example, a weight of "about 100 grams" can include weights between 90 grams and 110 grams. Further, when a listing of values is described herein (e.g., about 50%, 60%, 70%, 80%, 85% or 86%) the listing includes all intermediate and fractional values thereof (e.g., 54%, 85.4%). Thus, it should be understood that although the present technology has been specifically disclosed by representative embodiments and optional features, modification and variation of the concepts herein disclosed may be resorted to by those skilled in the art, and such modifications and variations are considered within the scope of this technology.

Certain embodiments of the technology are set forth in the claim(s) that follow(s).

What is claimed is:

1. A method for proliferating epithelial cells ex vivo, comprising:
  expanding the number of cells in an originating epithelial cell population under serum-free and feeder-cell free expansion culture conditions, thereby generating an expanded epithelial cell population, wherein (i) the originating epithelial cell population comprises epithelial progenitor cells, wherein the cells have non-detectable expression of one or more genes chosen from LGR5, Axin2, and Prom1 during expansion, and (ii) the expansion culture conditions comprise one or more agents that inhibit transforming growth factor beta (TGF-beta) signaling in the population.

2. The method of claim 1, the one or more agents that inhibit transforming growth factor beta (TGF-beta) signaling in the population comprise one or more inhibitors of ALK5, ALK4, and/or ALK7.

3. The method of claim 2, wherein the one or more inhibitors of ALK5, ALK4, and/or ALK7 are selected from A83-01, GW788388, RepSox, and SB 431542.

4. The method of claim 1, wherein the expansion culture conditions comprise a second agent that modulates cytoskeletal structure in the population.

5. The method of claim 4, wherein the second agent comprises an inhibitor selected from a Rho-associated protein kinase inhibitor, a p21-activated kinase (PAK) inhibitor, and a myosin II inhibitor.

6. The method of claim 5, wherein the Rho-associated protein kinase inhibitor is selected from Y-27632, SR 3677, thiazovivin, HA1100 hydrochloride, HA1077 and GSK-429286.

7. The method of claim 5, wherein the PAK inhibitor is IPA3.

8. The method of claim 5, wherein the myosin II inhibitor is blebbistatin.

9. The method of claim 1, wherein the expansion culture conditions further comprise a beta-adrenergic receptor agonist.

10. The method of claim 9, wherein the beta-adrenergic receptor agonist is isoproterenol.

11. The method of claim 1, wherein the expansion culture conditions comprise calcium at a concentration below 100 µM.

12. The method of claim 1, wherein the expansion culture conditions comprise one or more mitogenic growth factors.

13. The method of claim 12, wherein the one or more mitogenic growth factors comprise EGF, FGF, or EGF and FGF.

14. The method of claim 1, wherein the expansion culture conditions comprise inhibitors consisting of an ALK5 inhibitor and a Rho-associated protein kinase inhibitor; an ALK5 inhibitor and a p21-activated kinase (PAK) inhibitor; or an ALK5 inhibitor and a myosin II inhibitor.

15. A method for proliferating epithelial cells ex vivo, comprising:
  expanding the number of cells in an originating epithelial cell population under serum-free and feeder-cell free expansion culture conditions, thereby generating an expanded epithelial cell population, wherein (i) the originating epithelial cell population comprises epithelial progenitor cells, wherein the cells have non-detectable expression of one or more genes chosen from LGR5, Axin2, and Prom1 during expansion, and (ii) the expansion culture conditions comprise:
    a) one or more transforming growth factor beta (TGF-beta) inhibitors;
    b) one or more agents that modulate cytoskeletal structure;
    c) a beta-adrenergic receptor agonist;
    d) one or more mitogenic growth factors; and
    e) calcium at a concentration below 100 µM.

16. The method of claim 15, wherein the one or more transforming growth factor beta (TGF-beta) inhibitors comprise one or more inhibitors of ALK5, ALK4, and/or ALK7; and the one or more agents that modulate cytoskeletal structure comprise one or more inhibitors selected from a Rho-associated protein kinase inhibitor, a p21-activated kinase (PAK) inhibitor, and a myosin II inhibitor.

17. The method of claim 16, wherein the one or more inhibitors of ALK5, ALK4, and/or ALK7 are selected from A83-01, GW788388, RepSox, and SB 431542; the Rho-associated protein kinase inhibitor is selected from Y-27632, SR 3677, thiazovivin, HA1100 hydrochloride, HA1077 and GSK-429286; the PAK inhibitor is IPA3; and the myosin II inhibitor is blebbistatin.

18. A composition comprising
  a) a cell population comprising epithelial progenitor cells, wherein the cells have non-detectable expression of one or more genes chosen from LGR5, Axin2, and Prom1;
  b) one or more transforming growth factor beta (TGF-beta) inhibitors; and
  c) one or more agents that modulate cytoskeletal structure.

19. The composition of claim 18, wherein the one or more transforming growth factor beta (TGF-beta) inhibitors comprise one or more inhibitors of ALK5, ALK4, and/or ALK7; and the one or more agents that modulate cytoskeletal structure comprise one or more inhibitors selected from a Rho-associated protein kinase inhibitor, a p21-activated kinase (PAK) inhibitor, and a myosin II inhibitor.

20. The composition of claim 19, wherein the one or more inhibitors of ALK5, ALK4, and/or ALK7 are selected from A83-01, GW788388, RepSox, and SB 431542; the Rho-associated protein kinase inhibitor is selected from Y-27632, SR 3677, thiazovivin, HA1100 hydrochloride, HA1077 and GSK-429286; the PAK inhibitor is IPA3; and the myosin II inhibitor is blebbistatin.

* * * * *